United States Patent
Meng et al.

(10) Patent No.: US 10,067,130 B2
(45) Date of Patent: *Sep. 4, 2018

(54) INFECTIOUS GENOMIC DNA CLONE AND SEROLOGICAL PROFILE OF TORQUE TENO SUS VIRUS 1 AND 2

(71) Applicant: Virginia Tech Intellectual Properties, Inc., Blacksburg, VA (US)

(72) Inventors: Xiang-Jin Meng, Blacksburg, VA (US); Yaowei Huang, Blacksburg, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/978,413

(22) Filed: Dec. 22, 2015

(65) Prior Publication Data

US 2016/0266116 A1 Sep. 15, 2016

Related U.S. Application Data

(60) Division of application No. 13/840,805, filed on Mar. 15, 2013, now Pat. No. 9,249,192, which is a continuation-in-part of application No. 12/861,378, filed on Aug. 23, 2010, now Pat. No. 9,228,242.

(60) Provisional application No. 61/588,988, filed on Jan. 20, 2012, provisional application No. 61/316,519, filed on Mar. 23, 2010, provisional application No. 61/235,833, filed on Aug. 21, 2009.

(51) Int. Cl.
*G01N 33/569* (2006.01)
*A61K 39/12* (2006.01)
*C12Q 1/70* (2006.01)
*C12N 15/86* (2006.01)
*C12N 7/00* (2006.01)
*C07K 14/005* (2006.01)
*A61K 39/00* (2006.01)

(52) U.S. Cl.
CPC ....... *G01N 33/56983* (2013.01); *A61K 39/12* (2013.01); *C07K 14/005* (2013.01); *C12N 7/00* (2013.01); *C12N 15/86* (2013.01); *C12Q 1/701* (2013.01); *A61K 2039/53* (2013.01); *A61K 2039/552* (2013.01); *C12N 2750/00021* (2013.01); *C12N 2750/00022* (2013.01); *C12N 2750/00034* (2013.01); *C12N 2750/00043* (2013.01); *G01N 2333/01* (2013.01); *G01N 2469/20* (2013.01)

(58) Field of Classification Search
CPC combination set(s) only.
See application file for complete search history.

(56) References Cited

U.S. PATENT DOCUMENTS

2011/0150913 A1 6/2011 Nitzel et al.

FOREIGN PATENT DOCUMENTS

WO WO-2008127279 A2 10/2008
WO WO-2008150275 A2 12/2008

OTHER PUBLICATIONS

Kakkola L, Bondén H, Hedman L, Kivi N, Moisala S, Julin J, Ylä-Liedenpohja J, Miettinen S, Kantola K, Hedman K, Söderlund-Venermo M. Expression of all six human Torque teno virus (TTV) proteins in bacteria and in insect cells, and analysis of their IgG responses. Virology. Dec. 20, 2008;382(2):182-9. Epub Oct. 22, 2008.*
Anderson, et al., "Failure to genotype herpes simplex virus by real-time PCR assay and melting curve analysis due to sequence variation within probe binding sites". Journal of Clinical Microbiology, 2003, pp. 2135-2137 vol. 41, American Society for Microbiology.
Bao, et al., "Virus Classification by Pairwise Sequence Comparison (PASC)", 2008, pp. 342-348, vol. 5, Elsevier Ltd. Oxford, U.K.
Biagini, et al., "Classification of TTV and related viruses (anelloviruses)". Current Topics in Microbiology Immunology, 2009, pp. 21-33, vol. No. 331, Springer-Verlag Berlin Heidelberg.
Biagini, et al., "Distribution and genetic analysis of TTV and TTMV major phylogenetic groups in French blood donors". Journal of Medical Virology, 2006, pp. 298-304, vol. No. 78, Issue No. 2, Journal of Medical Virology, Marseille, France.
Biagini, et al., "Circular genomes related to anelloviruses identified in human and animal samples by using a combined rolling-circle amplification/sequence-independent single primer amplification approach". Journal of General Virology, 2007, pp. 2696-2701, vol. 88, Pt 10, Marseille, France.
Brassard, et al., "Development of a real-time TaqMan PCR assay for the detection of porcine and bovine Torque teno virus", Journal of Applied Microbiology, Agriculture and Agri-food Canada, Nov. 2009, pp. 2191-2198, Food Research and Development Centre, Saint-Hyacinthe, QC, Canada.

(Continued)

*Primary Examiner* — Rachel B Gill
(74) *Attorney, Agent, or Firm* — Blank Rome LLP

(57) ABSTRACT

The present invention also provides infectious DNA clones, biologically functional plasmid or viral vector containing the infectious nucleic acid genome molecule of Torque teno sus virus (TTsuV). The present invention also provides methods for diagnosing TTsuV infection via immunological methods, e.g., enzyme-linked immunoabsorbent assay (ELISA) and Western blot using PTTV specific antigens for detecting serum PTTV specific antibodies which indicate infections TTsuV1, TTsuV2, and individual TTsuV1 genotypes.

12 Claims, 27 Drawing Sheets

Specification includes a Sequence Listing.

(56) References Cited

OTHER PUBLICATIONS

Davidson, et al., "Unraveling the puzzle of human anellovirus infections by comparison with avian infections with the chicken anemia virus", Virus Research, 2008, pp. 1-15, vol. 137, Issue 1, Israel.

De Smit, et al., "Apoptosis-inducing proteins in chicken anemia virus and TT virus". Current Topics in Microbiology and Immunology, 2009, pp. 131-149, vol. 331.

Ellis, et al., "Effect of coinfection with genogroup 1 porcine torque teno virus on porcine circovirus type 2-associated postweaning multisystemic wasting syndrome in gnotobiotic pigs". American Journal of Veterinary Research, Dec. 2008, pp. 1608-1614, vol. 69, Issue 12, Schaumburg, IL.

Gallei, et al., "Porcine Torque teno virus: Determination of viral genomic loads by genogroup-specific multiplex rt-PCR, detection of frequent multiple infections with genogroups 1 or 2, and establishment of viral full-length sequences". Veterinary Microbiology, 2010, pp. 202-212, vol. 143, Veterinary Microbiology, Munster, Germany.

Gibellini, et al., "Simultaneous detection of HCV and HIV-1 by SYBR Green real time multiplex RT-PCR technique in plasma samples". Molecular and Cellular Probes, Mar. 2006, pp. 223-229, vol. 20.

Hino, et al., "Torque teno virus (TTV): current status". Reviews in Medical Virology, 2007, pp. 45-57, vol. 17, Wiley Interscience.

Hino, et al., "Relationship of Torque teno virus to chicken anemia virus". Current Topics in Microbiology and Immunology, 2009, pp. 117-130, vol. 331, Springer Verlag Berlin Heidelberg.

Ilyina, et al., "Conserved sequence motifs in the initiator proteins for rolling circle DNA replication encoded by diverse replicons from eubacteria, eucaryotes and archaebacteria". Nucleic Acids Research, pp. 3279-3285, vol. 20, No. 13, NIH, Bethesda, MD.

Inami, et al., "Full-length nucleotide sequence of a simian TT virus isolate obtained from a chimpanzee: evidence for a new TT virus-like species". Virology, 2000, pp. 330-335, vol. 277, No. 2, Academic Press.

Jelcic, et al., "Isolation of multiple TT virus genotypes from spleen biopsy tissue from a Hodgkin's disease patient: genome reorganization and diversity in the hypervariable region". Journal of Virology, 2004, pp. 7498-7507, vol. 78, No. 14, American Society for Microbiology.

Kakkola, et al., "Replication of and protein synthesis by TT viruses". Current Topics in Microbiology and Immunology, 2009, pp. 53-64, vol. 331, Springer Verlag Berlin Heidelberg.

Kekarainen, et al., "Detection of swine Torque teno virus genogroups 1 and 2 in boar sera and semen". Theriogenology, 2007, pp. 966-971, vol. 68, No. 4.

Kekarainen, et al., "Prevalence of swine Torque teno virus in post-weaning multisystemic wasting syndrome (PMWS)-affected and non-PMWS-affected pigs in Spain". Journal of General Virology, 2006, pp. 833-837, vol. 87, Part 4, UK.

Krakowka, et al., "Evaluation of the effects of porcine genogroup 1 torque teno virus in gnotobiotic swine". American Journal of Veterinary Research, 2008, pp. 1623-1629, vol. 69.

Krakowka, et al., "Evaluation of induction of porcine dermatitis and nephropathy syndrome in gnotobiotic pigs with negative results for porcine circovirus type 2". American Journal of Veterinary Research, 2008, pp. 1615-1622, vol. 69, Part 12.

Maggi, et al., "Immunobiology of the Torque teno viruses and other anelloviruses". Current Topics in Microbiology and Immunology, 2009, pp. 65-90, vol. 331.

Martinez, "Simultaneous detection and genotyping of porcine reproductive and respiratory syndrome virus (PRRSV) by real-time RT-PCR and amplicon melting curve analysis using SYBR Green". Research in Veterinary Science, 2008, pp. 184-193 vol. 85, Issue 1.

McKeown, et al., "Molecular characterization of porcine TT virus, an orphan virus, in pigs from six different countries". Veterinary Microbiology, 2004, pp. 113-117, vol. 104, Issues 1-2.

Mouillesseaux, et al., Improvement in the specificity and sensitivity of detection for the Taura syndrome virus and yellow head virus of penaeid shrimp by increasing the amplicon size in SYBR Green real-time RT-PCR. Journal of Virological Methods, 2003, pp. 121-127, vol. 111, Issue 2.

Mueller, et al., "Gene expression of the human Torque Teno Virus isolate P/1C1" Virology, 2008, pp. 36-45, vol. 381, Issue 1.

Ng, et al., "Novel anellovirus discovered from a mortality event of captive California sea lions". Journal of General Virology, 2009, pp. 1256-1261, vol. 90, Pt 5.

Niel, et al., "Rolling-circle amplification of Torque teno virus (TTV) complete genomes from human and swine sera and identification of a novel swine TTV genogroup". Journal of General Virology, 2005, pp. 1343-1347, vol. 86, Pt. 5.

Niel, et al., "Coinfection with multiple TT virus strains belonging to different genotypes is a common event in healthy Brazilian adults". Journal of Clinical Microbiology, 2000, pp. 1926-1930, vol. 38, No. 5.

Ninomiya, et al., "Analysis of the entire genomes of torque teno midi virus variants in chimpanzees: infrequent cross-species infection between humans and chimpanzees". Journal of General Virology, 2009, pp. 347-358, vol. 90, Pt 2.

Nishizawa, et al., "A novel DNA virus (TTV) associated with elevated transaminase levels in posttransfusion hepatitis of unknown etiology". Biochemical Biophysical Research Communications, 1997, pp. 92-97, vol. 241, No. 1.

Okamoto, et al., "History of discoveries and pathogenicity of TT viruses". Current Topics in Microbiology and Immunology, 2009, pp. 1-20, vol. 331.

Okamoto, et al., "TT viruses in animals". Current Topics in Microbiology and Immunology, 2009, pp. 35-52, vol. 331.

Okamoto, et al., "Genomic and evolutionary characterization of TT virus (TTV) in tupaias and comparison with species-specific TTVs in humans and non-human primates". Journal of General Virology, 2001, pp. 2041-2050, vol. 82, Pt 9.

Okamoto, et al., "Species-specific TT viruses in humans and non-human primates and their phylogenetic relatedness". Virology, 2000, pp. 368-378,vol. 277, No. 2.

Okamoto, et al., "TT virus mRNAs detected in the bone marrow cells from an infected individual". Biochemical and Biophysical Research Communications. 2000, pp. 700-707, vol. 279, No. 2.

Okamoto, et al., "Genomic characterization of TT viruses (TTVs) in pigs, cats and dogs and their relatedness with species-specific TTVs in primates and tupaias". Journal of General Virology, 2002, pp. pp. 700-707, vol. 83, Pt 6.

Opriessnig, et al., "Porcine circovirus type 2 associated disease: update on current terminology, clinical manifestations, pathogenesis, diagnosis, and intervention strategies". Journal of Veterinary Diagnostic Investestigation, 2007, pp. 591-615, vol. 19.

Pal, et al., "Development and validation of a duplex real-time PCR assay for the simultaneous detection and quantification of porcine circovirus type 2 and an internal control on porcine semen samples". Journal of Virological Methods, 2008, pp. 217-225, vol. 149.

Peters, et al., "Attenuation of chicken anemia virus by site-directed mutagenesis of VP2". Journal of General Virology, 2007, pp. 2168-2175, vol. 88, Pt. 8.

Peters, et al., "Site-directed mutagenesis of the VP2 gene of Chicken anemia virus affects virus replication, cytopathology and host-cell MHC class I expression". Journal of General Virology, 2006, pp. 823-831, vol. 87, Pt. 4.

Peters, et al., "Chicken anemia virus VP2 is a novel dual specificity protein phosphatase". Journal of Biological Chemistry, 2002, pp. 39566-39573, vol. 277, No. 42.

Pozzuto, et al., "In utero transmission of porcine torque teno viruses". Veterinary Microbiology, 2009, pp. 375-379, vol. 137.

Prasetyo, et al., "Replication of chicken anemia virus (CAV) requires apoptin and is complemented by VP3 of human torque teno virus (TTV)". Virology, 2009, pp. 85-92, vol. 385, No. 1.

Qiu, et al., "Human circovirus TT virus genotype 6 expresses six proteins following transfection of a full-length clone". Journal of Virology, 2005, pp. 6505-6510, vol. 79, No. 10.

(56) References Cited

OTHER PUBLICATIONS

Ririe, et al., "Product differentiation by analysis of DNA melting curves during the polymerase chain reaction". Analytical Biochemistry, 1997, pp. 154-160, vol. 245.

Sibila, et al., "Swine torque teno virus (TTV) infection and excretion dynamics in conventional pig farms". Veterinary Microbiology, 2009, pp. 213-228, vol. 139.

Takayama, et al., "Prevalence and persistence of a novel DNA TT virus (TTV) infection in Japanese haemophiliacs". British Journal of Haematology, 1999, vol. 104, No. 3, pp. 626-629.

Wilhelm, et al., "Real-time PCR protocol for the detection of porcine parvovirus in field samples". Journal of Virological Methods, 2006, pp. 257-260, vol. 134.

Okamoto, et al. "Genomic characterization of TT viruses (TTVs) in pigs, cats and dogs and their relatedness with species-specific TTVs in primates and tupias," Journal of General Virology, 2002, pp. 1291-1297, The Society for General Microbiology, Reading, UK.

Y.W. Huang, et al., Multiple infection of porcine Torque teno virus in a single pig and characterization of the full-length genomic sequences of four U.S. prototype PTTV strains: Implication for genotyping of PTTV, Nov. 2009, p. 289-297, Virology, vol. 396.

Huang, Y.W. et al., Multiple infectin of porcine Torque teno virus in a single pig and characterization of the full-length genomic sequences of four U.S. Prototype PTTV strains: Implication for genotyping of PTTV, Virology, vol. 396, No. 2., Nov. 13, 2009, p. 289-297.

Okamoto, H, "Torque teno virus ORF3, ORF2, ORF1 genes, complete cds. isolate Sd-TTV31", The Journal of General Virology, vol. 83, No. Pt , Jun. 2002, pages.

Huang, Y.W. et al., Multiple infection of porcine Torque teno virus in a single pig and characterization of the full-length genomic sequences of four U.S. prototype PTTV strains: Implication for genotyping of PTTV, Nov. 2009, p. 289-297, Virology, vol. 396.

Ninomiya, M. M., et al., "Development of PCR assays with nested primers specific for differential detection of three human anelloviruses and early acquisition of dual or triple infection during infancy." J Clin. Microbiol 46, pp. 507-514, 2008.

Huang, Y. W., et al., "Multiple infection of porcine Torque teno virus in a single pig and characterization of the full-length genomic sequences of four U.S. prototype PTTV strains: implication for genotyping of PTTV." Virology 396, pp. 287-297, 2010.

Niel, C. L., et al., "Rolling-circle amplification of Torque teno virus (TTV) complete genomes from human and swine sera and identification of a novel swine TTV genogroup," J Gen Virol 86, pp. 1343-1347, 2005.

Huang, Y. W., et al., "Expression of the putative ORF1 capsid protein of Torque teno sus virus 2 (TTSuV2) and development of Western blot and ELISA serodiagnostic assays: correlation between TTSuV2 viral load and IgG antibody level in pigs," Virus Res 158, pp. 79-88, 2011.

\* cited by examiner

TTSuV1

TTSuV2

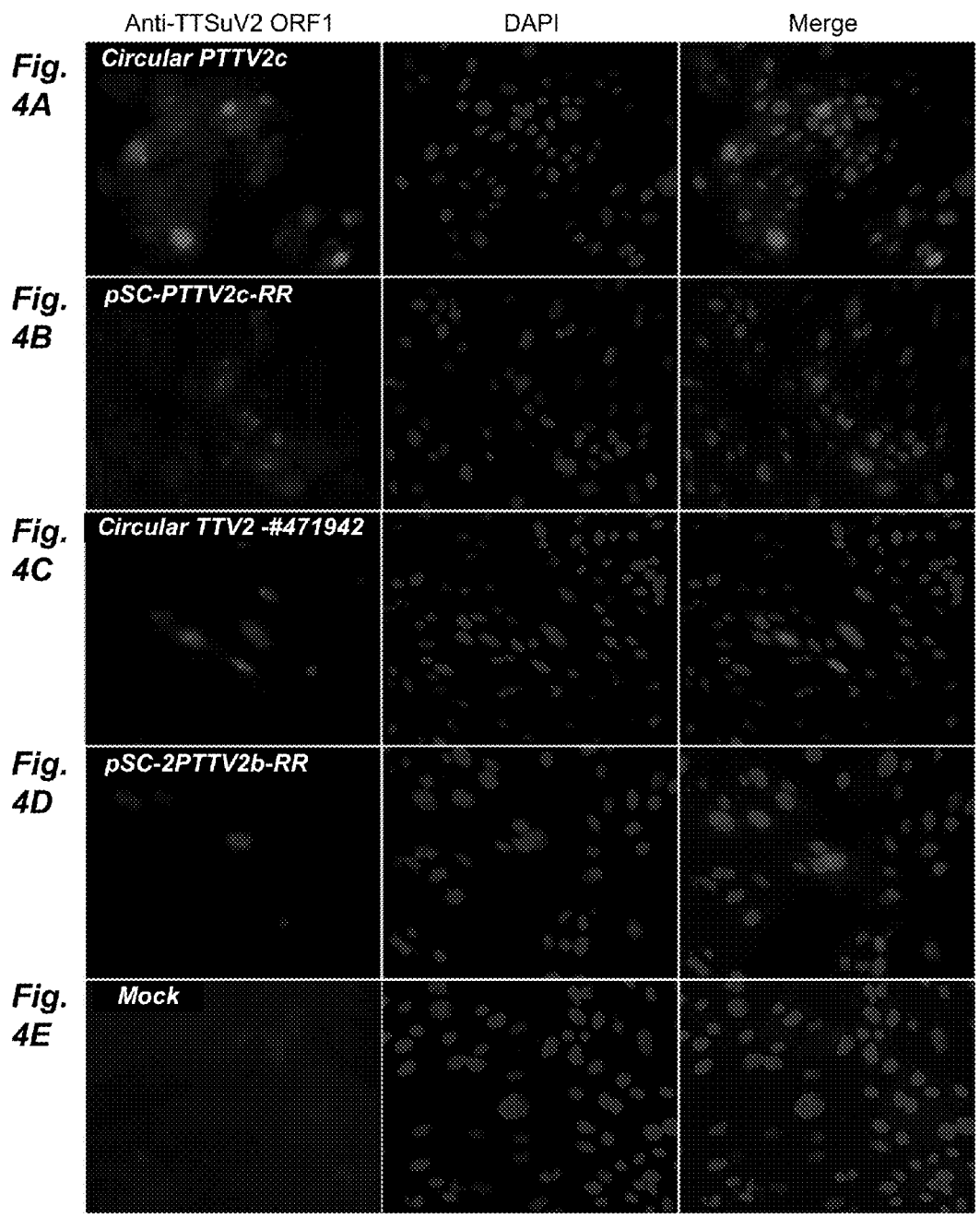

*Fig. 8A* *Fig. 8B* *Fig. 8C*
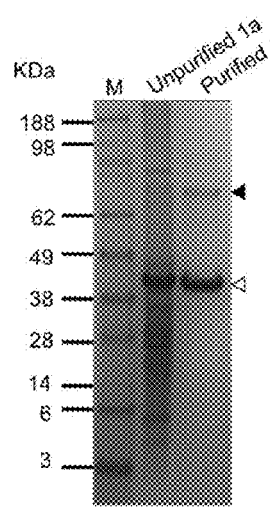
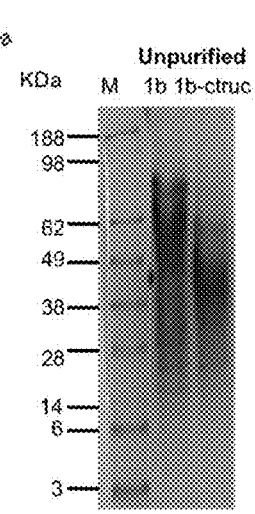
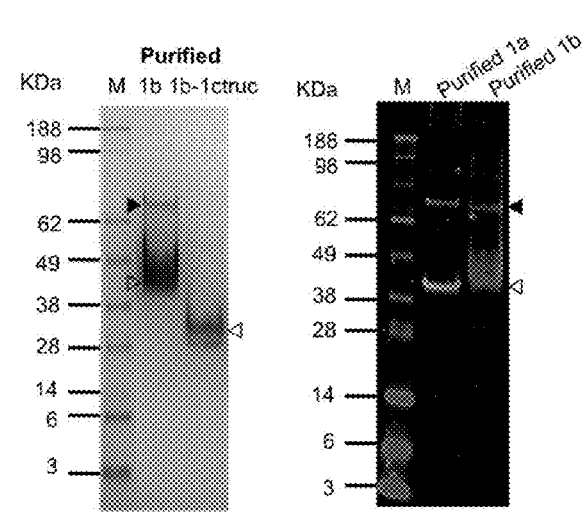

Gnotobiotic pigs

Conventional pigs from Wisconsin

*Fig. 10A*
| | TTSuV1 viremia | Anti-TTSuV1a IgG | Anti-TTSuV1b IgG | No. of diagnosed samples |
|---|---|---|---|---|
| Positive rate (Positive No./Total No.) | 31.9% (44/138) | 92.8% (128/138) | 87.7% (121/138) | |
| | + | + | + | 40 |
| | + | + | - | 2 |
| | + | - | + | 2 |
| | + | - | - | 0 |
| | - | + | + | 77 |
| | - | + | - | 9 |
| | - | - | + | 2 |
| | - | - | - | 6 |
*Fig. 10B*
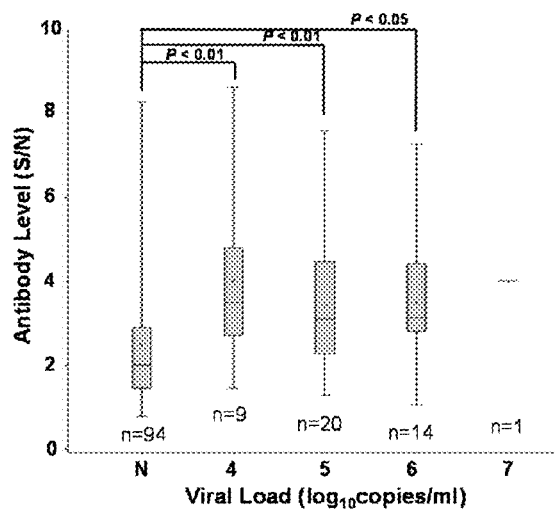
*Fig. 10C*
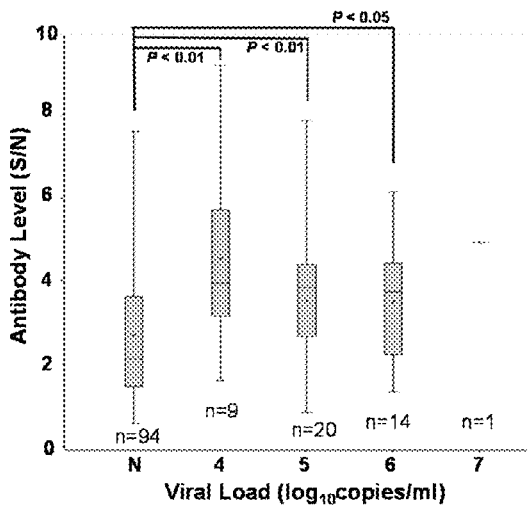

| | Anti-TTSuV1a IgG | Anti-TTSuV1b IgG | Anti-TTSuV2b IgG | No. of diagnosed samples |
|---|---|---|---|---|
| Positive rate (Positive No./Total No.) | 92.8% (128/138) | 87.7% (121/138) | 68.2% (90/132) | |
| | + | + | + | 82 |
| | + | + | - | 30 |
| | + | + | N/A | 5 |
| | + | - | N/A | 1 |
| | + | - | + | 1 |
| | + | - | - | 9 |
| | - | + | + | 1 |
| | - | + | - | 3 |
| | - | - | + | 6 |
| | - | - | - | 0 |

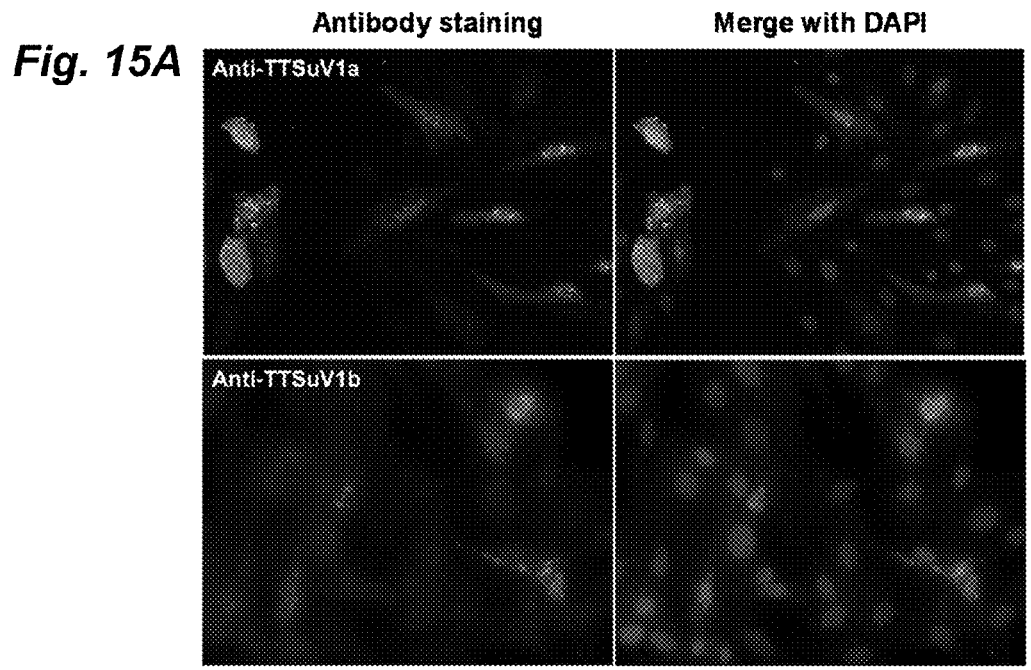
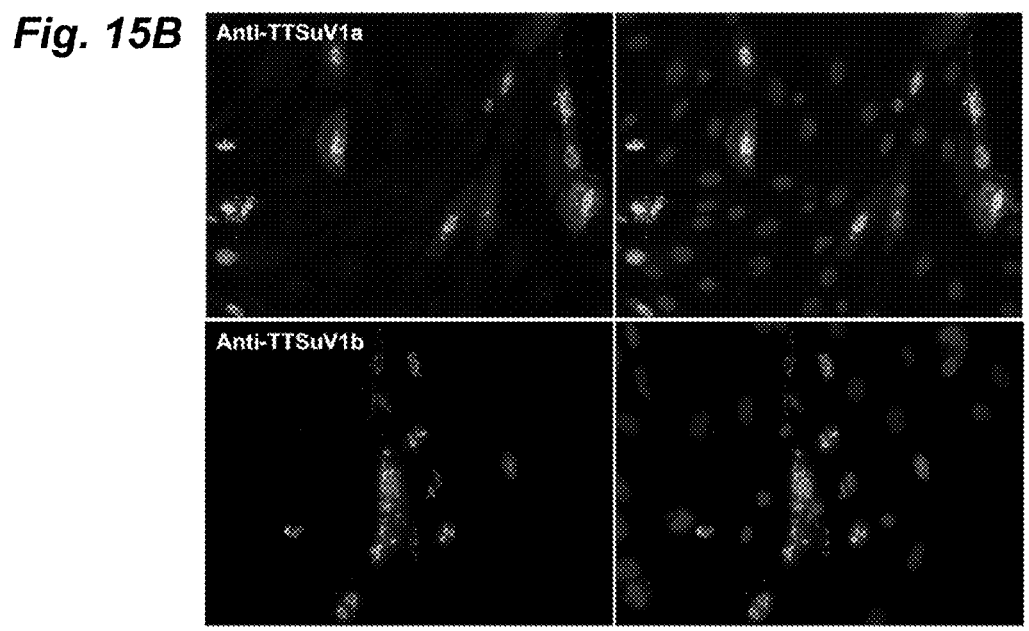
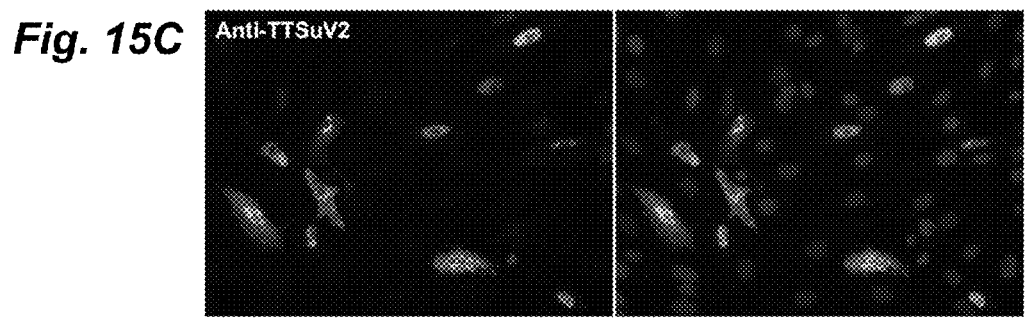
Fig. 15A
Fig. 15B
Fig. 15C

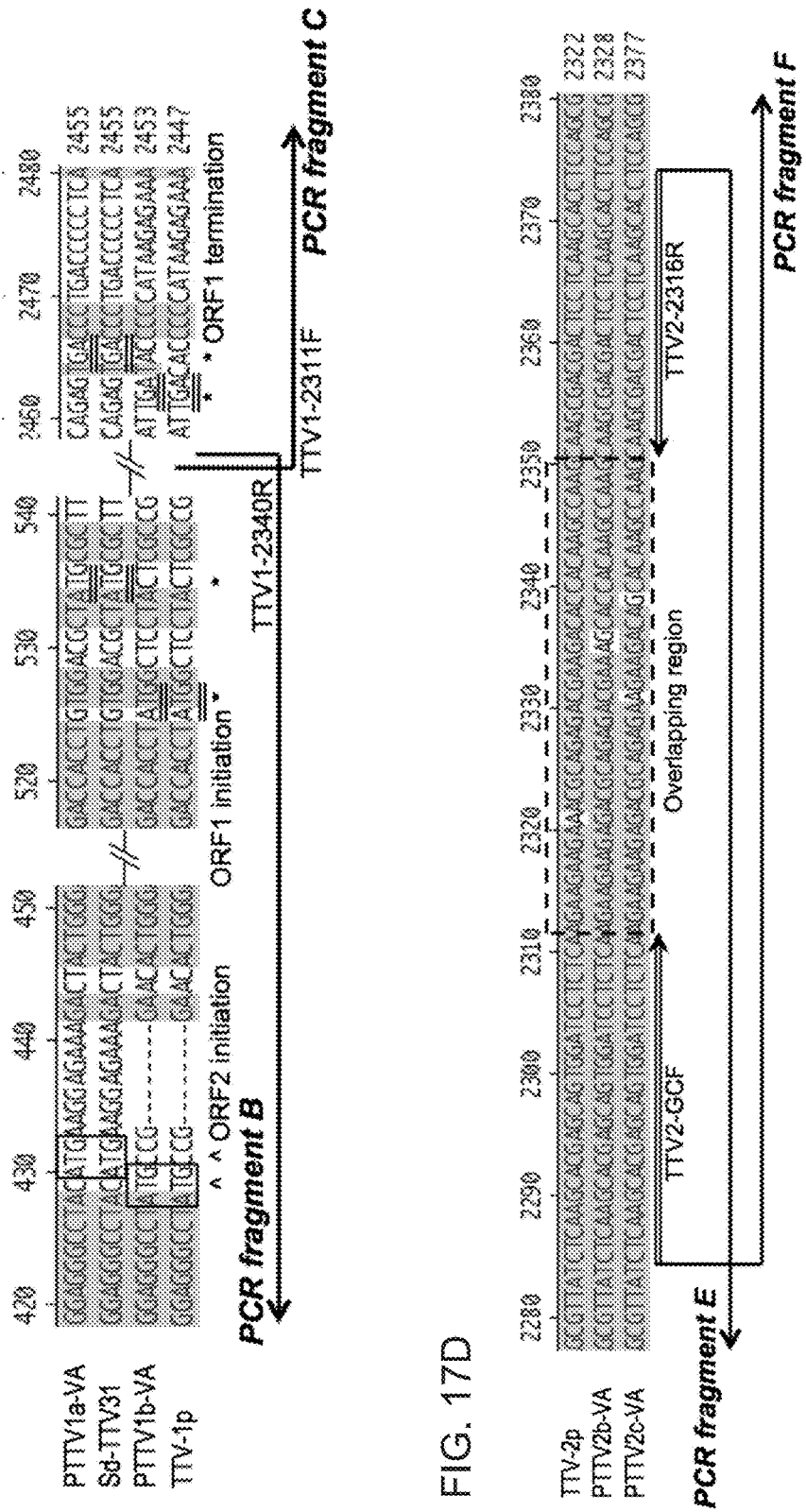

SEQUENCE LISTING

<160> NUMBER OF SEQ ID NOS: 68

<210> SEQ ID NO 1
<211> LENGTH: 32
<212> TYPE: DNA
<213> ORGANISM: Torque teno sus virus

<400> SEQUENCE: 1 cataggggtgt aaccaatcag atttaaggcg tt                32

<210> SEQ ID NO 2
<211> LENGTH: 27

<212> TYPE: DNA
<213> ORGANISM: Torque teno sus virus

<400> SEQUENCE: 2
ggtcatcaga cgatccatct ccctcag                                27

<210> SEQ ID NO 3
<211> LENGTH: 28
<212> TYPE: DNA
<213> ORGANISM: Torque teno sus virus

<400> SEQUENCE: 3
cttctgaggg agatggatcg tctgatga                               28

<210> SEQ ID NO 4
<211> LENGTH: 28
<212> TYPE: DNA
<213> ORGANISM: Torque teno sus virus

<400> SEQUENCE: 4
ttgagctccc gaccaatcag aattgact                               28

<210> SEQ ID NO 5
<211> LENGTH: 22
<212> TYPE: DNA
<213> ORGANISM: Torque teno sus virus

<400> SEQUENCE: 5
ttgtgccgga gctcctgaga gc                                     22

<210> SEQ ID NO 6
<211> LENGTH: 24
<212> TYPE: DNA
<213> ORGANISM: Torque teno sus virus

<400> SEQUENCE: 6
aggtgcttga ggagtcgtcg cttg                                   24

<210> SEQ ID NO 7
<211> LENGTH: 27
<212> TYPE: DNA
<213> ORGANISM: Torque teno sus virus

<400> SEQUENCE: 7
tacccaggcg gttagacact cagctct                                27

<210> SEQ ID NO 8
<211> LENGTH: 27
<212> TYPE: DNA
<213> ORGANISM: Torque teno sus virus

<400> SEQUENCE: 8
ctcaagcacg agcagtggat cctctca                                27

<210> SEQ ID NO 9
<211> LENGTH: 2878
<212> TYPE: DNA
<213> ORGANISM: Torque teno sus virus

<400> SEQUENCE: 9
tacacttccg ggttcaggag gctcaatttg gctagcttcg ctcgcaccac gtttgctgcc    60
aggcggacct gattgaagac tgaaaaccgt taaattcaaa tttgaaaatg gcgggcaaaa   120

```
tggcggaagg ggggcggagt ttatgcaaat taatttatgc aaagtaggag gagctcgatt      180
ttaatttatg caaagtagga ggagtcaatt ctgattggtc gggagctcaa gtcctcattt      240
gcatagggtg taaccaatca gatttaaggc gttcccccaa aagtgaatat aagtaagcgc      300
agttccgaat ggctgagttt atgccgccag cggtagacag aactgtctag cgactgggcg      360
ggtgccggag gatccctgat ccggagtcaa ggggcctatc gggcaggagc agctgagcgg      420
agggcctaca tgaaggagaa agactactgg gaggaagcct ggctgaccag ctgtacatct      480
atacacgacc accactgcaa ctgcggtagc tggagagacc acctgtggac gctatgcgct      540
ttagacgacg cagatttggc cgccgccgca gatattatag aaagagaaga ggcggatgga      600
ggagaagatt tcggattcgt agacggagac cctggagacg ctggcgggta aggagatggc      660
ggcgttccgt cttccgtaga gggggacgta gagcgcgccc ctaccgcatt agcgcttgga      720
accctaaggt tctcagaaac tgccgcatca cgggatggtg gccagttata cagtgtatgg      780
acgggatgga gtggataaaa tacaagccta tggacttaag agtcgaggca aactggatat      840
tcaataaaca ggacagtaaa atagagacag aacagatggg atacctgatg cagtatggag      900
gagggtggtc aagcggagta atcagcttag agggactatt caatgaaaac agactgtgga      960
gaaatatatg gtcaaaaagc aatgacggga tggacttggt cagatacttt ggctgtagaa     1020
ttagactata tccaacagag aatcaggact acttgttctg gtatgacaca gaatttgacg     1080
aacagcaaag gagaatgcta gatgaataca cacaacctag tgtgatgctg caggctaaaa     1140
actcgcgtct aatagtgtgt aaacagaaga tgccaattag acgcagagta aaaagtattt     1200
ttataccgcc gcctgcacag ttaacaactc agtggaaatt tcaacaggaa ctatgtcagt     1260
ttccactgtt taactgggcc tgtatctgca tagacatgga cacgccgttc gactacaacg     1320
gcgcatggcg aaatgcctgg tggctaatga aaggctgcaa aaacgaaaac atggagtaca     1380
tagaaagatg gggcagaata ccaatgacag gagacacaga actaccacca gcagacgact     1440
tcaaggcagg aggggtgaac aaaaaacttca aaccgacagg tattcaaaga atatacccga     1500
tagtagcggt atgccttgta gaagggaaca aaagagtagt caaatgggcc acagtacaca     1560
atggtcccat agacagatgg agaaaaaaac agacaggaac tttaaagctc tctaacctga     1620
gaggcctagt actgagagta tgctcagaga gtgaaacata ctataagtgg acaggatcag     1680
aatttacagg ggcatttcaa caagactggt ggccagtagg cggaacagaa tacccgcttt     1740
gtaccattaa aatggaccca gaatatgaaa accctacagt agaggtatgg tcctggaaag     1800
caaatatacc gacatcaggg actcttaaag actacttcgg actgagtaca gggcaacagt     1860
ggaaagacac tgactttgcg aggctgcaac tacctagaag cagccacaat gtggactttg     1920
gacataaagc tagatttggg ccattttgcg ttaaaaagcc tccagtagag ttcagagata     1980
cagccccaaa cccactaaat atatgggtaa aatacacgtt ctattttcag ttcggcggca     2040
tgtaccagcc tcccaccgga atccaagatc cctgcacttc taacccgacc tatcctgtca     2100
gaatggtcgg agcagttaca caccccaaat acgccgggca aggcggaatc acgacccaaa     2160
ttggagatca aggtatcacc gctgcctcta tccgtgccat cagtgcagct ccaccagata     2220
cctacacgca gtcggcgttc tcaaagccc ggaaaccga aaagaagag aaagagaga           2280 gtgagaccag tttcacgagt gccgaaagct cttctgaggg agatggatcg tctgatgacc     2340
aagcagagag acgcgctgcc agaaagcgag tcatcaagtt acttctcaag cgactcgctg     2400
acagacccgt ggacaacaag cgacgacgat tttcagagtg accctgaccc cctcaccaat     2460
aaacgcaaaa aacgcttgca attctaactc tgtctctgtg acttcattgg ggggtccgg      2520
```

-continued

```
ggggcttgc cccccgtta gttgggttct cgcactcccg cctgccaagt gaaactcggg    2580
gaggagtgag tgcgggacat cccgtgtaat ggctacataa ctacccggct ttgcttcgac    2640
agtggccgtg gctcgaccct cacacaaacac tgcagatagg gggcgcaatt gggatcgtta    2700
gaaaactatg gccgagcatg ggggggggctc cgccccccc aaccccccg gtggggggc     2760 caaggccccc cctacacccc cccatggggg gctgccgccc ccaaaccccc cgcgtcgga    2820 tgggggggc tgcgccccccc ccaaaccccc cttgcccggg gctgtgcccc ggacccccc    2878
```

<210> SEQ ID NO 10
<211> LENGTH: 2875
<212> TYPE: DNA
<213> ORGANISM: Torque teno sus virus

<400> SEQUENCE: 10

```
tacacttccg ggttcaggag gctcaatttg gctcgcttcg ctcgcaccac gtttgctgcc      60
aagcggacct gattgaagac tgacaaccgt tacattcaaa tttgaaaatg gcgcccaaac     120
atggcggcgg ggggcggagt ttatgcaaat taatttatgc aaagtaggag gagctccatt     180
ttaatttatg caaagtagga ggagtcaatt ctgattggtc gggagctcaa gtcctcattt     240
gcatagggtg taaccaatca gatttaaggc gttcccatta aagcgaatat aagtaagtga     300
ggttccgaat ggctgagttt atgccgccag cggtagacag aactgtctag cgactgggcg     360
ggtgccggag gatccctgat ccggagtcaa ggggcctatc gggcaggagc agctgagcgg     420
agggcctatg ccggaacact gggaggaagc ctggttggaa gctaccaagg gctggcacga     480
tctcgactgc cgctgcggta actggcagga ccacctatgg ctcctactcg ccgatggaga     540
cgccgctttg gccgccgccg tagacgctat agaaagagac gctatgggtg gagaagacgt     600
tactaccgct acagaccgcg ttactatagg agacgatggc tggtaaggag aaggcggcgt     660
tccgtctacc gtagaggtgg acgtagagcg cgcccctacc gaataagtgc tttaaccca     720 aaagtaatgc ggagggtggt gattagaggt tggtggccaa tattacagtg tctaaaagga     780
caggaatcac taagatatag accactgcag tgggacactg aaaaacagtg gagagtaaag     840
aaagactatg aggacaacta cggctacttg gtgcagtacg gaggaggttg ggggagtggt     900
gaagtgacat tggagggatt atatcaggaa cacttactct ggagaaactc ttggtcaaag     960
ggaaatgatg gcatggacct agtgagatac tttggctgca tagtataccct gtacccactg    1020 caggaccaag actactggtt ttggtgggat acagacttta agaactata cgcagagagc     1080 atcaaagaat actcccagcc aagtgttatg atgatggcca acgcactag actagtaata     1140 gctagagaca gagcaccaca cagaagaaga gtaagaaaaa ttttcatacc cccgccaagc     1200
agagacacca cacaatggca atttcagaca gacttctgca aaaggccact attcacatgg     1260
gcggcaggat taatagacat gcagaaacca tttgatgcaa acggagcgtt tagaaacgcc     1320
tggtggctag aaacaaggaa tgaccaggga gaaatgaaat acattgaact atggggaagg     1380
gtgccaccac agggtgacac agaactgcca aaacagagtg agtttaagaa gggagataat     1440
aaccctaact ataacataac ggaaggacat gaaaaaaata tttacccaat aatcatatac     1500
gttgaccaga aagaccagaa aacaagaaaa aaatactgtg tatgctacaa caaaacttta     1560
aatagatgga gaaaagccca ggcgagtaca ttagcaatag gagatcttca aggactagta     1620
ctgcgtcagc ttatgaatca ggagatgaca tactactgga atcgggaga gttttcctca     1680 ccattcctgc aaagatggaa aggaactagg ctaataacca tagacgcaag aaaggcagac     1740
```

```
acagaaaacc caaaagtaag ttcgtgggaa tgggggcaaa actggaacac aagcggaaca    1800
gtgctacagg aggtattcaa catttcactg aacaacactc aaataagaca ggatgacttt    1860
gcaaaattga cactgccaaa gtcaccacat gacatagact ttggacatca cagcagattt    1920
ggaccattct gtgttaaaaa cgaaccacta gaattccaac tactgcctcc aacaccaact    1980
aacctatggt ttcagtacaa atttctcttt cagtttggcg gtgaatacca gccaccaaca    2040
ggtatccgcg atccctgcat tgatacacca gcctatcctg tgccgcagtc aggaagtgtt    2100
acacacccca aattcgccgg aaagggcgga atgctcacgg aaacagaccg ttggggtatc    2160
actgctgcct cttccagaac cctcagtgca gatacaccca ccgaagcagc gcaaagtgca    2220
cttctcagag gggacgcgga aaagaaagga gaggaaaccg aggaaaccgc gtcatcgtcc    2280
agtatcacga gtgccgaaag ctctactgag ggagatggat cgtctgatga tgaagagaca    2340
atcagacgca gaaggaggac ctggaagcga ctcagacgga tggtcagaca gcagcttgac    2400
cgacgaatgg accacaagcg acagcgactt cattgatacc cccataagag aaagatgcct    2460
caataaaaaa caaaaaaaac gctaaacagt gtccgcctat tagtgggggg gtccgggggg    2520
gcttgccccc ccgtaagcgg ggttaccgca ctaactccct gccaagtgaa actcggggac    2580
gagtgagtgc gggacatccc gtgtaatggc tacataacta cccggctttg cttcgacagt    2640
ggccgtggct cgaccctcgc acaacactgc aggtagggg cgcaattggg atcgttagaa    2700
aactatggcc gagcatgggg ggggctccgc cccccccaac cccccggtg ggggggccaa    2760 ggccctccct acaccccccc atggggggct gccgccccccc aaaccccccg cgtcggatgg    2820 gggggctgc gcccccccca aaccccccctt gcccggggct gtgccccgga ccccc          2875

<210> SEQ ID NO 11
<211> LENGTH: 2750
<212> TYPE: DNA
<213> ORGANISM: Torque teno sus virus

<400> SEQUENCE: 11
taatgacagg gttcaccgga aaggctgcaa aattacagct aaaaccacaa tcataacaca      60
ataaaccaca aactattaca ggaaactgca ataaattaag aaataaatta cacataacca     120
cctaaccaca ggaaactttg caaaaaggg gaaataaatc tcattggctg gccagaagt       180 cctcattaga ataagaaaag aaccaatcag aaacacttcc tcttttagag tatataagta     240
agtgcgcaga cgaatggctg agtttatgcc gctggtggta gacacgaaca gagctgagtg     300
tctaaccgcc tgggcgggtg ccggagctcc tgagagcgga gtcaagggc ctatcgggca     360 ggcggtaatc cagcggaact gggcccccct ccatggaaga aagatggctg acggtagcgt     420
actgcgcgca cggattattc tgcgactgta aaaacccgaa aaaacatctt gaaaaatgcc     480
ttacagacgc tatcgccgac gccgaaggag accgacacgg agatggaggc accggaggtg     540
gagacgctac tttcgatatc ggtatcgacg cgctcctcgc cgccgccgcc caaaggtaag     600
gagacggagg aggaaagctc cggtcattca atggttccct cctagccgga gaacctgcct     660
catagagggc ttctggccgt tgagctacgg acactggttc cgtacctgtc tccctatgag     720
aaggctaaac ggactgattt tcacgggtgg aggatgtgac tggactcaat ggagtttaca     780
aaatttattc catgaaaaat taaactggag aaatatatgg acagcttcta atgtaggcat     840
ggagtttgct agattttta gaggaaaatt ttacttcttc agacacccct ggagaagcta     900
tatagtaaca tgggaccaag acatacctg taaaccgctc ccatatcaaa acttacaacc     960
tctattaatg ctcctcaaaa aacagcataa attagtcctc tctcaaaaag attgcaaccc    1020
```

```
gaacagaaaa caaaaaccag ttacattaaa attcaggcct ccaccaaaat taacatcaca    1080
gtggagacta agcagagaac tctcaaaaat acccttaata agactaggaa taagtctcat    1140
agacctgtca gaaccatggt tagaaggctg gggaaatgct ttttacagtg tactaggata    1200
tgaagctagt aaacacagtg gcagatggtc caactggaca caaatgaaat attttggat    1260 ctatgacaca ggcgtgggaa acgcagtcta cgttatttta ctgaaaaaag acgtgagtga    1320
caatccagga gacatggcta cacagtttgt aacaggctca ggacaacacc cagacgcaat    1380
agatcatata gaaatggtaa acgaaggatg gccttactgg ctattttttt atggacaatc    1440
agaacaagat ataaaaaaac tagcacatga ccaagatata gtcagagaat atgccagaga    1500
ccctaaatca aaaaattaa aaataggagt cataggatgg gccagcagta actacacaac    1560
agcagggagc aaccaaaaca gtgtacttca aacgccagaa gcaatacaag gtggatatgt    1620
agcttatgca ggatccagaa taccaggcgc aggatctatc acaaatttat ttcaaatggg    1680
atggccagga gatcaaaact ggccacccac aaaccaagac caaaccaatt ttaactgggg    1740
actcagagga ctttgtgtat aagagataa catgaaacta ggagcacaag agctagacga    1800
tgaatgcaca atgctctcct tatttggacc atttgttgaa aaagcaaaca cagcttttgc    1860
tacaaacgac ccaaaatatt ttaggcctga actaaaggac tacaacgtag taatgaaata    1920
tgcttttaaa tttcagtggg gaggacatgg caccgaaaga tttaaaacaa ccatcggaga    1980
tcccagcacc ataccatgtc cctttgaacc cggggaacgg taccaccacg gggtacaaga    2040
ccccgccaag gtacaaaaca cagtcctcaa cccttgggac tatgactgtg acgggattgt    2100
tagaacagat actctcaaaa gacttctcga actccccaca gagacggagg agacggagaa    2160
ggcgtaccca ctccttggac aaaaaacaga gaaagagcca ttatcagact ccgacgaaga    2220
gagcgttatc tcaagcacga gcagtggatc ctctcaagaa gaagagacgc agagacgaaa    2280
gcaccacaag ccaagcaagc gacgactcct caagcacctc cagcgggtgg taaagaggat    2340
gaaaacactg tgatagataa atacagaaac ctagcagacc cctcactcaa tgtcacagga    2400
cacatggaaa aattcatgca actacacata caaaacatac aagaaataag agctaaaaat    2460
gctaaaaaat ccctcaataa acttactttt tctgattaat agcggcctcc tgtgtccaat    2520
ctatttttcc tacacccctt caaaatggcg ggaggaacac aaaatggcgg agggactaag    2580
gggggggcaa gccccccccc ggggttgag ggggggtttc cccccctccc cccggtgcag    2640
ggggcggagc ccccgcaccc cccatgcggg ggctccgccc cctgcacccc cgggaggggg    2700 ggaaacccc cctcaacccc ccgcgggggg caagccccc tgcacccccc                2750
```

<210> SEQ ID NO 12
<211> LENGTH: 2803
<212> TYPE: DNA
<213> ORGANISM: Torque teno sus virus

<400> SEQUENCE: 12

```
tcatgacagg gttcaccgga agggctgcaa aattacagct aaaaccacaa gtctaacaca     60
ataaaccaca aagtattaca ggaaactgca ataaatttag aaatagatta cacataacca    120
ccaaaccaca ggaaacctac acataaccac caaaccacag gaaacataac caccaaacca    180
caggaaactg tgcaaaaaag gggaaataaa ttctattggc tgggcctgaa gtcctcatta    240
gaataataaa agaaccaatc agaagaactt cctctttttag agtatataag taagtgcgca    300
gacgaatggc tgagtttatg ccgctggtgg tagacacgaa cagagctgag tgtctaaccg    360
```

```
cctgggcggg tgccggagct cctgagagcg gagtcaaggg gcttatcggg caggcggtaa      420
tccagcggaa ccgggccccc ctcgatggaa gaaagatggc tgacggtagc gtactgcgcc      480
cacggattat tctgcggatg taaagacccg aaaaaacacc ttgaaaaatg ccttacagac      540
gctatcgcag acgccgaagg agaccgacac ggagatggag gcaccggagg tggagacgct      600
tctttcgata tcggtatcga cgcgctcctc gccgccgccg cacaaaggta aggagacgga      660
ggagaaaagc tccggtcata caatggttcc ctcctagccg gaggacctgc ctcatagagg      720
gcttctggcc gttgagctac ggacactggt tccgtacctg tctccctatg agaaggctga      780
acggactcat tttcacgggt ggcggttgtg actggacaca gtggagttta caaaacttat      840
accatgaaaa acttaactgg agaaatatat ggacagcttc taatgttggc atggaatttg      900
ctagattttt aagaggaaaa ttttacttct tcagacaccc ctggagaagc tatattatta      960
cttgggacca agacattcct tgcaaacctt taccatacca aaacttacat ccactactta     1020
tgctattaaa aaaacaacat aaacttgtac tatctcaaaa agactgtaat ccaaacagaa     1080
gacaaaaacc agtaacttta aaaataagac ctccaccaaa attaacatca cagtggagat     1140
taagcagaga actagcaaaa atgccacttg tcagactagg agtcagtcta atagacctct     1200
cagaaccatg gttagaaggc tggggaaatg cttttttacag cgtactggga tatgaagcta     1260
gtaaacactc agggagatgg tcaaactgga cacaaataaa atacttctgg atatatgaca     1320
caggagtagg aaatgcagtt tatgtcattt tattaaaaca agaggtggat gataatccag     1380
gggcaatggc aacaaaattt gtaactggac caggacaaca cccagatgcc atagacagga     1440
tcgaacaaat aaatgaagga tggccttact ggcttttctt ttacggacag tcagaacaag     1500
acataaaaaa attagcacac gatcaagaaa tagcaaggga atatgcaaac aatccaaaat     1560
ctaaaaaatt aaaaatagga gtgataggat gggctagcag taactttaca acagcaggca     1620
gctcacaaaa tcaaacacca caaacaccag aagccataca aggaggatac gtagcatatg     1680
caggctcaaa aatacaagga gcaggagcaa ttacaaactt atacacagat gcatggccgg     1740
gagaccaaaa ttggccacct ctaaatagag aacaaacaaa ctttaactgg ggcttaagag     1800
gactctgtat aatgagagat aatatgaaac tgggagctca agaactagat gatgaatgta     1860
caatgctcac acttttttgga cctttttgtgg aaaaagcaaa cacagctttt gctacaaatg     1920
accctaaata cttcagacca gaactcaaag actataacat agtaatgaaa tatgccttta     1980
aatttcagtg gggaggccac ggaaccgaaa gattcaaaac aaccatcgga gatcccagca     2040
ccataccatg tccctttgaa cccggggaac ggtaccacca cggggtacaa gaccccgcca     2100
aggtacaaaa cacagtcctc aacccttggg actatgactg tgacgggatt gttagaacag     2160
atactctcaa aagacttctc gaactcccca cagagacgga ggagacggag aaggcgtacc     2220
cactccttgg acaaaaaaca gagaaagagc cattatcaga ctccgacgaa gagagcgtta     2280
tctcaagcac gagcagtgga tcctctcaag aagaagagac gcagagaaga agacagcaca     2340
agccaagcaa gcgacgactc ctcaagcacc tccagcgggt ggtaaagaga atgaagacac     2400
tgtgatagat aaatatagaa acctagcaga cccctcactc aatgtcacag gacacatgga     2460
aaaattcatg caactgcaca tacaaaacgt acaagaaata agagctaaaa atgctaaaaa     2520
atccctcaat aaactttact tttctgatta ataccggcct cctgtgtcca atctatttt      2580 cctacacccc ttcaaaatgg cgggcgggac acaaatggc ggaggaaact aaggggggg      2640 caagccccc ccgggggtt gagggggggt tccccccct ccccccggtg caggggcgg        2700 agccccccgca ccccccctgc ggggggctccg ccccctgcac ccccggagg ggggggaaacc   2760
``` cccccctcaac cccccgcggg gggcaagccc ccctgcaccc ccc      2803

<210> SEQ ID NO 13
<211> LENGTH: 635
<212> TYPE: PRT
<213> ORGANISM: Torque teno sus virus

<400> SEQUENCE: 13

```
Met Arg Phe Arg Arg Arg Phe Gly Arg Arg Arg Tyr Tyr Arg
1               5                   10                  15

Lys Arg Arg Gly Gly Trp Arg Arg Phe Arg Ile Arg Arg Arg
            20                  25                  30

Pro Trp Arg Arg Trp Arg Val Arg Arg Trp Arg Arg Ser Val Phe Arg
        35                  40                  45

Arg Gly Gly Arg Arg Ala Arg Pro Tyr Arg Ile Ser Ala Trp Asn Pro
50                  55                  60

Lys Val Leu Arg Asn Cys Arg Ile Thr Gly Trp Trp Pro Val Ile Gln
65                  70                  75                  80

Cys Met Asp Gly Met Glu Trp Ile Lys Tyr Lys Pro Met Asp Leu Arg
                85                  90                  95

Val Glu Ala Asn Trp Ile Phe Asn Lys Gln Asp Ser Lys Ile Glu Thr
            100                 105                 110

Glu Gln Met Gly Tyr Leu Met Gln Tyr Gly Gly Gly Trp Ser Ser Gly
        115                 120                 125

Val Ile Ser Leu Glu Gly Leu Phe Asn Glu Asn Arg Leu Trp Arg Asn
130                 135                 140

Ile Trp Ser Lys Ser Asn Asp Gly Met Asp Leu Val Arg Tyr Phe Gly
145                 150                 155                 160

Cys Arg Ile Arg Leu Tyr Pro Thr Glu Asn Gln Asp Tyr Leu Phe Trp
                165                 170                 175

Tyr Asp Thr Glu Phe Asp Glu Gln Gln Arg Arg Met Leu Asp Glu Tyr
            180                 185                 190

Thr Gln Pro Ser Val Met Leu Gln Ala Lys Asn Ser Arg Leu Ile Val
        195                 200                 205

Cys Lys Gln Lys Met Pro Ile Arg Arg Arg Val Lys Ser Ile Phe Ile
210                 215                 220

Pro Pro Pro Ala Gln Leu Thr Thr Gln Trp Lys Phe Gln Gln Glu Leu
225                 230                 235                 240

Cys Gln Phe Pro Leu Phe Asn Trp Ala Cys Ile Cys Ile Asp Met Asp
                245                 250                 255

Thr Pro Phe Asp Tyr Asn Gly Ala Trp Arg Asn Ala Trp Trp Leu Met
            260                 265                 270

Arg Arg Leu Gln Asn Gly Asn Met Glu Tyr Ile Glu Arg Trp Gly Arg
        275                 280                 285

Ile Pro Met Thr Gly Asp Thr Glu Leu Pro Pro Ala Asp Asp Phe Lys
290                 295                 300

Ala Gly Gly Val Asn Lys Asn Phe Lys Pro Thr Gly Ile Gln Arg Ile
305                 310                 315                 320

Tyr Pro Ile Val Ala Val Cys Leu Val Glu Gly Asn Lys Arg Val Val
                325                 330                 335

Lys Trp Ala Thr Val His Asn Gly Pro Ile Asp Arg Trp Arg Lys Lys
            340                 345                 350

Gln Thr Gly Thr Leu Lys Leu Ser Asn Leu Arg Gly Leu Val Leu Arg
        355                 360                 365
```

Val Cys Ser Glu Ser Glu Thr Tyr Tyr Lys Trp Thr Gly Ser Glu Phe
    370                 375                 380

Thr Gly Ala Phe Gln Gln Asp Trp Trp Pro Val Gly Gly Thr Glu Tyr
385                 390                 395                 400

Pro Leu Cys Thr Ile Lys Met Asp Pro Glu Tyr Glu Asn Pro Thr Val
                405                 410                 415

Glu Val Trp Ser Trp Lys Ala Asn Ile Pro Thr Ser Gly Thr Leu Lys
                420                 425                 430

Asp Tyr Phe Gly Leu Ser Thr Gly Gln Gln Trp Lys Asp Thr Asp Phe
                435                 440                 445

Ala Arg Leu Gln Leu Pro Arg Ser Ser His Asn Val Asp Phe Gly His
    450                 455                 460

Lys Ala Arg Phe Gly Pro Phe Cys Val Lys Lys Pro Val Glu Phe
465                 470                 475                 480

Arg Asp Thr Ala Pro Asn Pro Leu Asn Ile Trp Val Lys Tyr Thr Phe
                485                 490                 495

Tyr Phe Gln Phe Gly Gly Met Tyr Gln Pro Pro Thr Gly Ile Gln Asp
                500                 505                 510

Pro Cys Thr Ser Asn Pro Thr Tyr Pro Val Arg Met Val Gly Ala Val
    515                 520                 525

Thr His Pro Lys Tyr Ala Gly Gln Gly Gly Ile Thr Thr Gln Ile Gly
    530                 535                 540

Asp Gln Gly Ile Thr Ala Ala Ser Ile Arg Ala Ile Ser Ala Ala Pro
545                 550                 555                 560

Pro Asp Thr Tyr Thr Gln Ser Ala Phe Leu Lys Ala Pro Glu Thr Glu
                565                 570                 575

Lys Glu Glu Arg Glu Ser Glu Thr Ser Phe Thr Ser Ala Glu Ser
                580                 585                 590

Ser Ser Glu Gly Asp Gly Ser Ser Asp Asp Gln Ala Glu Arg Arg Ala
    595                 600                 605

Ala Arg Lys Arg Val Ile Lys Leu Leu Leu Lys Arg Leu Ala Asp Arg
    610                 615                 620

Pro Val Asp Asn Lys Arg Arg Arg Phe Ser Glu
625                 630                 635

<210> SEQ ID NO 14
<211> LENGTH: 639
<212> TYPE: PRT
<213> ORGANISM: Torque teno sus virus

<400> SEQUENCE: 14

Met Ala Pro Thr Arg Arg Trp Arg Arg Arg Phe Gly Arg Arg Arg Arg
1               5                   10                  15

Arg Tyr Arg Lys Arg Arg Tyr Gly Trp Arg Arg Tyr Tyr Arg Tyr
                20                  25                  30

Arg Pro Arg Tyr Tyr Arg Arg Trp Leu Val Arg Arg Arg Arg
                35                  40                  45

Ser Val Tyr Arg Arg Gly Gly Arg Arg Ala Arg Pro Tyr Arg Ile Ser
    50                  55                  60

Ala Phe Asn Pro Lys Val Met Arg Arg Val Val Ile Arg Gly Trp Trp
65                  70                  75                  80

Pro Ile Leu Gln Cys Leu Lys Gly Gln Glu Ser Leu Arg Tyr Arg Pro
                85                  90                  95

Leu Gln Trp Asp Thr Glu Lys Gln Trp Arg Val Lys Lys Asp Tyr Glu

-continued

```
            100                 105                 110
Asp Asn Tyr Gly Tyr Leu Val Gln Tyr Gly Gly Gly Trp Ser Gly
            115                 120                 125
Glu Val Thr Leu Glu Gly Leu Tyr Gln Glu His Leu Leu Trp Arg Asn
        130                 135                 140
Ser Trp Ser Lys Gly Asn Asp Gly Met Asp Leu Val Arg Tyr Phe Gly
145                 150                 155                 160
Cys Ile Val Tyr Leu Tyr Pro Leu Gln Asp Gln Asp Tyr Trp Phe Trp
                165                 170                 175
Trp Asp Thr Asp Phe Lys Glu Leu Tyr Ala Glu Ser Ile Lys Glu Tyr
                180                 185                 190
Ser Gln Pro Ser Val Met Met Met Ala Lys Arg Thr Arg Leu Val Ile
            195                 200                 205
Ala Arg Asp Arg Ala Pro His Arg Arg Val Arg Lys Ile Phe Ile
        210                 215                 220
Pro Pro Pro Ser Arg Asp Thr Thr Gln Trp Gln Phe Gln Thr Asp Phe
225                 230                 235                 240
Cys Lys Arg Pro Leu Phe Thr Trp Ala Ala Gly Leu Ile Asp Met Gln
                245                 250                 255
Lys Pro Phe Asp Ala Asn Gly Ala Phe Arg Asn Ala Trp Trp Leu Glu
                260                 265                 270
Thr Arg Asn Asp Gln Gly Glu Met Lys Tyr Ile Glu Leu Trp Gly Arg
            275                 280                 285
Val Pro Pro Gln Gly Asp Thr Glu Leu Pro Lys Gln Ser Glu Phe Lys
        290                 295                 300
Lys Gly Asp Asn Asn Pro Asn Tyr Asn Ile Thr Glu Gly His Glu Lys
305                 310                 315                 320
Asn Ile Tyr Pro Ile Ile Ile Tyr Val Asp Gln Lys Asp Gln Lys Thr
                325                 330                 335
Arg Lys Lys Tyr Cys Val Cys Tyr Asn Lys Thr Leu Asn Arg Trp Arg
                340                 345                 350
Lys Ala Gln Ala Ser Thr Leu Ala Ile Gly Asp Leu Gln Gly Leu Val
            355                 360                 365
Leu Arg Gln Leu Met Asn Gln Glu Met Thr Tyr Tyr Trp Lys Ser Gly
        370                 375                 380
Glu Phe Ser Ser Pro Phe Leu Gln Arg Trp Lys Gly Thr Arg Leu Ile
385                 390                 395                 400
Thr Ile Asp Ala Arg Lys Ala Asp Thr Glu Asn Pro Lys Val Ser Ser
                405                 410                 415
Trp Glu Trp Gly Gln Asn Trp Asn Thr Ser Gly Thr Val Leu Gln Glu
                420                 425                 430
Val Phe Asn Ile Ser Leu Asn Asn Thr Gln Ile Arg Gln Asp Asp Phe
            435                 440                 445
Ala Lys Leu Thr Leu Pro Lys Ser Pro His Asp Ile Asp Phe Gly His
        450                 455                 460
His Ser Arg Phe Gly Pro Phe Cys Val Lys Asn Glu Pro Leu Glu Phe
465                 470                 475                 480
Gln Leu Leu Pro Pro Thr Pro Thr Asn Leu Trp Phe Gln Tyr Lys Phe
                485                 490                 495
Leu Phe Gln Phe Gly Gly Glu Tyr Gln Pro Pro Thr Gly Ile Arg Asp
                500                 505                 510
Pro Cys Ile Asp Thr Pro Ala Tyr Pro Val Pro Gln Ser Gly Ser Val
            515                 520                 525
```

```
Thr His Pro Lys Phe Ala Gly Lys Gly Gly Met Leu Thr Glu Thr Asp
    530                 535                 540

Arg Trp Gly Ile Thr Ala Ala Ser Ser Arg Thr Leu Ser Ala Asp Thr
545                 550                 555                 560

Pro Thr Glu Ala Ala Gln Ser Ala Leu Leu Arg Gly Asp Ala Glu Lys
                565                 570                 575

Lys Gly Glu Glu Thr Glu Glu Thr Ala Ser Ser Ser Ile Thr Ser
                580                 585                 590

Ala Glu Ser Ser Thr Glu Gly Asp Gly Ser Ser Asp Asp Glu Glu Thr
                595                 600                 605

Ile Arg Arg Arg Arg Thr Trp Lys Arg Leu Arg Met Val Arg
    610                 615                 620

Gln Gln Leu Asp Arg Arg Met Asp His Lys Arg Gln Arg Leu His
625                 630                 635

<210> SEQ ID NO 15
<211> LENGTH: 625
<212> TYPE: PRT
<213> ORGANISM: Torque teno sus virus

<400> SEQUENCE: 15

Met Pro Tyr Arg Arg Tyr Arg Arg Arg Arg Pro Thr Arg Arg
1               5                   10                  15

Trp Arg His Arg Arg Trp Arg Arg Tyr Phe Arg Tyr Arg Tyr Arg Arg
                20                  25                  30

Ala Pro Arg Arg Arg Pro Lys Val Arg Arg Arg Arg Lys Ala
                35                  40                  45

Pro Val Ile Gln Trp Phe Pro Pro Ser Arg Arg Thr Cys Leu Ile Glu
    50                  55                  60

Gly Phe Trp Pro Leu Ser Tyr Gly His Trp Phe Arg Thr Cys Leu Pro
65                  70                  75                  80

Met Arg Arg Leu Asn Gly Leu Ile Phe Thr Gly Gly Gly Cys Asp Trp
                85                  90                  95

Thr Gln Trp Ser Leu Gln Asn Leu Phe His Glu Lys Leu Asn Trp Arg
                100                 105                 110

Asn Ile Trp Thr Ala Ser Asn Val Gly Met Glu Phe Ala Arg Phe Leu
    115                 120                 125

Arg Gly Lys Phe Tyr Phe Phe Arg His Pro Trp Arg Ser Tyr Ile Val
    130                 135                 140

Thr Trp Asp Gln Asp Ile Pro Cys Lys Pro Leu Pro Tyr Gln Asn Leu
145                 150                 155                 160

Gln Pro Leu Leu Met Leu Leu Lys Lys Gln His Lys Leu Val Leu Ser
                165                 170                 175

Gln Lys Asp Cys Asn Pro Asn Arg Lys Gln Lys Pro Val Thr Leu Lys
                180                 185                 190

Phe Arg Pro Pro Lys Leu Thr Ser Gln Trp Arg Leu Ser Arg Glu
                195                 200                 205

Leu Ser Lys Ile Pro Leu Ile Arg Leu Gly Ile Ser Leu Ile Asp Leu
    210                 215                 220

Ser Glu Pro Trp Leu Glu Gly Trp Gly Asn Ala Phe Tyr Ser Val Leu
225                 230                 235                 240

Gly Tyr Glu Ala Ser Lys His Ser Gly Arg Trp Ser Asn Trp Thr Gln
                245                 250                 255

Met Lys Tyr Phe Trp Ile Tyr Asp Thr Gly Val Gly Asn Ala Val Tyr
```

```
              260                 265                 270
    Val Ile Leu Leu Lys Lys Asp Val Ser Asp Asn Pro Gly Asp Met Ala
        275                 280                 285

Thr Gln Phe Val Thr Gly Ser Gly Gln His Pro Asp Ala Ile Asp His
        290                 295                 300

Ile Glu Met Val Asn Glu Gly Trp Pro Tyr Trp Leu Phe Phe Tyr Gly
    305                 310                 315                 320

Gln Ser Glu Gln Asp Ile Lys Lys Leu Ala His Asp Gln Asp Ile Val
                    325                 330                 335

Arg Glu Tyr Ala Arg Asp Pro Lys Ser Lys Leu Lys Ile Gly Val
        340                 345                 350

Ile Gly Trp Ala Ser Ser Asn Tyr Thr Thr Ala Gly Ser Asn Gln Asn
        355                 360                 365

Ser Val Leu Gln Thr Pro Glu Ala Ile Gln Gly Gly Tyr Val Ala Tyr
        370                 375                 380

Ala Gly Ser Arg Ile Pro Gly Ala Gly Ser Ile Thr Asn Leu Phe Gln
    385                 390                 395                 400

Met Gly Trp Pro Gly Asp Gln Asn Trp Pro Pro Thr Asn Gln Asp Gln
                    405                 410                 415

Thr Asn Phe Asn Trp Gly Leu Arg Gly Leu Cys Val Leu Arg Asp Asn
                    420                 425                 430

Met Lys Leu Gly Ala Gln Glu Leu Asp Asp Glu Cys Thr Met Leu Ser
                    435                 440                 445

Leu Phe Gly Pro Phe Val Glu Lys Ala Asn Thr Ala Phe Ala Thr Asn
        450                 455                 460

Asp Pro Lys Tyr Phe Arg Pro Glu Leu Lys Asp Tyr Asn Val Val Met
    465                 470                 475                 480

Lys Tyr Ala Phe Lys Phe Gln Trp Gly His Gly Thr Glu Arg Phe
                    485                 490                 495

Lys Thr Thr Ile Gly Asp Pro Ser Thr Ile Pro Cys Pro Phe Glu Pro
                    500                 505                 510

Gly Glu Arg Tyr His His Gly Val Gln Asp Pro Ala Lys Val Gln Asn
        515                 520                 525

Thr Val Leu Asn Pro Trp Asp Tyr Asp Cys Asp Gly Ile Val Arg Thr
        530                 535                 540

Asp Thr Leu Lys Arg Leu Leu Glu Leu Pro Thr Glu Thr Glu Glu Thr
    545                 550                 555                 560

Glu Lys Ala Tyr Pro Leu Leu Gly Gln Lys Thr Glu Lys Glu Pro Leu
                    565                 570                 575

Ser Asp Ser Asp Glu Glu Ser Val Ile Ser Ser Thr Ser Ser Gly Ser
                    580                 585                 590

Ser Gln Glu Glu Glu Thr Gln Arg Arg Lys His His Lys Pro Ser Lys
                    595                 600                 605

Arg Arg Leu Leu Lys His Leu Gln Arg Val Val Lys Arg Met Lys Thr
        610                 615                 620

Leu
    625

<210> SEQ ID NO 16
<211> LENGTH: 625
<212> TYPE: PRT
<213> ORGANISM: Torque teno sus virus

<400> SEQUENCE: 16
```

-continued

```
Met Pro Tyr Arg Arg Tyr Arg Arg Arg Arg Arg Pro Thr Arg Arg
1               5                   10                  15

Trp Arg His Arg Arg Trp Arg Arg Phe Phe Arg Tyr Tyr Arg Arg
            20                  25                  30

Ala Pro Arg Arg Arg Thr Lys Val Arg Arg Arg Arg Lys Ala
        35                  40                  45

Pro Val Ile Gln Trp Phe Pro Pro Ser Arg Arg Thr Cys Leu Ile Glu
        50                  55                  60

Gly Phe Trp Pro Leu Ser Tyr Gly His Trp Phe Arg Thr Cys Leu Pro
65                  70                  75                  80

Met Arg Arg Leu Asn Gly Leu Ile Phe Thr Gly Gly Gly Cys Asp Trp
            85                  90                  95

Thr Gln Trp Ser Leu Gln Asn Leu Tyr His Glu Lys Leu Asn Trp Arg
            100                 105                 110

Asn Ile Trp Thr Ala Ser Asn Val Gly Met Glu Phe Ala Arg Phe Leu
            115                 120                 125

Arg Gly Lys Phe Tyr Phe Phe Arg His Pro Trp Arg Ser Tyr Ile Ile
            130                 135                 140

Thr Trp Asp Gln Asp Ile Pro Cys Lys Pro Leu Pro Tyr Gln Asn Leu
145                 150                 155                 160

His Pro Leu Leu Met Leu Leu Lys Lys Gln His Lys Leu Val Leu Ser
                165                 170                 175

Gln Lys Asp Cys Asn Pro Asn Arg Arg Gln Lys Pro Val Thr Leu Lys
                180                 185                 190

Ile Arg Pro Pro Lys Leu Thr Ser Gln Trp Arg Leu Ser Arg Glu
            195                 200                 205

Leu Ala Lys Met Pro Leu Val Arg Leu Gly Val Ser Leu Ile Asp Leu
            210                 215                 220

Ser Glu Pro Trp Leu Glu Gly Trp Gly Asn Ala Phe Tyr Ser Val Leu
225                 230                 235                 240

Gly Tyr Glu Ala Ser Lys His Ser Gly Arg Trp Ser Asn Trp Thr Gln
                245                 250                 255

Ile Lys Tyr Phe Trp Ile Tyr Asp Thr Gly Val Gly Asn Ala Val Tyr
            260                 265                 270

Val Ile Leu Leu Lys Gln Glu Val Asp Asp Asn Pro Gly Ala Met Ala
            275                 280                 285

Thr Lys Phe Val Thr Gly Pro Gly Gln His Pro Asp Ala Ile Asp Arg
            290                 295                 300

Ile Glu Gln Ile Asn Glu Gly Trp Pro Tyr Trp Leu Phe Phe Tyr Gly
305                 310                 315                 320

Gln Ser Glu Gln Asp Ile Lys Lys Leu Ala His Asp Gln Glu Ile Ala
                325                 330                 335

Arg Glu Tyr Ala Asn Asn Pro Lys Ser Lys Lys Leu Lys Ile Gly Val
            340                 345                 350

Ile Gly Trp Ala Ser Ser Asn Phe Thr Thr Ala Gly Ser Ser Gln Asn
            355                 360                 365

Gln Thr Pro Gln Thr Pro Glu Ala Ile Gln Gly Gly Tyr Val Ala Tyr
            370                 375                 380

Ala Gly Ser Lys Ile Gln Gly Ala Gly Ala Ile Thr Asn Leu Tyr Thr
385                 390                 395                 400

Asp Ala Trp Pro Gly Asp Gln Asn Trp Pro Pro Leu Asn Arg Glu Gln
                405                 410                 415

Thr Asn Phe Asn Trp Gly Leu Arg Gly Leu Cys Ile Met Arg Asp Asn
```

```
            420                 425                 430
Met Lys Leu Gly Ala Gln Glu Leu Asp Asp Glu Cys Thr Met Leu Thr
                435                 440                 445

Leu Phe Gly Pro Phe Val Glu Lys Ala Asn Thr Ala Phe Ala Thr Asn
            450                 455                 460

Asp Pro Lys Tyr Phe Arg Pro Glu Leu Lys Asp Tyr Asn Ile Val Met
465                 470                 475                 480

Lys Tyr Ala Phe Lys Phe Gln Trp Gly Gly His Gly Thr Glu Arg Phe
                485                 490                 495

Lys Thr Thr Ile Gly Asp Pro Ser Thr Ile Pro Cys Pro Phe Glu Pro
            500                 505                 510

Gly Glu Arg Tyr His His Gly Val Gln Asp Pro Ala Lys Val Gln Asn
                515                 520                 525

Thr Val Leu Asn Pro Trp Asp Tyr Asp Cys Asp Gly Ile Val Arg Thr
            530                 535                 540

Asp Thr Leu Lys Arg Leu Leu Glu Leu Pro Thr Glu Thr Glu Glu Thr
545                 550                 555                 560

Glu Lys Ala Tyr Pro Leu Leu Gly Gln Lys Thr Glu Lys Glu Pro Leu
                565                 570                 575

Ser Asp Ser Asp Glu Glu Ser Val Ile Ser Ser Thr Ser Ser Gly Ser
            580                 585                 590

Ser Gln Glu Glu Glu Thr Gln Arg Arg Arg Gln His Lys Pro Ser Lys
            595                 600                 605

Arg Arg Leu Leu Lys His Leu Gln Arg Val Val Lys Arg Met Lys Thr
            610                 615                 620

Leu
625

<210> SEQ ID NO 17
<211> LENGTH: 73
<212> TYPE: PRT
<213> ORGANISM: Torque teno sus virus

<400> SEQUENCE: 17

Met Lys Glu Lys Asp Tyr Trp Glu Glu Ala Trp Leu Thr Ser Cys Thr
1               5                   10                  15

Ser Ile His Asp His His Cys Asn Cys Gly Ser Trp Arg Asp His Leu
            20                  25                  30

Trp Thr Leu Cys Ala Leu Asp Asp Ala Asp Leu Ala Ala Ala Ala Asp
        35                  40                  45

Ile Ile Glu Arg Glu Glu Ala Asp Gly Gly Glu Asp Phe Gly Phe Val
    50                  55                  60

Asp Gly Asp Pro Gly Asp Ala Gly Gly
65                  70

<210> SEQ ID NO 18
<211> LENGTH: 72
<212> TYPE: PRT
<213> ORGANISM: Torque teno sus virus

<400> SEQUENCE: 18

Met Pro Glu His Trp Glu Glu Ala Trp Leu Glu Ala Thr Lys Gly Trp
1               5                   10                  15

His Asp Leu Asp Cys Arg Cys Gly Asn Trp Gln Asp His Leu Trp Leu
            20                  25                  30

Leu Leu Ala Asp Gly Asp Ala Ala Leu Ala Ala Ala Val Asp Ala Ile
```

```
                    35                  40                  45

Glu Arg Asp Ala Met Gly Gly Glu Asp Val Thr Thr Ala Thr Asp Arg
 50                  55                  60

Val Thr Ile Gly Asp Asp Gly Trp
 65                  70

<210> SEQ ID NO 19
<211> LENGTH: 68
<212> TYPE: PRT
<213> ORGANISM: Torque teno sus virus

<400> SEQUENCE: 19

Met Glu Glu Arg Trp Leu Thr Val Ala Tyr Cys Ala His Gly Leu Phe
  1               5                  10                  15

Cys Asp Cys Lys Asn Pro Lys Lys His Leu Glu Lys Cys Leu Thr Asp
             20                  25                  30

Ala Ile Ala Asp Ala Glu Gly Asp Arg His Gly Asp Gly Thr Gly
         35                  40                  45

Gly Gly Asp Ala Thr Phe Asp Ile Gly Ile Asp Ala Leu Leu Ala Ala
 50                  55                  60

Ala Ala Gln Arg
 65

<210> SEQ ID NO 20
<211> LENGTH: 68
<212> TYPE: PRT
<213> ORGANISM: Torque teno sus virus

<400> SEQUENCE: 20

Met Glu Glu Arg Trp Leu Thr Val Ala Tyr Cys Ala His Gly Leu Phe
  1               5                  10                  15

Cys Gly Cys Lys Asp Pro Lys Lys His Leu Glu Lys Cys Leu Thr Asp
             20                  25                  30

Ala Ile Ala Asp Ala Glu Gly Asp Arg His Gly Asp Gly Thr Gly
         35                  40                  45

Gly Gly Asp Ala Ser Phe Asp Ile Gly Ile Asp Ala Leu Leu Ala Ala
 50                  55                  60

Ala Ala Gln Arg
 65

<210> SEQ ID NO 21
<211> LENGTH: 174
<212> TYPE: PRT
<213> ORGANISM: Torque teno sus virus

<400> SEQUENCE: 21

Met Arg Phe Arg Arg Arg Arg Phe Gly Arg Arg Arg Tyr Tyr Arg
  1               5                  10                  15

Lys Arg Arg Gly Gly Trp Arg Arg Phe Arg Ile Arg Arg Arg
             20                  25                  30

Pro Trp Arg Arg Trp Arg Phe Gly Gly Met Tyr Gln Pro Thr Gly
         35                  40                  45

Ile Gln Asp Pro Cys Thr Ser Asn Pro Thr Tyr Pro Val Arg Met Val
 50                  55                  60

Gly Ala Val Thr His Pro Lys Tyr Ala Gly Gln Gly Gly Ile Thr Thr
 65                  70                  75                  80

Gln Ile Gly Asp Gln Gly Ile Thr Ala Ala Ser Ile Arg Ala Ile Ser
                 85                  90                  95
```

```
Ala Ala Pro Pro Asp Thr Tyr Thr Gln Ser Ala Phe Leu Lys Ala Pro
            100                 105                 110

Glu Thr Glu Lys Glu Glu Arg Glu Ser Glu Thr Ser Phe Thr Ser
        115                 120                 125

Ala Glu Ser Ser Glu Gly Asp Gly Ser Ser Asp Asp Gln Ala Glu
    130                 135                 140

Arg Arg Ala Ala Arg Lys Arg Val Ile Lys Leu Leu Leu Lys Arg Leu
145                 150                 155                 160

Ala Asp Arg Pro Val Asp Asn Lys Arg Arg Phe Ser Glu
                165                 170
```

<210> SEQ ID NO 22
<211> LENGTH: 182
<212> TYPE: PRT
<213> ORGANISM: Torque teno sus virus

<400> SEQUENCE: 22

```
Met Ala Pro Thr Arg Arg Trp Arg Arg Phe Gly Arg Arg Arg
1               5                   10                  15

Arg Tyr Arg Lys Arg Arg Tyr Gly Trp Arg Arg Tyr Tyr Arg Tyr
            20                  25                  30

Arg Pro Arg Tyr Tyr Arg Arg Trp Leu Phe Gly Gly Glu Tyr Gln
        35                  40                  45

Pro Pro Thr Gly Ile Arg Asp Pro Cys Ile Asp Thr Pro Ala Tyr Pro
50                  55                  60

Val Pro Gln Ser Gly Ser Val Thr His Pro Lys Phe Ala Gly Lys Gly
65                  70                  75                  80

Gly Met Leu Thr Glu Thr Asp Arg Trp Gly Ile Thr Ala Ala Ser Ser
                85                  90                  95

Arg Thr Leu Ser Ala Asp Thr Pro Thr Glu Ala Ala Gln Ser Ala Leu
            100                 105                 110

Leu Arg Gly Asp Ala Glu Lys Lys Gly Glu Glu Thr Glu Glu Thr Ala
        115                 120                 125

Ser Ser Ser Ser Ile Thr Ser Ala Glu Ser Ser Thr Glu Gly Asp Gly
    130                 135                 140

Ser Ser Asp Asp Glu Glu Thr Ile Arg Arg Arg Arg Thr Trp Lys
145                 150                 155                 160

Arg Leu Arg Arg Met Val Arg Gln Gln Leu Asp Arg Arg Met Asp His
                165                 170                 175

Lys Arg Gln Arg Leu His
            180
```

<210> SEQ ID NO 23
<211> LENGTH: 178
<212> TYPE: PRT
<213> ORGANISM: Torque teno sus virus

<400> SEQUENCE: 23

```
Met Pro Tyr Arg Arg Tyr Arg Arg Arg Arg Pro Thr Arg Arg
1               5                   10                  15

Trp Arg His Arg Arg Trp Arg Arg Tyr Phe Arg Tyr Tyr Arg Arg
            20                  25                  30

Ala Pro Arg Arg Arg Pro Lys Trp Gly Gly His Gly Thr Glu Arg
        35                  40                  45

Phe Lys Thr Thr Ile Gly Asp Pro Ser Thr Ile Pro Cys Pro Phe Glu
50                  55                  60
```

```
Pro Gly Glu Arg Tyr His His Gly Val Gln Asp Pro Ala Lys Val Gln
 65                  70                  75                  80

Asn Thr Val Leu Asn Pro Trp Asp Tyr Asp Cys Asp Gly Ile Val Arg
                 85                  90                  95

Thr Asp Thr Leu Lys Arg Leu Leu Glu Leu Pro Thr Glu Thr Glu Glu
            100                 105                 110

Thr Glu Lys Ala Tyr Pro Leu Leu Gly Gln Lys Thr Glu Lys Glu Pro
        115                 120                 125

Leu Ser Asp Ser Asp Glu Glu Ser Val Ile Ser Ser Thr Ser Ser Gly
    130                 135                 140

Ser Ser Gln Glu Glu Glu Thr Gln Arg Arg Lys His His Lys Pro Ser
145                 150                 155                 160

Lys Arg Arg Leu Leu Lys His Leu Gln Arg Val Val Lys Arg Met Lys
                165                 170                 175

Thr Leu

<210> SEQ ID NO 24
<211> LENGTH: 178
<212> TYPE: PRT
<213> ORGANISM: Torque teno sus virus

<400> SEQUENCE: 24

Met Pro Tyr Arg Arg Tyr Arg Arg Arg Arg Arg Pro Thr Arg Arg
 1               5                  10                  15

Trp Arg His Arg Arg Trp Arg Arg Phe Phe Arg Tyr Arg Tyr Arg Arg
                 20                  25                  30

Ala Pro Arg Arg Arg Arg Thr Lys Trp Gly Gly His Gly Thr Glu Arg
            35                  40                  45

Phe Lys Thr Thr Ile Gly Asp Pro Ser Thr Ile Pro Cys Pro Phe Glu
        50                  55                  60

Pro Gly Glu Arg Tyr His His Gly Val Gln Asp Pro Ala Lys Val Gln
 65                  70                  75                  80

Asn Thr Val Leu Asn Pro Trp Asp Tyr Asp Cys Asp Gly Ile Val Arg
                 85                  90                  95

Thr Asp Thr Leu Lys Arg Leu Leu Glu Leu Pro Thr Glu Thr Glu Glu
            100                 105                 110

Thr Glu Lys Ala Tyr Pro Leu Leu Gly Gln Lys Thr Glu Lys Glu Pro
        115                 120                 125

Leu Ser Asp Ser Asp Glu Glu Ser Val Ile Ser Ser Thr Ser Ser Gly
    130                 135                 140

Ser Ser Gln Glu Glu Glu Thr Gln Arg Arg Arg Gln His Lys Pro Ser
145                 150                 155                 160

Lys Arg Arg Leu Leu Lys His Leu Gln Arg Val Val Lys Arg Met Lys
                165                 170                 175

Thr Leu

<210> SEQ ID NO 25
<211> LENGTH: 224
<212> TYPE: PRT
<213> ORGANISM: Torque teno sus virus

<400> SEQUENCE: 25

Met Lys Glu Lys Asp Tyr Trp Glu Glu Ala Trp Leu Thr Ser Cys Thr
 1               5                  10

```
            20                  25                  30
Trp Thr Leu Cys Ala Leu Asp Asp Ala Asp Leu Ala Ala Ala Ala Asp
        35                  40                  45
Ile Ile Glu Arg Glu Glu Ala Asp Gly Gly Glu Asp Phe Gly Phe Val
    50                  55                  60
Asp Gly Asp Pro Gly Asp Ala Gly Gly Ser Ala Ala Cys Thr Ser Leu
65                  70                  75                  80
Pro Pro Glu Ser Lys Ile Pro Ala Leu Leu Thr Arg Pro Ile Leu Ser
                85                  90                  95
Glu Trp Ser Glu Gln Leu His Thr Pro Asn Thr Pro Gly Lys Ala Glu
            100                 105                 110
Ser Arg Pro Lys Leu Glu Ile Lys Val Ser Pro Leu Pro Leu Ser Val
        115                 120                 125
Pro Ser Val Gln Leu His Gln Ile Pro Thr Arg Ser Arg Arg Ser Ser
    130                 135                 140
Lys Pro Arg Lys Pro Arg Lys Lys Arg Lys Glu Arg Val Arg Pro Val
145                 150                 155                 160
Ser Arg Val Pro Lys Ala Leu Leu Arg Glu Met Asp Arg Leu Met Thr
                165                 170                 175
Lys Gln Arg Asp Ala Leu Pro Glu Ser Glu Ser Ser Tyr Phe Ser
            180                 185                 190
Ser Asp Ser Leu Thr Asp Pro Trp Thr Thr Ser Asp Asp Phe Gln
        195                 200                 205
Ser Asp Pro Asp Pro Leu Thr Asn Lys Arg Lys Lys Arg Leu Gln Phe
    210                 215                 220

<210> SEQ ID NO 26
<211> LENGTH: 228
<212> TYPE: PRT
<213> ORGANISM: Torque teno sus virus

<400> SEQUENCE: 26

Met Pro Glu His Trp Glu Ala Trp Leu Glu Ala Thr Lys Gly Trp
1               5                   10                  15
His Asp Leu Asp Cys Arg Cys Gly Asn Trp Gln Asp His Leu Trp Leu
            20                  25                  30
Leu Leu Ala Asp Gly Asp Ala Ala Leu Ala Ala Val Asp Ala Ile
        35                  40                  45
Glu Arg Asp Ala Met Gly Gly Glu Asp Val Thr Thr Ala Thr Asp Arg
    50                  55                  60
Val Thr Ile Gly Asp Asp Gly Cys Leu Ala Val Asn Thr Ser His Gln
65                  70                  75                  80
Gln Val Ser Ala Ile Pro Ala Leu Ile His Gln Pro Ile Leu Cys Arg
                85                  90                  95
Ser Gln Glu Val Leu His Thr Pro Asn Ser Pro Glu Arg Ala Glu Cys
            100                 105                 110
Ser Arg Lys Gln Thr Val Gly Val Ser Leu Leu Pro Leu Pro Glu Pro
        115                 120                 125
Ser Val Gln Ile His Pro Pro Lys Gln Arg Lys Val His Phe Ser Glu
    130                 135                 140
Gly Thr Arg Lys Arg Lys Glu Arg Lys Pro Arg Lys Pro Arg His Arg
145                 150                 155                 160
Pro Val Ser Arg Val Pro Lys Ala Leu Leu Arg Glu Met Asp Arg Leu
                165                 170                 175
```

```
Met Met Lys Arg Gln Ser Asp Ala Glu Gly Gly Pro Gly Ser Asp Ser
            180                 185                 190

Asp Gly Trp Ser Asp Ser Ser Leu Thr Asp Glu Trp Thr Thr Ser Asp
            195                 200                 205

Ser Asp Phe Ile Asp Thr Pro Ile Arg Glu Arg Cys Leu Asn Lys Lys
            210                 215                 220

Gln Lys Lys Arg
225

<210> SEQ ID NO 27
<211> LENGTH: 199
<212> TYPE: PRT
<213> ORGANISM: Torque teno sus virus

<400> SEQUENCE: 27

Met Glu Glu Arg Trp Leu Thr Val Ala Tyr Cys Ala His Gly Leu Phe
1               5                   10                  15

Cys Asp Cys Lys Asn Pro Lys Lys His Leu Glu Lys Cys Leu Thr Asp
            20                  25                  30

Ala Ile Ala Asp Ala Glu Gly Asp Arg His Gly Asp Gly Gly Thr Gly
            35                  40                  45

Gly Gly Asp Ala Thr Phe Asp Ile Gly Ile Asp Ala Leu Leu Ala Ala
        50                  55                  60

Ala Ala Gln Ser Gly Glu Asp Met Ala Pro Lys Asp Leu Lys Gln Pro
65                  70                  75                  80

Ser Glu Ile Pro Ala Pro Tyr His Val Pro Leu Asn Pro Gly Asn Gly
                85                  90                  95

Thr Thr Thr Gly Tyr Lys Thr Pro Pro Arg Tyr Lys Thr Gln Ser Ser
            100                 105                 110

Thr Leu Gly Thr Met Thr Val Thr Gly Leu Leu Glu Gln Ile Leu Ser
            115                 120                 125

Lys Asp Phe Ser Asn Ser Pro Gln Arg Arg Arg Arg Arg Arg Arg Arg
        130                 135                 140

Thr His Ser Leu Asp Lys Lys Gln Arg Lys Ser His Tyr Gln Thr Pro
145                 150                 155                 160

Thr Lys Arg Ala Leu Ser Gln Ala Arg Ala Val Asp Pro Leu Lys Lys
                165                 170                 175

Lys Arg Arg Arg Asp Glu Ser Thr Thr Ser Gln Ala Ser Asp Asp Ser
            180                 185                 190

Ser Ser Thr Ser Ser Gly Trp
        195

<210> SEQ ID NO 28
<211> LENGTH: 199
<212> TYPE: PRT
<213> ORGANISM: Torque teno sus virus

<400> SEQUENCE: 28

Met Glu Glu Arg Trp Leu Thr Val Ala Tyr Cys Ala His Gly Leu Phe
1               5                   10                  15

Cys Gly Cys Lys Asp Pro Lys Lys His Leu Glu Lys Cys Leu

Ala Ala Gln Ser Gly Glu Ala Thr Glu Pro Lys Asp Ser Lys Gln Pro
65                  70                  75                  80

Ser Glu Ile Pro Ala Pro Tyr His Val Pro Leu Asn Pro Gly Asn Gly
                85                  90                  95

Thr Thr Thr Gly Tyr Lys Thr Pro Pro Arg Tyr Lys Thr Gln Ser Ser
            100                 105                 110

Thr Leu Gly Thr Met Thr Val Thr Gly Leu Leu Glu Gln Ile Leu Ser
        115                 120                 125

Lys Asp Phe Ser Asn Ser Pro Gln Arg Arg Arg Arg Arg Arg Arg Arg
    130                 135                 140

Thr His Ser Leu Asp Lys Lys Gln Arg Lys Ser His Tyr Gln Thr Pro
145                 150                 155                 160

Thr Lys Arg Ala Leu Ser Gln Ala Arg Ala Val Asp Pro Leu Lys Lys
                165                 170                 175

Lys Arg Arg Arg Glu Glu Asp Ser Thr Ser Gln Ala Ser Asp Asp Ser
            180                 185                 190

Ser Ser Thr Ser Ser Gly Trp
        195

<210> SEQ ID NO 29
<211> LENGTH: 21
<212> TYPE: DNA
<213> ORGANISM: Torque teno sus virus

<400> SEQUENCE: 29
tccgaatggc tgagtttatg c                                           21

<210> SEQ ID NO 30
<211> LENGTH: 17
<212> TYPE: DNA
<213> ORGANISM: Torque teno sus virus

<400> SEQUENCE: 30
tccgctcagc tgctcct                                                17

<210> SEQ ID NO 31
<211> LENGTH: 18
<212> TYPE: DNA
<213> ORGANISM: Torque teno sus virus

<400> SEQUENCE: 31
ggtggtaaag aggatgaa                                               18

<210> SEQ ID NO 32
<211> LENGTH: 19
<212> TYPE: DNA
<213> ORGANISM: Torque teno sus virus

<400> SEQUENCE: 32
aatagattgg acacaggag                                              19

<210> SEQ ID NO 33
<211> LENGTH: 18
<212> TYPE: DNA
<213> ORGANISM: Torque teno sus virus

<400> SEQUENCE: 33
tatcgggcag gagcagct                                               18

<210> SEQ ID NO 34

```
<211> LENGTH: 18
<212> TYPE: DNA
<213> ORGANISM: Torque teno sus virus

<400> SEQUENCE: 34 tagggcgcg ctctacgt                                                  18

<210> SEQ ID NO 35
<211> LENGTH: 21
<212> TYPE: DNA
<213> ORGANISM: Torque teno sus virus

<400> SEQUENCE: 35
cctacatgaa ggagaaagac t                                             21

<210> SEQ ID NO 36
<211> LENGTH: 17
<212> TYPE: DNA
<213> ORGANISM: Torque teno sus virus

<400> SEQUENCE: 36
ccagcgtctc cagggtc                                                  17

<210> SEQ ID NO 37
<211> LENGTH: 17
<212> TYPE: DNA
<213> ORGANISM: Torque teno sus virus

<400> SEQUENCE: 37
aagctaccaa gggctgg                                                  17

<210> SEQ ID NO 38
<211> LENGTH: 19
<212> TYPE: DNA
<213> ORGANISM: Torque teno sus virus

<400> SEQUENCE: 38
gcggtctggt agcggtagt                                                19

<210> SEQ ID NO 39
<211> LENGTH: 22
<212> TYPE: DNA
<213> ORGANISM: Torque teno sus virus

<400> SEQUENCE: 39
cgaatggctg agtttatgcc gc                                            22

<210> SEQ ID NO 40
<211> LENGTH: 11
<212> TYPE: DNA
<213> ORGANISM: Torque teno sus virus

<400> SEQUENCE: 40
agtcctcatt t                                                        11

<210> SEQ ID NO 41
<211> LENGTH: 11
<212> TYPE: DNA
<213> ORGANISM: Torque teno sus virus

<400> SEQUENCE: 41
aaccaatcag a                                                        11
```

```
<210> SEQ ID NO 42
<211> LENGTH: 17
<212> TYPE: DNA
<213> ORGANISM: Torque teno sus virus

<400> SEQUENCE: 42
ctgggcgggt gccggag                                                  17

<210> SEQ ID NO 43
<211> LENGTH: 14
<212> TYPE: DNA
<213> ORGANISM: Torque teno sus virus

<400> SEQUENCE: 43
cggagtcaag gggc                                                     14

<210> SEQ ID NO 44
<211> LENGTH: 11
<212> TYPE: DNA
<213> ORGANISM: Torque teno sus virus

<400> SEQUENCE: 44
tatcgggcag g                                                        11

<210> SEQ ID NO 45
<211> LENGTH: 23
<212> TYPE: DNA
<213> ORGANISM: Torque teno sus virus

<400> SEQUENCE: 45
tacacttccg ggttcaggag gct                                           23

<210> SEQ ID NO 46
<211> LENGTH: 22
<212> TYPE: DNA
<213> ORGANISM: Torque teno sus virus

<400> SEQUENCE: 46
actcagccat tcggaacctc ac                                            22

<210> SEQ ID NO 47
<211> LENGTH: 22
<212> TYPE: DNA
<213> ORGANISM: Torque teno sus virus

<400> SEQUENCE: 47
caatttggct cgcttcgctc gc                                            22

<210> SEQ ID NO 48
<211> LENGTH: 25
<212> TYPE: DNA
<213> ORGANISM: Torque teno sus virus

<400> SEQUENCE: 48
tacttatatt cgctttcgtg ggaac                                         25

<210> SEQ ID NO 49
<211> LENGTH: 22
<212> TYPE: DNA
<213> ORGANISM: Torque teno sus virus

<400> SEQUENCE: 49
agttacacat aaccaccaaa cc                                            22
```

<210> SEQ ID NO 50
<211> LENGTH: 21
<212> TYPE: DNA
<213> ORGANISM: Torque teno sus virus

<400> SEQUENCE: 50
attaccgcct gcccgatagg c                                              21

<210> SEQ ID NO 51
<211> LENGTH: 21
<212> TYPE: DNA
<213> ORGANISM: Torque teno sus virus

<400> SEQUENCE: 51
ccaaaccaca ggaaactgtg c                                              21

<210> SEQ ID NO 52
<211> LENGTH: 20
<212> TYPE: DNA
<213> ORGANISM: Torque teno sus virus

<400> SEQUENCE: 52
cttgactccg ctctcaggag                                                20

<210> SEQ ID NO 53
<211> LENGTH: 2878
<212> TYPE: DNA
<213> ORGANISM: Torque teno sus virus

<400> SEQUENCE: 53
tacacttccg ggttcaggag gctcaatttg gctcgcttcg ctcgcaccac gtttgctgcc    60
aggcggacct gattgaagac tgaaaaccgt taaattcaaa tttgaaaatg gcgggcaaaa   120
tggcggacag ggggcgggga ttatgcaaat taatttatgc aaagtaggag gagctcgatt   180
ttaatttatg caaagtagga ggagtcattt ctgattggtc gggagctcaa gtcctcattt   240
gcatagggtg taaccaatca gatttaaggc gttcccacta aagtgaatat aagtgagtgc   300
agttccgaat ggctgagttt atgccgccag cggtagacag aactgtctag cgactgggcg   360
ggtgccggag gatcccagat ccggagtcaa ggggcctatc gggcaggagc agctgagcgg   420
agggcctaca tgaaggagaa agactactgg gaagaagcct ggctgaccag ctgtacatcc   480
atacacgacc accactgcga ctgcggtagc tggagagacc acctgtggac gctatgcgct   540
ttagacgacg cagatttggc cgccgccgca gatattatag aaagagaaga ggcggatgga   600
ggagaagatt tcggattcgt agacggcgac cctggagacg ctggcgggta aggagatggc   660
ggcgttccgt cttccgtaga aggggacgta gagcgcgccc ctaccgcatt agcgcgtgga   720
accctaaggt tctaagaaac tgccgcatca caggatggtg gccagtaata cagtgtatgg   780
acgggatgga gtggataaaa tacaagccga tggacttaag agtcgaggca aaccggatat   840
tcgataaaca gggcagtaag atagagacag aacagatggg atacttaatg cagtacggag   900
gaggatggtc aagcggagta atcagcttag agggactttt caatgaaaac agactgtgga   960
gaaacatatg gtctaaaagc aatgacggga tggacttggt cagatacttc gggtgcagaa  1020
ttagactata tccaacagag aatcagggct acttgttctg gtatgacaca gaatttgacg  1080
aacagcagag aagaatgtta gacgaatata cacaacctag tgtaatgctg caggctaaaa  1140
actcccgttt aatagtatgt aaacaaaaga tgccaattag acggagagta aagagcattt  1200
tcataccgcc accggcacag ttaacaacac agtggaagtt tcagcaggaa ctgtgtcaat  1260

```
ttccattatt taactgggcc tgtatctgta tagacatgga cacgccgttc gactacaacg    1320
gcgcatggcg aaatgcctgg tggctaatga aaggcttca aaacggaaac atggagtaca      1380
tagaaagatg gggcagaata ccgatgacag gagacacaga actgccacca gcagacgact    1440
tcaaggcagg aggggtgaac aaaaacttca aaccgacagg tattcagaga atataccta     1500 tagtagcagt atgcctagtg gagggaaaca agagagtagt gaaatgggcc acagtacaca    1560
atgggccaat agacagatgg agaaaaaaac agacaggaac gttaaaacta tctgcactga    1620
gaagactagt gcttagagta tgctcagaaa gtgagacata ctataagtgg acagcatcag    1680
aatttacagg agcatttcag caggactggt ggccagttag cggaacagaa tacccgttat    1740
gtacaattaa aatggagcca gaattcgaaa acccgacagt agaggtgtgg tcatggaaag    1800
caactatacc gacagcagga acactgaaag actatttcgg gctcagttca gggcaacagt    1860
ggaaggacac tgactttggc aggctgcaat acccagaag cagccacaat gttgactttg     1920
gacataaagc tagatttggc ccattttgtg tgaaaaagcc tccagtagaa ttcagagact    1980
cagcccccaa cccactaaat atctgggtga atacacatt ctattttcag ttcggcggca     2040
tgtaccagcc tcccaccgga atccaagatc cctgcacttc taacccgacc tatcctgtca    2100
gaatggtcgg agcagttaca caccccaaat acgccgggca aggcggaatc gcgacccaaa    2160
ttggagatca aggtatcacc gctgcctctc tccgtgccat cagtgcagct ccaccaaata    2220
cctacacgca gtcggcgttc ctcaaagccc cggaaaccga gaaagaagag gaaagagaga    2280
gtgagaccag tttcacgagt gccgaaagct cttctgaggg agatggatcg tctgatgacc    2340
aagcagagag acgcgctgcc agaaagcgag tcatcaagct acttctcaag cgactcgctg    2400
acagacccgt ggacaacaag cgacgacgat tttcagagtg accctgaccc cctcaccaat    2460
aaacgcaaaa agcgcttgca attctaattc gctgtccgtg tattcattgg ggggtccgg     2520 gggggcttgc ccccccgtta gttgggttct cgcactcccg cctgccaagt gaaagtcggg    2580
gacgagtgag tgcgggacat cccgtgtaat ggctacataa ctacccggct ttgcttcgac    2640
agtggccgtg gctcgaccct cacacaacaa tgcagatagg gggcgcaatt gggatcgtta    2700
gaaaactatg gccgagcatg gggggggctc cgccccccc aaccccccg gtgggggggc      2760 caaggccccc cctacacccc ccatgggg gctgctgccc ccaaacccc ccgcgtcgga      2820 tggggggggc tgcgccccc ccaaacccc cttgccgggg gctgtgcccc ggaccccc       2878
```

<210> SEQ ID NO 54
<211> LENGTH: 635
<212> TYPE: PRT
<213> ORGANISM: Torque teno sus virus

<400> SEQUENCE: 54

```
Met Arg Phe Arg Arg Arg Phe Gly Arg Arg Arg Tyr Tyr Arg
1               5                   10                  15

Lys Arg Arg Gly Gly Trp Arg Arg Phe Arg Ile Arg Arg Arg
            20                  25                  30

Pro Trp Arg Arg Trp Arg Val Arg Arg Trp Arg Ser Val Phe Arg
        35                  40                  45

Arg Arg Gly Arg Arg Ala Arg Pro Tyr Arg Ile Ser Ala Trp Asn Pro
    50                  55                  60

Lys Val Leu Arg Asn Cys Arg Ile Thr Gly Trp Trp Pro Val Ile Gln
65                  70                  75                  80

Cys Met Asp Gly Met Glu Trp Ile Lys Tyr Lys Pro Met Asp Leu Arg
```

|   | 85 |   |   |   | 90 |   |   |   | 95 |   |   |
|---|---|---|---|---|---|---|---|---|---|---|---|

Val Glu Ala Asn Arg Ile Phe Asp Lys Gln Gly Ser Lys Ile Glu Thr
            100                 105                 110

Glu Gln Met Gly Tyr Leu Met Gln Tyr Gly Gly Trp Ser Ser Gly
        115                 120                 125

Val Ile Ser Leu Glu Gly Leu Phe Asn Glu Asn Arg Leu Trp Arg Asn
        130                 135                 140

Ile Trp Ser Lys Ser Asn Asp Gly Met Asp Leu Val Arg Tyr Phe Gly
145                 150                 155                 160

Cys Arg Ile Arg Leu Tyr Pro Thr Glu Asn Gln Gly Tyr Leu Phe Trp
                165                 170                 175

Tyr Asp Thr Glu Phe Asp Glu Gln Arg Arg Met Leu Asp Glu Tyr
            180                 185                 190

Thr Gln Pro Ser Val Met Leu Gln Ala Lys Asn Ser Arg Leu Ile Val
            195                 200                 205

Cys Lys Gln Lys Met Pro Ile Arg Arg Val Lys Ser Ile Phe Ile
        210                 215                 220

Pro Pro Pro Ala Gln Leu Thr Thr Gln Trp Lys Phe Gln Gln Glu Leu
225                 230                 235                 240

Cys Gln Phe Pro Leu Phe Asn Trp Ala Cys Ile Cys Ile Asp Met Asp
                245                 250                 255

Thr Pro Phe Asp Tyr Asn Gly Ala Trp Arg Asn Ala Trp Trp Leu Met
            260                 265                 270

Arg Arg Leu Gln Asn Gly Asn Met Glu Tyr Ile Glu Arg Trp Gly Arg
        275                 280                 285

Ile Pro Met Thr Gly Asp Thr Glu Leu Pro Pro Ala Asp Asp Phe Lys
290                 295                 300

Ala Gly Gly Val Asn Lys Asn Phe Lys Pro Thr Gly Ile Gln Arg Ile
305                 310                 315                 320

Tyr Pro Ile Val Ala Val Cys Leu Val Glu Gly Asn Lys Arg Val Val
                325                 330                 335

Lys Trp Ala Thr Val His Asn Gly Pro Ile Asp Arg Trp Arg Lys Lys
            340                 345                 350

Gln Thr Gly Thr Leu Lys Leu Ser Ala Leu Arg Arg Leu Val Leu Arg
        355                 360                 365

Val Cys Ser Glu Ser Glu Thr Tyr Tyr Lys Trp Thr Ala Ser Glu Phe
        370                 375                 380

Thr Gly Ala Phe Gln Gln Asp Trp Trp Pro Val Ser Gly Thr Glu Tyr
385                 390                 395                 400

Pro Leu Cys Thr Ile Lys Met Glu Pro Glu Phe Glu Asn Pro Thr Val
                405                 410                 415

Glu Val Trp Ser Trp Lys Ala Thr Ile Pro Thr Ala Gly Thr Leu Lys
            420                 425                 430

Asp Tyr Phe Gly Leu Ser Ser Gly Gln Gln Trp Lys Asp Thr Asp Phe
            435                 440                 445

Gly Arg Leu Gln Leu Pro Arg Ser Ser His Asn Val Asp Phe Gly His
        450                 455                 460

Lys Ala Arg Phe Gly Pro Phe Cys Val Lys Lys Pro Val Glu Phe
465                 470                 475                 480

Arg Asp Ser Ala Pro Asn Pro Leu Asn Ile Trp Val Lys Tyr Thr Phe
                485                 490                 495

Tyr Phe Gln Phe Gly Gly Met Tyr Gln Pro Thr Gly Ile Gln Asp
        500                 505                 510

```
Pro Cys Thr Ser Asn Pro Thr Tyr Pro Val Arg Met Val Gly Ala Val
            515                 520                 525

Thr His Pro Lys Tyr Ala Gly Gln Gly Gly Ile Ala Thr Gln Ile Gly
        530                 535                 540

Asp Gln Gly Ile Thr Ala Ala Ser Leu Arg Ala Ile Ser Ala Ala Pro
545                 550                 555                 560

Pro Asn Thr Tyr Thr Gln Ser Ala Phe Leu Lys Ala Pro Glu Thr Glu
                565                 570                 575

Lys Glu Glu Glu Arg Glu Ser Glu Thr Ser Phe Thr Ser Ala Glu Ser
            580                 585                 590

Ser Ser Glu Gly Asp Gly Ser Ser Asp Asp Gln Ala Glu Arg Arg Ala
        595                 600                 605

Ala Arg Lys Arg Val Ile Lys Leu Leu Leu Lys Arg Leu Ala Asp Arg
    610                 615                 620

Pro Val Asp Asn Lys Arg Arg Arg Phe Ser Glu
625                 630                 635

<210> SEQ ID NO 55
<211> LENGTH: 73
<212> TYPE: PRT
<213> ORGANISM: Torque teno sus virus

<400> SEQUENCE: 55

Met Lys Glu Lys Asp Tyr Trp Glu Glu Ala Trp Leu Thr Ser Cys Thr
1               5                   10                  15

Ser Ile His Asp His His Cys Asp Cys Gly Ser Trp Arg Asp His Leu
            20                  25                  30

Trp Thr Leu Cys Ala Leu Asp Asp Ala Asp Leu Ala Ala Ala Ala Asp
        35                  40                  45

Ile Ile Glu Arg Glu Glu Ala Asp Gly Gly Glu Asp Phe Gly Phe Val
    50                  55                  60

Asp Gly Asp Pro Gly Asp Ala Gly Gly
65                  70

<210> SEQ ID NO 56
<211> LENGTH: 2872
<212> TYPE: DNA
<213> ORGANISM: Torque teno sus virus
<220> FEATURE:
<221> NAME/KEY: misc_feature
<222> LOCATION: (2719)..(2732)
<223> OTHER INFORMATION: n is a, c, g, or t

<400> SEQUENCE: 56
tacactttgg ggttcaggag gctcaatttg gctcgcttcg ctcgcaccac gtttgctgcc      60
aggcggacct gattgaagac tgaaaaccgt taaattcaaa attgaaaagg gcgggcaaaa     120
tggcggacag ggggcggagt ttatgcaaat taatttatgc aaagtaggag gagctcgatt     180
ttaatttatg caaagtagga ggagtcaaat ctgattggtc gggagctcaa gtcctcattt     240
gcatagggtg taaccaatca gaattaaggc gttcccacga aagcgaatat aagtaggtga     300
ggttccgaat ggctgagttt atgccgccag cggtagacag aactgtctag cgactgggcg     360
ggtgccggag gatccctgat ccggagtcaa ggggcctatc gggcaggagc agctaggcgg     420
agggcctatg ccggaacact gggaggaagc ctggttggaa gctaccaagg gctggcacga     480
tctcgactgc cgctgcggta actggcagga ccacctatgg ctcctactcg ccgatggaga     540
cgccgctttg gccgccgccg tagacgctat agaaagagac gctatggctg agacgacgc      600
```

```
tactaccgct acaggccgcg tgactatcgg cgacgatggc tggtaaggag aaggcggcgt     660
tccgtctacc gtagaggtgg acgtagagcg cgccctacc gactgtttaa tccaaaagta     720
atgcggagag tagtaattag ggggtggtgg cctattttac aatgcttaaa aggacaggag     780
gcactaagat atagacctct acagtgggac acagagagac agtggagagt gagatcagac     840
ttcgaagacc agtacggata cctcgtacaa tacggggag gttggggaag tggtgatgtg     900
acacttgaag gtctctacca agagcactta ttgtggagaa actcttggtc taaaggaaac     960
gatggaatgg acctagtaag atactttgga tgtgtagtat acctatatcc actaaaggac    1020
caggactatt ggttctggtg ggacacggac ttcaaagaat tatatgcaga aaacataaag    1080
gaatacagcc aaccatcagt aatgatgatg gcaaaaagaa caagaatagt aatagccaga    1140
gaaagggcac cacatagaag aaaagtaaga aaatattta ttccgccacc ttcgagagac    1200
acaacacagt ggcagtttca gacagatttc tgcaataaga agttatttac gtgggcagct    1260
ggtctaatag acatgcaaaa accgttcgat gctaatggag cctttagaaa tgcttggtgg    1320
ctggaacaga gaaatgatca gggagaaatg aaatacatag aactgtgggg aagagtaccc    1380
ccacaaggag attcagagct gcccaaaaaa aagaattct ccacaggaac agataaccca    1440
aactacaatg ttcaggacaa tgaggagaaa acatataccc cattataat atacgtagac    1500
caaaaagatc aaaaccaag aaaaaagtac tgcgtatgtt ataataagac cctcaacaga    1560
tggagactag gacaggcaag tactctaaag ataggaaacc tgaaaggact agtactaaga    1620
cagctgatga atcaagaaat gacgtatata tggaaagaag gagaatacag tgccccttt    1680
gtacaaaggt ggaaaggcag cagattcgct gtgatagacg caagaaaggc agaccaagaa    1740
aacccgaaag tatcaacatg gccaattgag ggaacgtgga acacacagga cacagtactg    1800
aaggatgtat tcggtattaa cttgcaaaat caacaattta gggcggcgga cttttggtaaa    1860
ctcacactac caaaatcacc gcatgactta gacttcggtc accacagcag atttgggcca    1920
ttttgtgtga aaatgaacc actggagttt caggtatacc ctccagaacc aactaacttg    1980
tggtttcagt acagattttt cttcagttt ggaggtgaat accaaccccc cacaggaatc    2040
cgggatccat gcgttgatac accagcctat cctgtgccgc agtcaggaag tattacacac    2100
cccaaattcg ccggaaaagg aggaatgctc acggaaacag accgttgggg tatcactgct    2160
gcctcttcca gagccctcag tgcagataca cccacagagg cagcgcaaag tgcacttctc    2220
cgagggact cggaagcgaa aggagaggaa accgaggaaa ccgcgtcatc gtccagtatc    2280
acgagtgccg aaagctctac tgagggagat ggatcgtctg atgatgaaga gacaatcaga    2340
cgcagaagga ggacctggaa gcgactcaga cgaatggtca gagagcagct tgaccgacga    2400
atggaccaca agcgacagcg acttcattga caccccata agagaaagat gcctcaataa    2460
aaaacaaaag aaacgctaaa cagtgtccga ttactaatgg gggggggtcc gggggggct    2520
tgccccccg caagctgggt taccgcacta actccctgcc aagtgaaact cggggacgag    2580
tgagtgcggg acatcccgtg taatggctac ataactaccc ggctttgctt cgacagtggc    2640
cgtggctcga ccctcacaca acactgcagg taggggcgc aattgggatc gttagaaaac    2700
tatgccgag catgggggnn nnnnnnnnn nnccaacccc ccggtgggg gggccaaggc    2760
ccccctaca ccccccatg ggggctgcc gcccccaaa ccccccgcgt cggatggggg    2820
gggctgcgcc cccccaaaac cccccttgcc cggggctgtg ccccggaccc cc           2872
```

<210> SEQ ID NO 57

<211> LENGTH: 637
<212> TYPE: PRT
<213> ORGANISM: Torque teno sus virus

<400> SEQUENCE: 57

```
Met Ala Pro Thr Arg Arg Trp Arg Arg Phe Gly Arg Arg Arg Arg Arg
1               5                   10                  15

Arg Tyr Arg Lys Arg Arg Tyr Gly Trp Arg Arg Tyr Tyr Arg Tyr
            20                  25                  30

Arg Pro Arg Asp Tyr Arg Arg Trp Leu Val Arg Arg Arg Arg
        35                  40                  45

Ser Val Tyr Arg Arg Gly Gly Arg Arg Ala Arg Pro Tyr Arg Leu Phe
    50                  55                  60

Asn Pro Lys Val Met Arg Arg Val Val Ile Arg Gly Trp Trp Pro Ile
65                  70                  75                  80

Leu Gln Cys Leu Lys Gly Gln Glu Ala Leu Arg Tyr Arg Pro Leu Gln
                85                  90                  95

Trp Asp Thr Glu Arg Gln Trp Arg Val Arg Ser Asp Phe Glu Asp Gln
            100                 105                 110

Tyr Gly Tyr Leu Val Gln Tyr Gly Gly Trp Gly Ser Gly Asp Val
        115                 120                 125

Thr Leu Glu Gly Leu Tyr Gln Glu His Leu Leu Trp Arg Asn Ser Trp
130                 135                 140

Ser Lys Gly Asn Asp Gly Met Asp Leu Val Arg Tyr Phe Gly Cys Val
145                 150                 155                 160

Val Tyr Leu Tyr Pro Leu Lys Asp Gln Asp Tyr Trp Phe Trp Trp Asp
                165                 170                 175

Thr Asp Phe Lys Glu Leu Tyr Ala Glu Asn Ile Lys Glu Tyr Ser Gln
            180                 185                 190

Pro Ser Val Met Met Met Ala Lys Arg Thr Arg Ile Val Ile Ala Arg
        195                 200                 205

Glu Arg Ala Pro His Arg Arg Lys Val Arg Lys Ile Phe Ile Pro Pro
    210                 215                 220

Pro Ser Arg Asp Thr Thr Gln Trp Gln Phe Gln Thr Asp Phe Cys Asn
225                 230                 235                 240

Arg Lys Leu Phe Thr Trp Ala Ala Gly Leu Ile Asp Met Gln Lys Pro
                245                 250                 255

Phe Asp Ala Asn Gly Ala Phe Arg Asn Ala Trp Trp Leu Glu Gln Arg
            260                 265                 270

Asn Asp Gln Gly Glu Met Lys Tyr Ile Glu Leu Trp Gly Arg Val Pro
        275                 280                 285

Pro Gln Gly Asp Ser Glu Leu Pro Lys Lys Lys Glu Phe Ser Thr Gly
    290                 295                 300

Thr Asp Asn Pro Asn Tyr Asn Val Gln Asp Asn Glu Glu Lys Asn Ile
305                 310                 315                 320

Tyr Pro Ile Ile Ile Tyr Val Asp Gln Lys Asp Gln Lys Pro Arg Lys
                325                 330                 335

Lys Tyr Cys Val Cys Tyr Asn Lys Thr Leu Asn Arg Trp Arg Leu Gly
            340                 345                 350

Gln Ala Ser Thr Leu Lys Ile Gly Asn Leu Lys Gly Leu Val Leu Arg
        355                 360                 365

Gln Leu Met Asn Gln Glu Met Thr Tyr Ile Trp Lys Glu Gly Glu Tyr
    370                 375                 380

Ser Ala Pro Phe Val Gln Arg Trp Lys Gly Ser Arg Phe Ala Val Ile
```

```
                385                 390                 395                 400
        Asp Ala Arg Lys Ala Asp Gln Glu Asn Pro Lys Val Ser Thr Trp Pro
                        405                 410                 415

Ile Glu Gly Thr Trp Asn Thr Gln Asp Thr Val Leu Lys Asp Val Phe
                        420                 425                 430

Gly Ile Asn Leu Gln Asn Gln Gln Phe Arg Ala Ala Asp Phe Gly Lys
                        435                 440                 445

Leu Thr Leu Pro Lys Ser Pro His Asp Leu Asp Phe Gly His His Ser
                450                 455                 460

Arg Phe Gly Pro Phe Cys Val Lys Asn Glu Pro Leu Glu Phe Gln Val
        465                 470                 475                 480

Tyr Pro Pro Glu Pro Thr Asn Leu Trp Phe Gln Tyr Arg Phe Phe Phe
                        485                 490                 495

Gln Phe Gly Gly Glu Tyr Gln Pro Pro Thr Gly Ile Arg Asp Pro Cys
                        500                 505                 510

Val Asp Thr Pro Ala Tyr Pro Val Pro Gln Ser Gly Ser Ile Thr His
                        515                 520                 525

Pro Lys Phe Ala Gly Lys Gly Met Leu Thr Glu Thr Asp Arg Trp
                530                 535                 540

Gly Ile Thr Ala Ala Ser Ser Arg Ala Leu Ser Ala Asp Thr Pro Thr
        545                 550                 555                 560

Glu Ala Ala Gln Ser Ala Leu Leu Arg Gly Asp Ser Glu Ala Lys Gly
                        565                 570                 575

Glu Glu Thr Glu Glu Thr Ala Ser Ser Ser Ile Thr Ser Ala Glu
                        580                 585                 590

Ser Ser Thr Glu Gly Asp Gly Ser Ser Asp Asp Glu Glu Thr Ile Arg
                595                 600                 605

Arg Arg Arg Arg Thr Trp Lys Arg Leu Arg Arg Met Val Arg Glu Gln
                        610                 615                 620

Leu Asp Arg Arg Met Asp His Lys Arg Gln Arg Leu His
        625                 630                 635

<210> SEQ ID NO 58
<211> LENGTH: 72
<212> TYPE: PRT
<213> ORGANISM: Torque teno sus virus

<400> SEQUENCE: 58

Met Pro Glu His Trp Glu Glu Ala Trp Leu Glu Ala Thr Lys Gly Trp
1               5                   10                  15

His Asp Leu Asp Cys Arg Cys Gly Asn Trp Gln Asp His Leu Trp Leu
                20                  25                  30

Leu Leu Ala Asp Gly Asp Ala Ala Leu Ala Ala Val Asp Ala Ile
            35                  40                  45

Glu Arg Asp Ala Met Ala Gly Asp Asp Ala Thr Thr Ala Thr Gly Arg
        50                  55                  60

Val Thr Ile Gly Asp Asp Gly Trp
65                  70

<210> SEQ ID NO 59
<211> LENGTH: 2735
<212> TYPE: DNA
<213> ORGANISM: Torque teno sus virus
<220> FEATURE:
<221> NAME/KEY: misc_feature
<222> LOCATION: (2596)..(2622)
<223> OTHER INFORMATION: n is a, c, g, or t
```

<400> SEQUENCE: 59

```
tcatgacagg gttcaccgga agggctgcaa aattacagct aaaaccacaa gtctaacaca      60
ataaaccaca aagtattaca ggaaactgca ataaatttag aaataagtta cacataacca     120
ccaaaccaca ggaaactgtg caaaaaagag gaaataaatt tcattggctg ggcctgaagt     180
cctcattaga ataataaaag aaccaatcag aagaacttcc tcttttagag tatataagta     240
agtgcgcaga cgaatggctg agtttatgcc gctggtggta gacacgaaca gagctgagtg     300
tctaaccgcc tgggcgggtg ccggagctcc tgagagcgga gtcaaggggc ctatcgggca     360
ggcggtaatc cagcggaacc gggccccccct cgatggaaga agatggctg acggtagcgt     420
actgcgcaca cggattattc tgcagctgta aagacccgaa aaacatctt gaaaatgcc      480
ttacagacgc tatcgcagac gccgaagaag accgacacgg agatggaggc accgaggtg     540
gagacgctac tttcgatatc ggtatcgacg cgctcctcgc cgccgccgca caaggtaag     600
gagacggagg aaaaaagctc cggtcataca atggttccct cctagccgga gaacctgcct     660
catagaggga ttttggccgt tgagctacgg acactggttc cgtacctgtc tcccctttag     720
gcggttaaat ggactagtat tcccgggtgg aggttgtgac tggagccagt ggagtttaca     780
aaacctttac aatgaaaaac ttaactggag aaatatatgg acagctagta atgttggaat     840
ggaattcgct agattttaa aaggaaagtt ttactttttc agacatccat ggagaaatta     900
tataataact tgggatcaag atataccatg caggccacta ccttatcaaa acctgcatcc     960
actcctaatg ctactaaaaa aacagcacaa aattgtactt tcacagcaaa actgtaaccc    1020
aaacagaaaa caaaaacctg tcacattaaa attcaaacct ccgccaaaac taacatcaca    1080
atggagacta agtagagaat tagcaaagat gccactaata agacttggag taagcttat    1140
agacctaaca gaaccatggg tagaagggtg gggaaatgca ttttattccg tgctaggata    1200
tgaagcagta aaagaccaag gacactggtc aaactggaca caaataaaat actattggat    1260
ctatgacacg ggagtaggaa atgcagtata tgttatacta ttaaaaaaag acgttactga    1320
taatccagga acatggcaa caacctttaa agcatcagga ggacagcatc cagatgcaat    1380
agatcacatt gaattgataa accaaggatg gccttactgg ttatactttt atggtaaaag    1440
tgaacaagac attaaaaaag aggcacacag cgcagaaata tcaagagaat atactagaga    1500
cccaaaatct aaaaaactaa aaataggaat agtaggatgg gcatcttcaa actcacaac    1560
aacaggcagt gatcaaaaca gtggtggatc aacatcagct atacaaggtg gatatgtagc    1620
atatgcaggt tccggggtca taggagcagg gtcaatagga aatttatatc aacaaggatg    1680
gccatctaat caaaactggc ctaatacaaa cagagacaaa acaaactttg actggggaat    1740
acgaggacta tgtatactca gagataacat gcacttagga agccaagaat tagatgatga    1800
atgcacaatg ctcacattgt tcggaccctt tgtagaaaaa gcaaatccaa tatttgcaac    1860
aacagaccct aaattcttta aacctgaact caaagactat aatataatca tgaaatatgc    1920
ctttaaattt cagtggggag gacatggcac agaaagattt aaaaccaaca tcggagaccc    1980
cagcaccata ccctgcccct tcgaacccgg ggaccgcttc cacagcggga tacaagaccc    2040
ctccaaggta caaacaccg tcctcaaccc ctggactat gactgtgatg ggattgttag    2100
aaaagatact ctcaaaagac ttctcgaact ccccacagag acagaggagg aggagaaggc    2160
gtacccactc cttggacaaa aaacagagaa gagccattta tcagactccg acgaagagag    2220
cgttatctca agcacgagca gtggatcctc tcaagaagaa gaaacgcaga gacgaagaca    2280
```

```
ccacaagcca agcaagcgac gactcctcaa gcacctccag cgggtggtaa agaggatgaa    2340
aacactgtga tagataaata tagaaaccta gcagacccct cactcaatgt cacaggacac    2400
atggaaaaat tcatgcagtt acatattcaa aacgtacaag aaataagagc taaaaatgct    2460
aaaaaatccc tcaataaact ttactttttct gattaatagc ggcctcctgt gtccaaccta    2520
```
```
ttttcctaa accccttcaa aatggcgggc gggacacaaa atggcggagg gactaagggg    2580
ggggcaagcc ccctnnnnn nnnnnnnnnn nnnnnnnnnn nngggggggcg accccccgc     2640 accccccct gcggggctc cgcccctgc accccggga gggggggaaa cccccctca         2700 accccccgcg ggggcaagc ccccctgcac ccccc                                2735
```

<210> SEQ ID NO 60
<211> LENGTH: 624
<212> TYPE: PRT
<213> ORGANISM: Torque teno sus virus

<400> SEQUENCE: 60

```
Met Pro Tyr Arg Arg Tyr Arg Arg Arg Arg Pro Thr Arg Arg
1               5                   10                  15

Trp Arg His Arg Arg Trp Arg Arg Tyr Phe Arg Tyr Tyr Arg Arg
            20                  25                  30

Ala Pro Arg Arg Arg Arg Thr Lys Val Arg Arg Arg Lys Lys Ala
        35                  40                  45

Pro Val Ile Gln Trp Phe Pro Pro Ser Arg Arg Thr Cys Leu Ile Glu
    50                  55                  60

Gly Phe Trp Pro Leu Ser Tyr Gly His Trp Phe Arg Thr Cys Leu Pro
65                  70                  75                  80

Phe Arg Arg Leu Asn Gly Leu Val Phe Pro Gly Gly Cys Asp Trp
                85                  90                  95

Ser Gln Trp Ser Leu Gln Asn Leu Tyr Asn Glu Lys Leu Asn Trp Arg
            100                 105                 110

Asn Ile Trp Thr Ala Ser Asn Val Gly Met Glu Phe Ala Arg Phe Leu
            115                 120                 125

Lys Gly Lys Phe Tyr Phe Phe Arg His Pro Trp Arg Asn Tyr Ile Ile
    130                 135                 140

Thr Trp Asp Gln Asp Ile Pro Cys Arg Pro Leu Pro Tyr Gln Asn Leu
145                 150                 155                 160

His Pro Leu Leu Met Leu Leu Lys Lys Gln His Lys Ile Val Leu Ser
                165                 170                 175

Gln Gln Asn Cys Asn Pro Asn Arg Lys Gln Lys Pro Val Thr Leu Lys
            180                 185                 190

Phe Lys Pro Pro Pro Lys Leu Thr Ser Gln Trp Arg Leu Ser Arg Glu
            195                 200                 205

Leu Ala Lys Met Pro Leu Ile Arg Leu Gly Val Ser Phe Ile Asp Leu
    210                 215                 220

Thr Glu Pro Trp Val Glu Gly Trp Gly Asn Ala Phe Tyr Ser Val Leu
225                 230                 235                 240

Gly Tyr Glu Ala Val Lys Asp Gln Gly His Trp Ser Asn Trp Thr Gln
                245                 250                 255

Ile Lys Tyr Tyr Trp Ile Tyr Asp Thr Gly Val Gly Asn Ala Val Tyr
            260                 265                 270

Val Ile Leu Leu Lys Lys Asp Val Thr Asp Asn Pro Gly Asn Met Ala
    275                 280                 285

Thr Thr Phe Lys Ala Ser Gly Gly Gln His Pro Asp Ala Ile Asp His
```

```
    290                 295                 300

Ile Glu Leu Ile Asn Gln Gly Trp Pro Tyr Trp Leu Tyr Phe Tyr Gly
305                 310                 315                 320

Lys Ser Glu Gln Asp Ile Lys Lys Glu Ala His Ser Ala Glu Ile Ser
                325                 330                 335

Arg Glu Tyr Thr Arg Asp Pro Lys Ser Lys Lys Leu Lys Ile Gly Ile
            340                 345                 350

Val Gly Trp Ala Ser Ser Asn Tyr Thr Thr Thr Gly Ser Asp Gln Asn
        355                 360                 365

Ser Gly Gly Ser Thr Ser Ala Ile Gln Gly Gly Tyr Val Ala Tyr Ala
    370                 375                 380

Gly Ser Gly Val Ile Gly Ala Gly Ser Ile Gly Asn Leu Tyr Gln Gln
385                 390                 395                 400

Gly Trp Pro Ser Asn Gln Asn Trp Pro Asn Thr Asn Arg Asp Lys Thr
                405                 410                 415

Asn Phe Asp Trp Gly Ile Arg Gly Leu Cys Ile Leu Arg Asp Asn Met
            420                 425                 430

His Leu Gly Ser Gln Glu Leu Asp Asp Glu Cys Thr Met Leu Thr Leu
        435                 440                 445

Phe Gly Pro Phe Val Glu Lys Ala Asn Pro Ile Phe Ala Thr Thr Asp
    450                 455                 460

Pro Lys Phe Phe Lys Pro Glu Leu Lys Asp Tyr Asn Ile Ile Met Lys
465                 470                 475                 480

Tyr Ala Phe Lys Phe Gln Trp Gly Gly His Gly Thr Glu Arg Phe Lys
                485                 490                 495

Thr Asn Ile Gly Asp Pro Ser Thr Ile Pro Cys Pro Phe Glu Pro Gly
            500                 505                 510

Asp Arg Phe His Ser Gly Ile Gln Asp Pro Ser Lys Val Gln Asn Thr
        515                 520                 525

Val Leu Asn Pro Trp Asp Tyr Asp Cys Asp Gly Ile Val Arg Lys Asp
    530                 535                 540

Thr Leu Lys Arg Leu Leu Glu Leu Pro Thr Glu Thr Glu Glu Glu Glu
545                 550                 555                 560

Lys Ala Tyr Pro Leu Leu Gly Gln Lys Thr Glu Lys Glu Pro Leu Ser
                565                 570                 575

Asp Ser Asp Glu Glu Ser Val Ile Ser Ser Thr Ser Ser Gly Ser Ser
            580                 585                 590

Gln Glu Glu Glu Thr Gln Arg Arg Arg His His Lys Pro Ser Lys Arg
        595                 600                 605

Arg Leu Leu Lys His Leu Gln Arg Val Val Lys Arg Met Lys Thr Leu
    610                 615                 620

<210> SEQ ID NO 61
<211> LENGTH: 68
<212> TYPE: PRT
<213> ORGANISM: Torque teno sus virus

<400> SEQUENCE: 61

Met Glu Glu Arg Trp Leu Thr Val Ala Tyr Cys Ala His Gly Leu Phe
1               5                   10                  15

Cys Ser Cys Lys Asp Pro Lys Lys His Leu Glu Lys Cys Leu Thr Asp
            20                  25                  30

Ala Ile Ala Asp Ala Glu Glu Asp Arg His Gly Asp Gly Gly Thr Gly
        35                  40                  45
```

```
Gly Gly Asp Ala Thr Phe Asp Ile Gly Ile Asp Ala Leu Leu Ala Ala
            50                  55                  60

Ala Ala Gln Arg
 65

<210> SEQ ID NO 62
<211> LENGTH: 625
<212> TYPE: PRT
<213> ORGANISM: Torque teno sus virus

<400> SEQUENCE: 62

Met Pro Tyr Arg Arg Tyr Arg Arg Arg Arg Pro Thr Arg Arg
 1               5                  10                  15

Trp Arg His Arg Arg Trp Arg Arg Tyr Phe Arg Tyr Arg Tyr Arg Arg
                20                  25                  30

Ala Pro Arg Arg Arg Arg Ala Lys Val Arg Arg Arg Arg Lys Ala
                35                  40                  45

Pro Val Ile Gln Trp Asn Pro Pro Ser Arg Arg Thr Cys Leu Ile Glu
            50                  55                  60

Gly Phe Trp Pro Leu Ser Tyr Gly His Trp Phe Arg Thr Cys Leu Pro
 65                  70                  75                  80

Met Arg Arg Leu Asn Gly Leu Ile Phe Thr Gly Gly Cys Asp Trp
                85                  90                  95

Thr Gln Trp Ser Leu Gln Asn Leu Phe His Glu Lys Leu Asn Trp Arg
                100                 105                 110

Asn Ile Trp Thr Ala Ser Asn Val Gly Met Glu Phe Ala Arg Phe Leu
                115                 120                 125

Arg Gly Lys Phe Tyr Phe Phe Arg His Pro Trp Arg Ser Tyr Ile Val
            130                 135                 140

Thr Trp Asp Gln Asp Ile Pro Cys Lys Pro Leu Pro Tyr Gln Asn Leu
145                 150                 155                 160

Gln Pro Leu Leu Met Leu Leu Lys Lys Gln His Lys Leu Val Leu Ser
                165                 170                 175

Gln Lys Asp Cys Asn Pro Ser Arg Lys Gln Lys Pro Val Thr Leu Lys
                180                 185                 190

Phe Arg Pro Pro Lys Leu Thr Ser Gln Trp Arg Leu Ser Arg Glu
            195                 200                 205

Leu Ser Lys Ile Pro Leu Ile Arg Leu Gly Ile Ser Leu Ile Asp Leu
            210                 215                 220

Ser Glu Pro Trp Leu Glu Gly Trp Gly Asn Ala Phe Tyr Ser Val Leu
225                 230                 235                 240

Gly Tyr Glu Ala Ser Lys His Ser Gly Arg Trp Ser Asn Trp Thr Gln
                245                 250                 255

Met Lys Tyr Phe Trp Ile Tyr Asp Thr Gly Val Gly Asn Ala Val Tyr
            260                 265                 270

Val Ile Leu Leu Lys Lys Asp Val Asp Asp Asn Pro Gly Asp Met Ala
            275                 280                 285

Thr Lys Phe Val Thr Gly Gln Gly Gln His Pro Asp Ala Ile Asp His
            290                 295                 300

Ile Glu Met Val Asn Glu Gly Trp Pro Tyr Trp Leu Phe Phe Tyr Gly
305                 310                 315                 320

Gln Ser Glu Gln Asp Ile Lys Lys Leu Ala His Asp Gln Asp Ile Ala
                325                 330                 335

Arg Glu Tyr Ala Arg Asp Pro Lys Ser Lys Lys Leu Lys Ile Gly Val
            340                 345                 350
```

-continued

```
Ile Gly Trp Ala Ser Ser Asn Tyr Thr Thr Ala Gly Ser Asn Gln Asn
        355                 360                 365
Thr Thr Ala Gln Thr Pro Glu Ala Ile Gln Gly Gly Tyr Val Ala Tyr
    370                 375                 380
Ala Gly Ser Arg Ile Pro Gly Ala Gly Ser Ile Thr Asn Leu Phe Gln
385                 390                 395                 400
Met Gly Trp Pro Gly Asp Gln Asn Trp Pro Pro Thr Asn Gln Glu Gln
                405                 410                 415
Thr Asn Phe Asn Trp Gly Leu Arg Gly Leu Cys Val Leu Arg Asp Asn
        420                 425                 430
Met Lys Leu Gly Ala Gln Glu Leu Asp Asp Glu Cys Thr Met Leu Ser
    435                 440                 445
Leu Phe Gly Pro Phe Val Glu Lys Ala Asn Thr Ala Phe Ala Thr Asn
450                 455                 460
Asp Pro Lys Tyr Phe Arg Pro Glu Leu Lys Asp Tyr Asn Val Val Met
465                 470                 475                 480
Lys Tyr Ala Phe Lys Phe Gln Trp Gly Gly His Gly Thr Glu Arg Phe
                485                 490                 495
Lys Thr Thr Ile Gly Asp Pro Ser Thr Ile Pro Cys Pro Phe Glu Pro
        500                 505                 510
Gly Glu Arg Tyr His His Gly Val Gln Asp Pro Ala Lys Val Gln Asn
    515                 520                 525
Thr Val Leu Asn Pro Trp Asp Tyr Asp Cys Asp Gly Ile Val Arg Thr
530                 535                 540
Asp Thr Leu Lys Arg Leu Glu Leu Pro Thr Glu Thr Glu Glu Thr
545                 550                 555                 560
Glu Lys Ala Tyr Pro Leu Leu Gly Gln Lys Thr Glu Lys Glu Pro Leu
                565                 570                 575
Ser Asp Ser Asp Glu Glu Ser Val Ile Ser Ser Thr Ser Ser Gly Ser
        580                 585                 590
Ser Gln Glu Glu Glu Thr Gln Arg Arg Gln His Lys Pro Ser Lys
    595                 600                 605
Arg Arg Leu Leu Lys His Leu Gln Arg Val Val Lys Arg Met Lys Thr
    610                 615                 620
Leu
625

<210> SEQ ID NO 63
<211> LENGTH: 10
<212> TYPE: DNA
<213> ORGANISM: Artificial Sequence
<220> FEATURE:
<223> OTHER INFORMATION: Synthetically synthesized sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 63 nngttaacnn                                                          10

<210> SEQ ID NO 64
<211> LENGTH: 10
<212> TYPE: DNA
```

```
<213> ORGANISM: artificial sequence
<220> FEATURE:
<223> OTHER INFORMATION: PST1site
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 64 nnctgcagnn                                                            10

<210> SEQ ID NO 65
<211> LENGTH: 10
<212> TYPE: DNA
<213> ORGANISM: Artificial Sequence
<220> FEATURE:
<223> OTHER INFORMATION: MfeIsite
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 65 nncaattgnn                                                            10

<210> SEQ ID NO 66
<211> LENGTH: 28
<212> TYPE: DNA
<213> ORGANISM: Torque teno sus virus

<400> SEQUENCE: 66
gaagaaagat ggctgacggt agcgtact                                        28

<210> SEQ ID NO 67
<211> LENGTH: 25
<212> TYPE: DNA
<213> ORGANISM: Torque teno sus virus

<400> SEQUENCE: 67
tgacacagga cgtaggaaat gcagt                                           25

<210> SEQ ID NO 68
<211> LENGTH: 26
<212> TYPE: DNA
<213> ORGANISM: Torque teno sus virus

<400> SEQUENCE: 68
tgaagtattt agggtcattt gtagca                                          26
```

INFECTIOUS GENOMIC DNA CLONE AND SEROLOGICAL PROFILE OF TORQUE TENO SUS VIRUS 1 AND 2

REFERENCE TO RELATED APPLICATION

This application is a divisional of U.S. patent application Ser. No. 13/840,805, filed Mar. 15, 2013, which is a continuation-in-part of U.S. patent application Ser. No. 12/861,378, which claims the benefit of U.S. Provisional Patent Application No. 61/235,833, filed on Aug. 21, 2009, and U.S. Provisional Patent Application 61/316,519, filed on Mar. 23, 2010. The disclosures of the above mentioned priority applications are hereby incorporated by reference in their entirety into the present disclosure.

FIELD OF INVENTION

The present invention relates to infectious DNA clones of Torque teno sus virus (TTsuV), also known as porcine Torque teno virus (PTTV), and diagnosis of Torque teno sus virus (TTsuV) infection, particularly diagnosis of species- or type-specific TTsuV infection, and simultaneous infection of multiple strains from different genotypes.

BACKGROUND OF THE INVENTION

Anelloviruses are small, single-stranded, circular DNA viruses that infect a wide range of animal species from humans to domestic animals including pigs (Hino, S., and H. Miyata. 2007. Torque teno virus (TTV): current status. Rev Med Virol 17:45-57; Okamoto, H. 2009. TT viruses in animals. Curr Top Microbiol Immunol 331:35-52). Most recently, all human and other animal anelloviruses have been assigned into a newly established family Anelloviridae that includes nine genera (Biagini, P., et al. 2011. Anelloviridae, p. 331-341. In A. M. Q. King, et al (ed.), Virus Taxonomy, 9th Report of the ICTV. Elsevier Academic Press, London). Human anelloviruses include Torque teno virus (TTV), Torque teno mini virus (TTMV) and Torque teno midi virus (TTMDV) that belong to three different genera. Human TTV, TTMV and TTMDV are non-enveloped spherical viruses with DNA genomes of 3.6-3.9, 2.8-2.9 and 3.2 kb in length, respectively (Okamoto, H. 2009. History of discoveries and pathogenicity of TT viruses. Curr Top Microbiol Immunol 331:1-20.). These three groups of human anelloviruses show a high degree of genetic diversity, and infections of TTV, TTMV and TTMDV at a high prevalence in human populations have been documented worldwide (Ninomiya, M., et al. 2008. Development of PCR assays with nested primers specific for differential detection of three human anelloviruses and early acquisition of dual or triple infection during infancy. J Clin Microbiol 46:507-14.; Okamoto, H. 2009. Curr Top Microbiol Immunol 331:1-20). On the other hand, porcine anelloviruses or Torque teno sus viruses (TTSuV) is assigned into a new genus *Iotatorquevirus* comprising two species (TTSuV1 and TTSuV2), each also characterized by high genetic diversity with a genomic size of approximately 2.8 kb (Huang, Y. W., et al. 2010. Multiple infection of porcine Torque teno virus in a single pig and characterization of the full-length genomic sequences of four U.S. prototype PTTV strains: implication for genotyping of PTTV. Virology 396:287-97, Niel, C., et al. 2005. Rolling-circle amplification of Torque teno virus (TTV) complete genomes from human and swine sera and identification of a novel swine TTV genogroup. J Gen Virol 86:1343-7). TTSuV1 and TTSuV2 are highly prevalent in pig populations in many countries (Gallei, A., et al. 2010. Porcine Torque teno virus: determination of viral genomic loads by genogroup-specific multiplex rt-PCR, detection of frequent multiple infections with genogroups 1 or 2, and establishment of viral full-length sequences. Vet Microbiol 143:202-12; Kekarainen, T., et al. 2006. Prevalence of swine Torque teno virus in post-weaning multisystemic wasting syndrome (PMWS)-affected and non-PMWS-affected pigs in Spain. J Gen Virol 87:833-7; McKeown, N. E., et al. 2004. Molecular characterization of porcine TT virus, an orphan virus, in pigs from six different countries. Vet Microbiol 104:113-7).

Human and porcine anelloviruses share the same genomic structure, which consists of at least four presumed open reading frames (ORFs), ORF1, ORF2, ORF1/1 and ORF2/2, as well as a short stretch of high GC content in the untranslated region (UTR) (Huang, Y. W., et al. 2010. Virology 396:287-97; Okamoto, H., et al. 2002. Genomic characterization of TT viruses (TTVs) in pigs, cats and dogs and their relatedness with species-specific TTVs in primates and tupaias. J Gen Virol 83:1291-7; Qiu, J., et al. 2005. Human circovirus TT virus genotype 6 expresses six proteins following transfection of a full-length clone, J Virol 79:6505-10). The transcription pattern and related translational products of human TTV genogroup 1 have been experimentally determined by using two full-length TTV DNA clones (Mueller, B., et al. 2008. Gene expression of the human Torque Teno Virus isolate P/1C1. Virology 381:36-45; Qiu, J., et al. 2005. J Virol 79:6505-10). It was shown that the human TTV genome expresses three or more spliced mRNAs encoding at least six proteins, ORF1, ORF2, ORF1/1, ORF2/2, ORF1/2 and ORF2/3 (Mueller, B., et al. 2008. Virology 381:36-45). The transcriptional analysis and protein expression profile using cloned full-length genomic DNA have not been reported for TTSuV.

The ORF1 of TTSuV is believed to encode a viral capsid and replication-associated protein (Huang, Y. W., et al. 2010. Virology 396:287-97; Okamoto, H., et al. 2002. J Gen Virol 83:1291-7). IgG antibodies against the ORF1 of TTV and TTSuV have been detected in human and pig sera, respectively (Huang, Y. W., et al. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88; Kakkola, L., et al. 2008. Expression of all six human Torque teno virus (TTV) proteins in bacteria and in insect cells, and analysis of their IgG responses. Virology 382:182-9; Ott, C., et al. 2000. Use of a TT virus ORF1 recombinant protein to detect anti-TT virus antibodies in human sera. J Gen Virol 81:2949-58).

The pathogenic potential of anellovirus is still controversial. Currently, human TTV is not considered to be directly associated with a particular disease, although recent studies suggested TTV may serve as an immunological trigger of multiple sclerosis (Maggi, F., and M. Bendinelli. 2010. Human anelloviruses and the central nervous system. Rev Med Virol 20:392-407). Similarly, whether TTSuV is associated with a swine disease is still debatable. TTSuV1 was shown to partially contribute to the experimental induction of porcine dermatitis and nephropathy syndrome (PDNS) and postweaning multisystemic wasting syndrome (PMWS or porcine circovirus associated disease, PCVAD) in a gnotobiotic pig model (Ellis, J. A., et al. 2008. Effect of coinfection with genogroup 1 porcine torque teno virus on porcine circovirus type 2-associated postweaning multisystemic wasting syndrome in gnotobiotic pigs. Am J Vet Res 69:1608-14; Krakowka, S., et al. 2008. Evaluation of induction of porcine dermatitis and nephropathy syndrome in gnotobiotic pigs with negative results for porcine circovirus type 2. Am J Vet Res 69:1615-22). PMWS-affected pigs in Spain had a higher prevalence and viral loads of TTSuV2 than the PMWS-unaffected pigs (Aramouni, M., et al. 2011. Torque teno sus virus 1 and 2 viral loads in postweaning multisystemic wasting syndrome (PMWS) and porcine dermatitis and nephropathy syndrome (PDNS) affected pigs. Vet Microbiol 153:377-81; Kekarainen, T., et al. 2006. J Gen Virol 87:833-7). Moreover, a significantly lower level of anti-TTSuV2 antibody was found in PCVAD-affected pigs than in PCVAD-unaffected pigs (Huang, Y. W., et al. 2011. Virus Res 158:79-88). However, results from other studies did not support a direct association of TTSuV1 or TTSuV2 with PCVAD or association of type 2 porcine circovirus (PCV2) and TTSuV with porcine reproductive failures (Gauger, P. C., et al. 2011. Postweaning multisystemic wasting syndrome produced in gnotobiotic pigs following exposure to various amounts of porcine circovirus type 2a or type 2b. Vet Microbiol 153:229-39; Huang, Y. W., et al. 2012. Serological profile of Torque teno sus virus species 1 (TTSuV1) in pigs and antigenic relationships between two TTSuV1 genotypes (1a and 1b), between two species (TTSuV1 and 2), and between porcine and human anelloviruses. J. Virol. Submitted Manuscript; Lee, S. S., et al. 2010. Quantitative detection of porcine Torque teno virus in Porcine circovirus-2-negative and Porcine circovirus-associated disease-affected pigs. J Vet Diagn Invest 22:261-4; Ritterbusch, G. A., et al. 2011. Natural co-infection of torque teno virus and porcine circovirus 2 in the reproductive apparatus of swine. Res Vet Sci. doi:10.1016/j.rvsc.2011.04.001).

Due to the lack of a cell culture system to propagate anelloviruses, little is known regarding the molecular biology and pathogenesis of anelloviruses. In order to definitively characterize diseases associated with anellovirus infection, an appropriate animal model is needed. Since multiple infections of different genotypes or subtypes of human TTV or TTSuV are common events (Gallei, A., et al. 2010. Vet Microbiol 143:202-12; Huang, Y. W., et al. 2010. Virology 396:287-97; Ninomiya, M., et al. 2008. J Clin Microbiol 46:507-14), a biologically pure and isolated form of a specific anellovirus generated from full-length infectious DNA clone is also required for a pathological study of a single phenotype. Although infectious DNA clones of human TTV in cultured cells have been reported (de Villiers, E. M., et al. 2011. The diversity of torque teno viruses: in vitro replication leads to the formation of additional replication-competent subviral molecules. J Virol 85:7284-95; Kakkola, L., et al. 2007. Construction and biological activity of a full-length molecular clone of human Torque teno virus (TTN) genotype. FEBS J 274:4719-30; Leppik, L., et al. 2007. In vivo and in vitro intragenomic rearrangement of TT viruses. J Virol 81:9346-56), it is important to construct an infectious TTSuV DNA clone so that TTSuV can be used as a useful model to study the replication and transcription mechanisms and to dissect the structural and functional relationships of anellovirus genes. More importantly, the availability of a TTSuV infectious DNA clone will afford us an opportunity to use the pig as a model system to study the replication and pathogenesis of TTSuV or even human TTV.

Multiple infections of human TTV with different genotypes in a single human individual or TTSuV with different genotypes or subtypes in a single pig have been documented (Ball, J. K., et al. 1999. TT virus sequence heterogeneity in vivo: evidence for co-infection with multiple genetic types. J Gen Virol 80 (Pt 7): 1759-68; Forns, X., et al. 1999. High prevalence of TT virus (TTV) infection in patients on maintenance hemodialysis: frequent mixed infections with different genotypes and lack of evidence of associated liver disease. J Med Virol 59:313-7; Gallei, A., et al. 2010. Vet Microbiol 143:202-12; Huang, Y. W., et al. 2010. Virology 396:289-97; Jelcic, I., et al. 2004. Isolation of multiple TT virus genotypes from spleen biopsy tissue from a Hodgkin's disease patient: genome reorganization and diversity in the hypervariable region. J Virol 78:7498-507; Niel, C., et al. 2000. Coinfection with multiple TT virus strains belonging to different genotypes is a common event in healthy Brazilian adults. J Clin Microbiol 38:1926-30; Ninomiya, M., et al. 2008. J Clin Microbiol 46:507-14). These findings raise the question whether the anti-ORF1 capsid antibodies recognized by the antigen from a particular TTV or TTSuV species/geno types also comprise anti-ORF1 antibodies against other distinct TTV or TTSuV species/genotypes and whether the anti-ORF1 antibodies from one TTV or TTSuV genotype can cross-protect against infection with another genotype. To our knowledge, for human TTV or TTSuV infection there is no information on this topic available to date. Furthermore, the antigenic diversity and relationship of anelloviruses have never been assessed (Maggi, F. and M. Bendinelli. 2009. Immunobiology of the Torque teno viruses and other anelloviruses. Curr Top Microbiol Immunol 331: 65-90). It is reasonable to speculate that there is little, if any, antigenic cross-reactivity between different anellovirus species/genotypes, due to the fact that concurrent infections with multiple anelloviruses in a single individual or animal exist.

The inventors have previously developed and validated serum Western blot (WB) and indirect ELISA assays for detection of the IgG antibody against TTSuV2 in porcine sera using the purified recombinant TTSuV2-ORF1 protein expressed in $E.\ coli$ (Huang, Y. W., et al. 2011. Virus Res 158:79-88). By using TTSuV2-specific real-time quantitative PCR (qPCR) and ELISA, The inventors further presented the combined virological and serological profile of TTSuV2 infection under natural or diseased conditions using 160 porcine sera collected from different sources (Huang, Y. W., et al. 2011. Id.). In the present invention, the inventors initially aimed to assess the serological profiles of the two TTSuV1 genotypes (TTSuV1a and TTSuV1b) in pigs, respectively. Subsequently, the inventors aimed to compare the virological and serological profiles of TTSuV1a and TTSuV1b with that of TTSuV2, and to determine the degree of correlation of IgG antibody levels between anti-TTSuV1a and -TTSuV1b and between anti-TTSuV1a or -1b and anti-TTSuV2. Finally, for the first time, the inventors assessed the antigenic relationships between two TTSuV1 genotypes (TTSuV1a and TTSuV1b), between two species (TTSuV1 and TTSuV2), and between porcine and human genogroup 1 anelloviruses using ELISA and immunofluorescence assay with antibody cross-reactions in PK-15 cells transfected with recombinant plasmids expressing the ORF1 s from TTSuV1a, TTSuV1b and TTSuV2, respectively.

SUMMARY OF THE INVENTION

The present invention provides an infectious nucleic acid molecule of porcine Torque teno virus (PTTV), also known as, and referred to herein interchangeably as, Torque teno sus virus (TTsuV) comprising a nucleic acid molecule encoding an infectious TTsuV which contains at least one copy of genomic sequence having at least 85% homology to a genomic sequence of TTsuV2.

The present invention provides an infectious nucleic acid molecule ("infectious DNA clone") of porcine Torque teno virus (PTTV) comprising a nucleic acid molecule encoding an infectious PTTV which contains at least one copy of genomic sequence having at least 80% homology to a genomic sequence selected from the group consisting of genotypes of PTTV1a-VA, PTTV1b-VA, PTTV2b-VA, and PTTV2c-VA.

According to one aspect of the present invention, the infectious DNA clones of PTTV of set forth in claim 1, wherein the genomic sequence is selected from sequences set forth in SEQ ID NO:9, SEQ ID NO:10, SEQ ID NO:11, and SEQ ID NO:12.

The present invention provides a biologically functional plasmid or viral vector containing the infectious PTTV genomes.

The present invention provides a suitable host cell transfected with the infectious clone DNA plasmid or viral vector.

The present invention provides an infectious PTTV produced by cells transfected with the PTTV infectious DNA clones.

The present invention also provides a viral vaccine comprising a nontoxic, physiologically acceptable carrier and an immunogenic amount of a member selected from the group consisting of (a) a nucleic acid molecule containing at least one copy of genomic sequence having at least 80% homology to a genomic sequence selected from the group consisting of PTTV genotypes or subtypes PTTV1a-VA, PTTV1b-VA, PTTV2b-VA, and PTTV2c-VA, or its complementary strand, (b) a biologically functional plasmid or viral vector containing a nucleic acid molecule containing at least one copy of genomic sequence having at least 80% homology to a genomic sequence selected from the group consisting of PTTV genotypes or subtypes PTTV1a-VA, PTTV1b-VA, PTTV2b-VA, and PTTV2c-VA, or its complementary strand, and (c) an avirulent, infectious nonpathogenic PTTV which contains at least one copy of genomic sequence having at least 80% homology to a genomic sequence selected from the group consisting of PTTV genotypes or subtypes PTTV1a-VA, PTTV1b-VA, PTTV2b-VA, and PTTV2c-VA.

According to one aspect of the present invention, the vaccine contains live PTTV virus derived from the PTTV infectious clones. According to another aspect of the present invention, the vaccine contains killed PTTV virus derived from the PTTV infectious clones.

The present invention provides purified recombinant proteins expressed from the ORF1 capsid genes of PTTV genotypes or subtypes PTTV1a-VA, PTTV1b-VA, and PTTV2c-VA in bacterial expression system, and the use of these recombinant capsid proteins as subunit vaccines against PTTV infections. In one embodiment of the present invention, the recombinant capsid proteins for the use as subunit vaccines are expressed in baculovirus expression system and other expression vector systems.

According to a further aspect of the present invention, further contains an adjuvant.

The present invention further provides a method of immunizing a pig against PTTV viral infection, comprising administering to a pig an immunologically effective amount of the viral vaccine.

According to one aspect of the present invention, the method comprising administering the recombinant subunit capsid protein, the infectious nucleic acid molecule or live PTTV virus to the pig.

According to another aspect of the present invention, the method comprising administering the vaccine parenterally, intranasally, intradermally, or transdermally to the pig. According a further aspect of the present invention, the method comprising administering the vaccine intralymphoidly or intramuscularly to the pig.

The present invention also provides an isolated polynucleotide consisting of the sequence of the nucleotide sequence of PTTV1a-VA set forth in SEQ ID NO:9.

The present invention also provides an isolated polynucleotide consisting of the sequence of the nucleotide sequence of PTTV1b-VA set forth in SEQ ID NO:10

The present invention also provides an isolated polynucleotide consisting of the sequence of the nucleotide sequence of PTTV2b-VA set forth in SEQ ID NO:11.

The present invention also provides an isolated polynucleotide consisting of the sequence of the nucleotide sequence of PTTV2c-VA set forth in SEQ ID NO:12.

The present invention further provides a subunit vaccine comprising an immunogentic fragment of a polypeptide sequence or a complete protein translated according to a polynucleotide sequence selected from the group consisting of ORF1, ORF2, ORF1/1, and ORF2/2 of PTTV genotypes or subtypes PTTV1a-VA, PTTV1b-VA, PTTV2b-VA, and PTTV2c-VA, particularly the ORF1 encoding the capsid protein.

According to one aspect of the present invention, the polynucleotide sequence is selected from the group consisting of ORF1 of PTTV genotypes or subtypes PTTV1a-VA, PTTV1b-VA, PTTV2b-VA, and PTTV2c-VA.

According to another aspect of the present invention, the polynucleotide sequence is ORF1 of PTTV genotype PTTV1a-VA. According to a further aspect of the present invention, the polynucleotide sequence is ORF1 of PTTV genotype PTTV1b-VA. According to yet another aspect of the present invention, the polynucleotide sequence is ORF1 of PTTV subtype PTTV2c-VA.

According to one aspect of the present invention, the polypeptide sequence is selected from the group consisting of sequence set forth in SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28.

According to another aspect of the present invention, the polypeptide sequence is set forth in SEQ ID NO:13. According to another aspect of the present invention, the polypeptide sequence is set forth in SEQ ID NO:14. According to a further aspect of the present invention, the polypeptide sequence is set forth in SEQ ID NO:16. In one specific embodiment of the present invention, the polypeptide sequence is C-terminal region (aa 310-625) of SEQ ID NO:16. According to yet another aspect of the present invention, the polypeptide sequence is set forth in SEQ ID NO:20.

According to an additional aspect of the present invention, the vaccine further contains an adjuvant.

The present invention further provides method of immunizing a pig against PTTV viral infection, comprising administering to a pig an immunologically effective amount of the vaccine comprising an immunogenic fragment of a polypeptide sequence or a complete protein translated according to a polynucleotide sequence selected from the group consisting of ORF1, ORF2, ORF1/1, and ORF2/2 of PTTV genotypes or subtypes PTTV1a-VA, PTTV1b-VA, PTTV2b-VA, and PTTV2c-VA.

According to one aspect of the present invention, the method comprises administering the immunogenic fragment or recombinant capsid protein to the pig.

According to another aspect of the present invention, the method comprises administering the vaccine parenterally, intranasally, intradermally, or transdermally to the pig. According to a further aspect of the present invention, the method comprises administering the vaccine intralymphoidly or intramuscularly to the pig.

The present invention additionally provides a method for diagnosing PTTV1 infection and quantification of PTTV1 load, comprising extracting DNA from a sample suspected of PTTV1 infection, performing polymerase chain reaction (PCR) using primers comprising the sequences set forth in SEQ ID NO:29 and SEQ ID NO:30, and detecting PTTV1 specific amplification. According to one aspect of the present invention, the polymerase chain reaction is a SYBR green real-time PCR.

The present invention further provides a method for diagnosing PTTV2 infection and quantification of PTTV2 load, comprising extracting DNA from a sample suspected of PTTV2 infection, performing polymerase chain reaction (PCR) using primers comprising the sequences set forth in SEQ ID NO:29, SEQ ID NO:30, SEQ ID NO:31 and SEQ ID NO:32, and detecting PTTV2 specific amplification. According to one aspect of the present invention, the polymerase chain reaction is a SYBR green real-time PCR.

The present invention also provides a method for simultaneously detecting and diagnosing PTTV1 and PTTV2 infection, comprising extracting DNA from a sample suspected of PTTV infection, performing polymerase chain reaction (PCR) using primers comprising the sequences set forth in SEQ ID NO:31 and SEQ ID NO:32, and detecting PTTV1 and PTTV2 specific amplification. According to one aspect of the present invention, the polymerase chain reaction is a SYBR green real-time PCR.

The present invention, in addition, provides a method for simultaneously detecting and diagnosing PTTV1a and PTTV1b infection, comprising extracting DNA from a sample suspected of PTTV1 infection, performing a first polymerase chain reaction (PCR) using primers comprising the sequences set forth in SEQ ID NO:33 and SEQ ID NO:34, performing a second PCR using primers comprising the sequences set forth in SEQ ID NO:35, SEQ ID NO:36, SEQ ID NO:37, and SEQ ID NO:38, and detecting PTTV1a and PTTV1b specific amplification.

The present invention provides a method for diagnosing PTTV infection, comprising immobilizing an immunogenic fragment of a polypeptide sequence translated according to a polynucleotide sequence selected from the group consisting of ORF1, ORF2, ORF1/1, and ORF2/2 of PTTV genotypes or subtypes PTTV1a-VA, PTTV1b-VA, PTTV2b-VA, and PTTV2c-VA; contacting a serum sample from a pig suspected of PTTV infection with the immobilized immunogenic fragment, and detecting captured antibody specific to the immunogenic fragment.

According to one aspect of the present invention, the polynucleotide sequence is selected from the group consisting of ORF1 of PTTV genotypes or subtypes PTTV1a-VA, PTTV2b-VA, and PTTV2c-VA.

According to one embodiment of the present invention, the polynucleotide sequence is ORF1 of PTTV genotype PTTV1a-VA. According to another aspect of the present invention, the polynucleotide sequence is ORF1 of PTTV genotype PTTV1b-VA. According to a further embodiment of the present invention, the polynucleotide sequence is ORF1 of PTTV subtype PTTV2c-VA According to another aspect of the present invention, the polypeptide sequence is selected from the group consisting of sequence set forth in SEQ ID NO:13, SEQ ID NO:14, SEQ ID NO:15, SEQ ID NO:16, SEQ ID NO:17, SEQ ID NO:18, SEQ ID NO:19, SEQ ID No:20, SEQ ID No:21, SEQ ID NO:22, SEQ ID NO:23, SEQ ID NO:24, SEQ ID NO:25, SEQ ID NO:26, SEQ ID NO:27, and SEQ ID NO:28.

According to one embodiment of the present invention, the polypeptide sequence is set forth in SEQ ID NO:13. According to another aspect of the present invention, the polypeptide sequence is set forth in SEQ ID NO:14. According to another embodiment of the present invention, the polypeptide sequence is set forth in SEQ ID NO:16. According to a further embodiment of the present invention, the immunogenic fragment is C-terminal region (aa 310-625) of SEQ ID NO:16. According to yet another embodiment of the present invention, the polypeptide sequence is set forth in SEQ ID NO:20.

The present invention provides three standardized enzyme-linked immunosorbent assays (ELISA) to diagnose PTTV infections and detect antibodies in serum of pigs infected by PTTV genotypes PTTV1a-VA, PTTV1b-VA, and all known subtypes in PTTV species 2.

The ELISA diagnostic tests are based on the bacterial-expressed or baculovirus-expressed recombinant ORF1 capsid protein of PTTV genotypes PTTV1a-VA, PTTV1b-VA, and PTTV2c-VA.

According to another aspect of the present invention, the detecting captured antibody is via Western blot. According to yet another aspect of the present invention, the detecting captured antibody is via enzyme-linked immunosorbent assay (ELISA).

According to one embodiment, the at least one copy of genomic sequence has at least 95% homology to the genomic sequence of TTsuV2.

According to another embodiment, the genomic sequence of TTsuV2 is a genomic clone of PTTV2c-VA. In one specific example, the genomic sequence is selected from sequences set forth in SEQ ID NO: 12.

According to a further embodiment, the genomic sequence of TTsuV2 is of genomic clone of TTV2-#471942. In a specific example, the genomic sequence is selected from sequences set forth in SEQ ID NO: 62.

According to an additional embodiment, the genomic sequence of TTsuV2 comprising at least one genetic marker in intron 1. In a specific example, the genetic marker in intron 1 is an artificially introduced restriction site.

The present invention provides a biologically functional plasmid or viral vector containing an infectious nucleic acid molecule of Torque teno sus virus (TTsuV) comprising a nucleic acid molecule encoding an infectious TTsuV which contains at least one copy of genomic sequence having at least 85% homology to a genomic sequence of TTsuV2.

According to one embodiment, the biologically functional plasmid or viral vector contains more than one copy of the infectious nucleic acid molecule.

According to one embodiment, the biologically functional plasmid or viral vector contains tandem copies of genomic clone of PTTV2c-VA.

The present invention provides an infectious TTsuV produced by cells containing the infectious nucleic acid sequence of TTsuV2 is of genomic clone of PTTV2c-VA.

The present invention provides a method for diagnosing TTsuV infection, comprising immobilizing an immunogentic fragment or a complete protein of a polypeptide sequence of ORF1 protein of TTsuV 1 or 2, contacting a serum sample from a pig suspected of TTsuV infection with the immobilized immunogenic fragment or complete protein, and detecting captured antibody specific to the immunogenic fragment.

According to one embodiment, the polypeptide sequence is selected from the group consisting of ORF1 proteins of TTsuV genotypes or subtypes TTsuV1a \or TTsuV1b.

According to another embodiment, the polypeptide sequence is selected from the group consisting of N-terminal truncated ORF1 proteins of TTsuV genotypes or subtypes TTsuV1a, TTsuV1b or TTsuV2. In a specific example, the polypeptide sequence is amino acid No. 317-635 of ORF1 protein of TTsuV1a. In another example, the polypeptide sequence is amino acid No. 322-639 of ORF1 protein of TTsuV1b.

BRIEF DESCRIPTION OF THE DRAWINGS

The above-mentioned features of the invention will become more clearly understood from the following detailed description of the invention read together with the drawings in which:

FIG. 1(A) pSC-PTTV2c (from the U.S. TTSuV2 isolate PTTV2c-VA; GenBank accession no. GU456386). FIG. 1(B) pSC-2PTTV2c-RR (tandem-dimerized PTTV2C-VA genomes). FIG. 1(C) pSC-TTV2-#471942 (from the German TTSuV2 isolate TTV2-#471942; GenBank accession no. GUI 88046). FIG. 1(D) pSC-2PTTV2b-RR (tandem-dimerized TTV2-#471942 genomes). FIG. 1(E) pSC-TTV2-EU (derived from pSC-TTV2-#471942). A HpaI site as the silent genetic marker was introduced in this clone. FIG. 1(F) pSC-TTV2-US (derived from pSC-PTTV2c). PstI and MfeI sites as the silent genetic markers were introduced in this clone. FIG. 1(G) pSC-TTV2-AAA. A 104-bp deletion mutation was introduced between the AccI and ApaI sites ranging from the putative TATA box to the ORF1 start codon on the clone pSC-TTV2-US. The restriction enzymes (BamHI or EcoRV) used for plasmids constructions are shown. The plasmid backbone used for cloning was the pSC-B-amp/kan vector (indicated by black). Grey arrows indicate the TTsuV2 genomic copies.

FIG. 2(E) Detection of specific TTsuV1 or TTsuV2 qPCR products (marked by black arrowheads) by agarose gel electrophoresis.

FIG. 3(A) Comparisons of the HindIII single-digestion patterns between clones pSC-TTV2-#471942 and pSC-2PTTV2b-RR (left panel) and AflII single-digestion patterns between clones pSC-PTTV2c and pSC-2PTTV2c-RR (right panel) by agarose gel electrophoresis. M: DNA markers. The results were consistent to the predicted patterns of the digested fragments (shown by black arrowheads). The 2.8-Kb fragments indicate the intact single TTsuV2 genomic DNA from the clone pSC-2PTTV2b-RR or pSC-2PTTV2c-RR. FIG. 3(B) Quality assessment of concatemerized ligation products of the BamH1-digested and purified PTTV2c genomic DNA. The samples were electrophoresed in a 1% agarose gel before (linear DNA) and after (ligation mixture) T4 DNA ligase treatment. Linear DNA (~2.8 Kb) and formations of the putative one-copy (monomer), two-copy (dimer) and high-copy-number circular DNA are indicated by arrowheads.

FIG. 4(A)-FIG. 4(E) illustrate Immunofluorescence assay (IFA) results on PCV1-free PK-15 cells transfected with the ligation mixtures of linear TTSuV2 genomic DNA derived from clones pSC-PTTV2c FIG. 4(A) or pSC-TTV2-#471942 FIG. 4(C), with plasmids pSC-2PTTV2c-RR FIG. 4(B) or pSC-2PTTV2b-RR FIG. 4(D), or with Lipofectamine LTX only FIG. 4(E). Cells were stained with a rabbit anti-TTSuV2 ORF1 polyclonal antibody (Ab) and a Texas Red-conjugated goat anti-rabbit IgG (red) at 5 days post-transfection (the left panels), DAPI (blue) was used to stain the cell nucleus (the middle panels). The Ab and DAPI stainings are merged (right panels). Magnification=200×.

FIG. 5(A) Schematic diagram of three putative viral mRNAs and six viral proteins. The TATA box, splicing sites (SD: splicing donor; SA: splicing acceptor) and the positions of primers TTV2-448F (SEQ ID NO:66) and TTV2-2316R (SEQ ID NO:6) were indicated at the top. The three open reading frames (ORFs) are depicted by colored boxes. The sizes of the six ORFs and two introns are also shown. FIG. 5(B) Sequencing of the RT-PCR products amplified by primers TTV2-448F and TTV2-2316R verified the splicing of the putative intron 1. FIG. 5(C) Sequencing of the RT-PCR products amplified by primers TTV2-448F and TTV2-2316R identified an additional intron (intron 2). Arrows and numbers indicate the joint site of the exons.

FIG. 8(A)-FIG. 8(C) illustrate expression and purification of the amino-terminally truncated TTSuV1a and TTSuV1b ORF1 proteins, respectively. FIG. 8(A) SDS-PAGE analysis of unpurified and purified TTSuV1a-ORF1 products. FIG. 8(B) SDS-PAGE analysis of unpurified and purified TTSuV1b-ORF1 products. An amino- and carboxyl-terminally double-truncated TTSuV1b-ORF1 (1b-ctruc) of smaller product size served as the control. FIG. 8(C) Near-infrared fluorescent WB analysis of purified 1a- and 1b-GRF1 products using an anti-His-tagged mAb. Open arrowheads indicate the truncated ORF1 protein of the expected size whereas filled arrowheads show the presumably homodimers of the expected proteins. M: protein markers.

FIG. 9(A) WB analyses using the gnotobiotic pig serum samples from Virginia and a commercial OIE diseases-free porcine serum as the positive control reference serum (pos). FIG. 9(B) Representative results of TTSuV1a WB analyses of conventional pig sera from a farm in Wisconsin. Purified 1a-ORF1 protein was used as the antigen. Sera tested negative for both TTSuV1a and TTSuV1b antibodies by WB were pooled and used as the negative control reference serum. Open arrowheads indicate the truncated ORF1 protein of expected size. Only the bands in green color were considered as positive. M: protein markers. FIG. 9(C) TTSuV1a or TTSuV1b ELISA results of the seven Virginia gnotobiotic pig serum samples, positive and negative control reference sera.

FIG. 10(A)-FIG. 10(C) illustrate serological and virological profiles of TTSuV1 infection in 138 sera of pigs from three different herds. FIG. 10(A) Distribution of TTSuV1 viremia, anti-TTSuV1a and anti-TTSuV1b IgG among 138 serum samples. Box-and-Whisker-plots of TTSuV1a FIG. 10(B) and TTSuV1b FIG. 10(C) serum antibody level by TTSuV1 viral DNA load. N: Negative. The detection limit of the TTSuV1 real-time qPCR was 4 $\log_{10}$ copies/ml in this study.

FIG. 13(A) Distribution of anti-TTSuV1a, -TTSuV1b and -TTSuV2 IgG. FIG. 13(B) Scatter plots showing a good linear relationship of antibody level between anti-TTSuV1a and anti-TTSuV1b (p<0.0001).

FIG. 15(A)-FIG. 15 (C) illustrate Immunofluorescence assay (IFA) results of PCV1-free PK-15 cells transfected with the plasmids pTri-1aORF1 FIG. 15(A), pTri-1bORF1 FIG. 15(B) or pTri-2cORF1 FIG. 15(C) at 3 days post-transfection. pTri-1aORF1- or pTri-1 bORF1-transfected cells were stained with the rabbit anti-TTSuV1a and -TTSuV1b ORF1 antiserum, respectively, whereas pTri-2cORF1-transfected cells were stained with the rabbit anti-TTSuV2 ORF1 antiserum. The Alexa fluor 488-conjugated goat anti-rabbit IgG was used as the secondary Ab in IFA (all the left panels). Ab staining merged with nuclear staining using DAPI (blue) are shown in the right panels. Magnification=200×.

FIG. 17A-FIG. 17D represent the schematic diagram of genomic structures, strategies for genomic cloning and assemblies of four prototype U.S. strains of porcine TTV virus group 1 (species 1) and group 2 (species 2) strains. FIG. 17A represents a schematic diagram of genomic structures and strategies for genomic cloning of porcine TTV virus group 1 strains. FIG. 17B represents a schematic diagram of genomic structures and strategies for genomic cloning of porcine TTV virus group 2 strains. FIG. 17C illustrates differentiation and assembly of full-length genomic sequences of PTTV1 strains PTTV1a-VA and PTTV1b-VA with PCR fragments Band C that were subsequently cloned. (PTTV1a-VA=SEQ ID NO: 9, Sd-TTV31=SEQ ID NO: 53, PTTV1bVA=SEQ ID NO: 10, TTV-1p=SEQ ID NO: 56). FIG. 17D genomic sequences of PTTV2 strains PTTV2b-VA and PTTV2c-VA with PCR fragments E and F that were subsequently cloned. (TTV-2p=SEQ ID NO: 59, PTTV2b-VA=SEQ ID NO: 11, and PTTV2c-VA=SEQ ID NO: 12).

FIG. 21A: pSC-PTTV1a (from the US PTTV isolate PTTV1a-VA; GenBank accession no. GU456383). FIG. 21B: pSC-PTTV1b (from the US PTTV isolate PTTV1b-VA; GenBank accession no. GU456384). FIG. 21C: pSC-PTTV2c (from the US PTTV isolate PTTV2c-VA; GenBank accession no. GU456386). FIG. 21D: pSC-2PTTV2c-RR (tandem-dimerized genomes). FIG. 21E: TTV2-#471942-full (from the Germany PTTV isolate TTV2-#471942; a gift from Dr. Andreas Gallei, not generated by the applicants). FIG. 21F: pSC-2PTTV2b-RR (tandem-dimerized genomes; generated by the applicants based on the clone TTV2-#471942-full). The plasmid back-bone used for the cloning of (A)-(D), and (F) was the pSCB-amp/kan vector (indicated in black). Grey arrows indicated the PTTV genomic copies.

FIG. 22A shows changes of viremia or virus titers (copies/ml) as determined by PTTV2-specific real-time PCR for pSC-2PTTV2b-RR. FIG. 22B shows changes of viremia or virus titers (copies/ml) as determined by PTTV2-specific real-time PCR for pSC-2PTTV2cb-RR. FIG. 22C shows seroconversion to IgG anti-porcine TTV2 ORF1 antibodies in pigs infected with TTV2 DNA clone pSC-2PTTV2b-RR. FIG. 22D shows seroconversion to IgG anti-porcine TTV2 ORF1 antibodies in pigs infected with TTV2 DNA clone pSC-2PTTV2c-RR. Anti-PTTV2 antibody is plotted as the ELISA optical density (A405). The ELISA cutoff value, indicated by a dashed line in each panel, is 0.4.

DETAILED DESCRIPTION OF THE INVENTION

In accordance with the present invention, in one specific example, the aforementioned four novel porcine TTV subtypes are isolated from a single boar in Virginia.

Figure 17B:
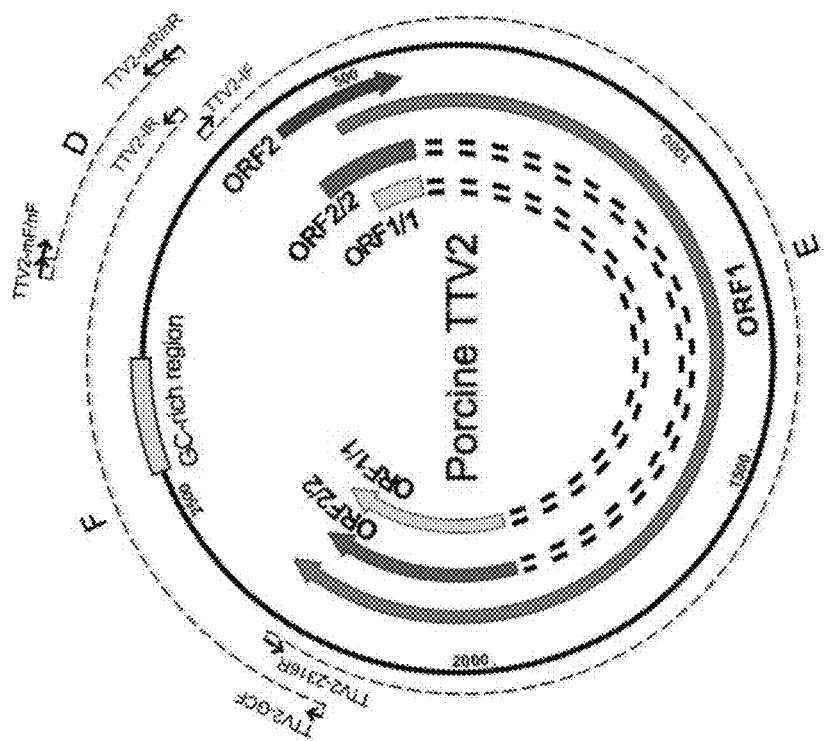
Figure 17A:
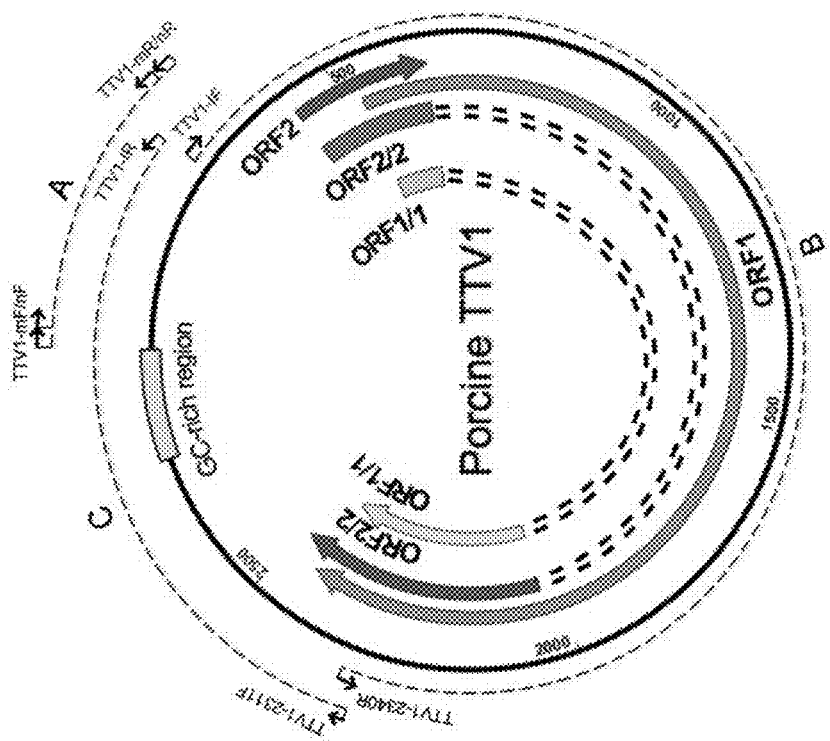

In FIG. 17A and FIG. 17B respectively, both the PTTV1 and PTTV2 genomes are shown in bold and the sizes and directions of the four putative ORFs (ORF1, ORF2, ORF1/1 and ORF2/2) are indicated by arrows. The GC-rich regions are also shown. Dashed-line arcs A and D represent the regions used for detection of PTTV1 and PTTV2 from serum and semen samples by nested PCR, respectively. Dashed-line arcs B and C represent the two overlapping PCR fragments for genomic cloning of PTTV1 whereas dashed-line arcs E and F represent the two overlapping PCR fragments for genomic cloning of PTTV2. The locations of the primers used in the study (see Table 1) are also shown in the corresponding positions.

One boar serum sample (SR#5) that was shown to be positive for both PTTV1 and PTTV2 in the first-round PCR, thus indicative of higher virus load, was used for subsequent full-length genomic cloning of PTTV. Surprisingly, initial attempts to utilize two primer sets (NG372/NG373 and NG384/NG385) of an inverse PCR (Okamoto et al., 2002, supra) designed for cloning of the first PTTV strain Sd-TTV31 to amplify the virus genomic DNA were not successful. No PCR product, was obtained after several trials. Based upon the initial sequence of the region A of PTTV1 and the region D of PTTV2, two new pairs of primers (TTV1-If (SEQ ID NO:1)/TTV1-2340R (SEQ ID NO:2) and TTV1-2311F (SEQ ID NO:3)/TTV1-IR (SEQ ID NO:4)) were subsequently designed to amplify regions B and C spanning the assumed PTTV1 genome, and two additional pairs of primers (TTV2-IF (SEQ ID NO:5)/TTV2-2316R (SEQ ID NO:6) and TTV2-GCF (SEQ ID NO:7)/TTV2-IR (SEQ ID NO:8)) to amplify regions E and F spanning the assumed PTTV2 genome, respectively (FIG. 17A-17D and Table 1). Primers TTV1-2340R (SEQ ID NO:2) and TTV1-2311F (SEQ ID NO:3) were deduced from a common sequence in PTTV1 stains Sd-TTV31 (Okamoto et al., 2002, supra) and TTV-1p (Niel et al., 2005) that is absent in PTTV2 strain TTV-2p (Niel et al., 2005, supra), whereas primers TTV2-2316R (SEQ ID NO:6) and TTV2-GCF (SEQ ID NO:7) were deduced from a sequence of strain TTV-2p that is absent in the two PTTV1 strains. The resulting four different PCR products with expected sizes were each inserted into a blunt-end cloning vector, and the resulting recombinant plasmids were transformed into *Escherichia coli*. Eight to fifteen positive (with white color) bacterial clones for each construct representing fragments B, C, E and F were identified and subsequently sequenced.

TABLE 1

Oligonucleotide primers used for nested PCR and genomic PCR amplifications of porcine TT viruses

| Primer ID | Sequence (5' to 3') | Used for: |
| --- | --- | --- |
| TTV1-mF (SEQ ID NO: 45) | TACACTTCCGGGTTCAGGAGGCT | Detection of porcine TTV1 |
| TTV1-mR (SEQ ID NO: 46) | ACTCAGCCATTCGGAACCTCAC | Detection of porcine TTV1 |
| TTV1-nF (SEQ ID NO: 47) | CAATTTGGCTCGCTTCGCTCGC | Detection of porcine TTV1 |
| TTV1-nR (SEQ ID NO: 48) | TACTTATATTCGCTTTCGTGGGAAC | Detection of porcine TTV1 |
| TTV2-mF (SEQ ID NO: 49) | AGTTACACATAACCACCAAACC | Detection of porcine TTV2 |
| TTV2-mR (SEQ ID NO: 50) | ATTACCGCCTGCCCGATAGGC | Detection of porcine TTV2 |
| TTV2-nF (SEQ ID NO: 51) | CCAAACCACAGGAAACTGTGC | Detection of porcine TTV2 |
| TTV2-nR (SEQ ID NO: 52) | CTTGACTCCGCTCTCAGGAG | Detection of porcine TTV2 |
| TTV1-IF (SEQ ID NO: 1) | CATAGGGTGTAACCAATCAGATTTAAGGCGTT | Genomic cloning (fragment B) |
| TTV1-2340R (SEQ ID NO: 2) | GGTCATCAGACGATCCATCTCCCTCAG | Genomic cloning (fragment B) |
| TTV1-2311F (SEQ ID NO: 3) | CTTCTGAGGGAGATGGATCGTCTGATGA | Genomic cloning (fragment C) |
| TTV1-IR (SEQ ID NO: 4) | TTGAGCTCCCGACCAATCAGAATTGACT | Genomic cloning (fragment C) |

TABLE 1-continued

Oligonucleotide primers used for nested PCR and genomic PCR
amplifications of porcine TT viruses

| Primer ID | Sequence (5' to 3') | Used for: |
| --- | --- | --- |
| TTV2-IF (SEQ ID NO: 5) | TTGTGCCGGAGCTCCTGAGAGC | Genomic cloning (fragment E) |
| TTV2-2316R (SEQ ID NO: 6) | AGGTGCTTGAGGAGTCGTCGCTTG | Genomic cloning (fragment E) |
| TTV2-GCF (SEQ ID NO: 7) | CTCAAGCACGAGCAGTGGATCCTCTCA | Genomic cloning (fragment F) |
| TTV2-IR (SEQ ID NO: 8) | TACCCAGGCGGTTAGACACTCAGCTCT | Genomic cloning (fragment F) |

Unexpectedly, two groups of sequence data from each construct were identified, indicating that there exist two types of PTTVs in genogroup 1 and genogroup 2 from the same pig. In order to differentiate and assemble the four PTTV strains, sequence comparisons were performed together with the three known PTTV strains, Sd-TTV31, TTV-1p and TTV-2p (FIGS. 17C and 17D).

FIG. 17C illustrates differentiation and assembly of full-length genomic sequences of PTTV1 strains PTTV1a-VA and PTTV1b-VA with PCR fragments B and C that were subsequently cloned. The initiation codons of ORF1 and ORF2 in the fragment B as well as the termination codons of ORF1 in the fragment C are marked by "^" or "*". The corresponding sequences of two known PTTV1 strains, Sd-TTV31 and TTV-1p, are also shown. Conserved sequences are shaded, and dashes indicate nucleotide deletions.

For PTTV1, the initiation codon ATG and the termination codon TGA of the putative ORF1 were located in fragments B and C, respectively (FIG. 17C). The positions of the codons were differed in two PTTV1 groups, the first one identical to Sd-TTV31 and the second one identical to TTV-1p (FIG. 17C). In addition, the ORF2 initiation codons in the two groups were also located at different positions consistent with that of ORF1. Moreover, phylogenetic analyses using four different sequences of the region B (two from the sequencing data and two from strains Sd-TTV31 and TTV-1p) and four different sequences of the region C supported that the first sequence was clustered with Sd-TTV31 and the second was clustered with TTV-1p (data not shown). Therefore, we were able to differentiate and assemble two groups of sequence data from both fragments B and C into two full-length PTTV1 genomes that were designated as strains PTTV1a-VA (SEQ ID NO:9) and PTTV1b-VA (SEQ ID NO:10), respectively (FIG. 17C).

FIG. 17D illustrates differentiation and assembly of full-length genomic sequences of PTTV2 strains PTTV2b-VA and PTTV2c-VA with PCR fragments E and F that were subsequently cloned. The corresponding sequence of TTV-2p strain is included and the conserved sequences are shaded. Dashes indicate nucleotide deletions. The unique nucleotides within the overlapping region (boxed with dashed-line) for each strain (a continuous "AG" nucleotides for PTTV2b-VA (SEQ ID NO:11) and two single "A" and "G" nucleotides for PTTV2c-VA (SEQ ID NO:12)) are shown, respectively.

Differentiation of the two PTTV2 strains was easier. A unique continuous "AG" nucleotides located in the overlapping region of two PCR fragments was shared by two groups of sequence data from fragments E and F, respectively (FIG. 17D). The assembled full-length genomic sequence represented a PTTV2 strain and was designated as PTTV2b-VA (SEQ ID. NO:11). Similarly, the complete genomic sequence of a second strain designated as PTTV2c-VA (SEQ ID NO:12) was assembled based upon two unique single "A" and "G" nucleotides shared in the overlapping region by another set of sequence data from fragments E and F, respectively (FIG. 17D). Phylogenetic analyses using four sequences from fragments E and F together with the two corresponding sequences from TTV-2p also supported this assignment (data not shown).

The present invention provides four isolated porcine TTV virus genotypes or subtypes that are associated with viral infections in pigs. This invention includes, but is not limited to, porcine TTV virus genotypes or subtypes PTTV1a-VA, PTTV1b-VA, PTTV2b-VA, and PTTV2c-VA, the virus genotypes or subtypes which have nucleotide sequences set forth in SEQ ID NO:9 (PTTV1a-VA), SEQ ID NO:10 (PTTV1b-VA), SEQ ID NO:11 (PTTV2b-VA), and SEQ ID NO:12 (PTTV2c-VA), their functional equivalent or complementary strand. It will be understood that the specific nucleotide sequence derived from any porcine TTV will have slight variations that exist naturally between individual viruses. These variations in sequences may be seen in deletions, substitutions, insertions and the like.

The proposed genomic structure for each of the four PTTV strains was analyzed in detail and summarized in Table 2, together with the three known PTTV strains, Sd-TTV31, TTV-1p and TTV-2p. All the four U.S. strains of PTTV have a similar genomic size of 2,878 by (PTTV1a-VA SEQ ID NO:9), 2,875 by (PTTV1b-VA SEQ ID NO:10), 2,750 by (PTTV2b-VA SEQ ID NO:11), and 2,803 by (PTTV2c-VA SEQ ID NO:12), respectively. Both PTTV1a-VA (SEQ ID NO:9) and Sd-TTV31 have the same genomic length. The published sequences of the strains TTV-1p and TTV-2p all have many undetermined nucleotides in the GC-rich region of the UTR. After artificial filling of these nucleotides with the consensus sequences corresponding to PTTV1 and PTTV2, it was shown that the TTV-1p is more closely-related to PTTV1b-VA (SEQ ID NO:10), and that TTV-2p is more closely-related to PTTV2b-VA (SEQ ID NO:11) in, genomic length, respectively (data not shown).

The assembled genomic sequences of porcine TTV virus genotypes or subtypes PTTV1a-VA (SEQ ID NO:9), PTTV1b-VA (SEQ ID NO:10), PTTV2b-VA (SEQ ID NO:11), and PTTV2c-VA(SEQ ID NO:12) are submitted to Genbank® (Nucleic Acids Research, 2008 January: 36(Database issue):D25-30) with accession numbers GU456383, GU456384, GU456385, and GU456386, respectively.

ID NO:43); TATCGGGCAGG of 11 nt (SEQ ID NO:44)) are located between the proposed 5'-end of mRNA and the

TABLE 2

Comparison of the genomic organization and ORFs of the seven porcine TTV strains

| Virus | Porcine TTV species 1 | | | | Porcine TTV species 2 | | |
|---|---|---|---|---|---|---|---|
| | Type 1a | | Type 1b | | Subtype 2a | Subtype 2b | Subtype 2c |
| Strain | PTTV1a-VA | Sd-TTV31 | PTTV1b-VA | TTV-1p | TTV-2p | PTTV2b-VA | PTTV2c-VA |
| Country | USA | Japan | USA | Brazil | Brazil | USA | USA |
| Full-length (nt) | 2878 | 2878 | 2875 | Uncompleted | Uncompleted | 2750 | 2803 |
| GenBank accession # | GU456383 | AB076001 | GU456384 | AY823990 | AY823991 | GU456385 | GU456386 |
| TATA box | 288-291 | 288-291 | 288-291 | 288-291 | 233-236 | 233-236 | 285-288 |
| Putative mRNA 5'-end | 316 | 316 | 316 | 316 | 261 | 261 | 313 |
| ORF1 | | | | | | | |
| Size (aa) | 635 | 635 | 639 | 637 | 624 | 625 | 625 |
| Exon # | 1 | 1 | 1 | 1 | 1 | 1 | 1 |
| Initiation | 534 | 534 | 517 | 517 | 476 | 476 | 528 |
| Termination | 2441 | 2441 | 2436 | 2430 | 2350 | 2353 | 2405 |
| ORF2 | | | | | | | |
| Size (aa) | 73 | 73 | 72 | 72 | 68 | 68 | 68 |
| Exon # | 1 | 1 | 1 | 1 | 1 | 1 | 1 |
| Initiation | 430 | 430 | 428 | 428 | 393 | 393 | 445 |
| Termination | 651 | 651 | 646 | 646 | 599 | 599 | 651 |
| ORF1/1 | | | | | | | |
| Size (aa) | 174 | 174 | 182 | 182 | 178 | 178 | 178 |
| Exon # | 2 | 2 | 2 | 2 | 2 | 2 | 2 |
| Initiation | 534 | 534 | 517 | 517 | 476 | 476 | 528 |
| Splicing | 647/648 | 647/648 | 642/643 | 642/643 | 595/596 | 595/596 | 647/648 |
| | 2030/2031 | 2030/2031 | 2013/2014 | 2007/2008 | 1933/1934 | 1936/1937 | 1988/1989 |
| Termination | 2441 | 2441 | 2436 | 2430 | 2350 | 2353 | 2405 |
| ORF2/2 (ORF3) | | | | | | | |
| Size (aa) | 224 | 224 | 228 | 228 | 199 | 199 | 199 |
| Exon # | 2 | 2 | 2 | 2 | 2 | 2 | 2 |
| Initiation | 430 | 430 | 428 | 428 | 393 | 395 | 445 |
| Splicing | 647/648 | 647/648 | 642/643 | 642/643 | 595/596 | 595/596 | 647/648 |
| | 2030/2031 | 2030/2031 | 2013/2014 | 2007/2008 | 1933/1934 | 1936/1937 | 1988/1989 |
| Termination | 2487 | 2487 | 2485 | 2479 | 2330 | 2333 | 2385 |
| Polyadenylation signal (AATAAA) | 2458-2463 | 2458-2463 | 2462-2467 | 2456-2461 | 2473-2478 | 2476-2481 | 2528-2533 |

The numbers (except sizes of the full-length genome, ORFs and the exon numbers) indicate the nucleotide (nt) positions on the genome of respective PTTV strains.

Two recent studies have identified the transcribed viral mRNAs and the expression of at least six viral proteins during human TTV replication (Mueller et al., 2008, supra; Qiu et al., 2005, supra), which is more than the predicted number of ORFs encoded by human TTV (Okamoto, H., et al. (2000b). TT virus mRNAs detected in the bone marrow cells from an infected individual. Biochem Biophys Res Commun 279(2), 700-7), therefore we included the new human TTV genomic information for comparison with the PTTV sequences. The 5'-ends of the mRNA transcripts of human TTV strain P/1C1 were mapped to an "A" that is 25 nt downstream of the TATA-box (Mueller et al., 2008, supra). This starting point, its adjacent sequence (CGAATG-GCTGAGTTTATGCCGC (SEQ ID NO:39); the starting point was underlined) and the distance to the upstream TATA-box (24 nt; Table 2) are very conserved in all seven PTTV strains, suggesting that PTTV and human TTV may utilize a common 5'-end of mRNA for translation.

Five additional completely-conserved regions were identified in the vicinity of the TATA-box among all seven PTTV strains. Two regions of 11 nt each (AGTCCTCATTT (SEQ ID NO:40) and AACCAATCAGA (SEQ ID NO:41)) are located in the upstream of the TATA-box, whereas the remaining three regions (CTGGGCGGGTGCCGGAG of 17 nt (SEQ ID NO:42); CGGAGTCAAGGGGC of 14 nt (SEQ ID NO:43); TATCGGGCAGG of 11 nt (SEQ ID NO:44)) are located between the proposed 5'-end of mRNA and the initiation codon of ORF2. These conserved PTTV-specific sequences may contain the common elements regulating the viral gene expression.

Previously, three ORFs (ORFs 1-3) were proposed in the genome of the three known PTTV strains, respectively (Niel et al., 2005, supra; Okamoto et al., 2002, supra). The four prototype U.S. strains of PTTV identified in this study possess this structure. The corresponding ORF3 in human TTV has been renamed as ORF2/2 since it initiates at the same ATG in ORF2 and remains in the same ORF (extending ORF2) after the splicing (FIG. 17A-17B) (Mueller et al., 2008, supra; Qiu et al., 2005, supra). We follow the nomenclature of human TTV for revising PTTV classification in this study. Human TTV ORF1/1 is a newly identified viral protein that is encoded by two exons in ORF1 (Qiu et al., 2005, supra). ORF1/1 share the identical N- and C-terminal part with ORF1. The PTTV ORF1/1 counterpart was readily identified in all seven PTTV strains (FIG. 17A-17B and Table 2).

The ORF1 and ORF2 are encoded by a ~2.8 kb viral mRNA whereas the ORF1/1 and ORF2/2 are encoded by a spliced viral mRNA with .about.1.2 kb in human TTV (Mueller et al., 2008, supra; Qiu et al., 2005, supra). Since these four ORFs were also deduced in PTTV genomes, and since the sequences and positions of the putative splice donor and acceptor sites in the seven PTTV strains are very conserved (Table 2), it is speculated that porcine TTV probably also encodes the two corresponding mRNAs.

Most of the human TTV strains share a genetic similarity with the CAV, encoding a TTV apoptosis-inducing protein (TAIP) in which its CAV counterpart was named apoptin (de Smit, M. H., and Noteborn, M. H. (2009). Apoptosis-inducing proteins in chicken anemia virus and TT virus. Curr Top Microbiol Immunol 331, 131-49). The ORF of TAIP is embedded within the ORF2. However, the corresponding TAIP does not exist in porcine TTV. A recent study showed that the expression of apoptin or TAIP was required for CAV replication in cultured cells (Prasetyo, A. A., et al. (2009). Replication of chicken anemia virus (CAV) requires apoptin and is complemented by VP3 of human torque teno virus (TTV). Virology 385(1), 85-92).

Pairwise sequence comparisons (PASC) is a useful method that plots the frequency distribution of pairwise nucleotide sequence identity percentages from all available genomic sequence of viruses in the same family (Bao, Y., Kapustin, Y., and Tatusova, T. (2008). Virus Classification by Pairwise Sequence Comparison (PASC). In "Encyclopedia of Virology, 5 vols." (B. W. J. Mahy, and M. H. V. Van Regenmortel, Eds.), Vol. 5, pp. 342-8. Elsevier, Oxford). The different peaks generated by the PASC program usually represent groups of virus genera, species, types, subtypes and strains. In this study, we performed PASC analyses of TTV using 121 full-length genomic sequences of human and animal TTV-related strains available in GenBank database. Assuming that TTV members are classified into a separate family, Anelloviridae, the two major peaks, at 36-55% and 55-67% nucleotide sequence identities, represent groups of genera and species, respectively. Accordingly, a TTV type is defined as a group of TTV having 67-85% nucleotide sequence identity whereas a TTV subtype may be defined as a group of TTV sequences sharing 85-95% nucleotide sequence identity. TTV strains sharing more than 95% nucleotide sequence identity may be further classified into variants. A similar classification has been proposed using sequences of 103 TTV isolates by Jelcic et al (Jelcic, I., et al. (2004). Isolation of multiple TT virus genotypes from spleen biopsy tissue from a Hodgkin's disease patient: genome reorganization and diversity in the hypervariable region. J Virol 78(14), 7498-507).

This proposed criteria of TTV classification were applied to phylogenetic analyses of the genomic sequences of the 4 prototype U.S. strains of PTTV and the 3 other known PTTV strains. Pairwise comparison of full-length nucleotide sequences among these strains showed that the four PTTV1 strains have 54.0-56.4% nucleotide sequence identity compared to the three PTTV2 strains (Table 3). Therefore, the previously designated "genogroup" of PTTV in the literature will probably be more appropriate to designate as "species", and PTTV1 and PTTV2 probably should represent porcine TTV species I and species 2, respectively. PTTV species 1 consists of two types of viruses designated as type 1a (including Sd-TTV31 and PTTV1a-VA (SEQ ID NO:9)) and type 1b (including TTV-1p and PTTV1b-VA (SEQ ID NO:10)), respectively, since the nucleotide sequence identity between these two types of viruses is between 69.8-70.7% (Table 3). Sd-TTV31 and TTV1a-VA (SEQ ID NO:9) are recognized as variant strains of the same species due to their higher sequence identity (95.1%). However, the two type 1b strains, TTV-1p and PTTV1b-VA (SEQ ID NO:10), may belong to two different subtypes (nucleotide sequence identity=86.4%). For PTTV species 2, three strains are likely to be classified into separate subtypes (TTV-2p for subtype 2a, PTTV2b-VA (SEQ ID NO:11) for subtype 2b, and PTTV2c-VA (SEQ ID NO:12) for subtype 2c, respectively) based upon their 86.5-90.9% nucleotide sequence identity. This proposed new classification system for PTTV was clearly evident in the phylogenetic tree. Phylogenetic trees constructed based upon the deduced amino acid sequences of ORF1, ORF1/1, ORF2 and ORF2/2 of PTTV were also consistent with this proposed classification.

TABLE 3

Pairwise sequence comparison of the full-length genomic sequence of the seven porcine TTV strains

| | Porcine TTV species 1 | | | | Porcine TTV species 2 | | |
| --- | --- | --- | --- | --- | --- | --- | --- |
| | Type 1a | | Type 1b | | Subtype 2a | Subtype 2b | Subtype 2c |
| | PTTV1a-VA | Sd-TTV31 | PTTV1b-VA | TTV-1p | TTV-2p | PTTV2b-VA | PTTV2c-VA |
| Type 1a | | | | | | | |
| PTTV1a-VA | — | 95.1 | 70.5 | 69.8 | 55.7 | 55.1 | 56.2 |
| Sd-TTV31 | | — | 70.7 | 70.1 | 55.9 | 56.0 | 56.4 |
| Type 1b | | | | | | | |
| PTTV1b-VA | | | — | 86.4 | 54.0 | 54.7 | 55.2 |
| TTV-1p | | | | — | 55.2 | 54.7 | 55.4 |
| Subtype 2a | | | | | | | |
| TTV-2p | | | | | — | 86.5 | 86.8 |
| Subtype 2b | | | | | | | |
| PTTV2b-VA | | | | | | — | 90.9 |
| Subtype 2c | | | | | | | |
| PTTV2c-VA | | | | | | | — |

The data were generated by using the PASC program, and the values indicate % nucleotide sequence identities.

Unique mutations and deletions and/or insertions are scattered throughout the genomes between PTTV species, types and subtypes. For example, the location of ORF1 initiation and termination codons and the ORF2 initiation codons between PTTV type 1a and 1b, which was shown in FIG. 17C as mentioned above, are different. The two PTTV1b strains also have a 2-codon deletion after the ORF2 initiation compared to PTTV1a (FIG. 17C).

Remarkably, both TTV-2p and PTTV2b-VA have a large 52-nt deletion, which is 39 nt upstream of the first 11-nt conserved sequence (AGTCCTCATTT (SEQ ID NO:40)) in the UTR, compared to PTTV2c-VA. Due to this deletion, the genomic size of PTTV2b-VA (probably TTV-2p as well) was significantly smaller than that of PTTV2c-VA (Table 2). A number of "subviral" human TTV clones have been isolated from serum samples that are considered as fulllength TTV genomes since the ORFs in a majority of these subviral molecules usually remain intact (de Villiers et al., 2009; Leppik et al., 2007). They have variable lengths in the UTR that are completely or partially deleted. The situation of TTV-2p and PTTV2b-VA appears to resemble that of the human TTV subviral molecules, implying that subtypes PTTV2a and PTTV2b might be the subviral molecules derived from subtype PTTV2c. Of note, the 3'-terminal sequence of a nested-PCR primer TTV2-nF (Table 1) that is commonly used for detection of the PTTV2 from field samples by other groups (Ellis et al., 2008, supra; Kekarainen et al., 2007, supra; Kekarainen et al., 2006, supra; Krakowka et al., 2008, supra) is located at both sides of the deletion. Therefore, the current nested-PCR assay for PTTV2 detection is likely not sufficient to identify the genetically diverse strains of PTTV2c subtype.

The source of the isolated virus strain is serum, fecal, saliva, semen and tissue samples of pigs having the porcine TTV viral infection. However, it is contemplated that recombinant DNA technology can be used to duplicate and chemically synthesize the nucleotide sequence. Therefore, the scope of the present invention encompasses the isolated polynucleotide which comprises, but is not limited to, a nucleotide sequence set forth in SEQ ID NO:9, SEQ ID NO:10, SEQ ID NO:11, and SEQ ID NO:12, or its complementary strand; a polynucleotide which hybridizes to and which is at least 67% complementary to the nucleotide sequence set forth in SEQ ID NO:9, SEQ ID NO:10, SEQ ID NO:11, and SEQ ID NO:12, preferably 85% complementary, or more preferably 95% complementary; or an immunogenic fragment selected from the group consisting of an amino acid sequence of ORF1 protein set forth in SEQ ID NO:13 (PTTV1a-VA), SEQ ID NO:14 (PTTV1b-VA), SEQ ID NO:15 (PTTV2b-VA), SEQ ID NO:16 (PTTV2c-VA), an amino acid sequence of ORF2 protein set forth in SEQ ID NO:17 (PTTV1a-VA), SEQ ID NO:18 (PTTV1b-VA), SEQ ID NO:19 (PTTV2b-VA), SEQ ID NO:20 (PTTV2c-VA), an amino acid sequence of ORF1/1 protein set forth in SEQ ID NO:21 (PTTV1a-VA), SEQ ID NO:22 (PTTV1b-VA), SEQ ID NO:23 (PTTV2b-VA), SEQ ID NO:24 (PTTV2c-VA), an amino acid sequence of ORF2/2 protein set forth in SEQ ID NO:25 (PTTV1a-VA), SEQ ID NO:26 (PTTV1b-VA), SEQ ID NO:27 (PTTV2b-VA), SEQ ID NO:28 (PTTV2c-VA). The immunogenic or antigenic coding regions or fragments can be determined by techniques known in the art and then used to make monoclonal or polyclonal antibodies for immunoreactivity screening or other diagnostic purposes. The invention further encompasses the purified, immunogenic protein encoded by the isolated polynucleotides. Desirably, the protein may be an isolated or recombinant ORF1 protein or an ORF2 protein of at least one of the above isolated porcine TTV subtypes, more desirably ORF1 protein.

Figure 18A:
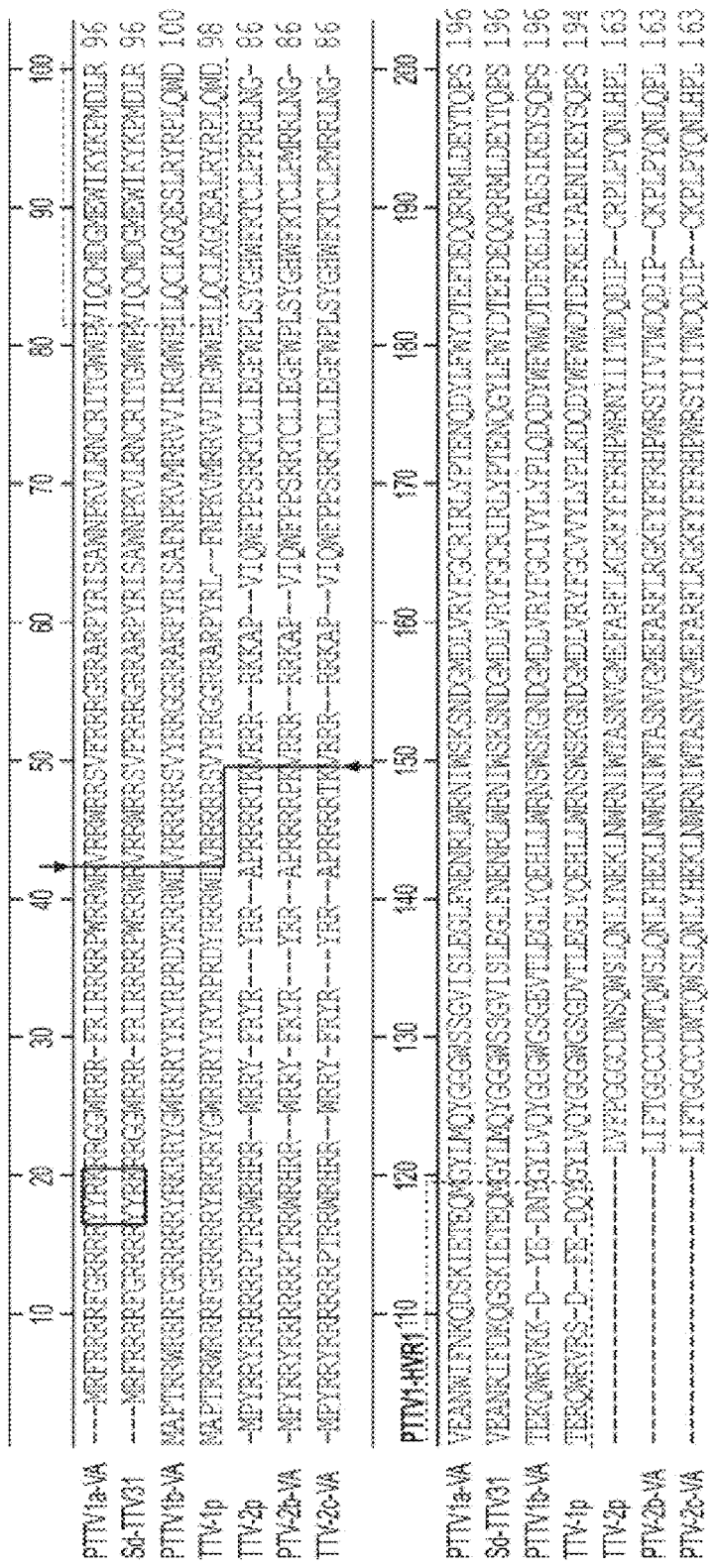
FIG. 18A-FIG. 18C represent an alignment of the full-length amino acid sequences of ORF1 among seven PTTV strains. (PTTV1a-VA=SEQ ID NO:13, Sd-TTV31=SEQ ID NO:54, PTTV1b-VA=SEQ ID NO: 14, TTV-1p=SEQ ID NO: 57, TTV-2p=SEQ ID NO:60, PTTV2b-VA=SEQ ID NO:15, and PPTV2c-VA=SEQ ID NO: 16).
Figure 18B:
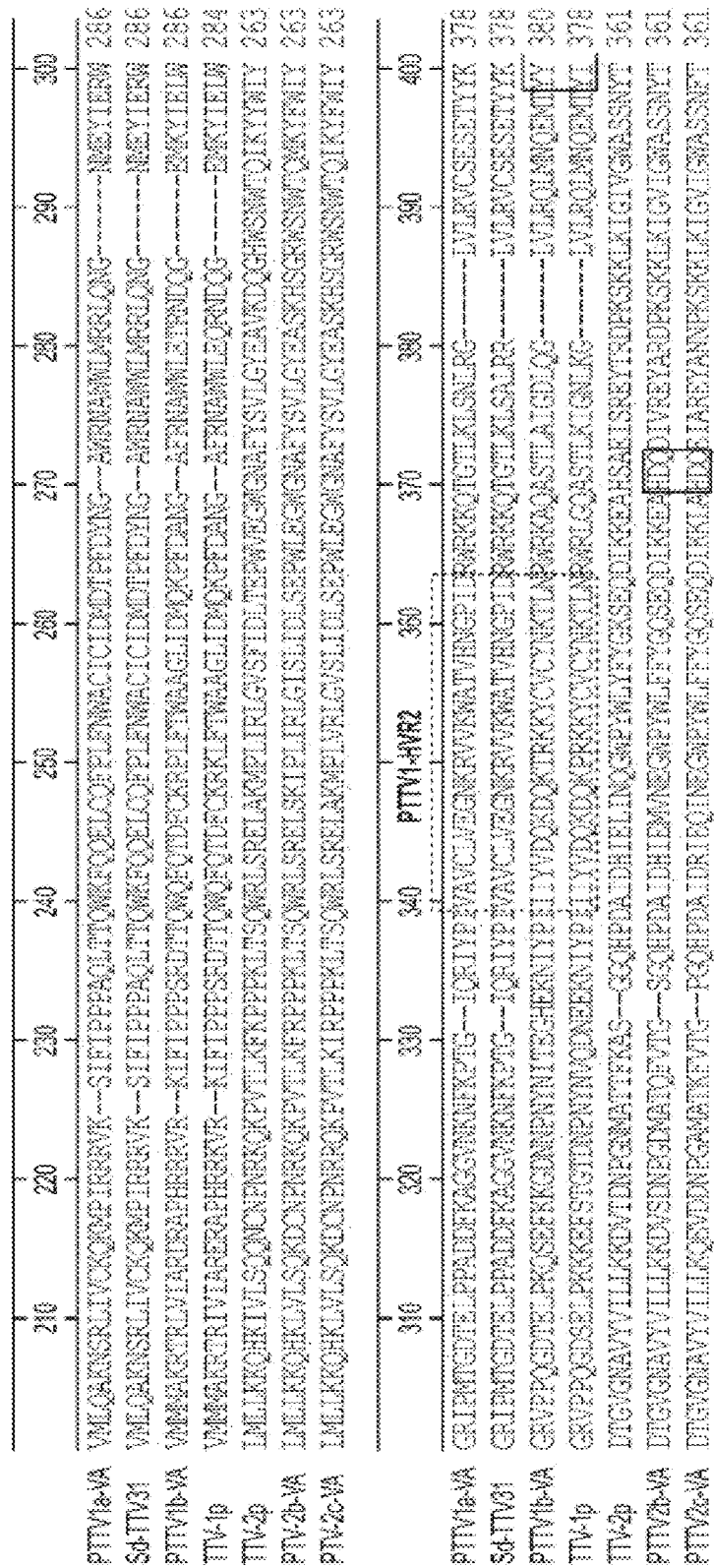
Figure 18C:
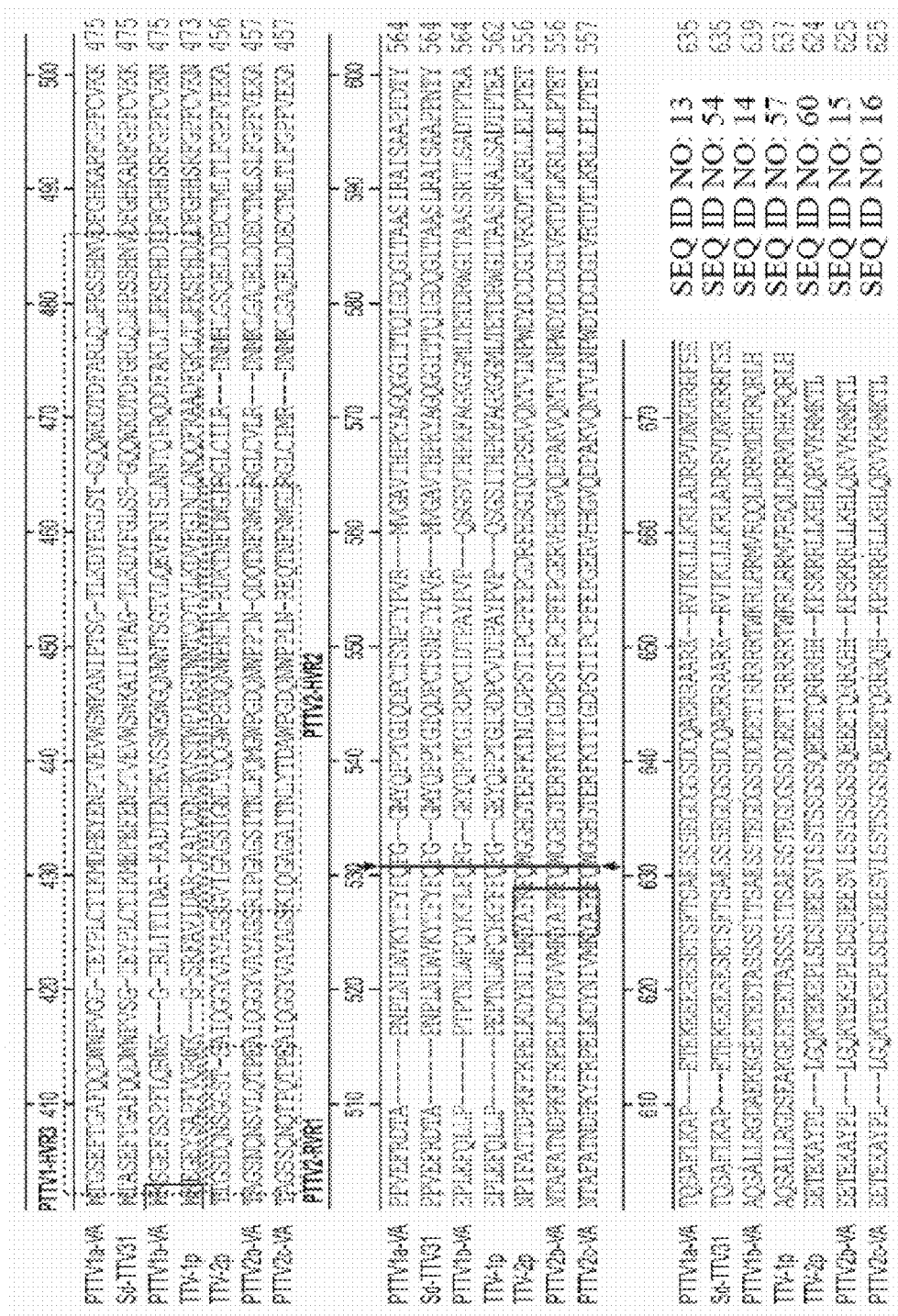

The ORF1 of porcine TTV is believed to encode a structural and replication-associated protein (Maggi, F. and Bendinelli, M. (2009). Immunobiology of the Torque teno viruses and other anelloviruses. Curr Top Microbiol Immunol 331, 65-90). The ORF1-encoding products of seven PTTV strains have 624-635 aa in length and possess a high number of arginine residues at the N-terminus that are thought to have the DNA-binding activity (FIG. 18A-18C). In FIG. 18A-C, conserved sequences are shaded. Dashes indicate amino acid deletions. The RCR motifs are boxed with solid lines. Three HVRs (PTTV1-HVRs 1, 2 and 3) of PTTV1 strains and two HVRs (PTTV2-HVRs 1 and 2) of PTTV2 strains are boxed with dashed lines. The connection boundaries of ORF1/1 are indicated by arrows. The predicted rolling-circle replication (RCR) motifs (Ilyina, T. V., and Koonin, E. V. (1992). Conserved sequence motifs in the initiator proteins for rolling circle DNA replication encoded by diverse replicons from eubacteria, eucaryotes and archaebacteria. Nucleic Acids Res 20(13), 3279-85) are presented at different positions in different PTTV types and subtypes that may be type- or subtype-specific. RCR motif-III (YxxK) is conserved in the PTTV type 1a (aa position 14-17 of PTTV1a-VA SEQ ID NO:13) and type 1b strains (aa position 379-382 of PTTV1b-VA SEQ ID NO:14), respectively, whereas the same conserved motif identified in all three PTTV2 strains is located at aa position 482-485 of PTTV2b-VA SEQ ID NO:15 (FIG. 4). Both PTTV2b-VA SEQ ID NO:15 and PTTV2c-VA SEQ ID NO:16 also have a conserved RCR motif-II (HxQ) at aa position 331-333 of PTTV2b-VA that is absence in TTV-2p (FIG. 18A-C).

The ORF1 proteins of PTTV strains between species 1 and species 2 share very low aa sequence identity with only 22.4 to 25.8%, which makes it difficult to identify significantly conserved aa sequences between the two species (FIG. 18A-C). In PTTV species 1, the aa identity of ORF1 between type 1a and 1b strains are 50.3-52.7%. Three major hypervariable regions (HVR), PTTV1-HVRs 1 to 3, with a relatively high number of aa substitutions, were identified among the four PTTV1 strains, whereas two HVRs (PTTV2-HVRs 1 and 2) were observed among the three PTTV2 strains (FIG. 18A-C): The three PTTV2 strains have an approximately 20-aa deletion in the corresponding PTTV1-HVR1 region. Moreover, the two HVRs of PTTV2 are within the corresponding PTTV1-HVR3 region (FIG. 18A-C). These HVRs are located only in the ORF1 but not in the truncated ORF1/1. They likely play a role in evading the host immune surveillance and helping PTTV to establish a persistent infection, as suggested by studies of human TTV.

Figure 19:
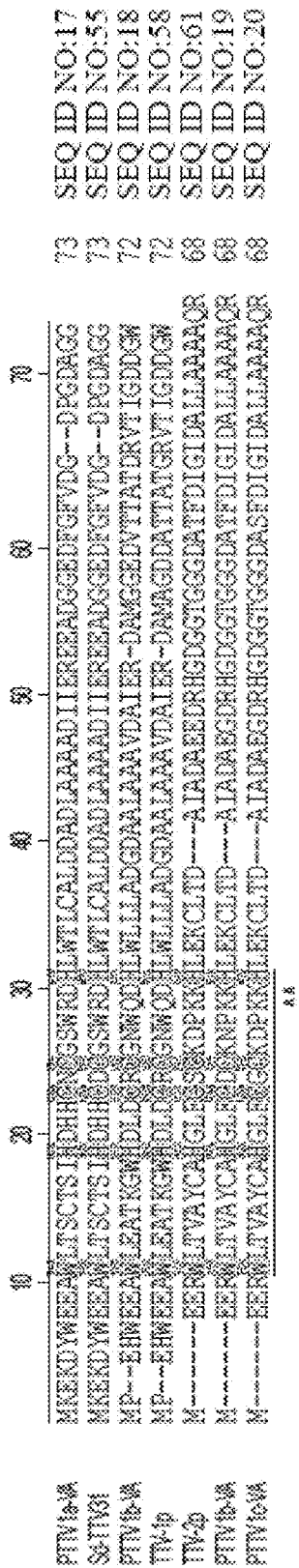
FIG. 19 represents an alignment of the full-length amino acid sequences of ORF2 among seven PTTV strains. (PTTV1a-VA=SEQ ID NO:17, Sd-TTV31=SEQ ID NO:55, PTTV1b-VA=SEQ ID NO:18, TTV-1p=SEQ ID NO: 58, TTV-2p=SEQ ID NO:61, PTTV2b-VA=SEQ ID NO:19, and PTTV2c-VA=SEQ ID NO:20).

The aa sequences of ORF2 differed considerably between the four PTTV1 (PTTV1a-VA SEQ ID NO:17; PTTV1b-VA SEQ ID NO:18) and three PTTV2 (PTTV2b-VA SEQ ID NO:19; PTTV2c-VA SEQ ID NO:20) strains (FIG. 19). However, they share a conserved protein-tyrosine phosphatase (PTPase)-like motif ($Wx_7Hx_3CxCx_5H$) at the N-terminus (FIG. 18A-C). This motif is also conserved among all human TTV, TTMV and TTMDV strains as well as CAV. The TTMV or CAV ORF2 protein also exhibited a serine/threonine phosphatase (S/T PPase) activity (Peters, M. A., Jackson, D. C., Crabb, B. S., and Browning, G. F. (2002). Chicken anemia virus VP2 is a novel dual specificity protein phosphatase. J Biol Chem 277(42), 39566-73). The dual specificity of the ORF2 protein is thought to regulate host gene transcription, signal transduction and cytokine responses during viral replication. Recently, mutagenesis analyses of two conserved basic aa residues before the last histidine residue of the motif in CAV revealed that the two residues affect virus replication, cytopathology in vitro and attenuation in vivo (Peters, M. A., Crabb, B. S., Washington, E. A., and Browning, G. F. (2006). Site-directed mutagenesis of the VP2 gene of Chicken anemia virus affects virus replication, cytopathology and host-cell MHC class I expression. J Gen Virol 87(Pt 4), 823-31; Peters, M. A., Crabb, B. S., Tivendale, K. A., and Browning, G. F. (2007). Attenuation of chicken anemia virus by site-directed mutagenesis of VP2. J Gen Virol 88(Pt 8), 2168-75). The two basic aa residues ("KK") are conserved in the three PTTV2 strains. However, only the first basic residue ("R") is retained in the two PTTV1a strains whereas both basic residues are substituted in the PTTV1b strains (FIG. 19). In FIG. 19, dashes indicate amino acid deletions. The five conserved amino acids within the common motif $Wx_7Hx_3CxCx_5H$ (underlined) identified in TTV, TTMV and CAV are shaded. The positions of the two basic aa residues before the last histidine of the motif, which have been shown to affect virus replication, cytopathology or in vivo attenuation in CAV, are indicated by " ".

In summary, the present invention has determined the full-length genomic sequences of four porcine TTV strains representing different genotypes or subtypes in a serum sample of a single boar in Virginia. The finding from this study clearly indicates that, similar to human TTV, multiple PTTV infections with distinct genotypes or subtypes exist and probably are common in pigs. We have also provided new information regarding the genomic organization, the degree of variability and the characteristics of conserved nucleotide and amino acid motifs of PTTV, which will improve the current PCR detection assay, aid in developing reagents for serological diagnostics and help initiate the structural and functional study of PTTV. A new classification of PTTV is also proposed in this study based upon the phylogenetic and genetic analyses of the genomic sequences of seven known PTTV strains.

The present invention also provides methods for diagnostics of porcine TTV infection by detecting viral DNA in samples of porcine TTV infected pigs or other mammals. One preferred embodiment of the present invention involves methods for detecting porcine TTV nucleic acid sequences in a porcine or other mammalian species using oligonucleotide primers for polymerase chain reaction (PCR) to further aid in the diagnosis of viral infection or disease. The diagnostic tests, which are useful in detecting the presence or absence of the porcine TTV viral nucleic acid sequence in the porcine or other mammalian species, comprise isolating viral DNA from samples of porcine TTV infected pigs, or pigs suspected of infection of TTV, and performing SYBR green real-time quantitative PCR using PTTV1-specific (SEQ ID NO:29/SEQ ID NO:30) or PTTV2-specific (SEQ ID NO:31/SEQ ID NO:32) primers.

In another embodiment of the present invention, the diagnostic method may be adapted to simultaneously detect PTTV1 and PTTV2 by using PTTV1/PTTV2 duplex real-time PCR. More specifically, the method comprises isolating viral DNA from samples of porcine TTV infected pigs or pigs suspected of infection of TTV, performing real-time PCR using both PTTV1-specific (SEQ ID NO:29/SEQ ID NO:30) or PVVT2-specific (SEQ ID NO:31/SEQ ID NO:32) primers in the same real-time PCR reaction. Since the T.sub.m value between PTTV1 and PTTV2 can be distinguished by MCA, the presence of PTTV1 and PTTV2 DNA can be simultaneously detected.

In a further embodiment of the present invention, the diagnostic method may employ duplex nested PCR. The method comprises isolating viral DNA from samples of porcine TTV infected pigs or pigs suspected of infection of TTV, performing a first round of PCR using one pair of primers P1ab-mF (SEQ ID NO:33)/P1ab-mR (SEQ ID NO:34), and performing a second round of PCR using a mixture of two pairs of primers, P1a-nF (SEQ ID NO:35)/P1a-nR (SEQ ID NO:36) for detection of PTTV1a, and P1b-nF (SEQ ID NO:37)/P1b-nR (SEQ ID NO:38) for detection of PTTV1b, and visualizing the PCR products.

The above diagnostics methods maybe optimized by one skilled in the art according to well known methods in the art.

Accordingly, an embodiment of the present invention develops two novel singleplex SYBR green real-time PCR assays to quantify the viral loads of two porcine TTV species, respectively. PTTV1- and PTTV2-specific primers were designed to target the extremely conserved regions across six PTTV1 and four PTTV2 full-length genomes available to date, respectively. Another embodiment of the present invention combines the two singleplex assays into a duplex real-time PCR assay followed by MCA of the viral amplicons that can be identified by their distinct melting temperatures for simultaneous detection of the two porcine TTV species, PTTV1a and PTTV1b. In a third embodiment, a duplex nested PCR assay for simultaneous amplification of the viral DNAs from two types of PTTV1 in the first round PCR and differential detection of types 1a and 1b in the second round PCR was developed for the identification of two types of porcine TTV species, PTTV1a and PTTV1b, in a single sample. These assays represent simple and practical tools for diagnoses of species- or type-specific porcine TTVs.

Potential primers sequences were identified by multiple sequence alignments of 10 available porcine TTV full-length genomes. PTTV1-specific primers TTV1F (SEQ ID NO:29) and TTV1R (SEQ ID NO:30) were designed based upon two conserved genomic regions immediately before the putative ORF2 across six PTTV1 genomes, whereas PTTV2-specific primers TTV2F4 (SEQ ID NO:31) and TTV2R4 (SEQ ID NO:32) were designed based upon two conserved genomic regions immediately after the putative ORF2/2 across four PTTV2 genomes (Table 4). Primers showed no potentials for self- and cross-dimerization. The expected amplicon sizes were a 118-bp fragment from the PTTV1 primers corresponding to the PTTV1b-VA genome and a 200-bp fragment from the PTTV2 primers corresponding to the PTTV2c-VA genome, respectively.

TABLE 4

Oligonucleotide primers used for real-time PCR and duplex nested PCR detections of porcine TTVs.

| Primer ID | Sequence (5' to 3') | Purpose |
|---|---|---|
| TTV1F<br>SEQ ID NO: 29 | TCCGAATGGCTGAGTTTATGC | PTTV1-specific real-time PCR |
| TTV1R<br>SEQ ID NO: 30 | TCCGCTCAGCTGCTCCT | PTTV1-specific real-time PCR |
| TTV2F4<br>SEQ ID NO: 31 | GGTGGTAAAGAGGATGAA | PTTV2-specific real-time PCR |
| TTV2R4<br>SEQ ID NO: 32 | AATAGATTGGACACAGGAG | PTTV2-specific real-time PCR |
| P1ab-mF<br>SEQ ID NO: 33 | TATCGGGCAGGAGCAGCT | Duplex nested PCR |
| P1ab-mR<br>SEQ ID NO: 34 | TAGGGGCGCGCTCTACGT | Duplex nested PCR |
| P1a-nF<br>SEQ ID NO: 35 | CCTACATGAAGGAGAAAGACT | Duplex nested PCR |

TABLE 4-continued

Oligonucleotide primers used for real-time PCR and duplex nested PCR detections of porcine TTVs.

| Primer ID | Sequence (5' to 3') | Purpose |
|---|---|---|
| P1a-nR SEQ ID NO: 36 | CCAGCGTCTCCAGGGTC | Duplex nested PCR |
| P1b-nF SEQ ID NO: 37 | AAGCTACCAAGGGCTGG | Duplex nested PCR |
| P1b-nR SEQ ID NO: 38 | GCGGTC(T/G)GTAGCGGTAGT | Duplex nested PCR |

According to one specific embodiment of the present invention, SYBR green simplex real-time PCR using PTTV1- and PTTV2-specific primers can be used specifically to detect porcine TTV1 and TTV2 DNA, respectively. For PTTV1, a standard curve was established over a range of target DNA concentrations per 25 µl. The linear range was shown to span $4.4 \times 10^1$ to $4.4 \times 10^8$ copies. The minimum detection limit (44 copies) corresponded to a threshold cycle ($C_t$) of 37.57. For PTTV2, standard curve was also generated and used to detect DNA concentration ranging from $8.6 \times 10^0$ to $8.6 \times 10^8$ copies per 25 µl reaction. The corresponding $C_t$ of minimum detection limit (8.6 copies) was 36.53.

According to another specific embodiment of the present invention, SYBR green duplex real-time PCR is utilized for the simultaneous detection of porcine TTV1 and TTV2 DNA. The 7-degree difference of $T_m$ value between PTTV1 (87.0° C.) and PTTV2 (80.0° C.) made it feasible to distinguish them from one another by the MCA. Therefore, two singleplex assays can be coupled into a duplex real-time PCR assay for the simultaneous detection of PTTV1 and PTTV2. A positive sample was one that had a symmetrical melt peak within the known $T_m$, for that product. This new assay was first validated by using a 10-fold dilution of PTTV1 and PTTV2 standards mixture. The non-template negative control using sterile water as the template showed a non-specific amplification caused by cross-dimerization between the PTTV1 and PTTV2 primers not seen in the singleplex assays. This produced a distinct melt peak between 72.0° C. and 76.0° C.

Figure 20:
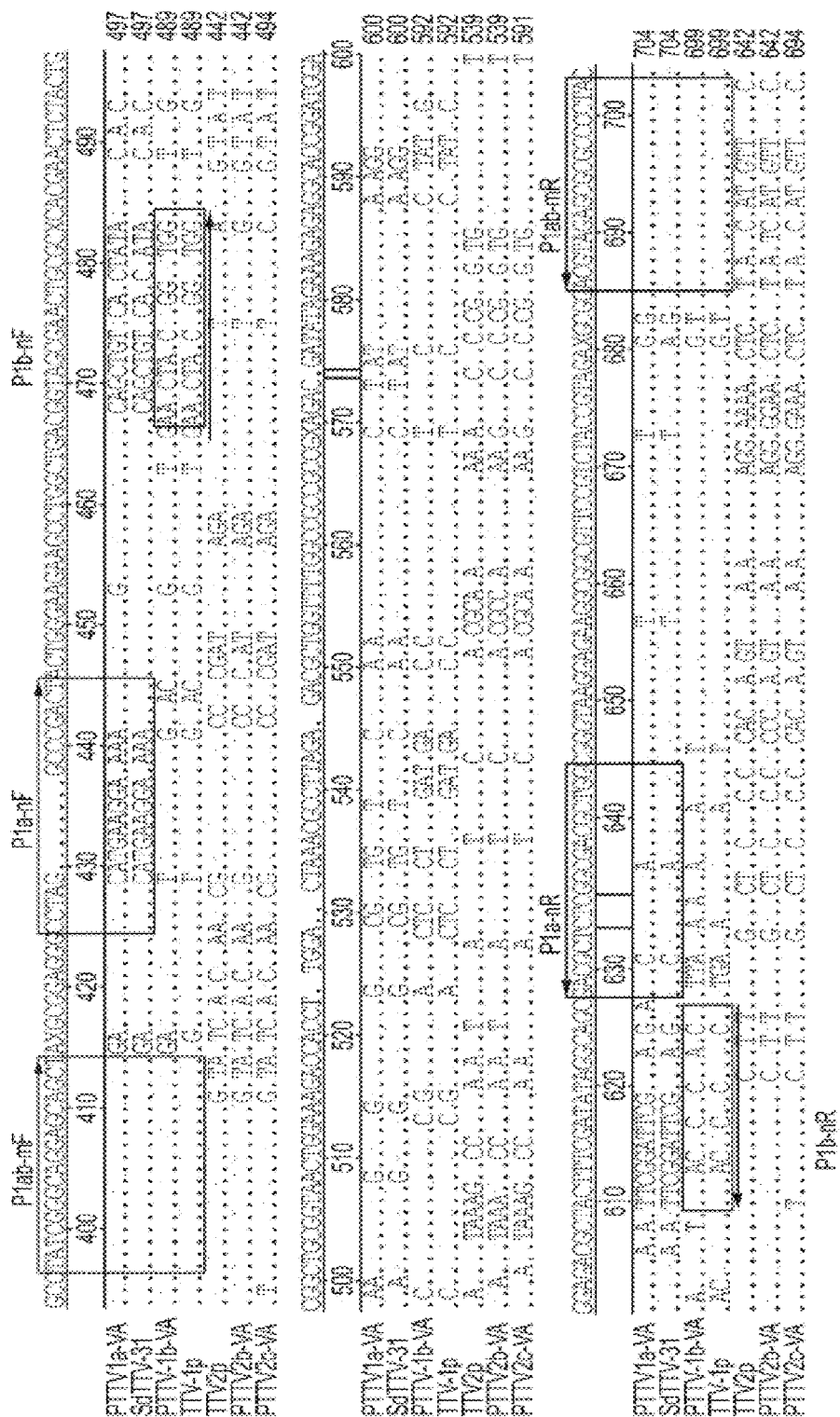
FIG. 20 represents an alignment of nucleotide sequences located at the N-terminal part of the putative ORF1 among seven PTTV strains. (PTTV1a-VA=SEQ ID NO:9, Sd-TTV31=SEQ ID NO:53, PTTV1bVA=SEQ ID NO:10, TTV-1p=SEQ ID NO:56, TTV-2p=SEQ ID NO:59, PTTV2b-VA=SEQ ID NO:11, and PTTV2c-VA=SEQ ID NO:12).

The inventors of the present invention demonstrated the existence of two distinct genotypes, tentatively named PTTV1a and PTTV1b, in porcine TTV species 1. To further determine whether the co-infection of PTTV1a and PTTV1b is common in pigs, a novel duplex nested PCR assay to quickly distinguish between the two was developed. Alignment of porcine TTV genomic DNA sequences identified a conserved genomic region located at the N-terminal part of the putative ORF1 encoding the viral capsid protein (FIG. 20). This region also contains the entire ORF2 and the partial UTR in the upstream. Primers P1ab-mF (SEQ ID NO:33)/P1ab-mR (SEQ ID NO:34) were designed to simultaneously amplify both PTTV1a and PTTV1b DNAs in the first-round PCR. A mixture of PTTV1a-specific primers P1a-nF (SEQ ID NO:35)/P1a-nR (SEQ ID NO:36) and PTTV1b-specific primers P1b-nF (SEQ ID NO:37)/P1b-nR (SEQ ID NO:38) was used to differentially amplify each genotype in the second-round PCR. The final PCR products of PTTV1a and PTTV1b were 162 by and 96 by in sizes, respectively, which could be easily distinguished by gel electrophoresis on a 1% agarose gel stained with ethidium bromide. This assay was not expected to detect PTTV2 DNA due to the specificity of primers (FIG. 20). In FIG. 20, conserved sequences were indicated by dots and shaded. Dashes indicated nucleotide deletions. The locations and directions of three pairs of primers used for duplex nested PCR were marked by arrows.

In one example, the 20 serum samples from adult boars that were subjected to the duplex nested PCR assay were all found to be positive for both PTTV1a and PTTV1b, as determined by visualizing two bands of the expected sizes and subsequent sequencing confirmation of PCR products (data not shown). No PCR products were amplified in the 19 semen samples, which was consistent with the results of PTTV1 conventional nested PCR and real-time PCR assays described above.

Infection of pigs with the two species of porcine TTV has been found back to 1985 in Spanish pig farms according to a retrospective investigation (Segales et al., 2009, supra). However, whether porcine TTVs are associated with any particular pig diseases remains elusive. Since both of porcine TTV species have a high prevalence in domestic pigs, determination of TTV viral loads is presumably more important than assessing the presence of TTV DNA. The level of viral loads in serum and semen samples has been indicated as an important marker for PCVAD in PCV2 infection (Opriessnig et al., 2007, supra). Therefore, establishment of quantitative PTTV-specific real-time PCR assays would help identify potential disease conditions associated with porcine TTVs.

Two TaqMan probe-based real-time PCR assays have recently been described. The singleplex assay developed by a Canadian group was not species-specific and was only designed to quantify the total viral loads of two PTTV species (Brassard et al., 2009, supra). The duplex assay established by a Germany group allowed the specific and simultaneous detection of both species (Gallei et al., 2009, supra). The target sequences of primers used in those two assays were determined by alignment of the three porcine TTV genomic sequences (Sd-TTV31, TTV-1p and TTV-2p) and were located in the UTR. In the present study, with 7 additional complete PTTV genomic sequences available (4 PTTV1 and 3 PTTV2 sequences), we analyzed and re-determined the conserved regions across the 10 full-length PTTV genomes. Based upon the updated alignment result from this study, two species-specific singleplex SYBR green-based real-time PCR assays were developed to quantify the viral loads of PTTV1 and PTTV2, respectively. The primers used in our assays were designed to bind to conserved genomic regions distinct from the previous studies, which may increase the accuracy of quantification. Our assays showed a considerable species-specificity and sensitivity of detection with 44 genomic copies for PTTV1 and 8.8 genomic copies for PTTV2 per 25-.mu.l reaction, whereas the detection limit of 10 genomic copies per reaction was reported in the TaqMan probe-based duplex real-time PCR (Gallei et al., 2009, supra). In addition, the SYBR green-based real-time PCR assay is a flexible and inexpensive approach that can be directly carried out without the need to use fluorescently labeled probes. Finally, considering porcine TTVs exhibit a high degree of genetic diversity, the results from SYBR green-based assays are unlikely affected by the different genetic background of porcine TTV variants that likely contain mutations in the probe-binding sequences in the TaqMan probe-based assays.

In spite of the presence of TTV DNA, all serum samples from healthy pigs tested in this study had low amounts of PTTV1 and PTTV2 that were less than $2 \times 10^6$ copies/ml. Moreover, only an extremely low titer of PTTV2 DNA was detected in three semen samples. Most of the tested serum samples were also positive for PCV2 DNA as determined by conventional nested PCR (data not shown). Many PCV2-positive pigs with low viral load do not develop clinical PCVAD. A proposed threshold for developing PCVAD is $10^7$ or greater PCV2 genomic copies/ml of serum (Opriessnig et al., 2007, supra). In addition, semen PCV2 DNA-positivity is also a notable marker of diseased status (Opriessnig et al., 2007, supra; Pal, N., et al. 2008. Development and validation of a duplex real-time PCR assay for the simultaneous detection and quantification of porcine circovirus type 2 and an internal control on porcine semen samples. J Virol Methods 149, 217-25). The situation of species-specific PTTV may be analogous to that of PCV2 and a high PTTV titer greater than $10^7$ copies/ml may be required for the induction of porcine diseases. The species-specific real-time PCR assays developed in this study will offer simple and practical tools for future investigations of PTTV association with diseases using a large number of clinical samples from various disease conditions.

Furthermore, by coupling the two species-specific singleplex assays, we developed and validated a quick, inexpensive and reliable screening for the simultaneous detection and differentiation of the two porcine TTV species, PTTV1 and PTTV2, in a MCA-based duplex real-time PCR assay. Although this assay is not intended for accurate quantification of both PTTV species, it is a more convenient approach that could replace the conventional nested PCR for detection purpose. In comparison with real-time PCR, the conventional nested PCR assay for porcine TTVs detection is time-consuming (requiring total 4 rounds of PCR), laborious and prone to sample contamination occurring during multiple rounds of PCR processing. Due to the difference of T.sub.m value between PTTV1 and PTTV2 species, an MCA following duplex PCR amplification is able to ensure distinct reaction specificity. Another advantage of this duplex real-time assay is that inclusion of PTTV1 and PTTV2 standards is dispensable when performing the described protocol, which makes it easier for much wider use in any diagnostic labs equipped with an automated real-time PCR instrument.

Multiple infection of porcine TTVs with distinct genotypes or subtypes of the same species has been demonstrated (Gallei et al., 2009, supra). In particular, our previous study showed that porcine TTV species 1 consists of two distinct types, PTTV1a (including strains Sd-TTV31 and PTTV1a-VA) and PTTV1b (including strains TTV-1p and PTTV1b-VA). The two newly published PTTV1 isolates with full-length genomes, swSTHY-TT27 (GQ120664) from Canada and FTV1 #471819 (GU188045) from Germany, were both classified into type 1b based upon the phylogenetic analysis (data not shown). The duplex nested PCR described in this study confirmed that dual infection of two PTTV1 genotypes frequently occurred in pigs. This novel assay is the first diagnostic PCR approach developed to distinguish between PTTV1a and 1b so far. Since it is currently not known whether one or both of PTTV1a and PTTV1b infection represents a relevant factor associated with diseases, our differential PCR assay should be of great value for future potential disease associations of these two PTTV types.

According to another aspect of the invention, porcine TTV ORF proteins were expressed and used in immunodetection assays to detect the presence of porcine TTV specific antibodies. In one embodiment of the present invention, three truncated and Histidine-tagged ORF1 proteins of PTTV1a, PTTV1b and PTTV2, were expressed and purified in *Escherichia coli* (*E. coli*), respectively. Furthermore, both serum Western blot and ELISA assays based on these recombinant antigens were developed and validated using porcine serum samples from different sources. In particular, serological testing using the PTTV1a-, PTTV1b- and PTTV2-specific ELISA provides an accurate and simple tool for revealing the association of porcine TTV infection with diseases.

According to a further aspect of the invention, porcine TTV ORF proteins were expressed and purified as recombinant ORF1 capsid protein in an *E. coli* expression system. Three truncated and His-tagged ORF1 capsid proteins of PTTV1a, PTTV1b and PTTV2, were expressed and purified in *Escherichia coli* (*E. coli*), respectively, and served as recombinant capsid subunit vaccines against PTTV infection.

Four porcine TTV2 strains, TTV-2p, TTV2#472142, PTTV2b-VA and PTTV2c-VA, had available complete genomic sequences to date. Although they are phylogenetically classified into three putative subtypes, a comparative analysis of hydrophilicity profiles of the ORF1 encoding amino acids from four PTTV2 showed that they shared three hydrophilic regions, an arginine-rich region from aa 1-49 at the N-terminal and two particular domains (I and II) located at the middle and C-terminal part, respectively. The C-terminal region used for truncated PTTV2c-VA ORF1 expression and the corresponding regions shared in other three PTTV2 strains were indicated by a dashed box. Alignments of amino acid sequences demonstrated high levels of sequence conservation of domains I (aa 322-349) and II (aa 536-625) across the four PTTV2 strains.

Since hydrophilic domains are believed to be important for the antigenicity of many proteins, the C-terminal region (aa 310-625) of the PTTV2c-VA ORF1 SEQ ID NO:16 containing the two domains was chosen for protein expression, which would be used as antigen for PTTV2-specific antibody detection in porcine serum. According to one aspect of the invention, expression of the truncated PTTV2c ORF1 was sufficient for detection of all PTTV2 subtypes (2a, 2b and 2c).

According to one embodiment of the present invention, the C-terminal part of the PTTV2c ORF1 gene fused with 8×His-tags was constructed and expressed in *E. coli*. The recombinant protein was insoluble and expressed within the bacterial inclusion bodies. SDS-PAGE of unpurified 2c-ORF1 products, purified 2c-ORF1 products and Western blot analysis of purified 2c-ORF1 products using an anti-His-tagged mAb was undertaken. The ORF1 protein with the expected size and its truncated product and the putative dimers of the expected and truncated proteins were observed. A band of ~40 KDa was consistent with the expected size of 2c-ORF1 whereas the ~30 KDa polypeptide was probably an N-terminally truncated product from the former. After purification with a nickel-affinity column, four polypeptides including the two described significant bands were showed in SDS-PAGE. They were also detected by western blot using an anti-His-tagged mAb. Two high-molecular-mass bands were the homodimers formed by the two polypeptides of ~40 KDa and ~30 KDa, respectively, based on the predicted sizes ~80 KDa and ~60 KDa). The results demonstrated that the purified C-terminal PTTV2c-ORF1 was successfully produced and could be used for porcine TTV2 antibody detection in porcine sera.

According to another aspect of the present invention, porcine TTV2 antibodies in various porcine serum samples can be detected by Western blot using purified C-terminal PTTV2c-ORF1. A total of more than 200 serum samples of conventional pigs (healthy or diseased), CD/CD pig's and gnotobiotic pigs from different sources were collected.

Samples were randomly selected for detection of anti-PTTV2c-ORF1 IgG antibodies using the purified C-terminal PTTV2c-ORF1 as antigen. Western blot analyses of selected porcine serum samples of conventional pigs, CD/CD pigs, and gnotobiotic pigs was undertaken. Purified PTTV2c-ORF1 products were used as the antigens. The two marked ~40 KDa and ~30 KDa bands were detected in most samples of the conventional pigs and CD/CD pigs, indicating widely PTTV2 infection in these pigs. However, all the gnotobiotic pigs from two different sources (Blacksburg, Va. and Ames, Iowa) had no detectable PTTV2 antibody. Additional low-molecular-mass bands were also observed. They were likely from non-specific reactivity in the Western blot.

According to yet another aspect of the present invention, PTTV2-specific ELISA can be used as a porcine TTV2 serological test. Seronegative results were also shown in a few samples from conventional pigs of a Wisconsin farm. These negative samples were pooled and used as a negative reference in development of a PTTV2-specific ELISA. The remaining samples from this source were positive. In addition, porcine sera from a commercial company used in cell culture (supposed to be OIE diseases-free) also displayed strong anti-PTTV2-ORF2 positivity, which was used as a positive control for ELISA. The concentrations of purified 2c-ORF1 antigen, porcine sera and IgG conjugate were determined by checkboard titration to present low background signal and give the highest difference of OD405 value between the positive and negative controls. The optimal antigen amount was 69 ng per well, and the optimal ELISA results were obtained by use of a 1:100 dilution of serum samples and a 1:4000 dilution of IgG conjugates. The ELISA cutoff values ranged from 0.25 to 0.5 in each trial.

138 conventional pig sera samples from 3 herds were chosen to analyze the correlation between PTTV2 viral load by real-time PCR and anti-PTTV2 IgG antibody level by ELISA. The results showed that pigs with undetectable or higher PTTV2 viral load ($10^8$ copies/ml) were more likely to have a lower serum PTTV2 antibody titer than pigs with middle values of PTTV2 viral load.

In particular, sera from 10 pigs in the same herd were also analyzed by comparing the PTTV2 viral loads and anti-PTTV2 antibody levels of their sera from their arrival in the new facility to two months after arrival. Nine of the 10 pigs had decreased viral loads (three had no detectable virus) after 2 months whilst the anti-PTTV2 antibody titers increased in nine of 10 pigs. The results suggested that the 10 pigs acquired PTTV2 infection at early stage, which induced humoral response and produced anti-ORF1 capsid IgG antibody progressively. The PTTV2-ORF1 IgG antibody was able to neutralize or even clear the virus, indicating the ORF1 indeed encode a viral capsid protein and may contain neutralizing epitopes against PTTV2.

According to one embodiment of the present invention, the C-terminal PTTV1a- and PTTV1b-ORF1 proteins were expressed and purified in E. coli system, respectively. SDS-PAGE and western blot analysis using an anti His-tagged mAb showed that both 1a- and 1b-ORF products had two polypeptides, one with expected size ~40 KDa) and another as the putative homodimer ~80 KDa). Compared to 2c-ORF1 expression, no truncated polypeptide was observed. As a comparative control, expression of a C-terminal-truncated 1 b-ORF1 region (1 b-ORF1ctruc) resulted in a lower-molecular-mass polypeptide compared to its C-terminal-non-truncated counterpart 1b-ORF1.

According one embodiment of the present invention, the purified C-terminal PTTV1a- and PTTV1b-ORF1 proteins were used to develop genotype-specific serum Western blots and ELISA as described for PTTV2 above.

Additionally, the present invention provides a useful diagnostic reagent for detecting the porcine TTV infection which comprise a monoclonal or polyclonal antibody purified from a natural host such as, for example, by inoculating a pig with the porcine TTV or the immunogenic composition of the invention in an effective immunogenic quantity to produce a viral infection and recovering the antibody from the serum of the infected pig. Alternatively, the antibodies can be raised in experimental animals against the natural or synthetic polypeptides derived or expressed from the amino acid sequences or immunogenic fragments encoded by the nucleotide sequence of the isolated porcine TTV. For example, monoclonal antibodies can be produced from hybridoma cells which are obtained from mice such as, for example, Balb/c, immunized with a polypeptide antigen derived from the nucleotide sequence of the isolated porcine TTV. Selection of the hybridoma cells is made by growth in hyproxanthine, thymidine and aminopterin in a standard cell culture medium like Dulbecco's modified Eagle's medium (DMEM) or minimal essential medium. The hybridoma cells which produce antibodies can be cloned according to procedures known in the art. Then, the discrete colonies which are formed can be transferred into separate wells of culture plates for cultivation in a suitable culture medium. Identification of antibody secreting cells is done by conventional screening methods with the appropriate antigen or immunogen. Cultivating the hybridoma cells in vitro or in vivo by obtaining ascites fluid in mice after injecting the hybridoma produces the desired monoclonal antibody via well-known techniques.

For another alternative method, porcine TTV capsid protein can be expressed in a baculovirus expression system or E. coli expression system according to procedures known in the art. The expressed recombinant porcine TTV capsid protein can be used as the antigen for diagnosis in an enzyme-linked immunoabsorbent Assay (ELISA). The ELISA assay based on the porcine recombinant capsid antigen, for example, can be used to detect antibodies to porcine TTV in porcine and mammalian species. Although the ELISA assay is preferred, other known diagnostic tests can be employed such as immunofluorescence assay (IFA), immunoperoxidase assay (IPA), etc.

Desirably, a commercial ELISA diagnostic assay in accordance with the present invention can be used to diagnose porcine TTV infection in pigs. The examples illustrate using purified ORF1 and ORF2 proteins of porcine TTV to develop an ELISA assay to detect anti-TTV antibodies in pigs. Sera collected from pigs infected with porcine TTV, and negative sera from control pigs are used to validate the assay. PTTV2 specific, PTTV1a specific, and PTTV1b specific antibodies were demonstrated to specifically recognize PTTV ORF proteins. Further standardization of the test by techniques known to those skilled in the art may optimize the commercialization of a diagnostic assay for porcine TTV.

Another aspect of the present invention is the unique immunogenic composition comprising the isolated porcine TTV or an antigenic protein encoded by an isolated polynucleotide described hereinabove and its use for raising or producing antibodies. The composition contains a nontoxic, physiologically acceptable carrier and, optionally, one or more adjuvants. Suitable carriers, such as, for example, water, saline, ethanol, ethylene glycol, glycerol, etc., are easily selected from conventional excipients and co-formulants may be added. Routine tests can be performed to ensure physical compatibility and stability of the final composition.

In accordance with the present invention, there are further provided infectious molecular and nucleic acid molecules of porcine Torque teno (TTV), live viruses produced from the nucleic acid molecule and veterinary vaccines to protect pigs from porcine TTV viral infection or disease caused by porcine TTV co-infection with other viruses. The invention further provides immunogenic polypeptide expression products that may be used as vaccines.

The novel infectious DNA molecule of porcine TTV comprises a nucleic acid molecule encoding at least a portion of an infectious PTTV1a-VA (SEQ ID NO:9), PTTV1b-VA (SEQ ID NO:10), PTTV2c-VA (SEQ ID NO:11), or PTTV2c-VA (SEQ ID NO:12) genome. The infectious PTTV DNA clone preferably contains at least one of ORF1, ORF2, ORF1/1, and ORF2/2 gene of the PTTV1 or PTTV2. Multiple copies of the PTTV1a-VA (SEQ ID NO:9), PTTV1b-VA (SEQ ID NO:10), PTTV2c-VA (SEQ ID NO:11), or PTTV2c-VA (SEQ ID NO:12) genome may be inserted into a single DNA molecule to construct tandem infectious PTTV clones.

The cloned genomic DNA of PTTV, particularly PTTV1a-VA, PTTV1b-VA, PTTV2c-VA, and tandem PTTV2b-RR, PTTV2c-RR, described herein is shown to be in vitro or in vivo infectious when transfected into PK-15 cells and given to pigs. This new, readily reproducible pathogenic agent lends itself to the development of a suitable vaccination program to prevent PTTV infection in pigs.

Figure 21A:
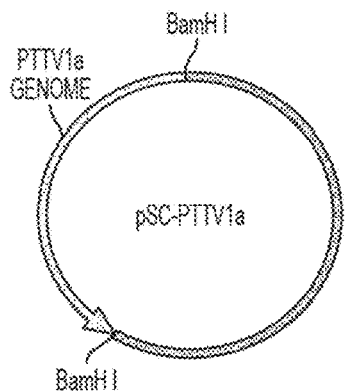
FIG. 21A-FIG. 21F represent the schematic diagrams of construction of full-length genomic DNA clones of porcine TTVs.
Figure 21B:
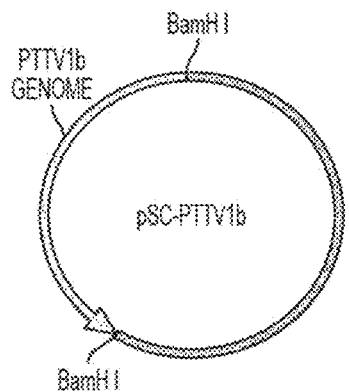
Figure 21C:
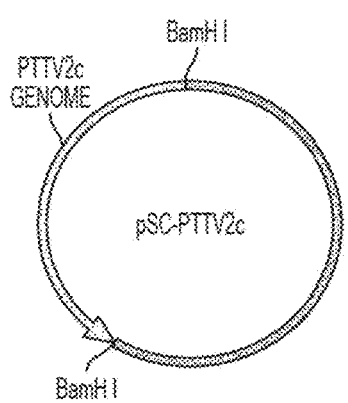

According to a further embodiment of the present invention, three one-genome-copy PTTV DNA clones were derived from the prototype US isolates PTTV1a-VA, PTTV1b-VA and PTTV2c-VA by fusion PCR, respectively. Each of the full-length genomic DNA was inserted into a cloning vector pSC-B-amp/kan by blunt-end ligation. The restriction site BamH1 is the unique site on the three PTTV genomes, which was engineered at both ends of the three genomes to facilitate the generation of concatemers and thus mimic the TTV circular genome. BamH1 single digestions of the selected plasmid DNA of each clone clearly resulted in two different fragments of 4.3-Kb and 2.8-Kb in size. The 4.3-Kb fragments represented the backbone vector whereas the 2.8-Kb fragments represented the inserted PTTV genomic DNA. The empty vector pSC-B-amp/kan digested with the same enzyme only showed a 4.3-Kb band. The resulting PTTV clones were designated pSC-PTTV1a, pSC-PTTV1b and pSC-PTTV2c, respectively (FIG. 21A-C).

Figure 21D:
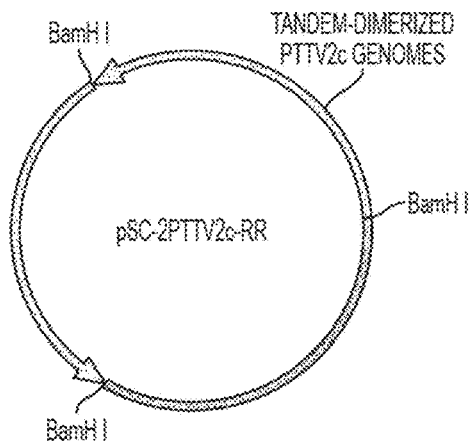

Furthermore, two copies of the full-length PTTV2c-VA genome derived from the clone pSC-PTTV2c were ligated in tandem into the pSC-B-amp/kan vector to generate the clone pSC-2PTTV2c-RR (FIG. 21D). Comparison of the Afl II single digestion patterns between pSC-PTTV2c and pSC-2PTTV2c-RR showed that the latter plasmid had an additional 2.8-Kb fragment representing the second copy of PTTV2c genome. Subsequently, we utilized the same cloning strategy to produce a tandem-dimerized PTTV2b DNA clone derived from the Germany TTV clone TTV2-#471942-full. An additional 2.8-Kb fragment representing the second copy of PTTV2b genome was presented in this construct, designated pSC-2PTTV2b-RR (FIG. 21F), which was digested with the Hind III alone when compared to its one-genome-copy counterpart, confirming the successful construction.

The replication competencies of the constructed PTTV infectious clones were tested by in vitro transfection of PK-15 cells. IFA using the commercially generated rabbit polyclonal antibodies against PTTV2c ORF1 confirmed that both the concatemers of clones TTV2-#471942-full and pSC-PTTV2c were replication competent, respectively. Passaging of the transfected cells did not eliminate or reduce the fluorescent signals, suggesting that the expression of ORF1 proteins was resulted from the PTTV2 concatemers that mimicked the natural PTTV2b or PTTV2c circular molecules. No fluorescent signals was observed in mock-transfected cells or DNA-transfected cells using pre-immune rabbit serum as the antibody for IFA detection (data not shown). The concatemers of the clone pSC-PTTV1a also showed to be replication-competent using an anti-PTTV1a ORF1 antibody. The positive fluorescent signals were located in the nucleus of transfected or passaged cells, indicating that porcine TTVs likely replicate in the cell nucleus. It is not unexpected because porcine circovirus (PCV) has a similar expression pattern in vitro.

Direct transfection of the tandem-dimerized clone pSC-2PTTV2b-RR or pSC-2PTTV2c-RR in PK-15 cells results in viral replication and produces the ORF1 capsid antigen. IFA using antibodies against PTTV2 ORF1 confirmed that both clones were also replication-competent and the positive ORF1 antigens were localized in the nuclei.

According to one embodiment of the present invention, infectious clones of porcine TTV can be used to inoculate pigs, which will then elicit an immune response of the host animal and stimulate production of neutralizing antibodies. In one particular embodiment of the present invention, the two tandem-dimerized PTTV2 clones were infectious when injected into the lymph nodes and muscles of conventional pigs.

Figure 22A:
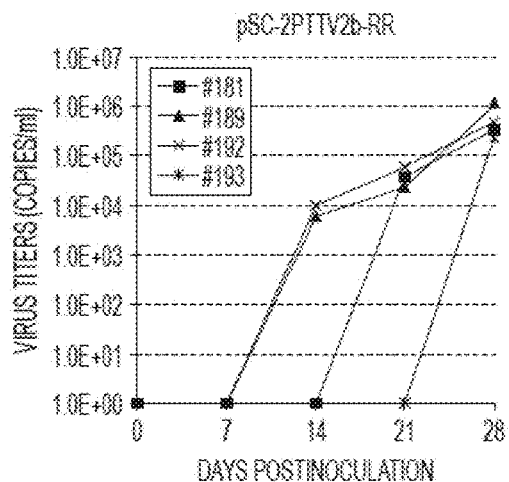
FIG. 22A-FIG. 22D represent the determination of the in vivo infectivity of the two porcine TTV2 DNA clones, pSC-2PTTV2b-RR and pSC-2PTTV2c-RR, in conventional pigs, respectively.
Figure 22B:
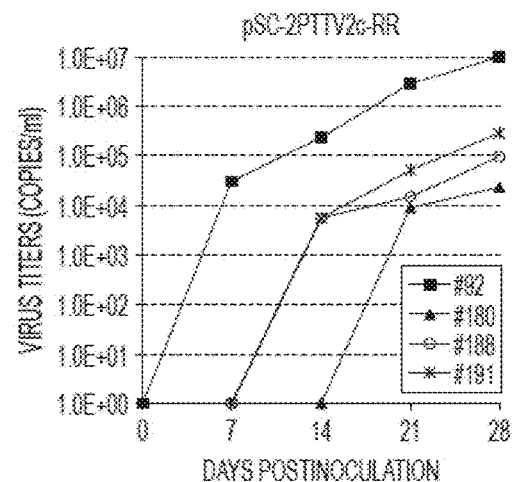

To test the in vivo infectivity of PTTV2 molecular clones, conventional pigs were inoculated with the clone pSC-2TTV2b-RR or pSC-2TTV2c-RR. Serum samples were collected from animals at 0, 7, 14, 21 and 28 days post-inoculation (DPI). PTTV2 DNA was detected in pSC-2TTV2c-RR-inoculated pigs beginning at 7 DPI (#92), 14 DPI (#188 and #191) and 21 DPI (#180), respectively (FIG. 22B). PTTV viremia appeared late for pigs inoculated with the clone pSC-2TTV2b-RR: two began at 14 DPI (#189 and #192), one at 21 DPI (#181) and one at 28 DPI (#193) (FIG. 22A). The viral loads increased during the course in all inoculated pigs that had the highest viral loads at 28 DPI before necropsy, as determined by PTTV2-specific real-time PCR (FIG. 22A and FIG. 22B). The real-time PCR products amplified from selected pigs were sequenced and found to have identical sequences to the corresponding regions of pSC-2TTV2b-RR or pSC-2TTV2c-RR (data not shown).

Figure 22C:
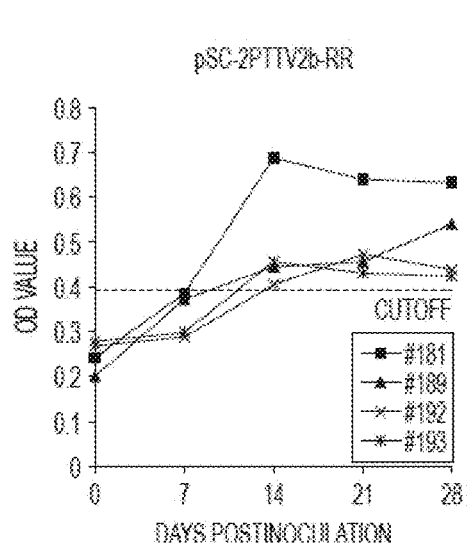
Figure 22D:
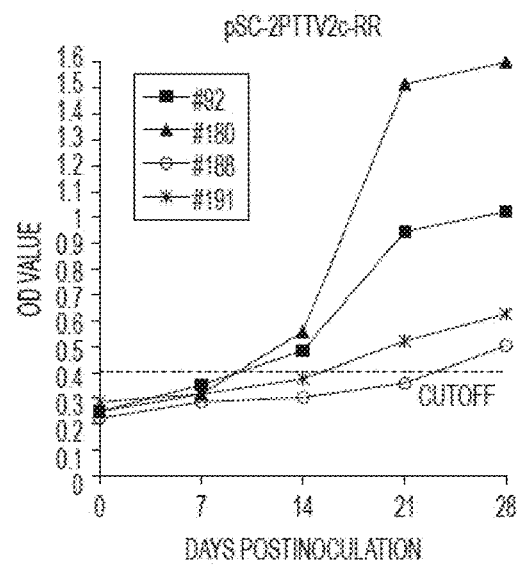

All inoculated pigs were negative for PTTV2 ORF1 antibodies at 0 and 7 DPI. At 14 DPI, all the four pSC-2TTV2b-RR-inoculated pigs seroconverted to anti-PTTV2 ORF1 IgG, whereas pigs in pSC-2TTV2c-RR-inoculated group seroconverted at 14 (#92 and #180), 21 (#191) and 28 (#188) DPI, respectively (FIG. 22C and FIG. 22D). The results indicated that active porcine TTV2b or TTV2c infection had occurred.

FIG. 1 is a schematic diagram of TTSuV2 constructs containing full-length TTSuV2 genomic DNA. FIG. 1(A) pSC-PTTV2c (from the U.S. TTSuV2 isolate PTTV2c-VA; GenBank accession no. GU456386; SEQ ID NO:12). FIG. 1(B) pSC-2PTTV2c-RR (tandem-dimerized PTTV2C-VA genomes). FIG. 1(C) pSC-TTV2-#471942 (from the German TTSuV2 isolate TTV2-#471942; GenBank accession no. GUI88046; SEQ ID NO:62). FIG. 1(D) pSC-2PTTV2b-RR (tandem-dimerized TTV2-#471942 genomes). FIG. 1(E) pSC-TTV2-EU (derived from pSC-TTV2-#471942). A HpaI site as the silent genetic marker was introduced in this clone.

Figure 1A:
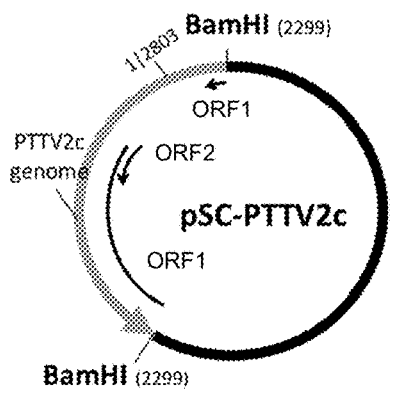
FIG. 1(A)-FIG. 1(G) represent schematic diagrams of TTSuV2 constructs containing full-length TTSuV2 genomic DNA.
Figure 1B:
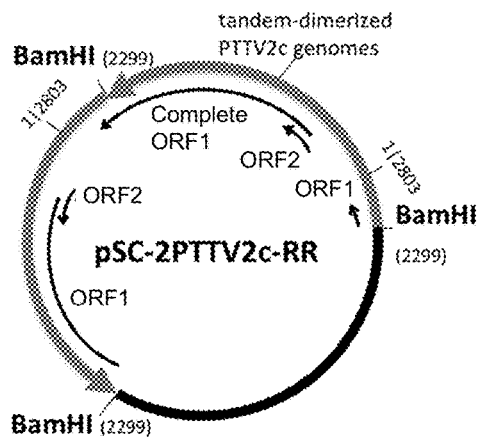
Figure 1C:
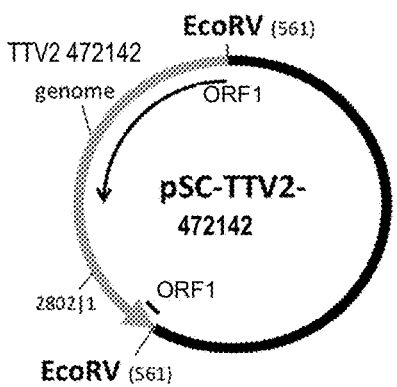
Figure 1D:
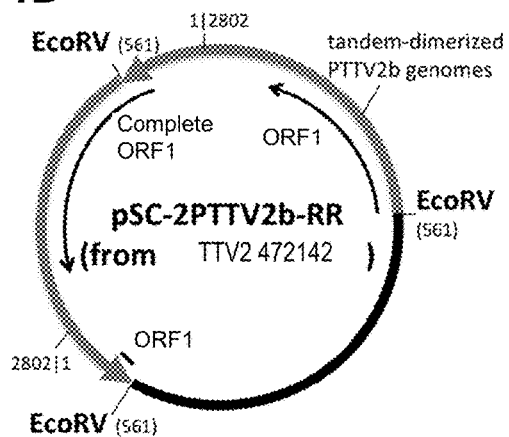
Figure 1E:
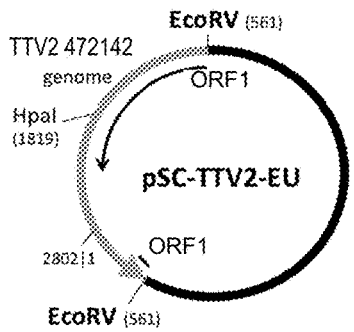
Figure 1F:
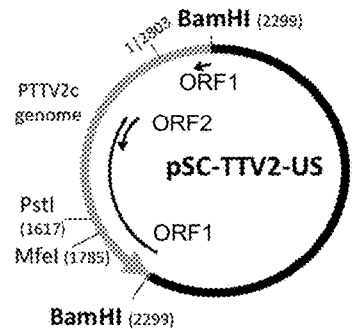
Figure 1G:
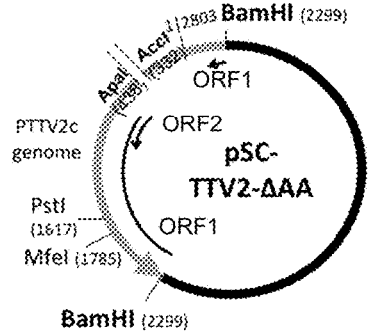
Figure 2A:
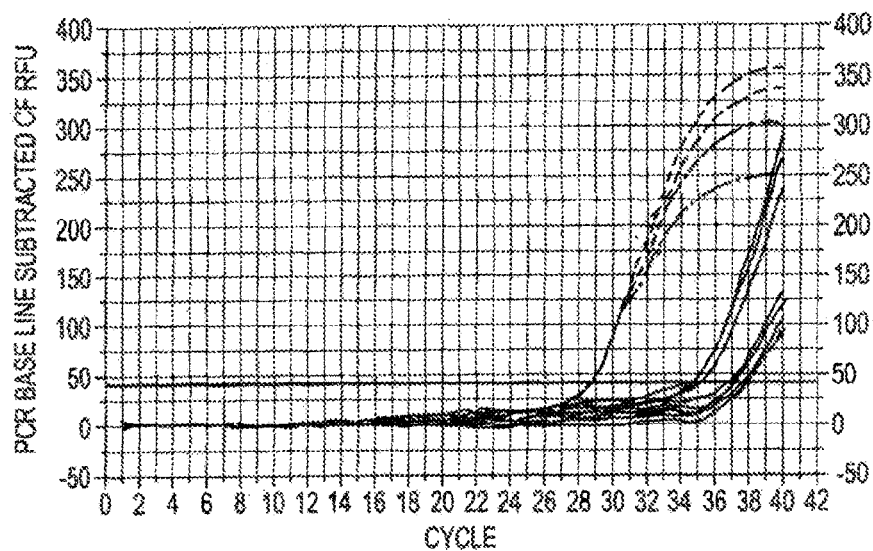
FIG. 2(A)-FIG. 2(E) illustrate detection of TTsuV1 or TTsuV2 contamination in live different cell lines (PCV1-free PK-15, 3D4/31, IPEC/J2, BHK-21 and MARC-145) and an CHE diseases-free porcine serum by real-time qPCR. Fluorescence curves (FIG. 2(A) and FIG. 2(C)) and melting curves (FIG. 2(B) and FIG. 2(D)) of TTsuV1 (FIG. 2(A) and FIG. 2(B)) or TTsuV2 (FIG. 2(C) and FIG. 2(D)) qPCR products are shown after 40 cycles of amplifications of the standard template with the minimum dilution limit ($10^{-4}$ pg; indicated by red), five different cell lines (blue) and the porcine serum (green). For each sample, duplicate determinations were made.
Figure 2B:
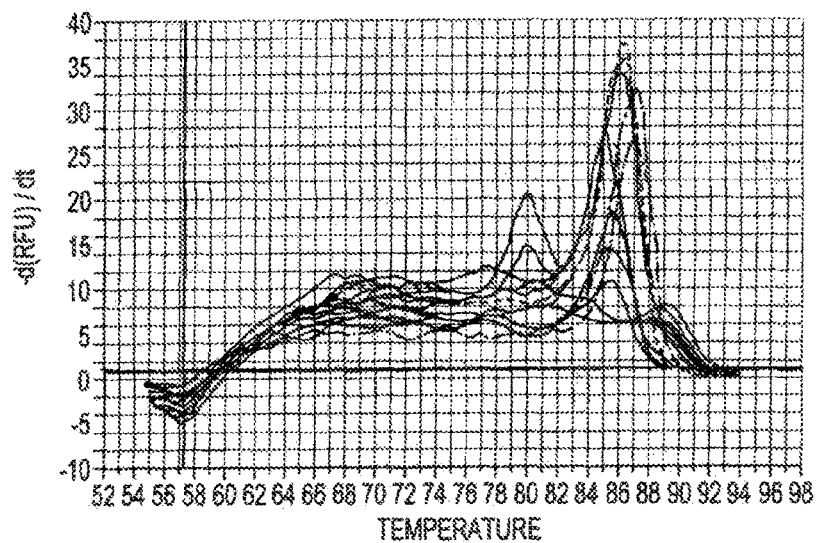
Figure 2C:
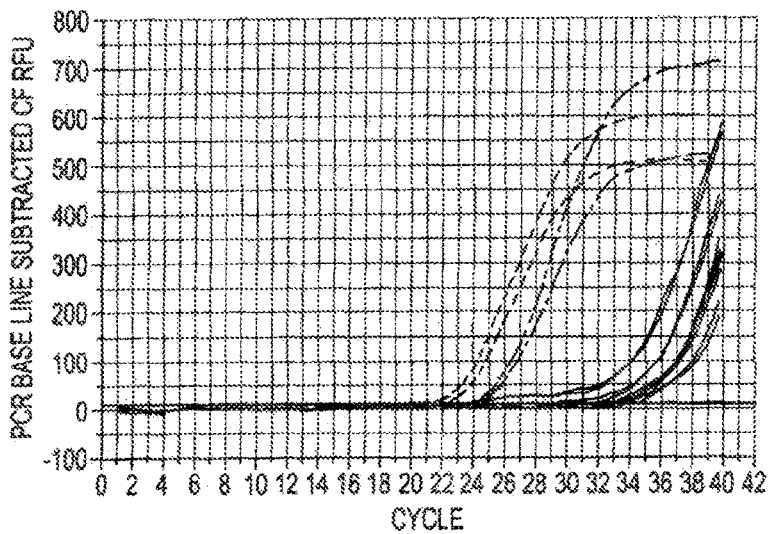
Figure 2D:
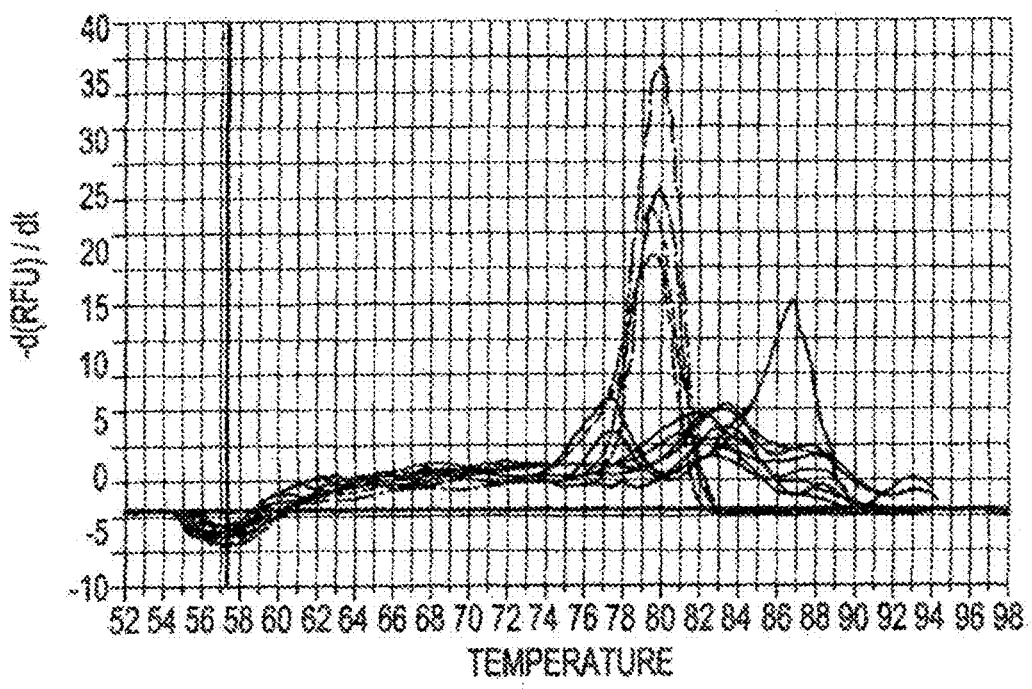
Figure 2E:
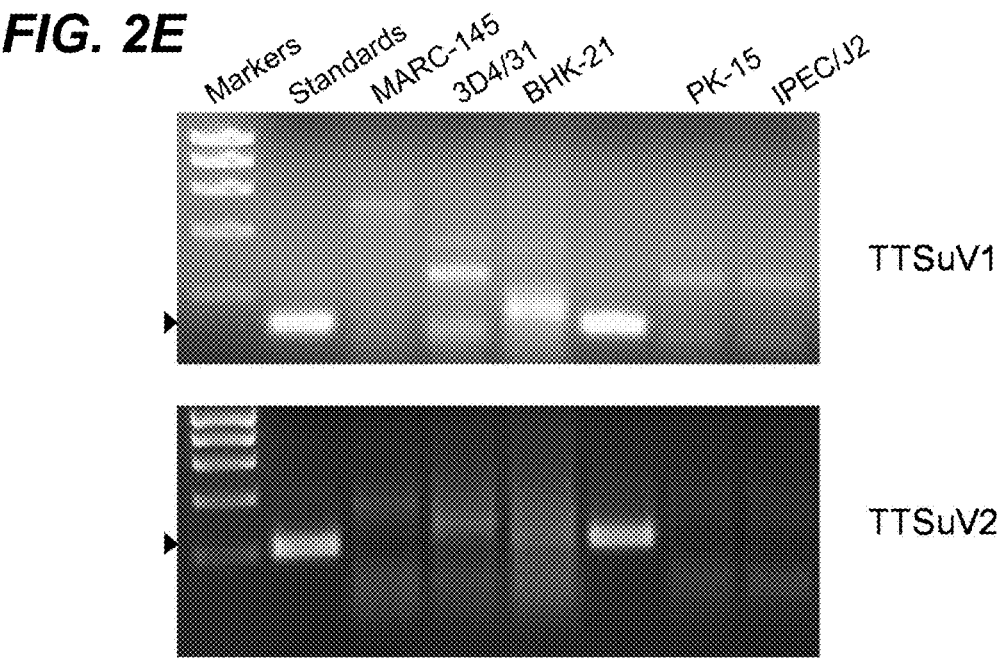

FIG. 1(F) pSC-TTV2-US (derived from pSC-PTTV2c). PstI and MfeI sites as the silent genetic markers were introduced in this clone. FIG. 1(G) pSC-TTV2-AAA. A 104-bp deletion mutation was introduced between the AccI and ApaI sites ranging from the putative TATA box to the ORF1 start codon on the clone pSC-TTV2-US. The restriction enzymes (BamHI or EcoRV) used for plasmids constructions are shown. The plasmid backbone used for cloning was the pSC-B-amp/kan vector (indicated by black). Grey arrows indicate the TTSuV2 genomic copies.

In the present invention, the inventors describe the construction and initial characterization of full-length DNA clones of TTSuV2 in vitro and in vivo. The inventors provide, for the first time, definite evidence of splicing of TTSuV2 mRNA and expression of the putative ORF1 capsid protein by transfection of the TTSuV2 full-length DNA clones in cultured cells. Furthermore, rescue of TTSuV2 containing the introduced genetic markers in pigs was confirmed by sequencing of viral DNA obtained from pigs experimentally inoculated with the circular TTSuV2 genomic DNA. Anellovirus is a group of single-stranded circular DNA viruses infecting human and various other animal species. Animal models combined with reverse genetics systems of anellovirus have not been developed. The inventors report here the construction and initial characterization of full-length DNA clones of a porcine anellovirus, Torque teno sus virus 2 (TTSuV2), in vitro and in vivo. The inventors first demonstrated that five cell lines including PK-15 are free of TTSuV1 or TTSuV2 contamination, as determined by real-time PCR and immunofluorescence assay (IFA) using rabbit anti-TTSuV ORF1 sera. Recombinant plasmids harboring monomeric or tandem-dimerized TTSuV2 genomic DNA that originated from the United States and Germany were constructed. Circular TTSuV2 genomic DNA with or without introduced genetic markers and tandem-dimerized TTSuV2 plasmids were transfected into the PK-15 cells, respectively. Splicing of viral mRNAs was identified in transfected cells. Expression of TTSuV2-specific ORF1 in cell nuclei, especially in nucleoli, was detected by IFA. However, evidence of productive TTSuV2 infection was not observed in 12 different cell lines including the 293TT cell line transfected with the TTSuV2 DNA clones. Transfection with circular DNA from a TTSuV2 deletion mutant did not produce ORF1 proteins, suggesting that the observed ORF1 expression in this study is driven by TTSuV2 DNA replication in cells. Pigs inoculated with either the tandem-dimerized plasmids or circular DNA derived from the U.S. strain of TTSuV2 containing genetic markers developed viremia, and the introduced genetic markers were retained in viral DNA extracted from the sera of infected pigs. The availability of an infectious DNA clone of TTSuV2 will facilitate future study of porcine anellovirus pathogenesis and biology.

Neither the viral DNA nor the expression of the putative ORF1 capsid protein of TTSuV1 or TTSuV2 was endogenously present in five representative cell lines tested in this study. The present study first aimed to identify potential permissive cell lines supporting the TTSuV propagation. The inventors selected five commonly-used cell lines including three that are of pig origin: PCV1-free PK-15, 3D4/31 and IPEC-J2, and two other cell lines including BHK-21 and MARC-145. These cell lines are known to be permissive for a wide variety of animal virus infections. In order to rule out the possibility of endogenous contamination of TTSuV1 or TTSuV2 in cultured cell lines, both viral DNA and ORF1 protein expression were subjected to TTSuV1 or TTSuV2 real-time qPCR and IFA detections, respectively. An OIE diseases-free porcine serum, which had been shown to have a high level of anti-TTSuV2 ORF1 antibody, was also included as a control (Huang, Y. W., et al. 2011. Virus Res 158:79-88). The results obtained with the qPCR analysis showed that none of the five cell lines tested in the study were positive for TTSuV1 or TTSuV2 DNA, as determined by the analyses of fluorescence curves, melting curves and agarose gel electrophoresis, since their fluorescence curves were below the minimum detection limit, their melting curves did not overlap with that of the standards, and there were no detectable specific bands corresponding to the expected PCR products (FIG. 2). In contrast, as expected, the commercial porcine serum was positive for TTSuV1 and TTSuV2 DNA (FIG. 2).

Neither the viral DNA nor the expression of the putative ORF1 capsid protein of TTSuV1 or TTSuV2 was endogenously present in five representative cell lines tested in this study. The present study first aimed to identify potential permissive cell lines supporting the TTSuV propagation. The inventors selected five commonly-used cell lines including three that are of pig origin: PCV1-free PK-15, 3D4/31 and IPEC-J2, and two other cell lines including BHK-21 and MARC-145. These cell lines are known to be permissive for a wide variety of animal virus infections. In order to rule out the possibility of endogenous contamination of TTSuV1 or TTSuV2 in cultured cell lines, both viral DNA and ORF1 protein expression were subjected to TTSuV1 or TTSuV2 real-time qPCR and IFA detections, respectively. An OIE diseases-free porcine serum, which had been shown to have a high level of anti-TTSuV2 ORF1 antibody, was also included as a control (Huang, Y. W., et al. 2011. Virus Res 158:79-88). The results obtained with the qPCR analysis showed that none of the five cell lines tested in the study were positive for TTSuV1 or TTSuV2 DNA, as determined by the analyses of fluorescence curves, melting curves and agarose gel electrophoresis, since their fluorescence curves were below the minimum detection limit, their melting curves did not overlap with that of the standards, and there were no detectable specific bands corresponding to the expected PCR products (FIG. 2). In contrast, as expected, the commercial porcine serum was positive for TTSuV1 and TTSuV2 DNA (FIG. 2).

To develop cell-based serological methods such as IFA or immunoperoxidase monolayer assay (IPMA) for TTSuV detection, the inventors raised three specific antisera against the putative ORF1 capsid protein of TTSuV1a, TTSuV1b (Huang, Y. W., et al. 2012. Serological profile of Torque teno sus virus species 1 (TTSuV1) in pigs and antigenic relationships between two TTSuV1 genotypes (1a and 1b), between two species (TTSuV1 and 2), and between porcine and human anelloviruses. J. Virol. Submitted Manuscript) or TTSuV2 in rabbits. When the five cell lines were stained with each of the three virus-specific antisera, respectively, no positive fluorescence signals were detected, indicating the absence of endogenous TTSuV1 or TTSuV2 ORF1 expression (data not shown). The IFA results were consistent with the qPCR detection, which demonstrated that the five selected cell lines were not contaminated with TTSuV1 or TTSuV2 and thus can be used for testing the susceptibility of TTSuV infection or replication by transfection with TTSuV2 DNA clones.

Construction and characterization of full-length TTSuV2 DNA clones in porcine kidney PK-15 cells. The inventors were particularly interested in characterizing the infectivity of TTSuV2 full-length DNA clone since TTSuV2 has been reported to be associated with PMWS or PCVAD at a high prevalence rate of viral DNA (Kekarainen, T., et al. 2006. J Gen Virol 87:833-7), a high viral load (Aramouni, M., et al. 2011. Vet Microbiol 153:377-81) and a low antibody level in disease-affected pigs with an unknown mechanism (Huang, Y. W., et al. 2011. Virus Res 158:79-88). The inventors first generated two monomeric full-length TTSuV2 DNA clones, pSC-PTTV2c and pSC-TTV2-#471942, derived from a prototype U.S. isolate PTTV2c-VA and a German isolate TTV2-#471942, respectively (FIGS. 1A & 1C) (Gallei, A., et al. 2010. Vet Microbiol 143:202-12; Huang, Y. W., et al. 2010. Virology 396:287-97). Each of the full-length TTSuV2 genomic DNA was inserted into a cloning vector pSC-B-amp/kan that does not contain a eukaryotic promoter. The restriction site BamHI or EcoRV is the unique site on the PTTV2c-VA or TTV2-#471942 genome, which was engineered at both ends of genomic DNA to facilitate the generation of concatemers and thus to mimic the TTSuV circular DNA genome. BamHI or EcoRV single digestion of the plasmid DNA of each clone clearly resulted in two different fragments of 4.3-Kb and 2.8-Kb in size. The 4.3-Kb fragment represented the backbone vector whereas the 2.8-Kb fragment represented the inserted monomeric TTSuV2 genomic DNA (data not shown).

Figure 3A:
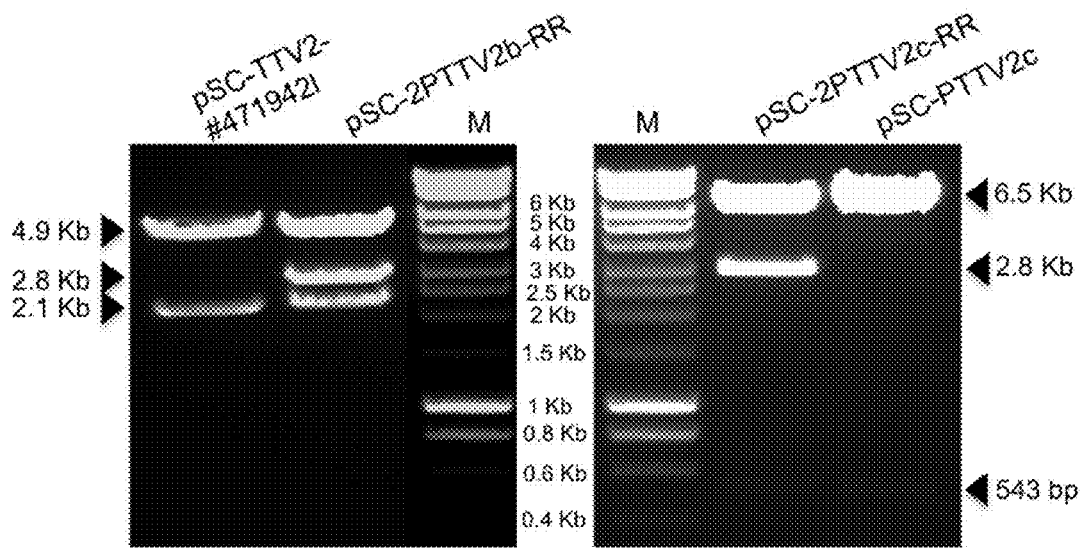
FIG. 3(A) and FIG. 3(B) illustrate identification and quality assessment of linear or circular TTsuV2 genomic DNA.

Subsequently, two copies of the full-length PTTV2c-VA genome from the clone pSC-PTTV2c were ligated in tandem into the pSC-B-amp/kan vector to generate the clone pSC-2PTTV2c-RR (FIG. 1B). Comparison of the AflII single digestion patterns between pSC-PTTV2c and pSC-2PTTV2c-RR showed that the latter clone had an additional 2.8-Kb fragment representing the intact single TTSuV2 genomic DNA (FIG. 3A, right panel). The inventors utilized the same cloning strategy to produce a tandem-dimerized TTSuV2 DNA clone, pSC-2PTTV2b-RR, derived from pSC-TTV2-#471942 (FIG. 1D). Similarly, when digested with HindIII alone, an additional 2.8-Kb fragment representing the intact single TTSuV2 genome was presented in this construct, compared to its monomeric parent clone (FIG. 3A, left panel), thus confirming the successful construction of the clone.

Figure 3B:
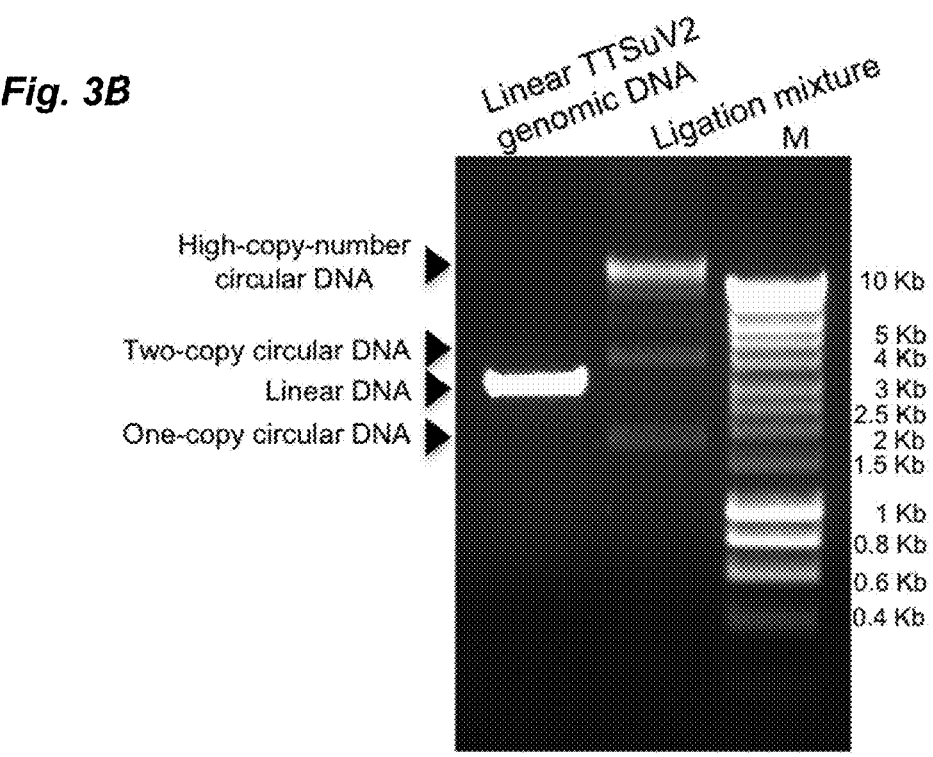

Circular TTSuV2 DNA was generated by tandem ligation of the purified linear TTSuV2 genomic DNA excised from the clone pSC-PTTV2c or pSC-TTV2-#471942. Typical monomer, dimer and high-copy-molecules of concatemerized TTSuV2 DNA were observed in the ligation products (FIG. 3B). The ligation mixture from PTTV2c-VA or TTV2-#471942 was transfected into PCV1-free PK-15 cells. IFA conducted at five days post-transfection, using the rabbit antiserum against PTTV2c-VA ORF1, indicated that TTSuV2 ORF1 antigen was expressed in the nuclei of the transfected cells with approximately 5% positive rate (FIGS. 4A & 4C). No fluorescent signal was observed in mock-transfected cells stained with the same anti-TTSuV2 serum (FIG. 4E) or in circular TTSuV2 DNA-transfected cells stained with the anti-TTSuV1a ORF1, anti-TTSuV1b ORF1 (Huang, Y. W., et al. 2012. Serological profile of Torque teno sus virus species 1 (TTSuV1) in pigs and antigenic relationships between two TTSuV1 genotypes (1a and 1b), between two species (TTSuV1 and 2), and between porcine and human anelloviruses. J. Virol. Submitted Manuscript) or pre-bleed rabbit serum (data not shown). Passaging of the transfected cells for two times did not eliminate but reduced the fluorescent signal (data not shown). When the transfected cells were continuously passaged for up to 20 passages, no positive signal was detectable, suggesting that TTSuV2 infection did not occur (data not shown).

The inventors next tested whether direct transfection of plasmid DNA of the tandem-dimerized clone pSC-2PTTV2c-RR or pSC-2PTTV2b-RR into PK-15 cells resulted in the synthesis of TTSuV2 ORF1. The tandem-dimerized double-stranded DNA does not represent genomic anellovirus DNA but might represent an infectious replicative intermediate. IFA at 5 days post-transfection using the same anti-TTSuV2 ORF1 antiserum confirmed that both DNA clones also expressed ORF1 in transfected PK-15 cells (FIGS. 4B & 4D). Again, the ORF1 was expressed in cell nuclei. However, the fluorescent intensity and positive rate were lower than that in circular TTSuV2 DNA-transfected cells (FIGS. 4B & 4D). The inventors did not observe the localization of ORF1 antigen in the cytoplasm of the transfected cells.

Experimental identification of two introns in the TTSuV2 genome. Although the transcriptional profile using cloned TTSuV full-length genomic DNA has not been reported, we previously speculated that TTSuV likely expresses two essential viral mRNA transcripts, mRNA1 and mRNA2, to produce the four known ORF counterparts of human TTV (FIG. 5A) (Huang, Y. W., et al. 2010. Virology 396:287-97). The continuous mRNA1 encodes ORF1 and ORF2 whereas removal of the putative intron of 1341 nt (designated intron 1 here), corresponding to nt positions 648-1988 in PTTV2c-VA genome, generates the putative mRNA2 that encodes two discontinuous ORFs, ORF 1/1 and ORF2/2 (Huang, Y. W., et al. 2010. Id.). The inventors also speculated that more spliced mRNAs and their encoding proteins of TTSuV may exist, as shown in human TTV (Mueller, B., et al. 2008. Virology 381:36-45; Qiu, J., et al. 2005. J Virol 79:6505-10).

Figure 5A:
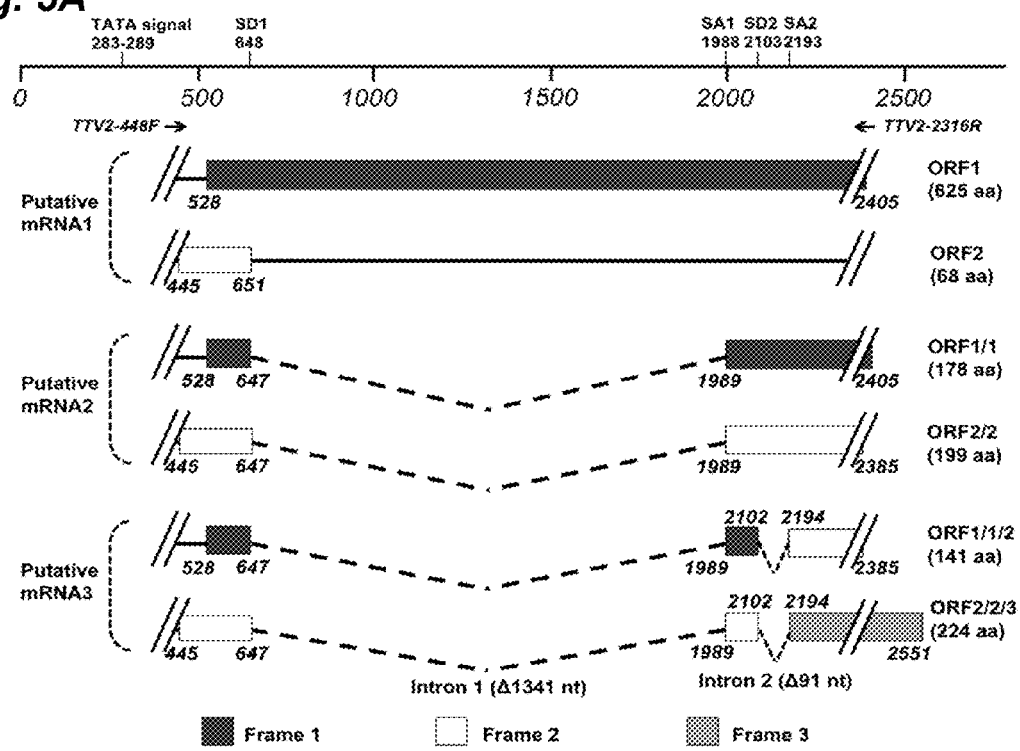
FIG. 5(A)-FIG. 5(C) illustrate the putative transcription profile and protein expression of TTSuV2 based on the PTTV2c-VA genome (a fragment of nucleotides which correspond to nucleotides 1-2500 of SEQ ID NO:12).
Figure 5B:
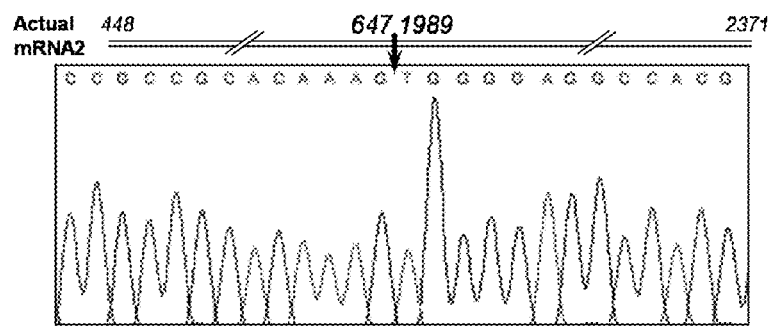
Figure 5C:
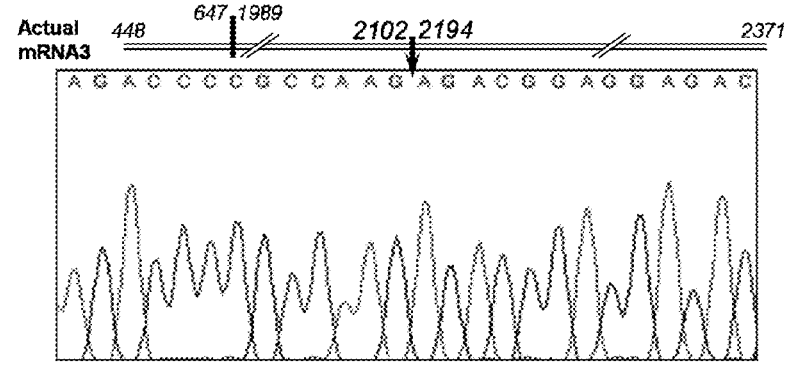

To verify whether the splicing of the putative intron 1 in TTSuV2 occurred, total RNA was extracted in PK-15 cells transfected with circular PTTV2c-VA DNA followed by DNase I treatment and RT-PCR analysis. Two PCR product bands of approximately 500 bp and 600 bp in sizes were visualized by agarose gel electrophoresis. Sequencing of the cloned PCR fragments resulted in the identification of two sequences. As expected, the large cDNA fragment of 583 bp was exactly the intron 1-spliced product (FIG. 5B), whereas the small cDNA product of 492 bp contained two splicing regions including the intron 1 and an additional 91-nt intron, corresponding to nt positions 2103-2193 in PTTV2c-VA genome, which was designated intron 2 in this study (FIG. 5C). The splicing sites are conserved among all published TTSuV2 sequences (data not shown). Therefore, in this study for the first time the inventors experimentally demonstrated the existence of splicing of intron 1 and the viral mRNA2 transcripts. The inventors also identified a novel viral mRNA transcript, termed mRNA3, which encodes two putative proteins, ORF1/1/2 and ORF2/2/3, and which switches reading frames from 1 to 2, and 2 to 3, respectively, due to splicing of intron 2 (FIG. 5A). The mRNA3 transcript contains at least three exons on the TTSuV2 genome. Since the inventors failed to determine the 5'- and 3'-ends of the viral mRNA transcripts by rapid amplification of cDNA ends (RACE)-PCR, it is possible that there exists an additional TTSuV2 intron in the upstream of ORF2, as known in human TTV transcripts (Mueller, B., et al. 2008. Virology 381:36-45). However, human TTV genome does not contain a short intron corresponding to the TTSuV intron 2 in the downstream of the large intron (intron 1).

Nevertheless, transfection of PK-15 cells with circularized TTSuV2 genomic DNA resulted in the synthesis of viral mRNA transcripts and the expression of ORF1 protein, indicating that the TTSuV2 concatemers mimicked the transcription and protein expression from the natural circular genome of TTSuV2.

A tandem-dimerized TTSuV2 clone, pSC-2PTTV2c-RR, is infectious when inoculated in the CD pigs. To test the infectivity of TTSuV2 DNA clones in pigs, the inventors first performed a pilot study with three groups of CD pigs with two pigs per group. The pigs were inoculated with PBS buffer (pig nos. 1 and 2) in group 1, the tandem-dimerized clone pSC-2TTV2c-RR (pig nos. 3 and 4) in group 2, and pSC-2TTV2b-RR (pig nos. 5 and 6) in group 3, respectively. Serum samples were collected from animals at 0, 7, 14, 21, 28, 35 and 42 days post-inoculation (DPI). Pig no. 2 died of septicemia due to an unidentified bacterial infection shortly after inoculation.

TTSuV2 DNA was detected in two pigs inoculated with pSC-2TTV2c-RR beginning at 28 DPI by real-time qPCR. The viral loads, although very low, increased weekly until 42 DPI before necropsy at 44 DPI in both pigs. The viral loads in serum of pig no. 3 increased from $1.93 \times 10^3$ at DPI 28 to $5.59 \times 10^3$ at DPI 35 and $4.36 \times 10^4$ at DPI 42 whereas the serum viral loads in pig no. 4 elevated from $5.07 \times 10^3$ at DPI 28 to $4.49 \times 10^4$ at DPI 35 and $8.87 \times 10^4$ at DPI 42. Moderate microscopic lesions in brain (lymphoplasmacytic encephalitis mainly perivascular), liver (lymphohistiocytic hepatitis) and kidney (lymphoplasmacytic interstitial nephritis) were observed in pig no. 3 but not in no. 4. The remaining three pigs including pigs inoculated with the clone pSC-2TTV2b-RR did not develop viremia throughout the study. However, pig no. 5 had mild lymphohistiocytic multifocal hepatitis. The results from this pilot pig experiment indicated that the clone pSC-2PTTV2c-RR originated from a U.S. strain of TTSuV2 is infectious.

Characterization of two TTSuV2 full-length DNA clones with engineered genetic markers and a derived mutant clone in vitro. To further rule out the possible contamination of other indigenous TTSuV2 infections in the pilot animal study, it is critical to introduce tractable genetic markers in the TTSuV2 genome so that the cloned virus and the potential indigenous contaminating virus in pigs can be discriminated in inoculated animals. The inventors introduced a unique HpaI restriction site and two unique restriction sites, PstI and MfeI, into two TTSuV2 monomeric DNA clones pSC-TTV2-#471942 and pSC-PTTV2c to produce two new clones pSC-TTV2-EU and pSC-TTV2-US, respectively (FIGS. 1E and 1F). The positions of these sites, located in the intron 1, were expected to not change the putative ORF1 capsid amino acid sequence. PK-15 cells were transfected with ligation mixtures of the linear TTSuV2 genomic DNA excised from these two marker clones, respectively. The ORF1 expression in nuclei of the transfected cells was detected by IFA at 3 days post-transfection, similar to the patterns of their parental clones (FIG. 6), indicating that the clones with introduced genetic markers are replication competent.

A mutant clone pSC-TTV2-AAA with a 104-bp deletion (nt positions 332-437) from the putative TATA box (nt positions 283-289; FIG. 5A) to the ORF1 (nt 528) and ORF2 (nt 445) start codons was generated based on the clone pSC-TTV2-US (FIG. 1G). When transfected into the PK-15 cells, the circularized DNA from this mutant clone did not express the ORF1 antigen (FIG. 6), suggesting that the deleted region likely contains a cis-acting element important for viral mRNA transcription or TTSuV2 ORF1 translation. The result of the deletion mutant clone also implied that the observed expression of ORF1 is likely driven by the replication-competent TTSuV2 DNA since the tandem-dimerized clone and concatemerized ligation products from the parental PTTV2c-VA genome were both infectious in pigs (see below).

Expression of the TTSuV2 ORF1 protein in various cell lines transfected with the circularized TTSuV2 DNA from the clone pSC-TTV2-US. From the in vitro transfection experiments described above, it appeared that, although the TTSuV2 putative ORF1 capsid protein is expressed, the PK-15 cells do not support the cell-to-cell spread of TTSuV2 recovered from the introduced TTSuV2 DNA clones. Alternatively, it is possible that the assembly of TTSuV2 virions in the transfected PK-15 cells may be deficient. To search for another cell line that may be permissive for TTSuV2 infection, the inventors subsequently transfected eleven other different cell lines with the circularized TTSuV2 DNA from the clone pSC-TTV2-US, respectively. These cell lines included the four cell lines (3D4131, IPEC-J2, BHK-21 and MARC-145) that were tested negative for TTSuV1 or TTSuV2 at both the DNA and protein levels. The plain cells of the other seven cell lines (ST, Vero, and 293TT, HeLa, Huh-7, HepG2 and CHO-K1) were also negative for TTSuV2 ORF1 as determined by IFA (data not shown).

After transfection, all the eleven cell lines expressed the ORF1 protein at 3 days post-transfection (FIG. 7; the results of BHK-21 and CHO-K1 not shown). The percentages of transfected cells with positive IFA signals were subjectively categorized into three levels: IPEC-J2, ST, PCV1-free PK-15, Huh-7 and HepG2 with a high level of positive rates (>5%); 3D4/31, Vero, MARC-145 and 293TT with a middle level of positive rates (between 2-5%); Hela, BHK-21 and CHO-K1 with a low level of positive rates (<2%). In general, TTSuV2-specific antibody staining patterns of individual positive cells by IFA could be divided into three different types: (i) cells displaying dense nuclear staining; (ii) cells displaying large nuclear inclusion staining; and (iii) cells displaying punctate nuclear staining. The last two patterns indicated the localization of ORF1 antigen in cell nucleoli. No cytoplasmic staining was observed in the transfected cells.

To test if some of these IFA-positive cells were susceptible to TTSuV2 infection, supernatants collected from cell lysates of PK-15, ST and 293TT cells transfected with circularized TTSuV2 DNA were inoculated into all cell lines with high level positive rates and some with middle level positive rates including the 293TT cell line, respectively. The inoculated cells were cultured for 3 to 5 days and examined by IFA. No fluorescent signal was detected in these cells (data not shown), indicating that none of the tested cell lines are susceptible to productive TTSuV2 infection.

Rescue of TTSuV2 from concatamerized TTSuV2 DNA of the clone pSC-TTV-US in CD/CD pigs. With the introduced genetic markers in the full-length DNA clones that can be used to distinguish between infections caused by the cloned virus and potential indigenous contaminating virus, the inventors performed an additional study in CD/CD pigs to further verify the in vivo infectivity of the TTSuV2 genomic DNA clones. Twelve CD/CD pigs were assigned into three groups with four pigs each. Pigs in each group were inoculated with PBS buffer, concatamerized "TTV2-EU DNA", and "TTV2-US DNA", respectively. Pre-inoculation serum samples for all pigs (collected at 30 days prior to inoculation) were tested negative for TTSuV1 or TTSuV2 DNA by real-time qPCR. Serum samples were collected from all animals at 0, 7, 14, 21, 28 and 35 DPI.

TTSuV2 DNA was detected in all eight inoculated pigs, but unfortunately, it was also detected in two negative control pigs, indicating contamination by other indigenous strains of TTSuV2 in the research facility or the source pigs, which is not uncommon. One pig (no. 133) inoculated with the concatamerized "TTV2-US DNA" had a detectable viremia even at 0 DPI, whereas the other pigs developed viremia at 14 or 21 DPI. Except for pig no. 133, the seven TTSuV2 DNA-inoculated pigs and the two TTSuV2-positive pigs in negative control group had an increased viral load until necropsy, indicating active virus infection. The inventors speculated that the source of the TTSuV2 contamination was likely due to the 1-month waiting period between the date of pre-inoculation serum sample testing (for which all animals were all negative) and 0 DPI.

However, thanks to the introduced genetic markers in the TTSuV2 DNA clones used in this study, the inventors were still able to determine if the TTSuV2 DNA clones were infectious in pigs, which was the main objective of our study. Since the inventors have previously demonstrated that a single pig can be infected by multiple strains of TTSuV2 and TTSuV1 (9, 17), then prior infection or concurrent infection of an indigenous TTSuV2 strain should not interfere with the infection of pigs by the TTSuV2 DNA clones the inventors intended to test in this study. To determine if the genetic markers of TTV2-EU or TTV2-US were present in viruses recovered from the sera of infected pigs under the mixed TTSuV2 infection status, the inventors amplified and sequenced a 620-bp region containing the engineered genetic markers from selected samples at 35 DPI from both inoculated and negative control pigs. The results showed that only the serum samples from pigs experimentally inoculated with the concatamerized "TTV2-US DNA" were found to have identical TTSuV2 sequences to the introduced genetic markers PstI and MfeI, whereas serum samples from the negative control group and from pigs inoculated with concatamerized "TTV2-EU DNA" did not contain any introduced genetic markers (data not shown). Therefore, this pig study further confirmed the initial pilot pig study that the TTSuV2-US full-length DNA clone is infectious in pigs. The results also experimentally verified, for the first time, that pigs can be co-infected by different strains of TTSuV2.

Little is known about the etiology and molecular biology of anelloviruses due to the lack of a cell culture system to propagate human TTV or TTSuV and the lack of a suitable animal model combined with reverse genetics systems for anellovirus studies. Reports of TTSuV DNA sequences detected in commercial porcine vaccine products, porcine-derived human drugs and in porcine-derived trypsin by nested PCR suggested a widespread contamination of TTSuV (Kekearainen, T., L. et al. 2009. Swine torque teno virus detection in pig commercial vaccines, enzymes for laboratory use and human drugs containing components of porcine origin. J Gen Virol 90:648-53; Krakowka, S., et al. 2008. Evaluation of Mycoplasma hyopneumoniae bacterins for porcine torque teno virus DNAs. Am J Vet Res 69:1601-7). Cell cultures may be one of the major sources for TTSuV contamination in biological products of pig origin. Therefore, the present study was first aimed at examining whether five selected cell lines harbor endogenous DNA and protein antigen of TTSuV1 or TTSuV2, and to further identify TTSuV-negative cell lines that are potentially permissive for TTSuV propagation.

Surprisingly, none of the five cell lines tested in the study were found to be positive for TTSuV1 or TTSuV2 DNA or ORF1 antigen (FIG. 2). Furthermore, screening of seven additional commonly-used cell lines also yielded negative results as determined by IFA detection, indicating that TTSuV contamination in cell cultures is probably not as common as the inventors originally thought. Our result was distinct from a recent study by a Brazilian group that reported TTSuV DNA contamination in 15 out of 25 cell lines (Teixeira, T. F., et al. 2011. Torque teno sus virus (TTSuV) in cell cultures and trypsin. PLoS One 6:e17501). In that study, the five cell lines that were also used here in our study, including PK-15, ST, BHK-21, Vero and MA-104 cells (from which the MARC-145 cell line is derived) had been shown to have detectable TTSuV1 and/or TTSuV2 sequences by using a one-round duplex PCR assay (Teixeira, T. F., Id.). It is unclear why there is such a major discrepancy between our results in this study and those by the Brazilian group. A reliable approach to prove the presence of a contaminating virus in cell cultures used in biological products is to determine its susceptibility to virus infection, which has been exemplified by PCV1 (Beach, N. M., et al. 2011. Productive infection of human hepatocellular carcinoma cells by porcine circovirus type 1. Vaccine 29:7303-6; Hattermann, K., et al. 2004. Infection studies on human cell lines with porcine circovirus type 1 and porcine circovirus type 2. Xenotransplantation 11:284-94; Ma, H., et al. 2011. Investigations of porcine circovirus type 1 (PCV1) in vaccine-related and other cell lines. Vaccine 29:8429-37; Tischer, I., et al. 1982. A very small porcine virus with circular single-stranded DNA. Nature 295:64-6). Theoretically, the possibility of TTSuV contamination in cell cultures is very low, since anellovirus has been shown to be extremely difficult to propagate in vitro. The present study utilized the (i) more sensitive qPCR assay (compared to the one-round PCR in the Teixeira et al study); (ii) the IFA; and (iii) transfection of circular TTSuV genomic DNA into the cells as the positive control (see below) to demonstrate the absence of TTSuV at both the DNA and amino acids levels in 12 representative cell lines including four of pig origin (PK-15, ST, 3D4/31 and IPEC-J2). Therefore, based on the results from this study, the inventors conclude that, contrary to what some may believe, there is very little, if any, endogenous TTSuV contamination in well-established continuous cell lineages. Instead, detection of contaminating TTSuV DNA sequences in biological products reported by other groups may come from the porcine-derived trypsin or serum (Kekearainen, T., et al. 2009. J Gen Virol 90:648-53; Teixeira, T. F., et al. 2011. PLoS One 6:e17501). The latter was actually confirmed in the present study for the first time (FIG. 2).

Figure 6:
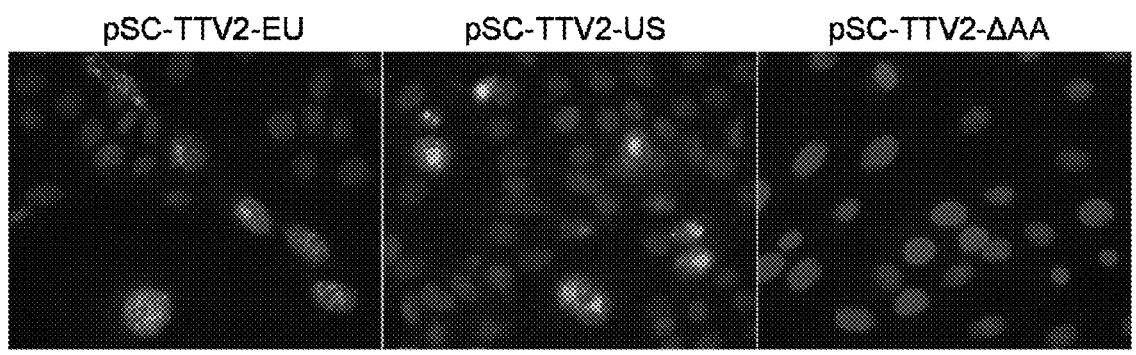
FIG. 6 illustrates IFA results of PCV1-free PK-15 cells transfected with the ligation mixtures of linear TTSuV2 genomic DNA derived from clones pSC-TTV2-EU, pSC-TTV2-US or pSC-TTV2-ΔAA. Cells were stained with an anti-TTSuV2 ORF1 antibody (Ab) and an Alexa fluor 488-conjugated goat anti-rabbit IgC (green) at 3 days post-transfection. DAPI (blue) was used to stain the cell nucleus. Only merge of Ab and DAPI stainings are shown. Magnification=200×.
Figure 7:
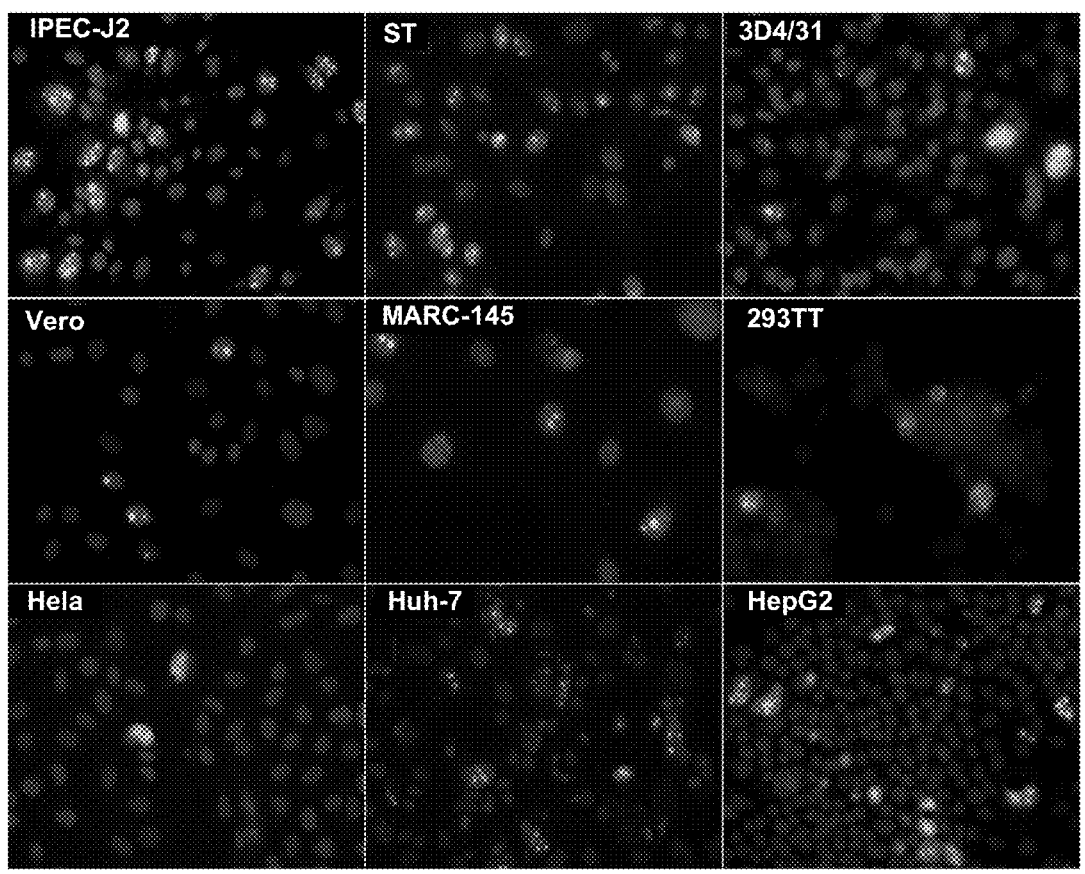
FIG. 7 illustrates transfection of nine different cell lines with the ligation mixture of linear TTSuV2 genomic DNA derived from the clone pSC-TTV2-US. Alexa fluor 488-conjugated antibody (Ab) staining (green) merged with nuclear staining using DAPI (blue) are shown. Magnification=200×.

Subsequently, the inventors demonstrated that all of these TTSuV-free cell lines supported TTSuV2 ORF1 expression by transfection with the circular TTSuV2 genomic DNA or the tandem-dimerized TTSuV2 plasmids (FIG. 4, FIG. 6 and FIG. 7). The TTSuV2 ORF1 protein was expressed in cell nuclei, especially in nucleoli, which is consistent with the localization of human TTV ORF1 in Huh-7 cells transfected with the circular full-length TTV genomic DNA by immunoblotting with the ORF1-specific antibody (Mueller, B., et al. 2008. Virology 381:36-45). Most recently, it was also reported that TTSuV1 or TTSuV2 ORF1-GFP fusion protein expressed from the recombinant construct was accumulated in nucleoli of the PK-15 cells (Martinez-Guino, L., et al. 2011. Expression profile and subcellular localization of Torque teno sus virus proteins. J Gen Virol 92:2446-57).

In addition, in this study TTSuV2-specific roRNA splicing events were detected intransfected PK-15 cells by RT-PCR, indicating the synthesis of viral mRNA transcripts in the transfected cells. While the inventors experimentally demonstrated the existence of two viral mRNAs transcripts (mRNA2 and mRNA3) (FIG. 5), the putative mRNA 1 encoding the full-length ORF1 of TTSuV2 was not detected (data not shown), which may suggest a lower quantity and integrity of mRNA1 than that of mRNA2 and mRNA3. In accordance with the result described by Martinez-Guino et al., splicing of the 91-nt intron 2 sequence in mRNA3 also occurred in the post-transcription of TTSuV2 ORF1-GFP fusion gene based on none-full-length viral clone (Martinez-Guino, et al. 2011. Id.).

The synthesis of viral mRNA transcripts and the subsequent expression of the ORF1 or ORF1-related viral proteins in transfected cells were driven by the endogenous TTSuV2 promoter. The processes were also regulated by the unidentified cis-acting elements, as we showed in this study that deletion of a 104-bp sequence downstream of the TATA box completely eliminated ORF1 expression (FIG. 6). To our knowledge, this is the first demonstration of porcine anellovirus viral mRNA and protein expression and mutagenesis analysis based on the viral DNA concatemers produced from circularized viral genomes or a tandem-dimerized full-length clone.

It appeared that both PTTV2c-VA and TTV2-#471942 DNA concatemers were replication-competent when transfected into cells since they mimicked the natural TTSuV2 circular genome. However, the rescue of PTTV2c-VA ("TTV2-US"), but not TTV2-#471942 ("TTV2-EU"), was only demonstrated in two in vivo animal experiments. The major sequence difference between these two TTSuV2 strains was in the GC-rich region. It has been proposed that the GC-rich region in anelloviruses forms unique stem-loop structures, which may play a significant role in viral replication (Miyata, H., et al. 1999. Identification of a novel GC-rich 113-nucleotide region to complete the circular, single-stranded DNA genome of TT virus, the first human circovirus. J Virol 73:3582-6; Okamoto, H., et al. 1999. The entire nucleotide sequence of a TT virus isolate from the United States (TUS01): comparison with reported isolates and phylogenetic analysis. Virology 259:437-48). Further in-depth mutagenesis analysis, which was not the scope of the present study, is required to explain this discrepancy between the two clones.

The inventors also showed that, although the three cell lines (PK-15, ST and 293TT) tested in the study supported a limited level of TTSuV2 replication, the infection of these cells by TTSuV2, if any, was non-productive since the supernatants of the transfected cells did not induce a second-round infection. Most recently, the 293TT cell line was shown to be susceptible for human TTV propagation due to its expression of SV40 large T antigen at a high level (5). The authors proposed that the human TTV genome contains a conserved octanucleotide in the UTR forming a stem-loop as the putative origin of replication. Five 4-bp motifs (CGGG and GGGC) were found adjacent to the stem-loop, which may act as the recognition sites for the SV40 large T antigen to facilitate TTV replication (de Villiers, E. M., et al. 2011. J Virol 85:7284-95). However, when the inventors performed a sequence alignment analysis of the corresponding sequences among human TTV, TTSuV, Torque teno canis virus (dog anellovirus) and Torque teno felis virus (cat anellovirus), neither the conserved octanucleotide nor the 4-bp motif was identified in the latter three anelloviruses (data not shown). Therefore, the SV40 large T protein expressed in 293TT cells likely does not provide the proposed helper effect on TTSuV replication. Further study is needed to screen whether additional cell lines are permissive to TTSuV2 infection.

Previous studies from our group and others have demonstrated that, even under strictly controlled experimental conditions in research facilities, TTSuV-negative pigs can easily acquire TTSuV infection due to the ubiquitous nature of this virus in pigs and environments (Gauger, P. C., et al. 2011. Vet Microbiol 153:229-39; Huang, Y. W., et al. 2011. Virus Res 158:79-88). Although our second in vivo experiment in the present study unfortunately "validated" these previous reports, our results did demonstrate the successful rescue of TTSuV2 in pigs inoculated with either the tandem-dimerized plasmids or circular TTSuV2 DNA with the introduced genetic markers. Unfortunately, due to the presence of indigenous TTSuV2 in the CD/CD pigs from the second animal study, the inventors could not analyze or correlate any pathological lesions in the inoculated pigs to TTSuV infection. Therefore, a future study using the germ-free gnotobiotic pig and the infectious DNA clone is warranted to characterize the pathological lesions solely attributable to TTSuV2 infection. The availability of the pig model combined with the reverse genetics system of anellovirus described in this study will facilitate future studies of porcine and even human anellovirus biology and pathogenesis.

The family Anelloviridae includes human and animal Torque teno viruses (TTV) with extensive genetic diversity. The antigenic diversity among anelloviruses has never been assessed. Using Torque teno sus virus (TTSuV) as a model, the inventors describe here the first investigation on antigenic relationships among different anelloviruses. Using the TTSuV1a or TTSuV1b ELISA based on the respective recombinant ORF1 antigen and TTSuV1-specific real-time PCR, the combined serological and virological profile of TTSuV1 infection in pigs was determined and compared with that of TTSuV2. TTSuV1 is likely not associated with porcine circovirus associated disease since both the viral loads and antibody levels were not different between affected and unaffected pigs and since there was no synergistic effect of concurrent PCV2/TTSuV1 infections. The inventors did observe a higher correlation of IgG antibody levels between anti-TTSuV1a and -TTSuV1b than between anti-TTSuV1a or -1b and anti-TTSuV2 in these serum samples, implying potential antigenic cross-reactivity. To confirm this, rabbit antisera against the putative ORF1 capsid proteins of TTSuV1a, TTSuV1b or TTSuV2 were raised and the antigenic relationships and diversity among these TTSuVs were analyzed by ELISA. Additionally, antibody cross-reactivity was analyzed using PK-15 cells transfected with one of the three TTSuV ORF1 constructs. The results demonstrate antigenic cross-reactivity between the two genotypes, TTSuV1a and TTSuV1b, but not between the two species, TTSuV1a or 1b and TTSuV2. In addition, an anti-genogroup 1 human TTV serum did not react with any of the three TTSuV antigens. The results add to the knowledge base on diversity among anelloviruses and have important implications for diagnosis, classification and vaccine development of TTSuVs.

Expression and purification of the N-terminally truncated TTSuV1a and TTSuV1b ORF1 proteins. Previously the inventors had successfully expressed a truncated TTSuV2 ORF1 protein in E. coli (Huang, Y. W., et al. 2011. Virus Res. 158:79-88). Using a similar strategy, the C-terminal region of the TTSuV1a-ORF1 or TTSuV1b-ORF1 gene with a C-terminally engineered 8×His-tag was inserted into the triple expression vector pTriEx1.1-Neo, resulting in two recombinant constructs, pTri-1aORF1 and pTri-1bORF1. The inventors also constructed an ORF1 C-terminally truncated version of 1b-ORF1 as a control, termed pTri-1bORF1-ctruc, which is 71-aa shorter than 1b-ORF1, to compare the size with that of pTri-1bORF1 in SDS-PAGE and WB analysis.

The three recombinant proteins, 1a-ORF1, 1b-ORF1 and 1bORF1-ctruc were found to be insoluble and expressed within the bacteria as inclusion bodies. Purification of the crude lysates from 1a-ORF1 products with a nickel-affinity column resulted in visualization of two bands of ~40 KDa (white arrowheads) and ~70 KDa (black arrowheads), as analyzed by Coomassie blue staining (FIG. 8A). The ~40 KDa band is the expected product of the truncated 1a-ORF1 protein, whereas the ~70 KDa polypeptide is an unknown product but should be derived from the former since it also reacted with an anti-His-tagged Mab (see below). Expression of 1b-ORF1 or 1bORF1-ctruc showed a smear in the crude lysates (FIG. 8B). After purification, two bands of ~40 KDa and ~70 KDa, similar to 1a-ORF1, were also identified in the purified 1b sample, whereas only a ~30 KDa polypeptide (white arrowheads) was detected in the purified 1 b-ctruc sample (FIG. 8B). The bands of ~40 KDa and ~30 KDa were consistent with the expected sizes of 1 b-ORF1 and 1 bORF1-ctruc protein products, respectively. All the identified polypeptides in the purified products were detected by WB using the anti-His-tagged Mab (FIG. 8C). The results indicated that both the truncated 1a-ORF1 and 1b-ORF1 proteins were successfully expressed in *E. coli* and thus can be used as antigens for TTSuV1a and TTSuV1b antibody detection in porcine sera.

Figure 9A:
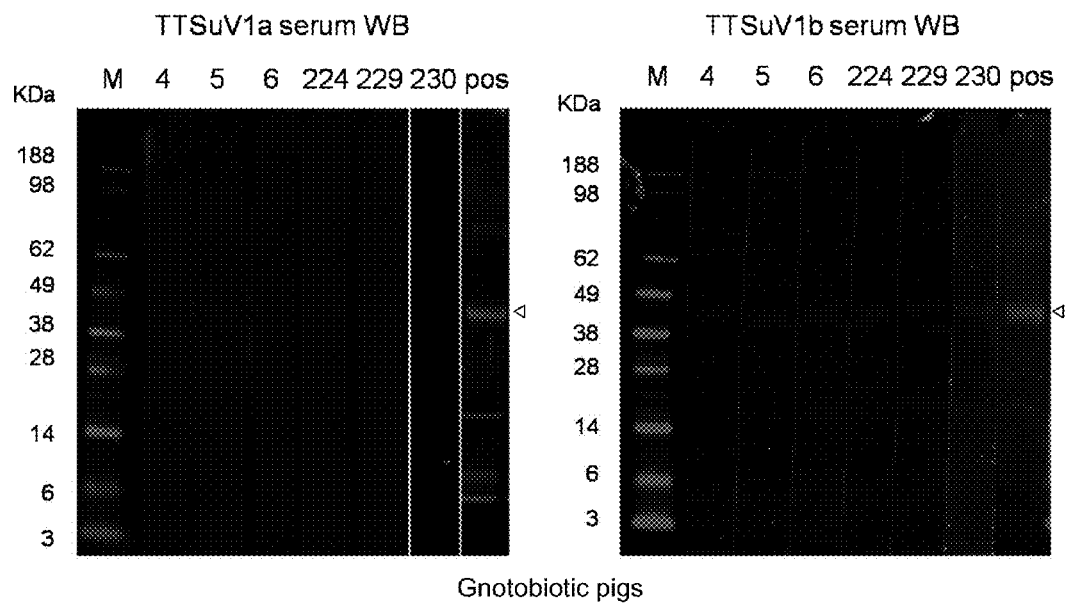
FIG. 9(A)-FIG. 9(C) illustrate TTSuV1a or TTSuV1b serum WB and ELISA.
Figure 9B:
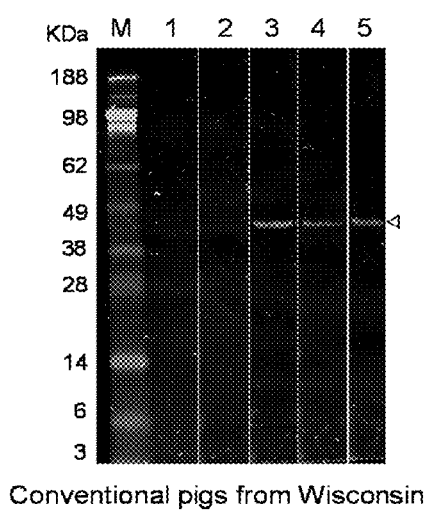

Development of TTSuV1a- and TTSuV1b-based serum WB and indirect ELISAs. In order to identify reference positive and negative sera as controls, a total of 100 serum samples from different sources including those from the gnotobiotic pigs were collected. Samples were screened for anti-TTSuV1a or anti-TTSuV1b IgG seropositivity by serum WB analysis using the purified 1a-ORF1 or 1b-ORF1 as the antigens, respectively. A TTSuV2-seropositive and TTSuV1/TTSuV2-DNA positive porcine serum (Huang, Y. W., et al. 2012. Rescue of a porcine anellovirus (Torque teno sus virus 2) from cloned genomic DNA in pigs. J Virol. Submitted Manuscript) showed reactivity with the 1a-ORF1 and the 1b-ORF1 antigen, as the ~40 KDa band was presented in the WB analysis (FIG. 9A; two rightmost lanes). Therefore, this serum was considered to be TTSuV1a- and TTSuV1b-seropositive and thus was used as a reference positive control for the ELISAs. All the seven Virginia and 12 Iowa gnotobiotic pigs had no detectable TTSuV1a and TTSuV1b antibodies (FIG. 9A). Except for a few serum samples from conventional pigs from a Wisconsin swine farm (FIG. 9B; the two lanes on the left), the remaining samples were tested positive for both TTSuV1a and TTSuV1b antibodies by the WB analysis. The dual-negative serum samples from Wisconsin conventional pigs were pooled and used as a negative control reference serum.

Figure 9C:
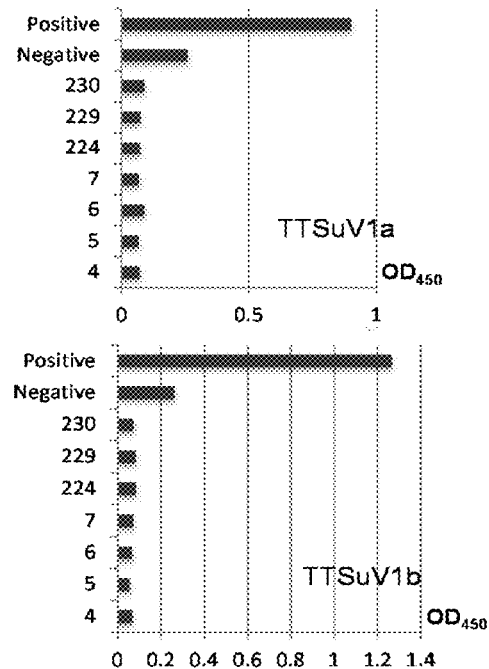

With the available positive and negative control reference sera, TTSuV1a- and TTSuV1b-based ELISAs were subsequently developed and standardized, respectively. The concentrations of the purified 1a-ORF1 or 1b-ORF1 antigen, porcine sera and IgG conjugate were determined by a checkerboard titration assay to ensure low background signal and to give the highest difference of OD450 values between the positive and negative controls. WB-negative gnotobiotic porcine sera showed very low OD values (<0.1) compared to the negative control reference serum (FIG. 9C), suggesting that these pig sera should not serve as a negative control reference for detection of porcine field samples in the ELISA test.

Association of TTSuV1 viral DNA loads and anti-TTSuV1a and anti-TTSuV1b IgG antibody levels. A total of 160 serum samples were collected and evaluated for the prevalence and viral DNA load of TTSuV1 by real-time qPCR and for seroprevalence and antibody levels (represented by S/N values) of anti-TTSuV1a and anti-TTSuV1b IgG by the ELISAs. Among the 160 samples, 138 sera in groups A to C were collected from three herds under field conditions whereas the remaining 22 sera in groups D (gnotobiotic pigs) and E were collected from pigs raised and housed under strictly controlled experimental conditions in research facilities.

None of the 12 TTSuV1a/TTSuV1b-seronegative gnotobiotic pigs in group D had a detectable viremia. In group E pigs, only one pig was viremic whereas six were seropositive for TTSuV1a and among them, one pig was also seropositive for TTSuV1b.

In groups A and C, 44 of 138 pigs were viremic (31.9%) whereas 128 were TTSuV1a-seropositive (92.8%) and 121 were TTSuV1b-seropositive (87.7%) (FIG. 10A). The incidence of TTSuV1 viremia was much lower than the TTSuV1a or 1b seropositive rate, suggesting previous clearance of the virus by neutralizing antibodies during the post-TTSuV1 infection convalescent period. Similar to the previously obtained results for TTSuV2 (Huang, Y. W., et al. 2011. Virus Res 158:79-88), pigs with undetectable TTSuV1 viral DNA load were more likely to have lower levels of TTSuV1a and TTSuV1b antibody titers than pigs with TTSuV1 viral DNA load at the levels of $10^4$ to $10^6$ copies/ml ($p<0.05$) in these three groups (FIGS. 10B & 10C).

All three markers of TTSuV1 infection, TTSuV1 DNA and TTSuV1a/1b antibodies, were found in 40 serum samples. Notably, the number of pigs that were TTSuV1a/TTSuV1b-dually seropositive but viral DNA-negative (77 samples) was higher than that of pigs with TTSuV1a- or TTSuV1b-seropositivity only (FIG. 10A). In addition, the total number of porcine sera with both antibodies was 117 (40+77) among the 138 serum samples, implying that (i) co-infection rates of pigs with TTSuV1a and TTSuV1b are high, which was expected; and (ii) a certain degree of cross-reactivity may exist between anti-TTSuV1a and anti-TTSuV1b IgG antibodies.

Figure 11A:
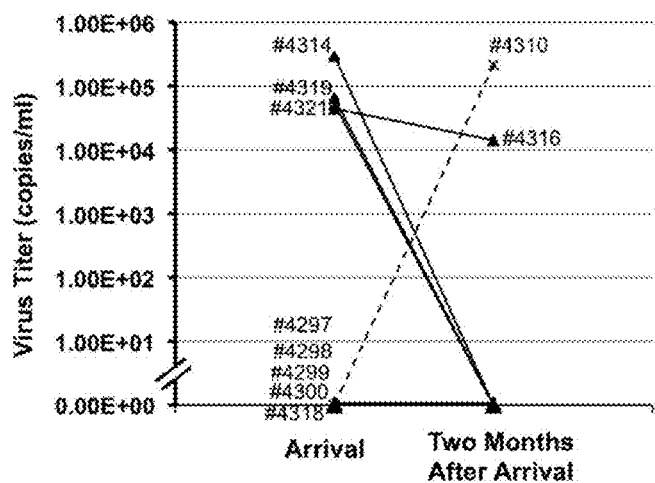
FIG. 11(A)-FIG. 11(C) illustrate a retrospective evaluation of TTSuV1 viral loads FIG. 11(A), antibody levels to the ORF1 protein of TTSuV1a FIG. 11(B) and TTSuV1b FIG. 11(C) in 10 pigs in group A from the time of their arrival at the research facility to two months after arrival.
Figure 11B:
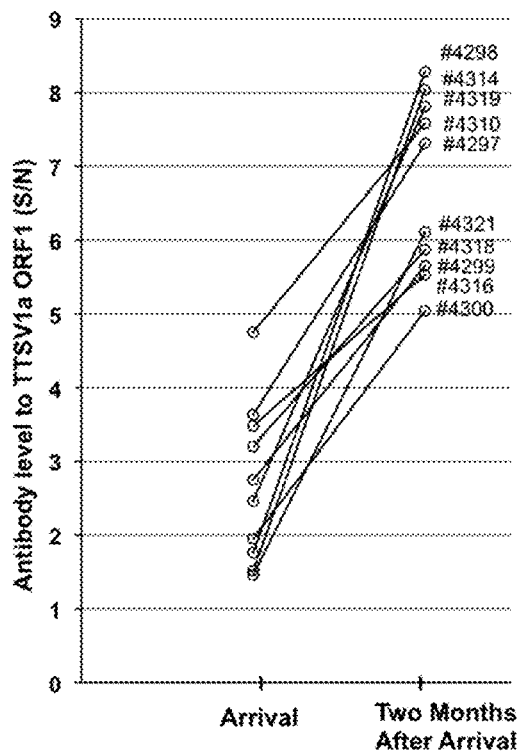
Figure 11C:
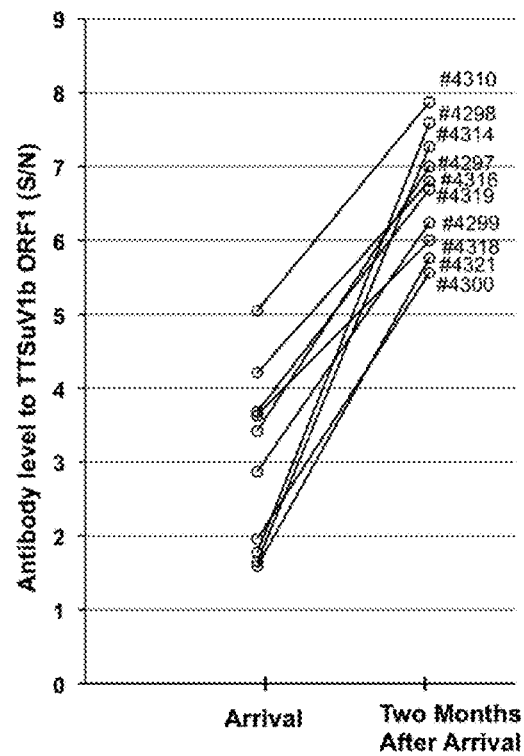

The inventors had previously demonstrated that, over a two-month period, the 10 group-A pigs had decreasing TTSuV2 viral loads that were associated with elevated anti-TTSuV2 ORF1 IgG antibody levels (Huang, Y. W., et al. 2011. Virus Res 158:79-88). Whether an analogous situation for TTSuV1 in these ten pigs existed was subsequently analyzed in this study, by comparing the TTSuV1 viral DNA loads and the anti-TTSuV1a or anti-TTSuV1b antibody levels in sera from the time of their arrival until two months later. Five of ten pigs were TTSuV1 DNA negative during the two months, and in four pigs (ID#4314, 4316, 4319 and 4321) the viral DNA loads decreased after two months, including in 3 pigs (ID#4314, 4319 and 4321) with no detectable TTSuV1 DNA (FIG. 11A). In contrast, both the anti-TTSuV1a and anti-TTSuV1b antibody titers increased in all 10 pigs (FIGS. 11B & 11C). These results were consistent with those of the TTSuV2 study.

Figure 12A:
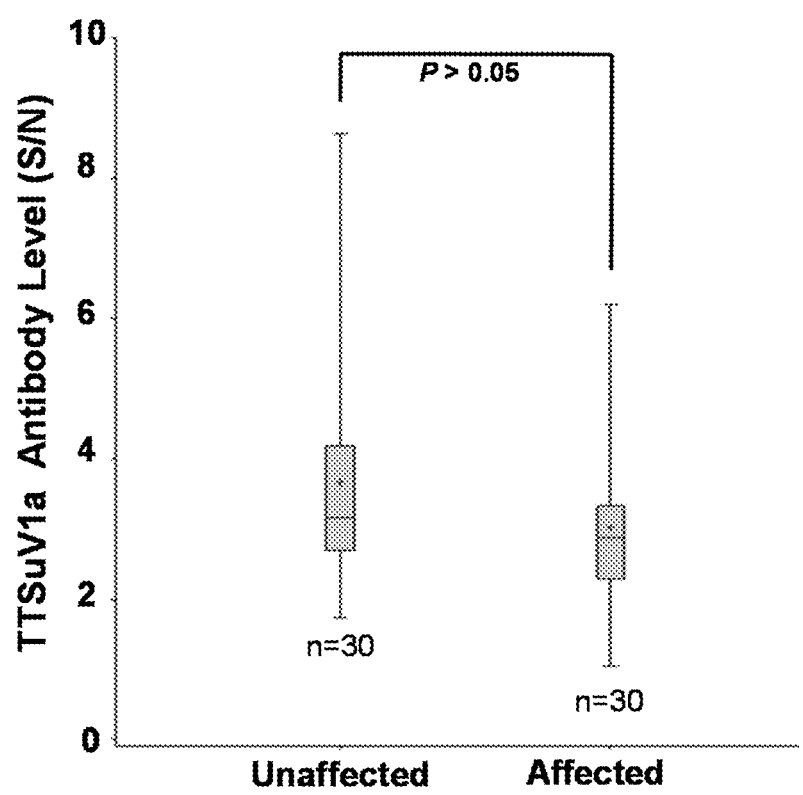
FIG. 12(A)-FIG. 12 (D) illustrate box plots showing the comparisons of anti-TTSuV1a FIG. 12(A) or anti-TTSuV1b FIG. 12(B) ORF1 antibody levels and TTSuV1 FIG. 12(C) or PCV2 FIG. 12(D) viral loads between the PCVAD-affected and -unaffected pigs.
Figure 12B:
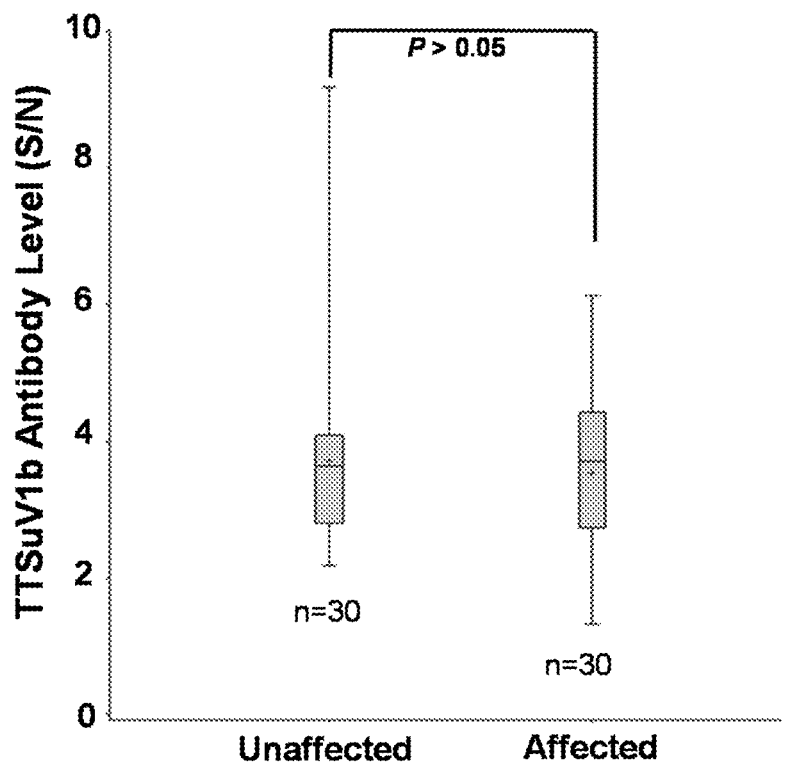
Figure 12C:
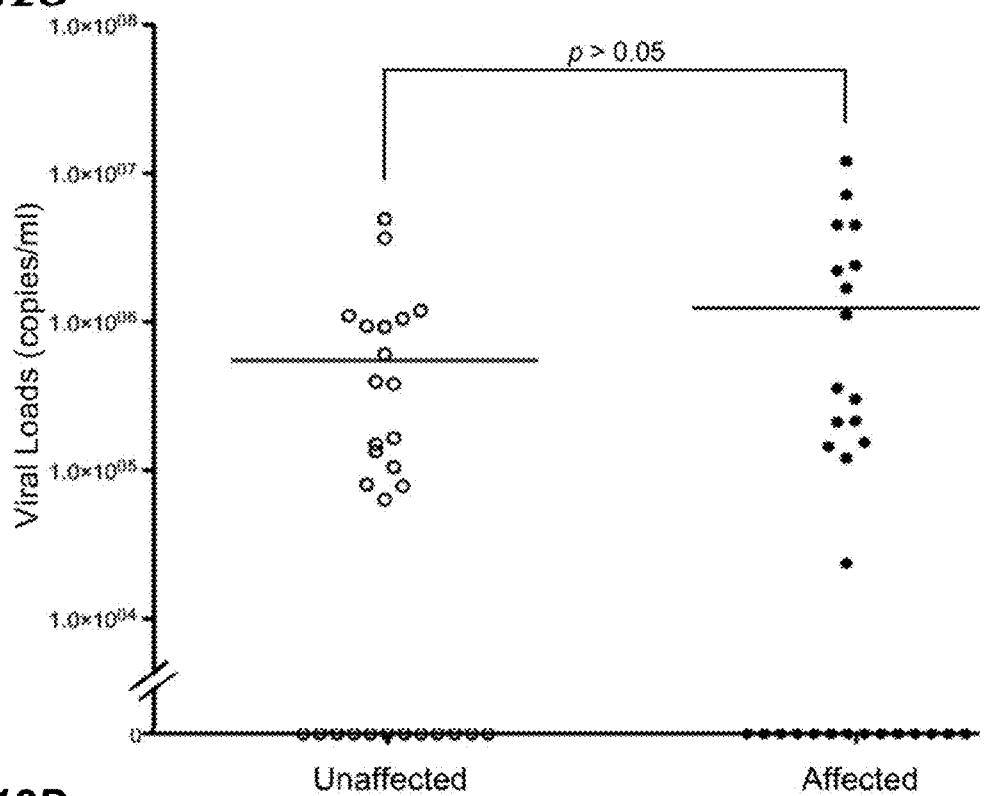
Figure 12D:
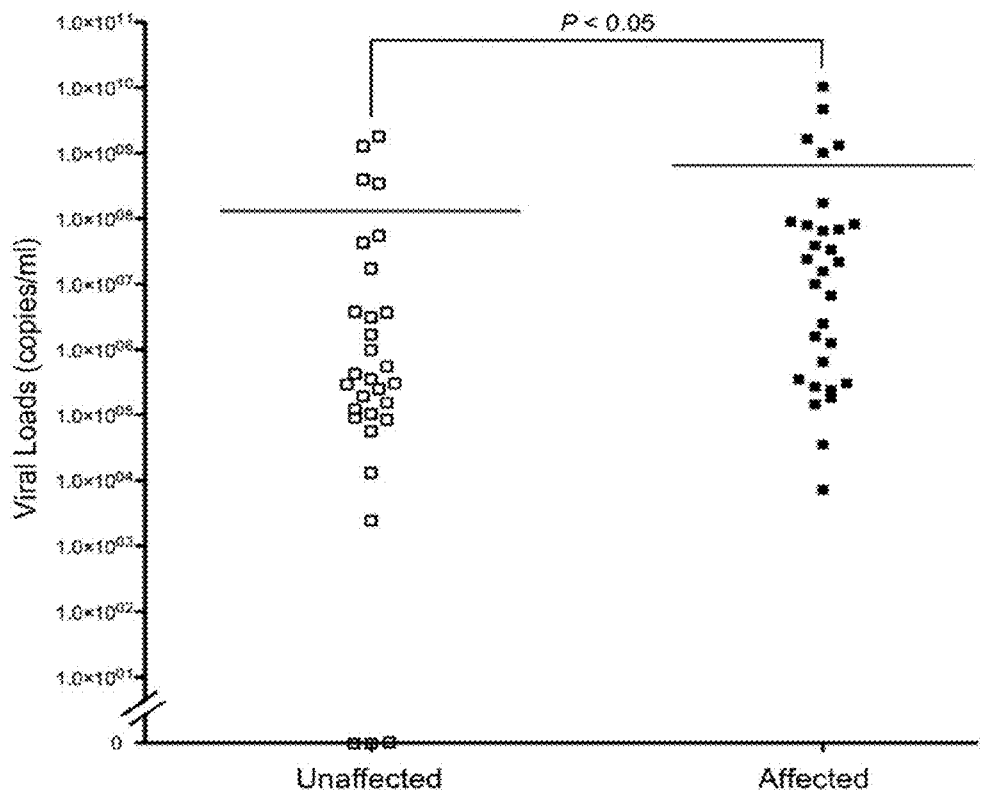

TTSuV1 is likely not associated with PCVAD. The inventors had previously found that PCVAD-affected pigs had a significantly lower level of TTSuV2 antibody than PCVAD-unaffected pigs in group B (Huang, Y. W., et al. 2011. Virus Res 158:79-88). However, determination of the levels of anti-TTSuV1a and anti-TTSuV1b IgG antibodies in these serum samples did not reveal a difference between the PCVAD-affected and -unaffected pigs (FIGS. 12A & 12B). In addition, there was no statistically significant difference of TTSuV1 viral loads between the PCVAD-affected and -unaffected pigs (FIG. 12C). In contrast, PCV2 viral load was significantly higher ($p<0.05$) in PCVAD-affected pigs compared to PCVAD-unaffected pigs (FIG. 12D).

The inventors further analyzed whether there existed a PCV2 and TTSuV1 synergistic effect associated with PCVAD. Serum viral DNA prevalence rates (viremia) of PCVAD-affected pigs were as follows: 50% (16/32) for PCV2 and TTSuV1, 56% (14/25) for PCV2 only, 0% (0/1) for TTSuV1 only, and 0% (0/2) for no detectable virus. These proportions were not significantly different (p=0.4339). The above results suggested that TTSuV1 is likely not associated with PCVAD.

Comparison and correlations of seroprevalence and antibody levels among anti-TTSuV1a, anti-TTSuV1b and anti-TTSuV2. Mixed infections of TTSuV1 and TTSuV2 are common in pigs, as determined by the presence of viral DNA of both TTSuV1 and TTSuV2 in the same pig using PCR (Gallei, A., et al. 2010. Vet Microbiol 143:202-12; Huang, Y. W., et al. 2010. Development of SYBR green-based real-time PCR and duplex nested PCR assays for quantitation and differential detection of species- or type-specific porcine Torque teno viruses. J Virol Methods 170: 140-6; Huang, Y. W., et al. 2011. Virus Res 158:79-88; Huang, Y. W., et al. 2010. Virology 396:289-97). In this study, the inventors provided the serological evidence to support this conclusion by analyzing the seroprevalence distribution of anti-TTSuV1a, -TTSuV1b and -TTSuV2 IgG in the 138 serum samples in groups A-C. As shown in FIG. 6A, 82 of 138 serum samples were triple-seropositive, indicating that these pigs had been infected by TTSuV1 (TTSuV1a and/or TTSuV1b) and TTSuV2.

Figures 13A, 13B:
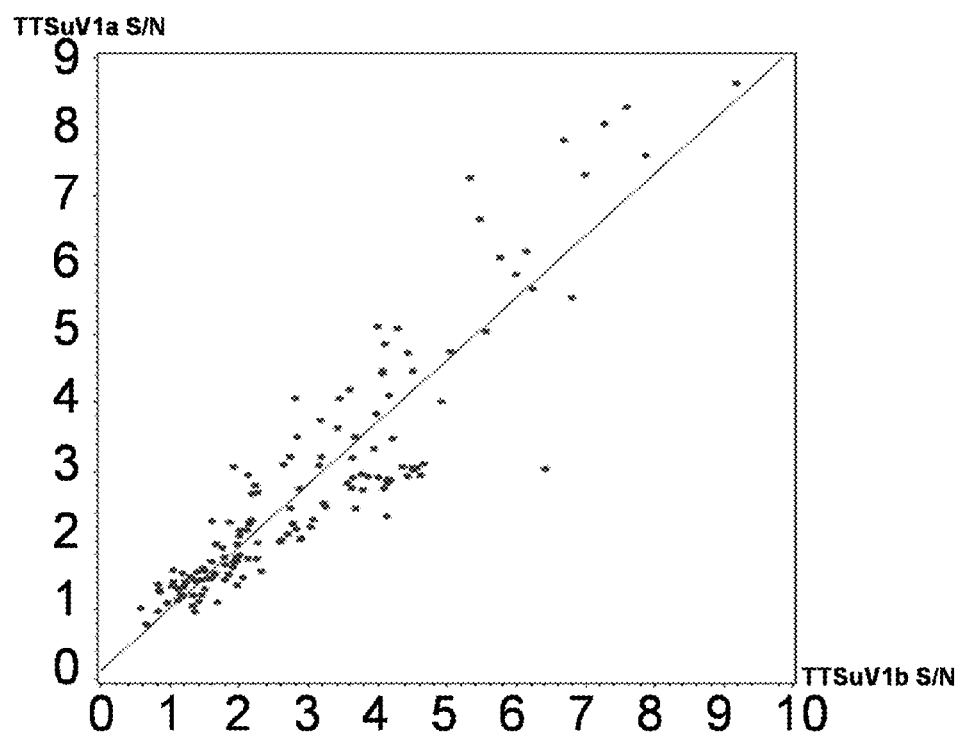
FIG. 13(A) and FIG. 13(B) illustrate a high correlation between anti-TTSuV1a and anti-TTSuV1b IgG in 138 serum samples.

The distribution of dual seropositive samples was significantly different. A total of 117 (82+30+5) porcine sera were dually-seropositive for both anti-TTSuV1a and anti-TTSuV1b, which was consistent with the number calculated in FIG. 10A. In contrast, dual seropositivity to anti-TTSuV1a and anti-TTSuV2, or to anti-TTSuV1b and anti-TTSuV2, each occurred in only one sample (FIG. 13A).

Furthermore, correlations of antibody levels between anti-TTSuV1a and anti-TTSuV1b, between anti-TTSuV1a and anti-TTSuV2, and between anti-TTSuV1b and anti-TTSuV2 were assessed in the 138 serum samples by using Spearman's correlation coefficient. A good linear relationship was observed between the anti-TTSuV1a and anti-TTSuV1b (FIG. 13B; Spearman's rank correlation coefficient=0.91, p<0.0001). When all the 160 samples were included, a better agreement was obtained (Spearman's rank correlation coefficient=0.93, p<0.0001). A lesser degree of correlation between anti-TTSuV1a and anti-TTSuV2 or between anti-TTSuV1b and anti-TTSuV2 was found when compared to that between anti-TTSuV1a and anti-TTSuV1b (data not shown). The results further revealed an association of sero-prevalence and antibody levels between anti-TTSuV1a and anti-TTSuV1b, and thus it is logical to hypothesize that there exists an antigenic cross-reactivity between the two TTSuV1a and TTSuV1b genotypes.

Figure 14A:
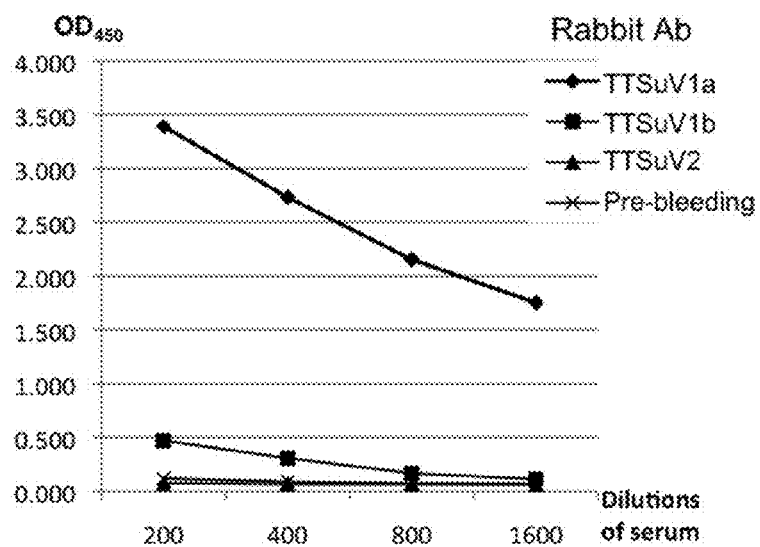
FIG. 14(A)-FIG. 14(C) illustrate reactivity of the three purified TTSuV ORF1 antigens: TTSuV1a FIG. 14(A), TTSuV1b FIG. 14(B) and TTSuV2 FIG. 14(C) with rabbit antisera against ORF1s of TTSuV1a, TTSuV1b or TTSuV2 or with pre-bleed rabbit serum with 2-fold serial dilutions by ELISAs. Each antigen was tested in duplicate against each serum sample. Mean OD values are presented.
Figure 14B:
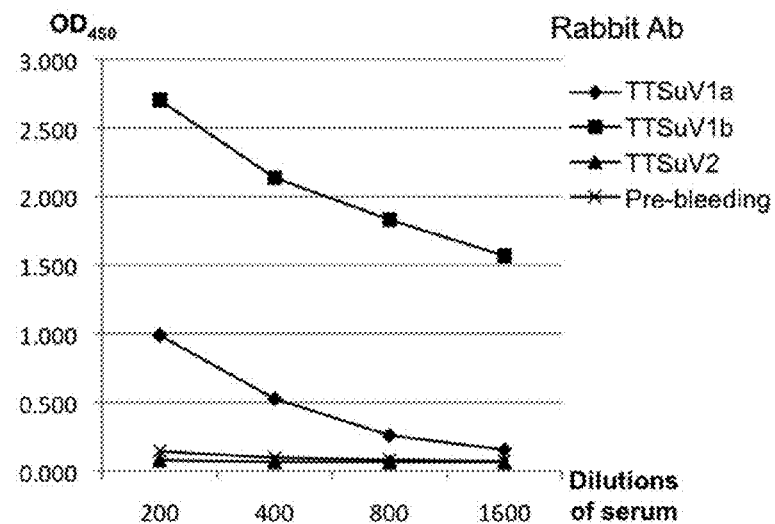

Analysis of antigenic relationships among TTSuV1a, TTSuV1b and TTSuV2 by ELISA. Three antisera against the truncated recombinant ORF1 s of TTSuV1a, TTSuV1b or TTSuV2 were raised by immunization of rabbits with the respective purified recombinant antigen. Cross-immunoreativity studies were initially performed to assess whether one of these antigens could cross-react with antisera against the other two antigens in an ELISA format. The pre-bleed rabbit serum was used as the negative control. As expected, each of three TTSuV antigens reacted with its corresponding homologous antiserum but not with the pre-bleed negative control serum (OD values<0.1) that were serially diluted from 1:200 to 1:1600 (FIG. 14A-14C).

Figure 14C:
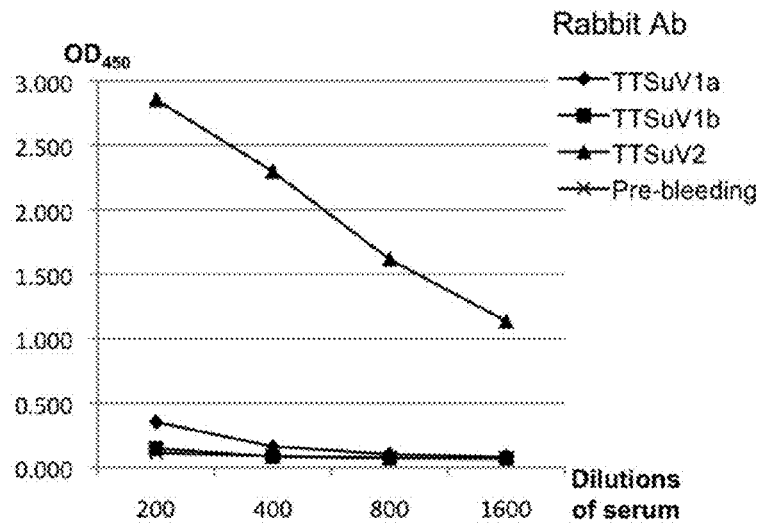

The TTSuV2 antigen did not appear to cross-react with TTSuV1a or TTSuV1b antiserum even at 1:200 dilution since the OD value was relatively low (FIG. 14C). In contrast, the TTSuV1b antigen did cross-react with the anti-TTSuV1a serum (as shown at 1:200 and 1:400 dilutions, both OD values>0.5) but not with the anti-TTSuV2 serum (FIG. 14B) whereas the TTSuV1a antigen likely cross-reacted with the anti-TTSuV1b serum (at 1:200 dilution) but not with the anti-TTSuV2 serum (FIG. 14A). The ELISA results strongly supported our hypothesis that there is an antigenic cross-reactivity between the two TTSuV1a and TTSuV1b genotypes but not between the two species TTSuV1a or 1b and TTSuV2.

Demonstration of antigenic relationships among TTSuV1a, TTSuV1b and TTSuV2, and between TTSuVs and a genogroup 1 human TTV by IFA. In order to definitely analyze the antigenic cross-reactivity among these viruses, an antibody cross-reactivity experiment was performed by using IFA staining. PK-15 cells were transfected with three plasmid constructs, pTri-1aORF1, pTri-1bORF1 and pTri-2cORF1, which harbor the truncated ORF1 capsid genes from TTSuV1a, TTSuV1b and TTSuV2, respectively. Three days post-transfection, cells were stained with anti-TTSuV1a, anti-TTSuV1b, anti-TTSuV2 and pre-bleed serum, respectively. As shown in FIG. 15, cells transfected with pTri-1aORF1 (FIG. 15A) or pTri-1bORF1 (FIG. 15B) stained positive with both anti-TTSuV1a and anti-TTSuV1b but not with the anti-TTSuV2 or the pre-bleed serum (data not shown), whereas cells transfected with pTri-2cORF1 only reacted with anti-TTSuV2 serum (FIG. 15C). Each TTSuV1 antiserum reacted stronger with its own homologous antigen than the heterologous antigen based on comparison of the positive cell numbers and fluorescence intensity (FIGS. 15A and 15B). The truncated ORF1s were expressed in both nuclei and cytoplasm of the transfected cells (FIG. 15), which was different from what we found in cells transfected with full-length TTSuV DNA clones (15), probably due to the lack of most of the putative nuclear localization signals (NLS) located at the N-terminal part of the ORF1 in the truncated genes (computer analysis; data not shown). Table 1 summarizes the results of the cross-reactive immunostaining study. In addition, when transfected cells were each stained with an anti-human genogroup 1 TTV ORF1 antiserum (AK47; raised in rabbits), no fluorescent signal was detected. Mock-transfected cells did not stain with any of the five antisera (Table 1). The IFA result further confirmed the presence of antigenic cross-reactivity between TTSuV1a and TTSuV1b as shown by the ELISA but not between the TTSuV1a or 1b and TTSuV2. The results also revealed that there was no antigenic cross-reactivity between genogroup 1 human TTV and porcine anelloviruses.

Identification of two putative antigenic sites on the ORF1 shared by TTSuV1a and TTSuV1b by sequence analyses. The full-length ORF1 proteins between TTSuV1 and TTSuV2 shared only 22.4-25.8% amino acid (aa) sequence identity with no significantly conserved regions identified (14). The ORF1 proteins of the two TTSuV species share only 19.1-21.0% aa sequence identity with that of the human genogroup 1 TTV isolate P/1C1 (GenBank accession no. AF298585). The high ORF1 sequence divergences between TTSuV1 and TTSuV2 and between porcine and human anelloviruses likely account for the absence of antigenic cross-reactivity observed in this study.

Figure 16:
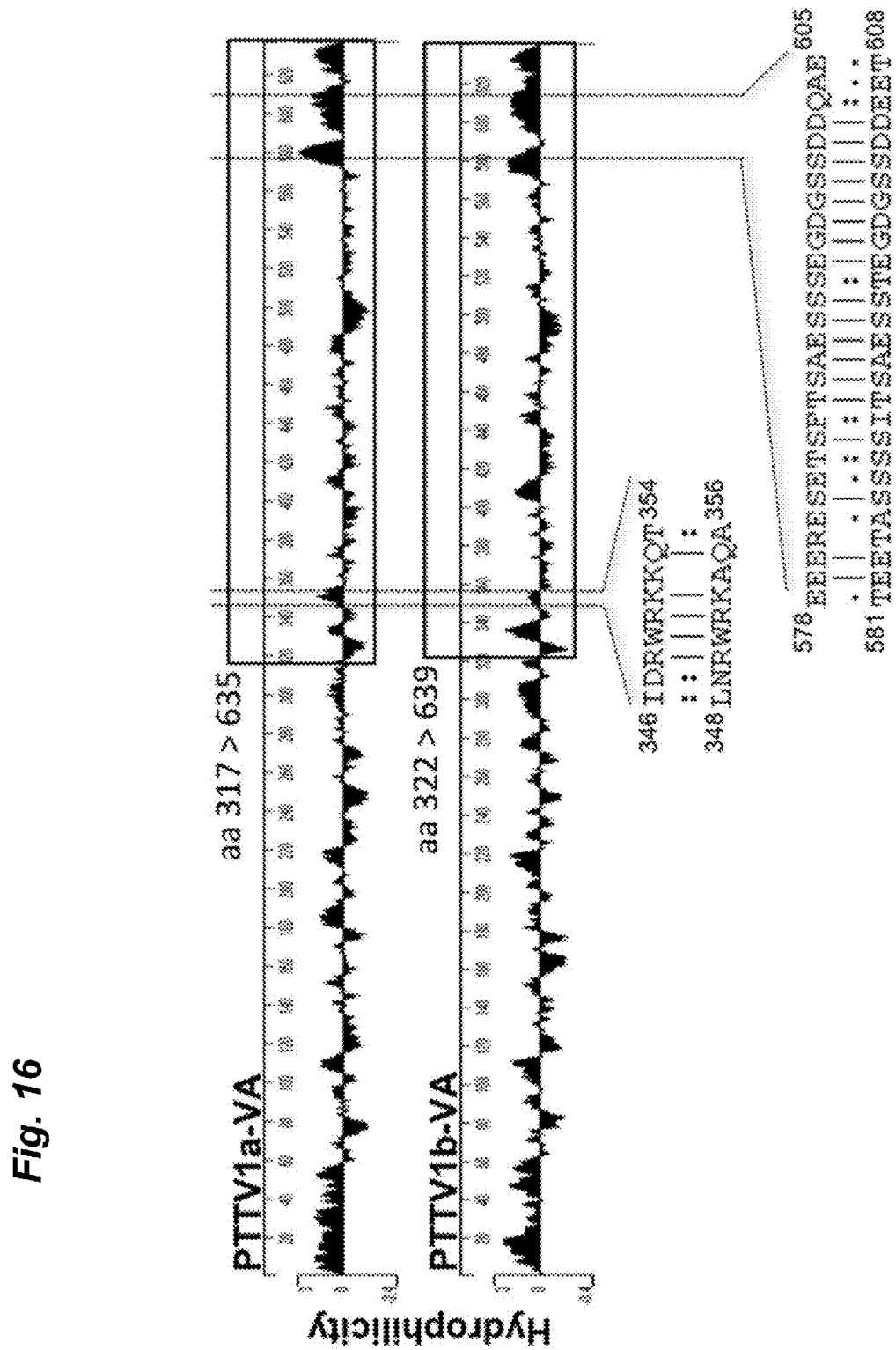
FIG. 16 illustrates comparison of hydrophilicity profiles of TTSuV1a (PTTV1a-VA strain) (SEQ ID NO:13) and TTSuV1b (PTTV1b-VA strain (SEQ ID NO:14) ORF1 and identification of two putative common antigenic domains in ORF1 of TTSuV1. The C-terminal region used for the expression of the truncated 1a- or 1b-ORF1 is indicated by a box. The corresponding alignment of amino acid (aa) sequences and aa positions of the two domains are also shown. Favorable mismatches of the aa were displayed as colons whereas neutral mismatches are depicted as periods.

However, the aa sequence identity of ORF1 between the two TTSuV1a and TTSuV1b genotypes (six isolates available in GenBank) ranged between 49.4-52.4%. The inventors have previously found that conserved sites exist in the ORF1 of different TTSuV1 stains except for the four proposed variable regions (30.0-37.5% aa identity) (Huang, Y. W., et al. 2010. Virology 396:289-97). In order to identify the common antigenic sites on the ORF1 between the genotypes TTSuV1a and TTSuV1b, the inventors performed a comparative analysis of hydrophilicity profiles of the ORF1 aa sequences between PTTV1a-VA and PTTV1b-VA. Two conserved hydrophilic regions located at the middle and C-terminal regions were identified (FIG. 16). The C-terminal antigenic domain appeared to be more antigenic than the domain in the middle region. Alignment of the two putative antigenic regions among all published TTSuV1 sequences revealed a high degree of sequence conservation (data not shown).

The immunology of anellovirus is poorly understood. Detection of specific adaptive immune responses can provide insights into anellovirus epidemiology. By analogy to the chicken anemia virus (CAV), another single-stranded circular DNA virus, the ORF1 product of anelloviruses is believed to function as the putative capsid protein and thus represents the major viral antigen (Crowther, R. A., et al. 2003. Comparison of the structures of three circoviruses: chicken anemia virus, porcine circovirus type 2, and beak and feather disease virus. J Virol 77:13036-41; Maggi, F. and M. Bendinelli. 2009. Curr Top Microbiol Immunol 331:65-90).

Detection of human TTV IgG antibodies in human populations based on the human TTV ORF1 as the antigen has been reported (Maggi, F. and M. Bendinelli. Id.). Handa et al reported a 38% prevalence of human TTV antibody among 100 American blood donors when using the N-terminal part (aa 1-411) containing the arginine-rich region of ORF1 of a human genotype 1b TTV isolate as the antigen (Handa, A., et al. 2000. Prevalence of the newly described human circovirus, TTV, in United States blood donors. Transfusion 40:245-51). In contrast, antibody reactivity in humans to the N-terminus of ORF1 (ORF1-N) of a human TTV genotype 6 was not detected by a Finish group. After removal of the arginine-rich region (aa 1-62), the arginine-deleted constructs (ORF1AArg and ORF1-NAArg) as well as the C-terminal portion (ORF1-C; aa 344-737) were expressed, 48% human TTV IgG prevalence was detected in sera of 21 healthy Finnish adults using the three products as the antigens (Kakkola, L., et al. 2008. Virology 382:182-9). Two other groups also utilized similar strategies targeting the C-terminal region to successfully express human TTV ORF1. Muller et al demonstrated that an ORF1-specific antiserum against the C-terminal part of ORF1 (aa 402-733) of the human TTV isolate P/1C1 generated in a rabbit was able to detect ORF1 expression in cell culture (21), whereas a French group reported the detection of anti-human TTV ORF1 IgG antibodies in 69 of 70 French subjects including 30 blood donors, 30 cryptogenic hepatitis patients and 10 healthy children using an ORF1 C-terminus-based WB analysis (Ott, C., et al. 2000. J Gen Virol 81:2949-58). Most recently, our group successfully used the C-terminal fragment of the ORF1 protein of a U.S. strain of TTSuV2 as the antigen to detect TTSuV2-specific IgG antibodies in pig sera by ELISA. Together with the present study for serological detections of the two porcine TTV species-1 genotypes TTSuV1a and TTSuV1b, the obtained data suggest that the C-terminal portion of ORF1 of anelloviruses is an appropriate target for the development of serodiagnostic assays.

Indeed, based on the CAV virion structure determined by cryo-electron microscopic images, the C-terminal half portion of the ORF1 is proposed to form the outer part of the capsid that is exposed to the virion surface whereas the basic N-terminal part of the CAV ORF1 is proposed to be inside the capsid to bind the viral DNA, and the middle part of the ORF1 is proposed to form the inner shell of the capsid (Crowther, R. A., et al. 2003. Comparison of the structures of three circoviruses: chicken anemia virus, porcine circovirus type 2, and beak and feather disease virus. J Virol 77:13036-41). The ORF1 polypeptide of anellovirus has been suggested to be organized in the same way as that of CAV (Crowther, R. A., 2003. Id.). This proposed structure is consistent with the computer analysis of the ORF1 hydrophilicity profiles of TTSuV1 (FIG. 16) and TTSuV2 (Huang, Y. W., et al. 2011. Virus Res 158:79-88). In either case, there are two conserved major hydrophilic regions located at the middle and C-terminal regions that span the C-terminal half portion of the ORF1.

Reliability and specificity of the established ELISAs for differential TTSuVs antibody detections were guaranteed by screening of the positive and negative reference sera through a serum WB. It was further demonstrated by triple seronegativity of TTSuV1a, TTSuV1b and TTSuV2 in gnotobiotic pigs of group D (FIG. 9). A high seropositive rate of TTSuV1a (92.8%) or TTSuV1b (87.7%) was revealed in the 138 groups A-C pigs (FIG. 10A), which was higher than that of TTSuV2 (~60%) (13), indicating a wider spread of actual TTSuV1 infection or the presence of long-persisting anti-TTSuV1 ORF1 antibodies in these pigs regardless of a low incidence of TTSuV1 viremia. Accordingly, these results, for the first time, provided serological evidence supporting multiple infections of TTSuV1a, TTSuV1b and TTSuV2 in the same pigs. To our knowledge, this is also the first study demonstrating multiple anellovirus infections in the same animals by using serological diagnosis in addition to the PCR assay. Therefore, the subsequent question raised was to determine the specificity of seropositivity and cross-antigenic reactivity among different TTSuV species and genotypes.

In this study, the inventors demonstrated by investigating four different aspects that indeed there exists antigenic cross-reactivity between the two TTSuV1a and TTSuV1b genotypes but not between the two TTSuV species (TTSuV1a or 1b and TTSuV2). First, when compared to the serum samples with single TTSuV1a- or TTSuV1b-seropositivity, the numbers of serum samples with TTSuV1a/1b-dual seropositivity was much higher (FIG. 10A), likely implying a certain degree of cross-antigenic reactivity between TTSuV1a and TTSuV1b antibodies. Secondly, the number of serum samples with dual TTSuV1a and TTSuV1b seropositivity was significantly higher than that of dual seropositivity to TTSuV1a and TTSuV2, or to TTSuV1b and TTSuV2 (FIG. 13A). In addition, a high correlation of antibody levels between anti-TTSuV1a and anti-TTSuV1b as assessed by Spearman's correlation coefficient was observed (FIG. 13B). These analyses were conducted under the background of multiple TTSuV infections in field samples, which led us to propose a logical hypothesis regarding the presence of an antigenic cross-reactivity between TTSuV1a and TTSuV1b. Thirdly, this hypothesis was experimentally confirmed by analysis of the antigenic relationships among TTSuV1a, TTSuV1b and TTSuV2 through antigen-specific ELISAs (FIG. 14), and antibody cross-reactivity studies in PK-15 cells transfected with the three TTSuV ORF1 constructs, respectively (FIG. 15 and Table 1). Finally, sequence comparison of ORF1 of the TTSuV also supported the observed epidemiologic and experimental data in this study: while there was no significant sequence homology of TTSuV1a or 1b ORF1 with that of TTSuV2, the inventors identified two putative antigenic sites on the ORF1 that are shared by TTSuV1a and TTSuV1b (FIG. 16).

In addition, in this study the inventors also demonstrated the absence of antigenic cross-reactivity between TTSuVs and a human genogroup 1 TTV by IFA. Taken together, the results from this study have important implications in predicting the antigenic cross-reactivity among different anelloviruses based on the ORF1 aa sequence homology. Currently, anelloviruses are classified into nine genera according to the infected host species (human/ape, tamarin, douroucouli, tupaia, pig, dog and cat), nucleotide sequence identity and the genome size of primate anelloviruses (TTV, TTMV and TTMDV) (Biagini, P., et al. 2011. Anelloviridae, p. 331-341. In A. M. Q. King, M. J. Adams, E. B. Carstens, and E. J. Lefkowitz (ed.), Virus Taxonomy, 9th Report of the ICTV. Elsevier Academic Press, London). The ORF1 of the TTSuV (Genus *Iotatorquevirus*) share 15.6-22.3% aa sequence identity with the other eight genera based on multiple sequence alignment (data not shown), which is similar to that between TTSuVs and the human genogroup 1 TTV (19.1-21.0%). Therefore, it is reasonable to deduce that porcine anellovirus is not antigenically cross-reactive with other anelloviruses in other animal species. The ORF1 aa sequence homologues among the nine genera range from 15.0% to 27.3% (data not shown), thus implying that antigenic diversity between different genera does exist.

The two TTSuV species (TTSuV1 and TTSuV2) do not share antigenicity in the ORF1 antigen since they only had 22.4-25.8% aa sequence identity, whereas the two TTSuV1 genotypes (TTSuV1a and 1b) were antigenically related and cross-reactive due to their higher aa sequence homology (49.4-52.4%). It is possible that the antigenic relationship of different anelloviruses in the same genus may depend on a threshold or a range of aa sequence homology. The available data using TTSuV as a model will provide insights into similar research of antigenic diversity on human anelloviruses (TTV, TTMV and TTMDV) in the future.

The present study on TTSuV1 together with our previous study on TTSuV2 (Huang, Y. W., et al. 2011. Virus Res 158:79-88) also revealed a broader picture of the nature of mixed TTSuVs infections under natural or clinically disease conditions by assessing the serological and virological profiles. It is not surprising to see in this study that several features of TTSuV1 infection were consistent with that of TTSuV2 (FIGS. 3 & FIG. 11). More importantly, the inventors provided new evidence to support the current opinion that TTSuV1 is likely not associated with PCVAD (1, 18, 23), by demonstrating that both viral loads and antibody levels were not significant different between PCVAD-affected and -unaffected pigs (FIG. 12), and that there was no significant PCV2/TTSuV1 synergic effect. It is not known whether the presence of ORF1 antibody is protective against homologous TTSuV infection. However, since antibodies to TTSuV1 or TTSuV2 ORF1 do not cross-react with the heterologous TTSuV antigen, it appears that TTSuV1 infection and the consequent humoral immune response do not interfere with TTSuV2 infection. Therefore, this may make the development of a single vaccine against the two recognized TTSuV species difficult. Together, the results from the present study have important implications in understanding the diversity of anellovirus, and in diagnosis and vaccine development of TTSuVs.

Vaccines of the infectious viral and infectious molecular DNA clones, and methods of using them, are also included within the scope of the present invention. Inoculated pigs are protected from viral infection and associated diseases caused by TTV2 infection or co-infection. The novel method protects pigs in need of protection against viral infection by administering to the pig an immunologically effective amount of a vaccine according to the invention, such as, for example, a vaccine comprising an immunogenic amount of the infectious TTsuV DNA, a plasmid or viral vector containing the infectious DNA clone of TTsuV, the recombinant TTsuV DNA, the polypeptide expression products, the bacteria-expressed or baculovirus-expressed purified recombinant ORF1 capsid protein, etc. Other antigens such as PRRSV, PPV, other infectious swine agents and immune stimulants may be given concurrently to the pig to provide a broad spectrum of protection against viral infections.

The vaccines comprise, for example, the infectious viral and molecular DNA clones, the cloned TTsuV infectious DNA genome in suitable plasmids or vectors such as, for example, the pSC-B vector, an avirulent, live virus, an inactivated virus, expressed recombinant capsid subunit vaccine, etc. in combination with a nontoxic, physiologically acceptable carrier and, optionally, one or more adjuvants. The vaccine may also comprise the infectious TTsuV2 molecular DNA clone described herein. The infectious TTsuV DNA, the plasmid DNA containing the infectious viral genome and the live virus are preferred with the live virus being most preferred. The avirulent, live viral vaccine of the present invention provides an advantage over traditional viral vaccines that use either attenuated, live viruses which run the risk of reverting back to the virulent state or killed cell culture propagated whole virus which may not induce sufficient antibody immune response for protection against the viral disease.

Vaccines and methods of using them are also included within the scope of the present invention. Inoculated mammalian species are protected from serious viral infection, may also provide protection for disease related to co-infection of TTsuV, such as porcine dermatitis and nephropathy syndrome (PDNS), postweaning multisystemic wasting syndrome (PMWS), and other related illness. The vaccines comprise, for example, an inactivated or attenuated TTsuV virus, a nontoxic, physiologically acceptable carrier and, optionally, one or more adjuvants.

The adjuvant, which may be administered in conjunction with the vaccine of the present invention, is a substance that increases the immunological response of the pig to the vaccine. The adjuvant may be administered at the same time and at the same site as the vaccine, or at a different time, for example, as a booster. Adjuvants also may advantageously be administered to the pig in a manner or at a site different from the manner or site in which the vaccine is administered. Suitable adjuvants include, but are not limited to, aluminum hydroxide (alum), immunostimulating complexes (ISCOMS), non-ionic block polymers or copolymers, cytokines (like IL-1, IL-2, IL-7, IFN-$\alpha$, IFN-$\beta$, IFN-$\gamma$, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

The vaccines may further contain additional antigens to promote the immunological activity of the infectious TTsuV DNA clones such as, for example, porcine reproductive and respiratory syndrome virus (PRRSV), porcine parvovirus (PPV), other infectious swine agents and immune stimulants.

The new vaccines of this invention are not restricted to any particular type or method of preparation. The cloned viral vaccines include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

As a further benefit, the preferred live virus of the present invention provides a genetically stable vaccine that is easier to make, store and deliver than other types of attenuated vaccines.

Another preferred vaccine of the present invention utilizes suitable plasmids for delivering the nonpathogenic DNA clone to pigs. In contrast to the traditional vaccine that uses live or killed cell culture propagated whole virus, this invention provides for the direct inoculation of pigs with the plasmid DNA containing the infectious viral genome.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from ORF1, ORF1/1, ORF2, ORF2/2, etc.). Such identified genes or immunodominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product. The recombinant subunit vaccines are based on bacteria-expressed (FIG. 10, FIG. 15) or baculovirus-expressed ORF1 capsid proteins of TTsuV1a, PTTsuV1b and TTsuV2.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

An immunologically effective amount of the vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to the TTsuV virus. Preferably, the pig is protected to an extent in which one to all of the adverse physiological symptoms or effects of the viral disease are significantly reduced, ameliorated or totally prevented.

The vaccine can be administered in a single dose or in repeated doses. Dosages may range, for example, from about 1 microgram to about 1,000 micrograms of the plasmid DNA containing the infectious chimeric DNA genome (dependent upon the concentration of the immuno-active component of the vaccine), preferably 100 to 200 micrograms of the TTsuV DNA clone, but should not contain an amount of virus-based antigen sufficient to result in an adverse reaction or physiological symptoms of viral infection. Methods are known in the art for determining or titrating suitable dosages of active antigenic agent to find minimal effective dosages based on the weight of the pig, concentration of the antigen and other typical factors. Preferably, the infectious viral DNA clone is used as a vaccine, or a live infectious virus can be generated in vitro and then the live virus is used as a vaccine. In that case, from about 50 to about 10,000 of the 50% tissue culture infective dose (TCID 50) of live virus, for example, can be given to a pig.

The new vaccines of this invention are not restricted to any particular type or method of preparation. The vaccines include, but are not limited to, modified live vaccines, inactivated vaccines, subunit vaccines, attenuated vaccines, genetically engineered vaccines, etc.

The advantages of live vaccines are that all possible immune responses are activated in the recipient of the vaccine, including systemic, local, humoral and cell-mediated immune responses. The disadvantages of live virus vaccines, which may outweigh the advantages, lie in the potential for contamination with live adventitious viral agents or the risk that the virus may revert to virulence in the field.

To prepare inactivated virus vaccines, for instance, the virus propagation and virus production can occur in cultured porcine cell lines such as, without limitation PK-15 cells. Serial virus inactivation is then optimized by protocols generally known to those of ordinary skill in the art or, preferably, by the methods described herein.

Inactivated virus vaccines may be prepared by treating the TTsuV with inactivating agents such as formalin or hydrophobic solvents, acids, etc., by irradiation with ultraviolet light or X-rays, by heating, etc. Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection.

The preparation of subunit vaccines typically differs from the preparation of a modified live vaccine or an inactivated vaccine. Prior to preparation of a subunit vaccine, the protective or antigenic components of the vaccine must be identified. In the present invention, antigenic components of TTsuV were identified as the ORF1 capsid proteins of TTsuV1a, TTsuV1b and TTsuV2, which were expressed and purified in *Escherichia coli* (*E. coli*) in this invention, and other expression system, such as baculovirus expression system, for use as subunit recombinant capsid vaccines. Such protective or antigenic components include certain amino acid segments or fragments of the viral capsid proteins which raise a particularly strong protective or immunological response in pigs; single or multiple viral capsid proteins themselves, oligomers thereof, and higher-order associations of the viral capsid proteins which form virus substructures or identifiable parts or units of such substructures; oligoglycosides, glycolipids or glycoproteins present on or near the surface of the virus or in viral substructures such as the lipoproteins or lipid groups associated with the virus, etc. Preferably, the ORF1 protein is employed as the antigenic component of the subunit vaccine. Other proteins may also be used such as those encoded by the nucleotide sequence in the ORF2, ORF1/1, and ORF2/2 gene. These immunogenic components are readily identified by methods known in the art. Once identified, the protective or antigenic portions of the virus (i.e., the "subunit") are subsequently purified and/or cloned by procedures known in the art. The subunit vaccine provides an advantage over other vaccines based on the live virus since the subunit, such as highly purified subunits of the virus, is less toxic than the whole virus.

If the subunit vaccine is produced through recombinant genetic techniques, expression of the cloned subunit such as the ORF1, ORF2. ORF1/1, and ORF2/2 genes, for example, may be expressed by the method provided above, and may also be optimized by methods known to those in the art (see, for example, Maniatis et al., "Molecular Cloning: A Laboratory Manual," Cold Spring Harbor Laboratory, Cold Spring Harbor, Mass. (1989)). On the other hand, if the subunit being employed represents an intact structural feature of the virus, such as an entire capsid protein, the procedure for its isolation from the virus must then be optimized. In either case, after optimization of the inactivation protocol, the subunit purification protocol may be optimized prior to manufacture.

To prepare attenuated vaccines, the live, pathogenic virus is first attenuated (rendered nonpathogenic or harmless) by methods known in the art or, preferably, as described herein. For instance, attenuated viruses may be prepared by the technique of the present invention which involves the novel serial passage through embryonated pig eggs. Attenuated viruses can be found in nature and may have naturally-occurring gene deletions or, alternatively, the pathogenic viruses can be attenuated by making gene deletions or producing gene mutations. The attenuated and inactivated virus vaccines comprise the preferred vaccines of the present invention.

Genetically engineered vaccines, which are also desirable in the present invention, are produced by techniques known in the art. Such techniques involve, but are not limited to, the use of RNA, recombinant DNA, recombinant proteins, live viruses and the like.

For instance, after purification, the wild-type virus may be isolated from suitable clinical, biological samples such as serum, fecal, saliva, semen and tissue samples by methods known in the art, preferably by the method taught herein using infected pigs or infected suitable cell lines. The DNA is extracted from the biologically pure virus or infectious agent by methods known in the art, and purified by methods known in the art, preferably by ultracentrifugation in a CsCl gradient. The cDNA of viral genome is cloned into a suitable host by methods known in the art (see Maniatis et al., id.), and the virus genome is then analyzed to determine essential regions of the genome for producing antigenic portions of the virus. Thereafter, the procedure is generally the same as that for the modified live vaccine, an inactivated vaccine or a subunit vaccine.

Genetically engineered vaccines based on recombinant DNA technology are made, for instance, by identifying the portion of the viral gene which encodes for proteins responsible for inducing a stronger immune or protective response in pigs (e.g., proteins derived from ORF1, ORF2, ORF1/1, and ORF2/2, etc.). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co. (1992)). The host cells are cultured, thus expressing the desired vaccine proteins, which can be purified to the desired extent and formulated into a suitable vaccine product.

Genetically engineered proteins, useful in vaccines, for instance, may be expressed in insect cells, yeast cells or mammalian cells. The genetically engineered proteins, which may be purified or isolated by conventional methods, can be directly inoculated into a porcine or mammalian species to confer protection against TTsuV.

An insect cell line (like sf9, sf21, or HIGH-FIVE) can be transformed with a transfer vector containing polynucleic acids obtained from the virus or copied from the viral genome which encodes one or more of the immuno-dominant proteins of the virus. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Alternatively, DNA from the isolated TTsuV which encode one or more capsid proteins can be inserted into live vectors, such as a poxvirus or an adenovirus and used as a vaccine.

An immunologically effective amount of the vaccine of the present invention is administered to an porcine or mammalian species in need of protection against said infection or syndrome. The "immunologically effective amount" can be easily determined or readily titrated by routine testing. An effective amount is one in which a sufficient immunological response to the vaccine is attained to protect the pig or other mammal exposed to the TTsuV virus, or TTsuV co-infection, which may cause porcine dermatitis and nephropathy syndrome (PDNS), postweaning multisystemic wasting syndrome (PMWS) or related illness. Preferably, the pig or other mammalian species is protected to an extent in which one to all of the adverse physiological symptoms or effects of the viral disease are found to be significantly reduced, ameliorated or totally prevented.

The vaccine can be administered in a single dose or in repeated doses. Dosages may contain, for example, from 1 to 1,000 micrograms of virus-based antigen (dependent upon the concentration of the immuno-active component of the vaccine), but should not contain an amount of virus-based antigen sufficient to result in an adverse reaction or physiological symptoms of viral infection. Methods are known in the art for determining or titrating suitable dosages of active antigenic agent based on the weight of the bird or mammal, concentration of the antigen and other typical factors.

The vaccine can be administered to pigs. Also, the vaccine can be given to humans such as pig farmers who are at high risk of being infected by the viral agent. It is contemplated that a vaccine based on the TTsuV can be designed to provide broad protection against both porcine and human TTV. In other words, the vaccine based on the TTsuV can be preferentially designed to protect against human TTV infection through the so-called "Jennerian approach" (i.e., cowpox virus vaccine can be used against human smallpox by Edward Jenner). Desirably, the vaccine is administered directly to a porcine or other mammalian species not yet exposed to the TTV virus. The vaccine can conveniently be administered orally, intrabuccally, intranasally, transdermally, parenterally, etc. The parenteral route of administration includes, but is not limited to, intramuscular, intravenous, intraperitoneal and subcutaneous routes.

When administered as a liquid, the present vaccine may be prepared in the form of an aqueous solution, a syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions which contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of mammalian body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives which can be employed in the present vaccine include, but are not limited to, dextrose, conventional antioxidants and conventional chelating agents such as ethylenediamine tetraacetic acid (EDTA). Parenteral dosage forms must also be sterilized prior to use.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

EXAMPLES

Example 1

Viral DNA Extraction, Nested PCR and Genomic PCR

Convenient serum and semen samples from 20 conventional adult boars from a Virginia pig farm were used in the study. Total DNA was isolated from 20 serum and 19 semen samples using QIAamp DNA mini kit (Qiagen). To screen for the positive PTTV-containing samples, nested PCR amplifications of the conserved regions in the UTR of PTTV1 and PTTV2 were initially performed by using AmpliTaq Gold polymerase (Applied Biosystems). The two primer pairs used to amplify the fragment A of PTTV1 were TTV1-mF (SEQ ID NO:45)/TTV1-mR (SEQ ID NO:46)(for the first-round PCR) and TTV1-nF (SEQ ID NO:47)/TTV1-nR (SEQ ID NO:48) (for the second-round PCR), whereas the two primer pairs used to amplify the fragment D of PTTV2 were TTV2-mF (SEQ ID NO:49)/TTV2-mR (SEQ ID NO:50) (for the first-round PCR) and TTV2-nF (SEQ ID NO:51)/TTV2-nR (SEQ ID NO:52) (for the second-round PCR; FIGS. 17 A and 17B, Table 1).

In order to amplify the full-length genomic sequences of both PTTV1 and PTTV2, we first performed an inverse genomic PCR using a pair of conserved gene-specific primers TTV1-IF (SEQ ID NO:1)/TTV1-IR (SEQ ID NO:4) located in region A for PTTV1 and another pair of gene-specific primers TTV2-IF (SEQ ID NO:5)/TTV2-IR (SEQ ID NO:8) located in region D for PTTV2, respectively, with Herculase II Fusion DNA Polymerase (Stratagene) according to the manufacturer's instructions. No PCR products with expected sizes were detected. Subsequently we designed new sets of primers to amplify two regions covering the complete PTTV1 and PTTV2 genomes in the second-round PCR, respectively (FIG. 17A-17B). The primer pairs used to amplify fragments B and C of PTTV1 were TTV1-IF (SEQ ID NO:1)/TTV1-2340R (SEQ ID NO:2) and TTV1-2311F (SEQ ID NO:3)/TTV1-IR (SEQ ID NO:4), respectively, whereas the primer pairs used to amplify fragments E and F of PTTV2 were TTV2-IF (SEQ ID NO:5)/TTV2-2316R (SEQ ID NO:6) and TTV2-GCF (SEQ ID NO:7)/TTV2-IR (SEQ ID NO:8), respectively (FIG. 17A-17B and Table 1). Fragments C and F contain the GC-rich regions of PTTV1 and PTTV2, respectively. The amplified PCR products were individually excised, purified, and subsequently cloned into a pSC-B-amp/kan vector (Stratagene) by StrataClone Blunt PCR cloning strategy according to the manufacturer's instructions (Stratagene) followed by DNA sequencing.

Example 2

Screening for Porcine TTV Positive Samples Collected from Boars in a Farm from Virginia Porcine TTV DNA was previously detected from pigs in different geographic regions by nested-PCR based on the UTR sequence of a Japanese PTTV1 strain Sd-TTV31 (McKeown et al., 2004, supra). With the recent identification of PTTV2, two different sets of nested-PCR primers have been used to amplify region A of PTTV1 and region D of PTTV2, respectively (FIG. 17A-17B) (Ellis et al., 2008, supra; Kekarainen, T., et al (2006). *J Gen Virol* 87(Pt 4), 833-7; Krakowka et al., 2008, supra). A similar detection approach was also utilized in the present study to identify PTTV strains from pigs in the United States. In order to screen for indigenous PTTV1- or PTTV2-positive samples for subsequent use to determine the full-length genomic sequences, 20 sera (SR#1-20) and 19 semen samples (SM#1-18, and SM#20) collected from 20 boars in a farm of Virginia were subjected to nested-PCR analyses. Surprisingly, all the 20 serum samples were positive for PTTV1 and 19 were also positive for PTTV2 (except for SR#18). In contrast, only 1 semen sample (SM#6) was PTTV1-positive and 3 semen samples (SM#8, 9 and 20) were PTTV2-positive. The result was consistent with a recent study in that boar semen samples were shown to be positive for PTTV DNA in Spain (Kekarainen, T., Lopez-Soria, S., and Segales, J. (2007). Detection of swine Torque teno virus genogroups 1 and 2 in boar sera and semen. *Theriogenology* 68(7), 966-71), and thus suggesting a potential vertical transmission of PTTV. However, the prevalence rates of both PTTV1 and PTTV2 in semen were much lower than that in sera, suggesting that there is no direct association for the presence of PTTV DNAs in sera and semen of the same pig.

Example 3

Sequence and Phylogenetic Analyses

Generic analyses and alignment of DNA and amino acid sequences were performed using Lasergene package (DNASTAR Inc., Madison, Wis.). The genomic sequences of three known PTTV strains and their corresponding GenBank accession numbers used for the alignment and comparison are Sd-TTV31 (AB076001), TTV-1p (AY823990) and TTV-2p (AY823991). Pairwise sequence comparisons (PASC) were performed using 121 full-length genomic sequences of human and animal TTV-related strains available in GenBank with an online program PASC (Pairwise Sequence Comparison) developed for analysis of pairwise identity distribution within viral families and available from the National Center for Biotechnology Information (NCBI) (Bao Y., Kapustin Y. & Tatusova T. (2008). Virus Classification by Pairwise Sequence Comparison (PASC). Encyclopedia of Virology, 5 vols. (B. W. J. Mahy and M. H. V. Van Regenmortel, Editors). Oxford: Elsevier. Vol. 5, 342-348).

Phylogenetic trees were constructed by the neighbor-joining method in the PAUP4.0 program (David Swofford, Smithsonian Institute, Washington, D.C., distributed by Sinauer Associate Inc.) based upon the full-length genomic sequences and the deduced amino acid sequences of 4 ORFs of seven PTTV strains. The data were obtained from 1000 re-sampling.

Example 4

Design of PCR Primers for Diagnosing Porcine PTTV Infection

Analyses and alignment of DNA sequences were performed using Lasergene package (DNASTAR Inc., Madison, Wis.). Full-length genomic sequences of ten porcine TTV strains and their corresponding GenBank accession numbers used for the alignment were as follows. Species PTTV1: Sd-TTV31 (AB076001), PTTV1a-VA (GU456383), TTV-1p (AY823990), PTTV1b-VA (GU456384), swSTHY-TT27 (GQ120664) and TTV1 #471819 (GU188045). Species PTTV2: PTTV2b-VA (GU456385), PTTV2c-VA (GU456386), TTV-2p (AY823991) and TTV2 #472142 (GU188046). The conserved sequences among the 6 PTTV1 and 4 PTTV2 genomes were identified, respectively, and subsequently used to guide real-time PCR primer selections using the Beacon Designer program (PREMIER Biosoft International, Palo Alto, Calif.). Primers used for the duplex nested PCR of PTTV1 were designed by the Lasergene package.

Example 5

Standard Curves of PTTV1 and PTTV2 Real-Time PCR

A region of 2091 bp corresponding to the PCR fragment B of PTTV1b-VA genome was re-amplified from the same PCR fragment using primers TTV1-IF (5'-CATAGGGTG-TAACCAATCAGATTTAAGGCGTT-3') and TTV1-2340R (5'-GGTCATCAGACGATCCATCTCCCTCAG-3') as described previously (Huang et al., 2010). The resulting amplicon was gel-purified by QIAquick Gel Extraction Kit (Qiagen) and quantified by a NanoDrop spectrophotometer that was used for the real-time PCR standard template of porcine TTV species 1. A full-length DNA clone of PTTV2c-VA strain, pSC-PTTV2c, was constructed by assembling PCR fragments E and F from PTTV2c-VA in the vector pSC-B-amp/kan (Huang et al., unpublished data). Plasmid pSC-PTTV2c (7082 bp) was used for the real-time PCR standard template of porcine TTV species 2 and the plasmid DNA concentration was measured by a NanoDrop spectrophotometer. A 10-fold dilution series of the two templates was used to generate the real-time PCR standard curves, respectively.

Example 6

Extraction of Viral DNA for PCR Assays

Total DNA was isolated from 20 serum and 19 semen samples collected from 20 conventional adult boars (with no clinical syndromes) from a Virginia pig farm using QIAamp DNA mini kit (Qiagen) as described previously (Huang et al., 2010). A sample volume of 400 μl for sera and semen was used to extract DNA with a final eluate of 50 μl sterile water. All extracted DNA samples were stored at −20° C. until real-time PCR testing. Detection of porcine TTVs in these samples by conventional nested PCR had been described previously (Huang et al., 2010). Total DNA extracted from a goat serum sample with the same procedure was used as the negative control.

Example 7

SYBR Green Real-Time Quantitative PCR Assays

PTTV1- and PTTV2-specific real-time PCR were performed, respectively, using SensiMix SYBR & Fluorescein kit (Quantace Ltd) and the MyiQ iCYCLER Real Time PCR instrument (BIO-RAD Laboratories). Each 25-μl reaction contained 12.5 μl of SYBR green Master Mix, 4 μl of extracted DNA, 0.5 μl of each primer (10 nM) and 7.5 μl of sterile water. The PCR condition for PTTV1 was 10 min at 95° C. followed by 40 cycles of amplification (15 sec at 95° C., 30 sec at 59.4° C., 10 sec at 72° C.). This was immediately followed by a melting point analysis obtained by gradually increasing the temperature form 55° C. to 95° C. with the fluorescence signal being measured every 0.5° C. The PCR condition for PTTV2 was the same as PTTV1 except that the annealing temperature was 56° C. PTTV1 and PTTV2 standard templates were included as positive controls in every run. Amplification and data analysis were carried out using MyiQ System software (BIO-RAD Laboratories). All samples were run in duplicate on the same plate.

Example 8

Specificity and Sensitivity of Two Singleplex Assays

The optimal annealing temperatures for amplification of PTTV1- and PTTV2-specific assays were 59.4° C. and 56° C., respectively, as determined by a 10-fold dilution of amplifications using a gradient of annealing temperatures. Amplification of the 118-bp product using primers TTV1F/TTV1R was obtained only with PTTV1 template whereas amplification of the 200-bp product with PTTV2 template was only observed when primers TTVF4/TTVR4 were used. Neither assay yielded any cross-amplification from the other, confirming the specificity of the primers and targets (data not shown).

A PTTV1 standard curve was established over a range of target DNA concentrations per 25 µl. The linear range was shown to span $4.4 \times 10^1$ to $4.4 \times 10^8$ copies. The minimum detection limit (44 copies) corresponded to a threshold cycle ($C_t$) of 37.57. Tested samples with $C_t > 37.57$ were considered as below the detection limit and were not quantifiable. Similarly, a PTTV2 standard curve was generated and used to detect DNA concentration ranging from $8.6 \times 10^0$ to $8.6 \times 10^8$ copies per 25 µl reaction. The corresponding $C_t$ of minimum detection limit (8.6 copies) was 36.53. All samples that were considered as PTTV1- or PTTV2-positive had copy numbers lower than the respective maximum detection limit. Melting curves using a 10-fold dilution of PTTV1 or PTTV2 standard template, as well as 20 boar serum samples, displayed melting temperatures ($T_m$) of 87.0° C. for PTTV1 and 80.0° C. for PTTV2, respectively. No peaks were observed for the negative controls using sterile water or goat serum DNA as templates.

Example 9

Quantification of Porcine TTV1 and TTV2 in Boar Serum and Semen Samples

Viral load was expressed as copy numbers of PTTV1 or PTTV2 genomes per ml of original boar serum samples. PTTV1 DNA were detected in all 20 serum samples ranging from $1.91 \times 10^3$ to $3.25 \times 10^5$ copies/ml whereas PTTV2 DNA were detected in 19 serum samples (except #10) ranging from $3.59 \times 10^2$ to $1.39 \times 10^6$ copies/ml. The result was consistent to our previous study by using conventional nested PCR (Table 5). None of the semen samples were PTTV1-positive whereas three semen samples were PTTV2-positive with very low viral loads (230, 244 and 357 copies/ml, respectively).

Example 10

PTTV1/PTTV2 Duplex Real-Time PCR Assay

PTTV1/PTTV2 duplex real-time PCR assay was performed in a 25 µl PCR system containing 12.5 µl of SYBR green Master Mix, 0.5 µl of each PTTV1 primers, 0.5 µl of each PTTV2 primers, 4 µl of DNA and 6.5 µl of sterile water. The duplex PCR condition and melting point analysis were the same as PTTV1 except that the annealing temperature was 58° C. The melting peaks were analyzed to distinguish the PTTV1- and PTTV2-specific amplicons.

Example 11

Duplex Nested PCR

The first-round PCR was performed with a Platinum PCR HiFi Supermix (Invitrogen) using 4 µl of extracted DNA in a total volume of 50 µl. The PCR condition was 30 cycles of 94° C. for 30 sec, 55° C. for 30 sec, 72° C. for 30 sec with an initial denaturation of the template DNA at 94° C. for 2 min. A 4-µl aliquot of the first-round PCR product was used for the second-round PCR with the same PCR reagents and condition. One pair of primers P1ab-mF/P1ab-mR was used in the first-round PCR whereas a mixture of two pairs of primers, P1a-nF/P1a-nR for detection of PTTV1a, and P1b-nF/P1b-nR for detection of PTTV1b, were used in the second-round PCR (Table 1). The amplification products were visualized by gel electrophoresis on a 1% agarose gel stained with ethidium bromide and two bands specific for each type were differentiated by UV light.

Example 12

Construction of PTTV1 and PTTV2 ORF Expression Plasmids

The C-terminal parts of ORF1 of PTTV1a, PTTV1b and PTTV2c were amplified from the respective full-length DNA clones (pSC-PTTV1a, pSC-PTTV1b and pSC-PTTV2c; described elsewhere). The amplified fragments were expected to encode protein products with 319 aa for PTTV1a (ORF1 aa positions 317-635 (SEQ ID NO:13); GenBank accession no. GU456383), 318 aa for PTTV1b (ORF1 aa positions 322-639 (SEQ ID NO:14); GenBank accession no. GU456384), and 316 aa for PTTV2c (ORF1 aa positions 310-625 (SEQ ID NO:16); GenBank accession no. GU456386), respectively. A C-terminal truncated fragment of PTTV1b encoding 248 aa (ORF1 aa positions 322-569 (SEQ ID NO:14)) was also amplified and used as a comparison control for SDS-PAGE analysis. All the plas-

TABLE 5

Comparison of porcine TTVs detection by different assays in 20 serum and 19 semen samples from adult boars in a Virginia Farm.

| Samples | No. of positive/total no. tested by different assay | | | | |
|---|---|---|---|---|---|
| | PTTV1 real-time PCR | PTTV1 nested PCR | PTTV2 real-time PCR | PTTV2 nested PCR | PTTV1/PTTV2 duplex real-time PCR |
| Serum PTTV1 | 20/20 | 20/20 | — | — | 20/20 |
| Serum PTTV2 | — | — | 19/20 | 19/20 | 19/20 |
| Semen PTTV1 | 0/19 | 1/19 | — | — | — |
| Semen PTTV2 | — | — | 3/19 | 3/19 | — | mids were constructed by cloning of the PCR products into an E. coli/baculovirus/mammalian cells triple expression vector pTriEx1.1-Neo (Novagen) between the NcoI and XhoI restriction sites to generate C-terminally 8×His-tagged fusion proteins. The four recombinant plasmids were designated pTri-PTTV1a-ORF1, pTri-PTTV1b-ORF1, pTri-PTTV1b-ORF1 ctruc and pTri-PTTV2c-ORF1. All cloned sequences were confirmed by DNA sequencing.

Example 13

Expression of Recombinant PTTV1 and PTTV2 Proteins

The four expression plasmids were transformed into Rosetta 2 (DE3) pLacI competent cells (Novagen), respectively, and the bacteria were plated on LB agar plates containing 100 ampicillin overnight at 37° C. A single transformation colony for each construct was used to inoculate 3 ml of LB medium containing 100 μg/ml of ampicillin (LB/amp), and grown 6-8 hours at 37° C. The turbid 3 ml culture for each construct was then used to make bacterial stocks by adding 25% filter sterilized glycerol, and freezing the culture down at −80° C. Prior to purification, 10 μl of the frozen bacterial stock for each construct was used to inoculate a 3 ml starter culture of LB/amp, and grown for 6-8 hours at 37° C. A 100-ml of Overnight Express TB Media (Novagen) was inoculated with the starter culture to induce protein expression, and was grown 16-18 hours at 37° C. After incubation, the autoinduction culture underwent centrifugation at 3400 rpm for 15 minutes at 4° C. The resulting supernatant for each construct was discarded, and each of the bacterial pellets was reserved at −20° C. until use.

Example 14

Purification and Dialysis of Recombinant Proteins

The recombinant proteins were insoluble and expressed within the bacterial inclusion bodies. Each of the bacterial pellets was treated with BugBuster and rLysozyme according to the manufacture's protocol (Novagen), and Benzonase Nuclease (Novagen) was added for degradation of DNA and RNA. Each of the inclusion body pellets was subsequently resuspended with 840 μl of lysis buffer (6M Guanidine Hydrochloride, 0.1M sodium phosphate, 0.01M Tris-Chloride, 0.01M imidazole, pH 8.0), and frozen at −80° C. for at least 30 minutes. It was then thawed, diluted with an additional 2.5 ml of lysis buffer and gently rotated for 30 minutes at room temperature. The lysate supernatants were collected by centrifugation at 15,000×g for 30 minutes at room temperature. A 50%-Ni-NTA His-bind slurry (Novagen) was added to each of the decanted supernatants, and the mixtures were shaken for 60 minutes at room temperature to promote his-tag binding. The lysate/resin mixtures were loaded into an empty chromatography column. After the initial flow-through, a 7-ml of lysis buffer was added to the column and allowed to flow through. Each column was then washed 2 times with 7 mL of wash buffer (8M Urea, 0.1M Sodium Phosphate, 0.15M Sodium Chloride, 0.02M imidazole, pH 8.0). Elution of the target protein was achieved by adding 4 separate 1 ml aliquots of elution buffer (8M Urea, 0.05M Sodium Phosphate, 1M Sodium Chloride, 0.5M Imidazole, pH 8.0) to the column. The four elution fractions were analyzed by SDS Page and Coomasie Blue Staining.

The elutions containing significant concentrations of the target protein were injected into a 0.5 ml-3 ml dialysis cassette with a 20,000 molecular weight cut-off (Pierce). A series of 4 dialysis buffers were used for dialysis; dialysis buffer 1 (6M Urea, 0.05M Sodium Phosphate, 0.8M Sodium Chloride, 0.3M Imidazole, pH 8.0), dialysis buffer 2 (4M Urea, 0.033M Sodium Phosphate, 0.533M Sodium Chloride, 0.2M Imidazole, pH 8.0), dialysis buffer 3 (2.67M Urea, 0.022M Sodium Phosphate, 0.356M Sodium Chloride, 0.133M Imidazole, pH 8.0) and dialysis buffer 4 (1.5M Urea, 0.0148 Sodium Phosphate, 0.237M Sodium Chloride, 0.089M Imidazole, pH 8.0). The dialysis cassette was sequentially submerged and rotated in each dialysis buffer for over 6 hours at 4° C. When dialysis was complete, the recombinant His-tagged fusion proteins were each removed from the cassettes, quantified using a NanoDrop and frozen at −80° C.

Example 15

SDS-PAGE and Anti-His-Tagged Western Blot

A western blot was developed to detect purified recombinant proteins by using an anti-6×His-tagged monoclonal antibody (Rockland). Equal volumes of each of the purified truncated ORF1 proteins and LDS/10% β-ME were mixed, and boiled at 95° C. for 10 minutes. A 10-μ1 of the boiled sample was added to each appropriate well of a 4-12% Bis-Tris Polyacrylamide Gel (Invitrogen), and was run at 200 volts for 43 minutes in 1×MES running buffer (Invitrogen). The proteins were transferred to a PVDF membrane (Bio-Rad) using a Trans blot semi dry transfer apparatus and 1×transfer buffer (Invitrogen). Once transfer was complete, the PVDF membrane was incubated in Odyssey blocking buffer (Li-Cor) at room temperature for 1 hour. The anti-6× His-tagged MAb was diluted at 1:1000 in Odyssey blocking buffer/0.2% tween 20, and transferred to the membrane after the previous Odyssey blocking buffer was removed. The MAb was left on a rocker to incubate with the membrane for either 2 hours at room temperature or 4° C. overnight, and then the membrane was washed 3 times with tris buffered saline/0.05% tween 20 (TBS-T, Sigma). A Goat anti-rabbit IgG IRDye 800 (Li-Cor) antibody was diluted at 1:5000 in Odyssey blocking buffer/0.2% tween 20/0.1% SDS. It was transferred to the freshly washed PVDF membrane, and allowed to incubate for 1 hour at room temperature while gently rocking. The membrane was washed 3 times with TBS-T, 1 time with TBS and imaged with the Li-Cor Odyssey.

Example 16

Serum Western Blot

A serum western blot was developed, and used to identify positive and negative serum controls for ELISA development. After SDS-PAGE as described above, the proteins were transferred to a PVDF membrane that was subsequently incubated in Odyssey blocking buffer (Li-Cor) at room temperature for 1 hour. A selected serum sample was diluted at 1:100 in Odyssey blocking buffer/0.2% tween 20, and transferred to the membrane after the previous Odyssey blocking buffer was removed. The serum sample was left on a rocker to incubate with the membrane for 2 hours at room temperature, and then the membrane was washed 3 times with tris buffered saline/0.05% tween 20 (TBS-T, Sigma). A goat anti-swine IgG IRDye 800 antibody (Rockland) was diluted at 1:2500 in Odyssey blocking buffer/0.2% tween 20/0.1% SDS. It was transferred to the freshly washed PVDF membrane, and allowed to incubate for 1 hour at room temperature while gently rocking. The membrane was washed 3 times with TBS-T, 1 time with TBS and imaged with the Li-Cor Odyssey.

Example 17

Indirect PTTV1a-, PTTV1b- and PTTV2-Specific ELISA

The optimal concentrations of the antigens used to coat the plates and dilutions of antisera and conjugates were determined by checkboard titration. The ELISA was initiated by diluting each of the purified recombinant His-tagged fusion proteins (PTTV1a, PTTV1b and PTTV2c, respectively) to 680 ng/ml in 1×Carbonate Coating Buffer (CCB) at a pH of 9.6, and coating medium binding ELISA plates (Greiner) with 100 µl/well. The plates were covered, and allowed to incubate at 37° C. for 2 hours. After coating, the diluted proteins were removed, and each well was washed 3 times with 300 µl of 1×TBS-T. Protein Free Blocking Buffer (Pierce) was then added at a volume of 300 µl/well, and the plates were allowed to incubate at 37° C. for 1 hour. Meanwhile, in a 96-well dilution block, the serum samples were diluted at 1:100 in 150 µl of protein free blocking buffer. The block was then removed, and 100 µl of each diluted serum sample was transferred to each corresponding well on the ELISA plates. The plates were allowed to incubate at 37° C. for 2 hours, after which each well was washed 3 times with 300 µl of TBS-T. Next, the HRP-conjugated anti-swine IgG antibody (Rockland) was diluted at 1:4000 in 12 ml of protein free block, and 100 µl was added to each well of the plates. This was incubated at 37° C. for 1 hour, and then each well was washed 3 times with 300 µl of TBS-T. In order to develop the ELISA, 100 µl of Sure Blue Reserve 1-Component (KPL) was added to each well of the plates. After 20 minutes, 100 µl of 1N HCL was added to each well to stop development. The plates were then read at 450 nm.

Example 18

Data Analyses

Porcine sera used in cell culture research from a commercial company (manufactured in New Zealand and considered free from all OIE diseases) were used as a positive control for the three ELISA protocols because the sera were all PTTV1a-, PTTV1b- and PTTV2-positive as detected by serum western blot and displayed high OD values (>2.0). We initially used pooled gnotobiotic pig sera as a negative control as they were negative in western blot detection. Subsequently, in comparison of the negative gnotobiotic pig sera, we screened some porcine sera collected from a conventional pig farm in Wisconsin. They were also negative in western blot detection and their OD values corresponded to that of negative gnotobiotic pig sera. These conventional porcine sera were pooled and used as a negative control. The cutoff value for each ELISA was calculated as the mean OD value of the negative control group (n=4) plus 3 times of the standard deviation.

Example 19

Construction of Full-Length Genomic DNA Clones of Porcine TTV1a, 1b and 2c

Figure 21E:
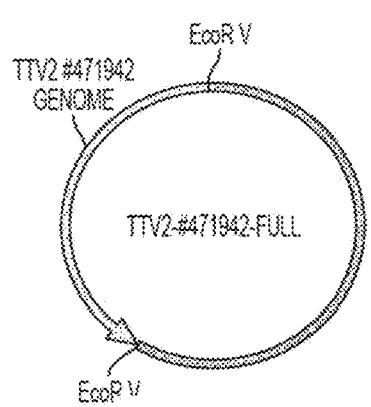

PCR fragments B and C from the US isolate PTTV1a-VA (GenBank accession no. GU456383) were re-amplified from the constructs described previously, and were subsequently assembled into a full-length genomic DNA with a BamH I site at the both ends of the genome by overlapping PCR using the Herculase II Fusion DNA Polymerase (Stratagene) on the vector pSC-B-amp/kan (Stratagene). The resulting construct was designated pSC-PTTV1a (FIG. 21A). Using the same strategy, the clone pSC-PTTV1b (FIG. 17B) originated from the US isolate PTTV1b-VA (GenBank accession no. GU456384) and the clone pSC-PTTV2c (FIG. 21C) originated from the US isolate PTTV2c-VA (GenBank accession no. GU456386) were constructed with the same restriction sites (BamH1) on the same backbone vector. Plasmid TTV2-#471942-full (FIG. 21E) containing a full-length genomic DNA originated from a Germany pathogenic porcine TTV2 isolate. TTV2-#471942 was a gift from Dr. Andreas Gallei (BIVI, Germany). TTV2-#471942 was classified into the porcine TTV subtype 2b together with the US isolate PTTV1b-VA based upon the phylogenetic analysis (data not shown).

Example 20

Construction of Tandem-Dimerized DNA Clones of Porcine TTV2b and 2c

Figure 21F:
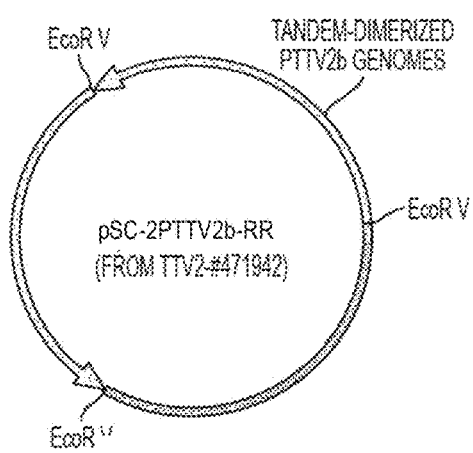

The full-length PTTV2c genome was excised from the clone pSC-PTTV2c by BamH I digestion, purified and ligated to form concatemers. Ligated concatemers were cloned into the BamH I-pre-digested pSC-B-amp/kan vector to produce a tandem-dimerized DNA clone, pSC-2PTTV2c-RR (FIG. 21D). Similarly, a tandem-dimerized DNA clone, pSC-2PTTV2b-RR, was generated from the clone TTV2-#471942-full using EcoR V restriction sites (FIG. 21F).

Example 21

Generation of PTTV1a-, PTTV1b- and PTTV2-Specific Anti-ORF1 Polyclonal Antibodies The ORF1-encoding product is the putative capsid protein of TTV. To generate PTTV1a-, PTTV1b- and PTTV2-specific anti-ORF1 polyclonal antibodies to detect the expression of PTTV ORF1 proteins and to determine the infectivity of PTTV DNA clones, the three ORF1 proteins from PTTV1a, PTTV1b and PTTV2c were expressed in *E. coli*, purified and were subsequently used to immunize New Zealand white rabbits, respectively, as a custom antibody production service at Rockland Immunochemicals (Gilbertsville, Pa.). Each anti-ORF1 polyclonal antibody was produced from serum of immunized rabbits.

Example 22

In Vitro Transfection of PTTV Infectious Clones

PK-15 cells were seeded at 2×10$^5$ cells per well onto a 6-well plate and grown until 60%-70% confluency before transfection. The DNA clones pSC-2PTTV2b-RR and pSC-2PTTV2c-RR were directly transfected into PK-15 cells, respectively, using Lipofectamine LTX (Invitrogen) according to the manufacturer's protocol. For clones pSC-PTTV1a, pSC-PTTV2c and TTV2-#471942-full, their ligated concatemers, produced as described above, were used for transfection, respectively. Cells were cultured for 3 to 5 days, and were then applied to an immunofluorescence assay (IFA) to detect the expression of ORF1 of porcine TTVs. Alternatively, transfected cells were passaged into new 6-well plates and continued to culture for 3 days before the IFA detection.

Example 23

Immunofluorescence Assay (IFA)

Transfected or passaged cells were washed 2 times with PBS and fixed with acetone. Five hundred microliters of the antibodies, specific to PTTV1a or PTTV2 at 1:500 dilution in PBS, was added over the cells and incubated for 1 hour at room temperature. Cells were washed 3 times with PBS and 500 µl Texas red- or Alexa Fluor 488-labeled goat anti-rabbit IgG (Invitrogen) at 1:200 dilution was then added. After 1-hour incubation at room temperature and washed with PBS, the cells were stained with 500 µl DAPI (KPL, Inc.) at 1:1000 dilution and visualized under a fluorescence microscope.

Example 24

In Vivo Inoculation of Conventional Pigs with the Tandem-Dimerized Porcine TTV2 Clones A pig inoculation study was performed to determine the infectivities of the two tandem-dimerized porcine TTV2 clones: pSC-2TTV2b-RR and pSC-2TTV2c-RR. Briefly, eight 4-week-old conventional pigs that were seronegative and viral DNA negative for porcine TTV2 were randomly assigned into two groups of four each. Each group of pigs was housed separately and maintained under conditions that met all requirements of the Institutional Committee on Animal Care and Use.

All pigs in each group were injected by a combination of both the intra-lymph node route and intramuscular route. The four pigs (nos. 181, 189, 192 and 193) were each injected with 200 µg of the pSC-2TTV2b-RR plasmid DNA whereas another four pigs (nos. 92, 180, 188 and 191) were each inoculated with 200 µg of the pSC-2TTV2c-RR clone. Pigs were monitored daily for clinical signs of disease for a total of 28 days. All pigs were necropsied at 28 days postinoculation.

Example 25

Cell Lines and Cell Cultures

A total of twelve continuous cell lines were used in this study. A type 1 porcine circovirus (PCV1)-free porcine kidney epithelial cell line PK-15 (Fenaux, M., T. et al. 2004. A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs. J Virol 78:6297-303), a swine testis cell line ST (ATCC CRL-1746, passage 6), a baby hamster kidney fibroblast cell line BHK-21 (ATCC CCL-10, passage 62), and an African green monkey kidney epithelial Vero cell (ATCC CCL-81, passage 95) were each grown in modified Eagle's medium (MEM) supplemented with 10% fetal bovine serum (FBS) and antibiotics. A porcine monocytic cell line 3D4/31 (ATC-CCRL-2844, passage 8), a porcine small intestinal epithelial cell line IPEC-J2 (a gift from Dr. Anthony Blikslager at North Carolina State University, Raleigh, N.C.) (Schierack, P., M. et al. 2006. Characterization of a porcine intestinal epithelial cell line for in vitro studies of microbial pathogenesis in swine. Histochem Cell Biol 125:293-305), and a hamster ovarycell line CHO-K1 (ATCC CCL-61, passage 12) were each cultured in Dulbecco's modified Eagle's medium (DMEM) and nutrient mixture F-12 (Ham) (1:1) with GlutaMAX™-I (Invitrogen, Carlsbad, Calif.) supplemented with 5% FBS and antibiotics. A monkey kidney cell line subclone MARC-145 (passage 42) derived from MA-104 (ATCC CRL-2378), a human cervical cancer cell line HeLa (ATCC CCL-2, passage 10), two human hepatocellular carcinoma cell lines Huh-7 (subclone 10-3; a gift from Dr. Suzanne U. Emerson at NIAID, NIH) (Emerson, S. U., H. et al. 2004. In vitro replication of hepatitis E virus (HEV) genomes and of an HEV replicon expressing green fluorescent protein. J Virol 78:4838-46) and HepG2 (ATCC CRL-10741, passage 7) were each grown in DMEM supplemented with 10% fetal bovine serum (FBS) and antibiotics. A human 293 cell line, 293TT, engineered to stably express high levels of SV40 large T antigen (a gift from Dr. John T. Schiller, Laboratory of Cellular Oncology, National Cancer Institute, Bethesda, Md.) (Buck, C. B., et al. 2004. Efficient intracellular assembly of papillomaviral vectors. J Virol 78:751-7), was cultured in DMEM-10 medium (DMEM with 10% inactivated FBS, 1% non-essential amino acids and 1% GlutaMAX-I) supplemented with 400 µg/ml hygromycin B and antibiotics. All cells were grown at 37° C. with 5% $CO_2$.

Example 26

Analysis of TTSuV1 or TTSuV2 Contamination in Cultured Cells by Real-Time Quantitative PCR (qPCR)

To ensure that the porcine-derived cell lines used in the study were free of TTSuV contamination, five cell lines, PCV1-free PK-15, 3D4/31, IPEC/J2, BHK-21 and MARC-145, were tested for TTSuV1 or TTSuV2 DNA by using two singleplex SYBR green-based real-time qPCR assays (Huang, Y. W., et al. 2010. J Virol Methods 170:140-6). Briefly, total DNA was extracted from each cell line using the QIAamp DNA mini kit (Qiagen) and was subsequently subjected to TTSuV1 or TTSuV2 qPCR detection in a 25 µl PCR system using SensiMix SYBR & Fluorescein kit (Quantace Ltd) as described previously (Huang, Y. W., et al. Id.). A TTSuV1 or TTSuV2 standard template and a porcine serum sample from a commercial company used in cell culture, which is supposed to be OIE (The World Organization for Animal Health) diseases-free, were included as controls. All samples were run in duplicate on the same plate.

Example 27

Generation of a Rabbit Anti-TTSuV2 ORF1 Antiserum

The inventors have previously expressed and purified a recombinant truncated ORF1 protein of TTSuV2 (PTTV2c-VA strain) (Huang, Y. W., et al. 2011. Virus Res 158:79-88). The purified protein products were used to immunize two New Zealand white rabbits as a custom antibody production service at Rockland Immunochemicals (Gilbertsville, Pa.). Serum samples from both rabbits were collected before immunization (pre-bleed) and at 45 days post-immunization.

Example 28

Construction of Full-Length Genomic DNA Clones of TTSuV2

Two PCR fragments (E and F) covering the full-length genome of the U.S. strain of TTSuV2 isolate PTTV2c-VA (GenBank accession no. GU456386; SEQ ID NO:12) were re-amplified from the constructs reported previously (Huang, Y. W., Virology 396:287-97), which were subsequently assembled into a full-length genomic DNA by overlapping PCR using the Herculase II Fusion DNA Polymerase (Stratagene) in the vector pSC-B-amp/kan (Stratagene). The monomeric TTSuV2 DNA fragment was flanked by a BamHI restriction site at both ends. The resulting construct was designated pSC-PTTV2c (FIG. 1A). The full-length PTTV2c genome was excised from the clone pSC-PTTV2c using BamHI digestion, purified and ligated head-to-tail to form concatemers. Two-copy concatemers were cloned into the BamHI-pre-digested pSC-B-amp/kan vector to produce a tandem-dimerized TTSuV2 DNA clone, pSC-2PTTV2c-RR (FIG. 1B). Similarly, two plasmids harboring monomeric and tandem-dimerized TTSuV2 genomic DNA originated from German TTSuV2 isolate TTV2-#471942 (GenBank accession no. GU188046; SEQ ID NO:62) (Gallei, A., et al. 2010. Vet Microbiol 143:202-12) were constructed with the EcoRV site on the same vector backbone, respectively. Since the TTV2-#471942 strain was classified into the TTSuV2 subtype 2b together with the U.S. isolate PTTV2b-VA based upon phylogenetic analysis (data not shown), the inventors designated these two clones pSC-TTV2-#472142 (FIG. 1C) and pSC-2PTTV2b-RR (FIG. 1D), respectively.

Example 29

Introduction of Genetic Markers into the Two TTSuV2 Monomeric DNA Clones and Construction of a TTSuV2 Deletion Mutant An HpaI restriction enzyme site was engineered into the putative spliced region (intron) of TTSuV2 genome in the clone pSC-TTV2-#472142 for introducing a genetic marker to discriminate between the cloned virus and the potential indigenous viruses in the subsequent animal study. To create the unique HpaI site (GTTAAC; mutations are underlined; SEQ ID NO:63), three point mutations, C to T, C to A and T to A at nucleotide (nt) positions 1817, 1819 and 1820 corresponding to the TTV2-#471942 genome were generated by a fusion PCR technique using two pairs of primers containing the desired mutations. The fusion PCR product replaced the corresponding region on the clone pSC-TTV2-#471942 by using the cloning site KpnI at both ends. The mutations did not change the putative ORF1 capsid amino acid sequence. The resulting full-length DNA clone was named pSC-TTV2-EU (FIG. 1E). Using the same strategy, two unique restriction sites, PstI (CTGCAG; SEQ ID NO:64) and MfeI (CAATTG; SEQ ID NO:65), were introduced into the putative intron of the PTTV2c-VA genome in the pSC-PTTV2c clone (FIG. 1F). The new clone, designed pSC-TTV2-US, contained three silent mutations at nt positions 1613 (A to T), 1784 (T to C) and 1787 (C to T) corresponding to the PTTV2c-VA genome. A mutant clone pSC-TTV2-AAA, with a 104-bp deletion (nt positions 332-437) from the putative TATA box to the ORF1/ORF2 start codon on the clone pSC-TTV2-US, was also generated by removing the short deletion fragment with double-digestion with the AccI and ApaI enzymes followed by formation of two blunt ends with a Klenow enzyme and self-ligation (FIG. 1G). All mutagenesis were confirmed by DNA sequencing.

Example 30

In Vitro Transfection of TTSuV DNA Clones

The PCV1-free PK-15 cells were seeded at $2 \times 10^5$ cells per well onto a 6-well plate and grown until 60%-70% confluency before transfection. Two micrograms of the tandem-dimerized clones pSC-2PTTV2b-RR and pSC-2PTTV2c-RR were directly transfected into the cells, respectively, using Lipofectamine LTX (Invitrogen) according to the manufacturer's protocol. For monomeric clones pSC-PTTV2c, pSC-TTV2-#471942, pSC-TTV2-EU, pSC TTV2-US and pSC-TTV2-AAA, the respective genomic fragment was excised by BamHI or EcoRV enzyme, gel-purified, and re-ligated with the T4 DNA ligase overnight. The ligation mixtures (~2 µg) were used for transfection using Lipofectamine LTX, respectively. Cells were cultured for 3 to 5 days, and then subjected to an immunofluorescence assay (IFA) to detect the expression of ORF1. Alternatively, transfected cells were passaged into new 6-well plates and were cultured for 3 days before detection of ORF1 expression by IFA. Transfection of the other 11 cell lines and IFA detection were similar.

Example 31

Immunofluorescence Assay (IFA)

Transfected or passaged cells on 6-well plates were washed times with PBS and fixed with acetone. Five hundred microliters of the anti-TTSuV2 ORF1 antiserum at a 1:500 dilution in PBS, was added to the cells for each well and incubated for 1 hour at room temperature. Cells were washed 3 times with PBS and 500 µl Texas Red- or Alexa Fluor 488-conjugated goat anti-rabbit IgG (Invitrogen) at a 1:300 dilution was subsequently added. After incubation for 1 hour at room temperature, the cells were washed with PBS, stained with 500 µl DAPI (KPL, Inc.) at a 1:1000 dilution and visualized under a fluorescence microscope.

Example 32

RT-PCR

Total RNA was extracted from PCV1-free PK-15 cells transfected with circular TTSuV2 DNA using the RNeasy mini kit (Qiagen) followed by an RNase-free DNase I treatment. The cDNA synthesis was performed using SuperScript II reverse transcriptase (Invitrogen) with oligo-dT as the reverse primer. PCR was performed in a 50-µL reaction with the Advantage 2 PCR kit (Clontech) using primers TTV2-448F (5'-GAAGAAAGATGGCTGACGGTAGCG-TACT-3'; SEQ ID NO:66) and TTV2-2316R (5'-AGGT-GCTTGAGGAGTCGTCGCTTG-3'; SEQ ID NO:6). The PCR products were gel-purified, cloned into a pCR2.1 vector (Invitrogen) by TA cloning strategy and sequenced.

Example 33

In Vivo Transfection of Colostrum Deprived (CD) Pigs with the Tandem-Dimerized TTSuV2 Clones It has been previously demonstrated that the infectivity of infectious DNA clones for viruses with a circular genome can be tested by direct inoculation of dimerized full-length genomic DNA into animals (Fenaux, M., T. et. al. 2004. A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs. J Virol 78:6297-303). Therefore, in this study, a pilot animal study was initially conducted to determine the infectivity of the two tandem-dimerized TTSuV2 clones pSC-2TTV2c-RR and pSC-2TTV2b-RR. Briefly, six, 26-day old, CD pigs that were seronegative and viral DNA-negative for TTSuV1 and TTSuV2 were assigned into three groups of two each. Each group of pigs was housed separately and maintained under conditions that met all requirements of the Institutional Animal Care and Use Committee. The pigs in each group were injected by using a combination of intra-lymphoid (superficial inguinal lymph nodes) and intramuscular routes with the plasmid DNA of the full-length TTSuV2 clones. The two pigs (nos. 1 and 2) in group 1 were each given 1 ml of PBS buffer and used as the negative control. The two pigs (nos. 3 and 4) in group 2 were each injected with 200 µg of the pSC-2TTV2c-RR plasmid DNA whereas the remaining two pigs (nos. 5 and 6) in group 3 were each inoculated with 200 µg of the pSC-2TTV2b-RR clone.

Pigs were monitored daily for evidence of TTSuV2 infection for a total of 44 days. All pigs were necropsied at 44 days post-inoculation. Serum samples were collected from all pigs prior to inoculation and weekly thereafter until termination of the study. The samples were tested for the presence of TTSuV DNA and quantified for viral loads by a singleplex TTSuV2-specific real-time qPCR (Huang, Y. W., et al. 2010. J Virol Methods 170:140-6). Samples of tissues including brain, lung, lymph nodes, liver, kidney, thymus, spleen, small intestines, large intestines, heart, tonsil, bone marrow were collected during necropsies and processed for microscopic examination. The tissues were examined in fashion blinded to the treatment status of the pigs and given a subjective score for severity of tissue lesions ranged from 0 (normal) to 3 (severe) (Fenaux, M., et al. A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs. J Virol 78:6297-303; Halbur, P. G., et al. 1995. Comparison of the pathogenicity of two US porcine reproductive and respiratory syndrome virus isolates with that of the Lelystad virus. Vet Pathol 32:648-60).

Example 34

In Vivo Transfection of Cesarean Derived, Colostrum Deprived (CD/CD) Pigs with the Circularized TTSuV2 Genomic DNA Containing Genetic Markers To further verify the results from the initial pilot pig study, the inventors introduced tractable genetic markers into the full-length DNA clones and conducted another CD/CD pig study. Approximately 600 µg of circular or concatamerized TTSuV2 genomic DNA derived from the clone pSC-TTV2-EU or pSC-TTV2-US was generated by ligation of the linearized TTSuV2 genomic DNA. To determine the infectivity of the full-length DNA clones, the inventors inoculated four, 40-day-old, CD/CD pigs (nos. 129, 135, 139 and 140 in group 1) each with 150 µg of concatamerized "TTV2-EU DNA" by a combination of both the intra-lymph node route and intramuscular route. Another four CD/CD pigs (nos. 133, 137, 138 and 141) in group 2, which were housed in a separate room, were each similarly inoculated with 150 µg of concatamerized "TTV2-US DNA". The remaining four CD/CD pigs (nos. 127, 132, 136 and 142) in group 3 were each injected with 1.5 ml of PBS buffer and served as negative controls. All pigs were monitored for evidence of TTSuV2 infection for a total of 35 days, at which time they were necropsied. Viremia was tested by a TTSuV2 real-time qPCR (Huang, Y. W., et al. 2010. J Virol Methods 170:140-6). A TTSuV2 genomic region of 620 bp containing the engineered genetic markers in TTV2-EU or TTV2-US was amplified from the sera of inoculated pigs by PCR using primers TTV2-tagF (5'-TGACACAGGA/CG-TAGGAAATGCAGT-3'; SEQ ID NO: 67) and TTV2-tagR (5'-TGAAGTATTTAGGGTCATTTGTAGCA-3'; SEQ ID NO: 68) from selected serum samples of pigs with viremia. The PCR products were gel-purified and cloned into a pCR2.1 vector by using the TA cloning strategy. The white bacterial clones on the X-gal-containing agar plates were picked up for subsequent DNA extraction and sequencing.

Example 35

Sources of Porcine Sera

Porcine sera used in this study were described previously (Huang, Y. W., et al. 2011. Virus Res 158:79-88). Briefly, serum samples for serum Western blot (WB) analysis were collected from 20 conventional adultboars with no clinical symptoms from a Virginia pig farm, seven gnotobiotic pigs from Virginia (nos. 4 to 7, 224, 229 and 230; kindly provided by Drs. Lijuan Yuan and Guohua Li fromVirginia Tech) and 12 from Iowa (group D), five cesarean-derived, colostrum-deprived (CD/CD) pigs and approximately 50 conventional piglets from a Wisconsin pig farm. A TTSuV2-seropositive porcine serum, which was manufactured in New Zealand and free of all known OIE (The World Organization for Animal Health) notifiable diseases, was also used in this study.

One hundred and sixty porcine serum samples were used for assessing the virological and serological profiles of TTSuV1a and TTSuV1b infection and were divided into five groups (A to E) as described previously (Huang, Y. W., et al. 2011. Virus Res 158:79-88): (i) Twenty group-A samples were from 10 specific-pathogen-free (SPF) pigs (60-80 days old at arrival) free of known pathogens and were collected at arrival in the facility and two months after arrival; (ii) Sixty group-B samples were collected from 105 days old pigs in a farm with an outbreak of porcine circovirus associated disease (PCVAD): 30 were from clinically affected pigs and 30 were were clinically unaffected pigs; (iii) Fifty-eight group-C samples were collected from 28 days old pigs with unknown disease status: 28 were clinically affected and 30 were clinically unaffected; (iv) Twelve group-D samples were from 14-42 days old gnotobiotic pigs located in Iowa; (v) Ten group-E sera were from 21-30 days old SPF pigs used for an experimental PCV2 infection study.

Example 36

Construction of the TTSuV1a- and TTSuV1b-ORF1 Expression Plasmids

The C-terminal part of the ORF1 of two TTSuV1 strains, PTTV1a-VA (GenBank accession no. GU456383; SEQ ID NO: 9) and PTTV1b-VA (GenBank accession no. GU456384; SEQ ID NO: 10) was amplified, respectively, from the available PCR fragments reported previously. The amplicon was expected to encode a truncated PTTV1a-VA ORF1 protein of 319 aa (positions 317-635 corresponding to PTTV1a-VA) or a truncated PTTV1b-VA ORF1 protein of 318 aa (positions 322-639 corresponding to PTTV1b-VA). An additional methionine was introduced at the N-terminus of each amplified fragments. Two ORF1 expression plasmids, designated pTri-1aORF1 and pTri-1bORF1, were each constructed by cloning the respective PCR product into a bacterial/insect/mammalian-triple expression vector pTriEx1.1-Neo (Novagen) between the NcoI and XhoI restriction sites to generate two C-terminally 8×His-tagged fusion proteins. The recombinant plasmids were confirmed by DNA sequencing. The TTSuV2 ORF1 expression construct, pTri-2cORF1, had been described previously (Huang, Y. W., et al. 2011. Virus Res 158:79-88).

Example 37

Expression and Purification of the Recombinant TTSuV1a- and TTSuV1b-ORF1 Proteins The two plasmids were each transformed into Rosetta 2 (DE3) pLacI competent cells (Novagen). The bacteria were grown in 100-ml of Overnight Express TB Media (Novagen) for 16-18 hours at 37° C. and then the bacterial culture was harvested by centrifugation at 3,400 rpm for 15 minutes at 4° C. The resulting bacterial pellet was treated with BugBuster and rLysozyme according to the manufacture's protocol (Novagen). Benzonase Nuclease (Novagen) was added to degrade DNA and RNA. The resulting inclusion bodies were lysed in 6M guanidine hydrochloride, 0.1 M sodium phosphate, 0.01 M Tris-Chloride, and 0.01 M imidazole with a pH value of 8.0. The lysate supernatants were collected by centrifugation and were used for His-tagged protein purification by a Ni-NTA His•Bind Resin 50% (Novagen) under denaturing condition with 8 M urea. Proteins were dialyzed as described previously. The recombinant His-tagged TTSuV1a- or TTSuV1b ORF1 proteins used as the antigen for ELISA and rabbit immunization were quantified using a NanoDrop spectrophotometry and frozen at −80° C. until use.

Example 38

Generation of Anti-ORF1 Antisera of TTSuV1a and TTSuV1b in Rabbits

The two ORF1 proteins of TTSuV1a and TTSuV1b expressed in *E. coli* were purified and used to immunize two New Zealand white rabbits, respectively, at a custom antibody production service at Rockland Immunochemicals (Gilbertsville, Pa.). Antisera were harvested at 50 days post-immunization.

Example 39

SDS-PAGE, Anti-His-Tagged WB and Serum WB Analysis

The unpurified or purified recombinant TTSuV1 ORF1 proteins were resolved on a 4-12% Bis-Tris Polyacrylamide Gel (Invitrogen) by electrophoresis and were subsequently transferred onto a polyvinylidene difluoride (PVDF) membrane. Proteins were detected on the PVDF membrane using an anti-6×His-tagged Mab at a 1:1000 dilution at 4° C., followed by incubation with an IRDye 800CW conjugated goat anti-rabbit IgG (LI-COR Biosciences) at a 1:10,000 dilution at room temperature. After three washing steps using Tris buffered saline/0.05% Tween 20 (TBS-T; Sigma), the membrane was analyzed using the Odyssey Infrared Imaging System (LI-COR Biosciences).

For serum WB analysis, the purified TTSuV1a- or TTSuV1b-ORF1 proteins were incubated with individual porcine sera at a 1:200 dilution and with IRDye 800CW conjugated rabbit F(ab')$_2$ anti-swine IgG (Rockland Immunochemicals, Inc.) at a 1:10,000 dilution at room temperature. The membrane was then analyzed using the Odyssey Infrared Imaging System.

Example 40

Indirect ELISAs

TTSuV1a- and TTSuV1b-based ELISAs were developed. The optimal concentration of the antigens and the optimal dilutions of sera and HRP conjugates were determined by checkerboard titrations. Similar to the TTSuV2-based ELISA reported previously, the optimal amount of the ORF1 antigen of TTSuV1a or TTSuV1b was 68 ng per well. The optimal ELISA results were obtained by using a 1:100 dilution of serum samples and a 1:4000 dilution of IgG conjugates.

The ELISA was initiated by diluting the purified ORF1 proteins in carbonate coating buffer (pH=9.6) that was used for coating 96-well ELISA plates (Greiner Bio-One) with 100 μl/well. After incubation at 37° C. for 2 hours, each well was washed 3 times with 300 μl of Tris-buffered saline-Tween 20 solution (TBS-T) and blocked with protein-free blocking buffer (Pierce) at a volume of 300 μl for 1 hour at 37° C. One hundred μl of each diluted serum sample was transferred to the corresponding well on the ELISA plates and incubated at 37° C. for 2 hours. After washing the wells three times with 300 μl of TBS-T buffer, the diluted HRP-conjugated rabbit anti-swine IgG (Rockland) was added to each well in a volume of 100 μl and the plate was incubated at 37° C. for 1 hour. A volume of 100 μl of Sure Blue Reserve 1-Component (KPL) was added to each well and incubated for 10 minutes at room temperature. The reaction was stopped by adding 100 μl/well of 1 N HCL. The plates were then read at 450 nm using a spectrophotometer. All serum samples were run in duplicates. Positive and negative controls run in quadruplicates were included on each plate. In general, the mean OD value of the negative control was less than 0.5 whereas the mean OD value of the positive control was greater than 1.5. The ELISA value was calculated as the S/N value that was expressed as a ratio of the mean OD value of a sample to the mean OD value of the negative control (n=4). A subjective cut-off S/N value of 1.2 was used to distinguish between positive and negative samples.

Example 41

Real-Time qPCR Assay for Quantitation of TTSuV1

A SYBR green-based TTSuV1-specific real-time quantitative PCR (qPCR) developed recently in our laboratory was used to measure the total TTSuV1 viral loads (both TTSuV1a and TTSuV1b) in the five groups of pig sera as described previously. The minimal detection limit was $1.0 \times 10^4$ copies per ml in this study. The TTSuV1 qPCR assay does not cross-amplify TTSuV2 DNA (Huang, Y. W., et al. 2010. J Virol Methods 170:140-6). Quantitation of TTSuV2 and PCV2 viral loads in group-B sera had been reported previously (Huang, Y. W., et al. 2011. Virus Res 158:79-88).

Example 42

Statistical Analyses

Data were analyzed using SAS software (version 9.2; SAS Institute Inc., Cary, N.C.) and GraphPad Prism software (version 5.0; San Diego, Calif.), respectively. Antibody levels (represented by S/N values) were compared between categories of $\log_{10}$ viral titers using the Kruskal-Wallis test followed by Dunn's procedure. For each group that contained clinically affected and non-affected pigs (groups B and C), $\log_{10}$ virus titers were compared between pigs with and without clinical signs using a Wilcoxon 2-sample test. Antibody levels were compared between pigs with and without disease using a 2-sample t-test. Using a cutoff point of 1.2, the proportion of pigs with antibodies was compared between affected and unaffected pigs using a Fisher's exact test.

Correlations between S/N values for TTSuV1a and S/N values for TTSuV1b, and between S/N values for TTSuV1a or TTSuV1b (separately) and TTSuV2 were assessed using Spearman's correlation coefficient. The correlations were separately generated for a combination of 3 groups (group-A to group-C).

To assess the synergistic effects between PCV2 and TTSuV1 on disease prevalence, the pigs in group B were categorized as follows: pigs positive for both PCV2 and TTSuV1, pigs only positive for PCV2, pigs only positive for TTSuV1, and pigs with neither PCV2 nor TTV1. Subsequently, the proportions of affected pigs were compared between the groups using Fisher's exact test. Statistical significance was set to alpha=0.05.

Example 43

Transfection of PK-15 Cell with TTSuV Expression Constructs

PK-15 cells were seeded onto a 6-well plate and grown until 70%-80% confluency before transfection. Two micrograms of each of the three constructs pTri-1aORF1, pTri-1bORF1 and pTri-2cORF1, mixed with 10 μl of Lipofectamine LTX (Invitrogen), were transfected into the cells, respectively. Cells were cultured for 3 days and were subjected to IFA to detect the ORF1 expression.

Example 44

Immunofluorescence Assay (IFA)

Five rabbit antisera were used for IFA staining, including anti-TTSuV1a, anti-TTSuV1b, anti-TTSuV2, pre-bleed rabbit negative control serum, and rabbit anti-human genogroup-1 TTV ORF1 antiserum (AK47; a generous gift from Dr. Annette Mankertz at the Robert Koch-Institute, Berlin, Germany). Transfected cells were fixed with acetone. Five hundred microliters of each of the five antisera, at a 1:500 dilution in PBS, was added on top of the cells in each well and incubated for 1 hour at room temperature. After three washing steps with PBS, the cells were incubated with 500 μl Alexa Fluor 488-labeled goat anti-rabbit IgG (Invitrogen) at a 1:200 dilution for 1 hour incubation at room temperature. Cells were stained with 500 μl DAPI (KPL, Inc.) at a 1:1000 dilution and visualized under a fluorescence microscope.

TABLE 6

Reactivity of anti-TTSuV1a, anti-TTSuV1b, anti-TTSuV2, pre-bleed rabbit and anti-human TTV (AK47) sera in PCV1-free PK-15 cells transfected with plasmids encoding truncated ORF1s from TTSuV1a, TTSuV1b and TTSuV2, respectively, as determined by IFA. The intensity of the fluorescent signal was determined visually and expressed ranging from – to ++.

| | Ab | | | | |
|---|---|---|---|---|---|
| Transfection | Anti-TTSuV1a | Anti-TTSuV1b | Anti-TTSuV2 | Pre-bleed rabbit serum | Anti-human TTV (AK47) |
| pTri-1aORF1 | ++ | + | – | – | – |
| pTri-1bORF1 | + | ++ | – | – | – |
| pTri-2cORF1 | – | – | ++ | – | – |
| Mock | – | – | – | – | – |

What is claimed is:

1. A method for diagnosing a Torque Teno Sus Virus (TTsuV) infection in a pig, or determining whether a pig has been exposed to one or more TTsuV genotypes or subtypes, comprising:

immobilizing an immunogenic fragment or a complete protein of a recombinantly expressed and purified polypeptide sequence of an ORF1 protein of one or more TTsuV genotypes or subtypes wherein the immunogenic fragment or complete polypeptide sequence comprises one or more of: amino acids 363 to 375 of a TTsuV2 ORF1 represented by SEQ ID NO: 16, and amino acids 388 to 423 of a TTsuV2 ORF1 represented by SEQ ID NO: 16;

contacting a serum sample from a pig suspected of TTsuV infection with the immobilized immunogenic fragment or complete protein; and detecting captured antibody specific to the immunogenic fragment.

2. The method of claim 1, wherein the TTsuV genotypes or subtypes include one or more of TTsuV1a and TTsuV1b in addition to the-TTsuV2 ORF1 immunogenic fragment or complete polypeptide sequence.

3. The method of claim 1, wherein the polypeptide comprises N-terminal truncated ORF1 proteins of one or more of TTsuV genotypes or subtypes TTsuV1a and TTsuV1b in addition to the TTsuV2 ORF1 immunogenic fragment or complete polypeptide sequence.

4. The method of claim 2, wherein the polypeptide sequence comprises amino acids 317-635 of the ORF1 protein of TTsuV1a as referenced by SEQ ID NO: 12.

5. The method of claim 2, wherein the polypeptide sequence comprises amino acids 322-639 of the ORF1 protein of TTsuV1b as referenced by SEQ ID NO: 13.

6. The method of claim 1, wherein the polypeptide sequence comprises amino acids 310-625 of the ORF1 protein of TTsuV2 as referenced by SEQ ID NO: 16.

7. The method of claim 1, wherein the detecting captured antibody is by Western blot.

8. The method of claim 1, wherein the detecting captured antibody is by enzyme-linked immunosorbent assay (ELISA).

9. A diagnostic reagent for use in the detection of Torque Teno Sus Virus (TTsuV) infection in a mammal, comprising ORF1 proteins or immunogenic fragments thereof of one or more TTsuV genotypes or subtypes wherein the immunogenic fragments or complete polypeptide sequences are recombinantly expressed and purified and comprise one or more of: amino acids 363 to 375 of a TTsuV2 ORF1 represented by SEQ ID NO: 16, and amino acids 388 to 423 of a TTsuV2 ORF1 represented by SEQ ID NO: 16.

10. The diagnostic reagent of claim 9, wherein the one or more TTsuV genotypes or subtypes include one or more of TTsuV1a and TTsuV1b in addition to the TTsuV2 immunogenic fragments or complete polypeptide sequences.

11. A method for simultaneously detecting TTsuV1 and TTsuV2 infection comprising:

extracting DNA from a sample suspected of TTsuV infection;

performing real-time polymerase chain reaction (RT-PCR) using a TTsuV1-specific primer pair according to SEQ ID NO:29 and SEQ ID NO:30 and a TTsuV2-specific primer pair according to SEQ ID NO:31 and SEQ ID NO:32 in the same real-time PCR reaction; and determining a presence of TTsuV1 and/or TTsuV2 DNA based on amplified primer specific sequences.

12. A method for simultaneously detecting TSSuV1 and TTSuV2 infection by duplex nested polymerase chain reaction (PCR) comprising:

isolating viral DNA from samples of pigs suspected of TTSuV infection;

performing a first round of PCR using one pair of primers Plab-mF according to SEQ ID NO:33 and Plab-mR according to SEQ ID NO:34;

performing a second round of PCR using a mixture of two pairs of primers, Pla-nF according to SEQ ID NO:35 and Pla-nR according to SEQ ID NO:36 for detection of TTSuV1a, and Plb-nF according to SEQ ID NO:37 and Plb-nR according to SEQ ID NO:38 for detection of TTSuV1b, and visualizing the PCR products.

* * * * *